United States Patent
Parmar et al.

(10) Patent No.: US 12,173,287 B2
(45) Date of Patent: Dec. 24, 2024

(54) COMPOSITIONS AND METHODS FOR IMPROVING STRAND BIASED

(71) Applicant: Alnylam Pharmaceuticals, Inc., Cambridge, MA (US)

(72) Inventors: Rubina G. Parmar, Cambridge, MA (US); Pawan Kumar, Cambridge, MA (US); Masaaki Akabane-Nakata, Cambridge, MA (US); Shigeo Matsuda, Cambridge, MA (US); Muthiah Manoharan, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 533 days.

(21) Appl. No.: 17/053,460

(22) PCT Filed: May 7, 2019

(86) PCT No.: PCT/US2019/031083
§ 371 (c)(1),
(2) Date: Nov. 6, 2020

(87) PCT Pub. No.: WO2019/217397
PCT Pub. Date: Nov. 14, 2019

(65) Prior Publication Data
US 2021/0238594 A1    Aug. 5, 2021

Related U.S. Application Data

(60) Provisional application No. 62/811,870, filed on Feb. 28, 2019, provisional application No. 62/667,972, filed on May 7, 2018.

(51) Int. Cl.
*C12N 15/113*    (2010.01)

(52) U.S. Cl.
CPC ........ *C12N 15/113* (2013.01); *C12N 2310/14* (2013.01); *C12N 2310/315* (2013.01);
(Continued)

(58) Field of Classification Search
CPC .............. C12N 15/113; C12N 2310/14; C12N 2310/315; C12N 2310/317;
(Continued)

(56) References Cited

U.S. PATENT DOCUMENTS

2009/0023675 A1*  1/2009  McSwiggen ............ A61P 31/10
                                                536/23.1
2011/0059187 A1   3/2011  Basu
(Continued)

FOREIGN PATENT DOCUMENTS

EP            1681347 A1   7/2006
WO    WO-2009044392 A2 *  4/2009  ................ A61P 1/02
(Continued)

OTHER PUBLICATIONS

Pei et al., Quantitative evaluation of siRNA delivery in vivo, 2010, RNA, 16, 2553-2563. (Year: 2010).*
(Continued)

*Primary Examiner* — J. E. Angell
*Assistant Examiner* — Keyur A Vyas
(74) *Attorney, Agent, or Firm* — Nixon Peabody LLP; David S. Resnick; Ravinderjit S. Braich

(57) ABSTRACT

One aspect of the present invention relates to double-stranded RNA (dsRNA) agent capable of inhibiting the expression of a target gene. Other aspects of the invention relate to pharmaceutical compositions comprising these dsRNA molecules suitable for therapeutic use, and methods of inhibiting the expression of a target gene by administering
(Continued)

these dsRNA molecules, e.g., for the treatment of various disease conditions.

20 Claims, 44 Drawing Sheets

Specification includes a Sequence Listing.

(52) U.S. Cl.
CPC .. *C12N 2310/317* (2013.01); *C12N 2310/322* (2013.01); *C12N 2310/3231* (2013.01); *C12N 2310/332* (2013.01); *C12N 2310/351* (2013.01)

(58) Field of Classification Search
CPC ...... C12N 2310/322; C12N 2310/3231; C12N 2310/332; C12N 2310/351
See application file for complete search history.

(56) References Cited

U.S. PATENT DOCUMENTS

| | | | |
|---|---|---|---|
| 2013/0130378 A1 | 5/2013 | Manoharan et al. |
| 2014/0170191 A1 | 6/2014 | Carter et al. |
| 2015/0247147 A1 | 9/2015 | Rusconi |
| 2015/0315594 A1 | 11/2015 | Prakash et al. |
| 2017/0275626 A1 | 9/2017 | Maier et al. |

FOREIGN PATENT DOCUMENTS

| | | |
|---|---|---|
| WO | 2016028649 A1 | 2/2016 |
| WO | 2016100716 A1 | 6/2016 |
| WO | 2018098328 A1 | 5/2018 |
| WO | 2021072395 A1 | 4/2021 |

OTHER PUBLICATIONS

Kaur et al., Perspectives on Chemistry and Therapeutic Applications of Locked Nucleic Acid (LNA), 2007, Chem. Rev., 107, 4672-4697. (Year: 2007).*

Raguraman et al. Alpha-I-Locked Nucleic Acid-Modified Antisense Oligonucleotides Induce Efficient Splice Modulation In Vitro, 2020, International J. of Molecular Sci., 21, 2434, p. 1-12 (Year: 2020).*

Schlegel et al. "Chirality Dependent Potency Enhancement and Structural Impact of Glycol Nucleic Acid Modification on siRNA", JACS (2017), vol. 139, pp. 8537-8546.

Supporting Information for Schlegel et al. "Chirality Dependent Potency Enhancement and Structural Impact of Glycol Nucleic Acid Modification on siRNA", JACS (2017), vol. 139, pp. 8537-8546.

Parmar et al., "5'-(E)-Vinyiphosphonate: A Stable Phosphate Mimic Can Improve the RNAi Activity of siRNA-GalNAc Conjugates." ChemBioChem 17.11 (2016): 985-989.

Haraszti et al., "5'-Vinylphosphonate improves tissue accumulation and efficacy of conjugated siRNAs in vivo." Nucleic acids research 45.13 (2017): 7581-7592.

Janas et al. "Selection of GalNAc-conjugated siRNAs with limited off-target-driven rat hepatotoxicity." Nature communications 9.1 (2018): 1-10.

Kumar et al. "5'-Morpholino modification of the sense strand of an siRNA makes it a more effective passenger." Chemical Communications 55.35 (2019): 5139-5142.

Clark et al. "Knockdown of TNFR1 by the sense strand of an ICAM-1 siRNA: dissection of an off-target effect." Nucleic acids research 36.4 (2008): 1081-1097.

Supplementary Information for Janas et al. "Selection of GalNAc-conjugated siRNAs with limited off-target-driven rat hepatotoxicity." Nature communications 9.1 (2018): 1-10.

Supporting Information for Parmar et al.,"5'-(E)-Vinylphosphonate: A Stable Phosphate Mimic Can Improve the RNAi Activity of siRNA-GalNAc Conjugates." ChemBioChem 17.11 (2016): 985-989.

OligoCalc: Oligonucleotide Properties calculator accessed Dec. 8, 2020 at <http://biotools.nubic.northwestern.edu/OligoCalc.html>, 5 pages.

Alagia et al., "Modulation of the RNA Interference Activity Using Central Mismatched siRNAs and Acyclic Threoninol Nucleic Acids (aTNA) Units." Molecules, 20, 7602-7619 (2015).

Bramsen et al. A screen of chemical modifications identifies position-specific modification by UNA to most potently reduce siRNA off-target effects. Nucleic Acids Res, 38, 5761-5773 (2010).

Egli et al. "Conformational influence of the ribose 2'-hydroxyl group: Crystal structures of DNA-RNA chimeric duplexes. Biochemistry, 32, 3221-3237 (1993).

Kenski et al., "Analysis of acyclic nucleoside modifications in siRNAs finds sensitivity at position 1 that is restored by 5'-terminal phosphorylation both in vitro and in vivo." Nucleic Acids Research, 38, 660-671 (2010).

Laursen et al. "Utilization of unlocked nucleic acid (UNA) to enhance siRNA performance in vitro and in vivo." Molecular BioSystems, 6, 862-870 (2010).

Lee et al. "Abasic pivot substitution harnesses target specificity of RNA interference." Nat. Commun., 6, 10154 (2015).

Mook et al. "In vivo efficacy and off-target effects of locked nucleic acid (LNA) and unlocked nucleic acid (UNA) modified siRNA and small internally segmented interfering RNA (sisiRNA) in mice bearing human tumor xenografts." Artif DNA PNA XNA, 1, 36-44 (2010).

Schirle et al. "Structural Analysis of Human Argonaute-2 Bound to a Modified siRNA Guide." J. Am. Chem. Soc., 138, 8694-8697 (2016).

Schlegel et al. "Improved Phosphoramidite Building Blocks for the Synthesis of the Simplified Nucleic Acid GNA." J. Org. Chem., 74, 4615-4618 (2009).

Seok et al. "Rationally designed siRNAs without miRNA-like off-target repression." BMB Rep, 49, 135-136 (2016).

Sheng et al. "Structural insights into the effects of 2'-5' linkages on the RNA duplex." Proc. Natl. Acad. Sci., 111, 3050-3055 (2014).

Ui-Tei et al. "Functional dissection of siRNA sequence by systematic DNA substitution: modified siRNA with a DNA seed arm is a powerful tool for mammalian gene silencing with significantly reduced off-target effect." Nucleic Acids Res., 36, 2136-2151 (2008).

Vaish et al. Improved specificity of gene silencing by siRNAs containing unlocked nucleobase analogs. Nucleic Acids Res., 39, 1823-1832 (2010).

Wahl et al. "B-form to A-form conversion by a 3'-terminal ribose: crystal structure of the chimera d(CCACTAGTG)r(G)." Nucleic Acids Res., 28, 4356-4363 (2000).

Wasner et al. "Physicochemical and Biochemical Properties of 2',5'-Linked RNA and 2',5'-RNA:3',5'-RNA "Hybrid" Duplexes." Biochemistry, 37, 7478-7486 (1998).

Zhang et al. "A Simple Glycol Nucleic Acid." J. Am. Chem. Soc., 127, 4174-4175 (2005).

Zhang et al. "Synthesis of Glycol Nucleic Acids." Synthesis, 2006, 645-653 (2006).

Elkayam et al., "siRNA carrying an €-vinylphosphonate moiety at the 5' end of the guide strand augments gene silencing by enhanced binding to human Argonaute-2", Nucleic Acid Research, 45, (6.), 3528-3536, (2016).

Adams et al. "Patisiran, an RNAi therapeutic, for hereditary transthyretin amyloidosis." New England Journal of Medicine 379.1 (2018): 11-21.

Breslow "Centenary lecture. Biomimetic chemistry." Chemical Society Reviews 1.4 (1972): 553-580.

Bumcrot et al. "RNAi therapeutics: a potential new class of pharmaceutical drugs." Nature Chemical Biology 2.12 (2006): 711-719.

Chen et al. "Strand-specific 5'-O-methylation of siRNA duplexes controls guide strand selection and targeting specificity." RNA 14.2 (2008): 263-274.

Chen et al. "Proof-of-concept studies for siRNA-mediated gene silencing for coagulation factors in rat and rabbit." Molecular Therapy—Nucleic Acids 4 (2015): e224.

Elbashir et al. "Duplexes of 21-nucleotide RNAs mediate RNA interference in cultured mammalian cells." Nature 411.6836 (2001): 494-498.

(56) References Cited

OTHER PUBLICATIONS

Elbashir et al. "Functional anatomy of siRNAs for mediating efficient RNAi in *Drosophila melanogaster* embryo lysate." The EMBO Journal 20.23 (2001): 6877-6888.
Elbashir et al. "RNA interference is mediated by 21- and 22-nucleotide RNAs." Genes & development 15.2 (2001): 188-200.
Elkayam et al. "The structure of human argonaute-2 in complex with miR-20a." Cell 150.1 (2012): 100-110.
Fitzgerald et al. "A highly durable RNAi therapeutic inhibitor of PCSK9." New England Journal of Medicine 376.1 (2017): 41-51.
Frank et al. "Structural basis for 5'-nucleotide base-specific recognition of guide RNA by human AGO2." Nature 165.7299 (2010): 818-822.
Hannon "RNA interference." Nature 418.6894 (2002): 244-251.
Hardcastle et al. "A single amide linkage in the passenger strand suppresses its activity and enhances guide strand targeting of siRNAs." ACS Chemical Biology 13.3 (2018): 533-536.
Manoharan "RNA interference and chemically modified small interfering RNAs." Current Opinion in Chemical Biology 8.6 (2004): 570-579.
Nair et al. "Multivalent N-acetylgalactosamine-conjugated siRNA localizes in hepatocytes and elicits robust RNAi-mediated gene silencing." Journal of the American Chemical Society 136.49 (2014): 16958-16961.
Parmar et al. "Facile synthesis, geometry, and 2'-substituent-dependent in vivo activity of 5'-(E)- and 5'-(Z)-vinylphosphonate-modified siRNA conjugates." Journal of Medicinal Chemistry 61.3 (2018): 734-744.
Pettersen et al. "UCSF Chimera—a visualization system for exploratory research and analysis." Journal of Computational Chemistry 25.13 (2004): 1605-1612.
Schirle et al. "The crystal structure of human Argonaute2." Science 336.6084 (2012): 1037-1040.
Snead et al. "5' Unlocked nucleic acid modification improves siRNA targeting." Molecular Therapy—Nucleic Acids 2 (2013): e103.
Soutschek et al. "Therapeutic silencing of an endogenous gene by systemic administration of modified SiRNAs." Nature 432.7014 (2004): 173-178.
Schwarz et al. "Asymmetry in the assembly of the RNAi enzyme complex." Cell 115.2 (2003): 199-208.
Suter et al. "Controlling miRNA-like off-target effects of an siRNA with nucleobase modifications." Organic & Biomolecular Chemistry 15.47 (2017): 10029-10036.
Weitzer "The human RNA kinase hClp1 is active on 3' transfer RNA exons and short interfering RNAs." Nature 447.7141 (2007): 222-226.
Westheimer "Why nature chose phosphates." Science 235.4793 (1987): 1173-1178.
Zimmermann et al. "RNAi-mediated gene silencing in non-human primates." Nature 441.7089 (2006): 111-114.

\* cited by examiner

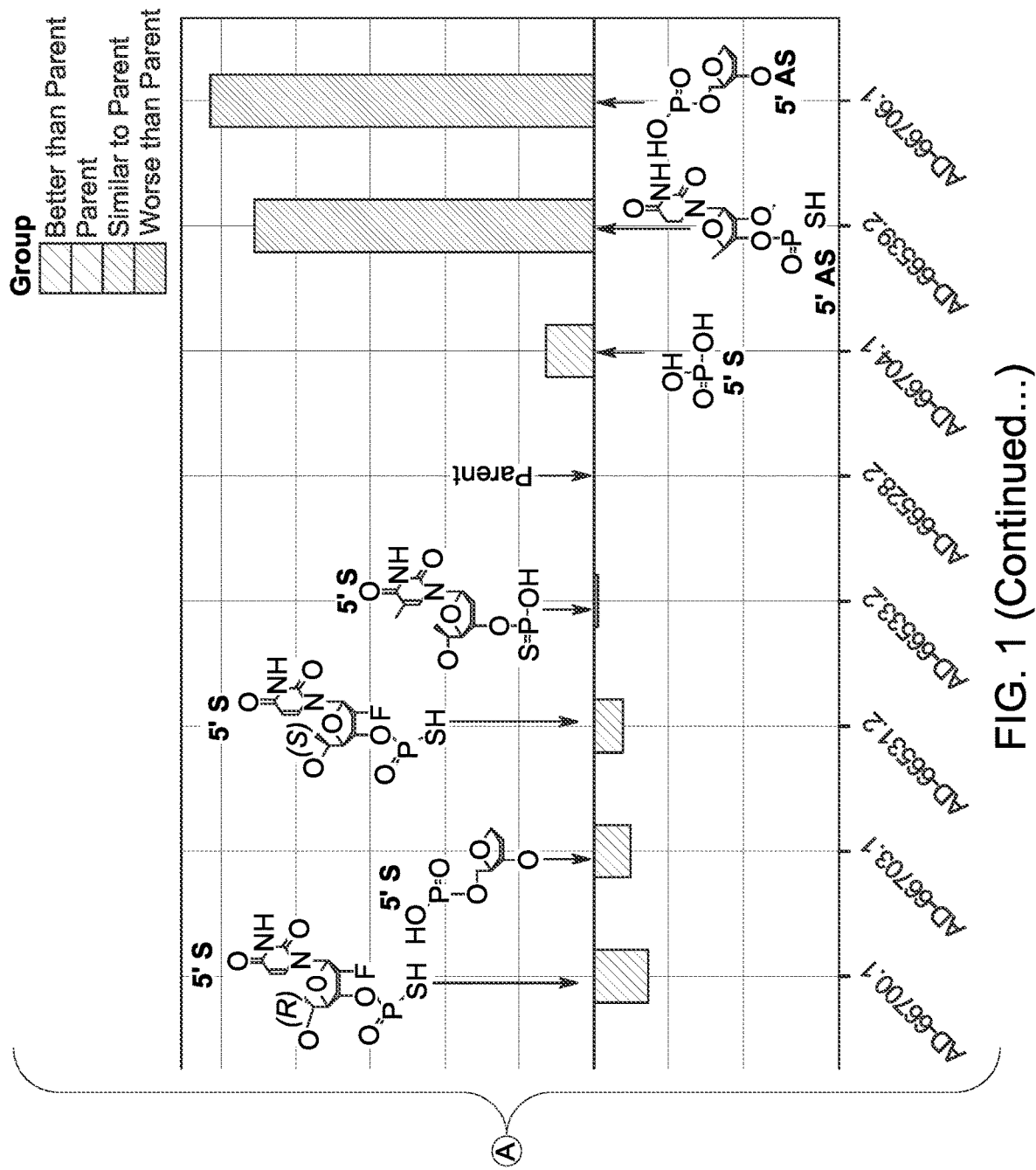
FIG. 1 (Continued...)

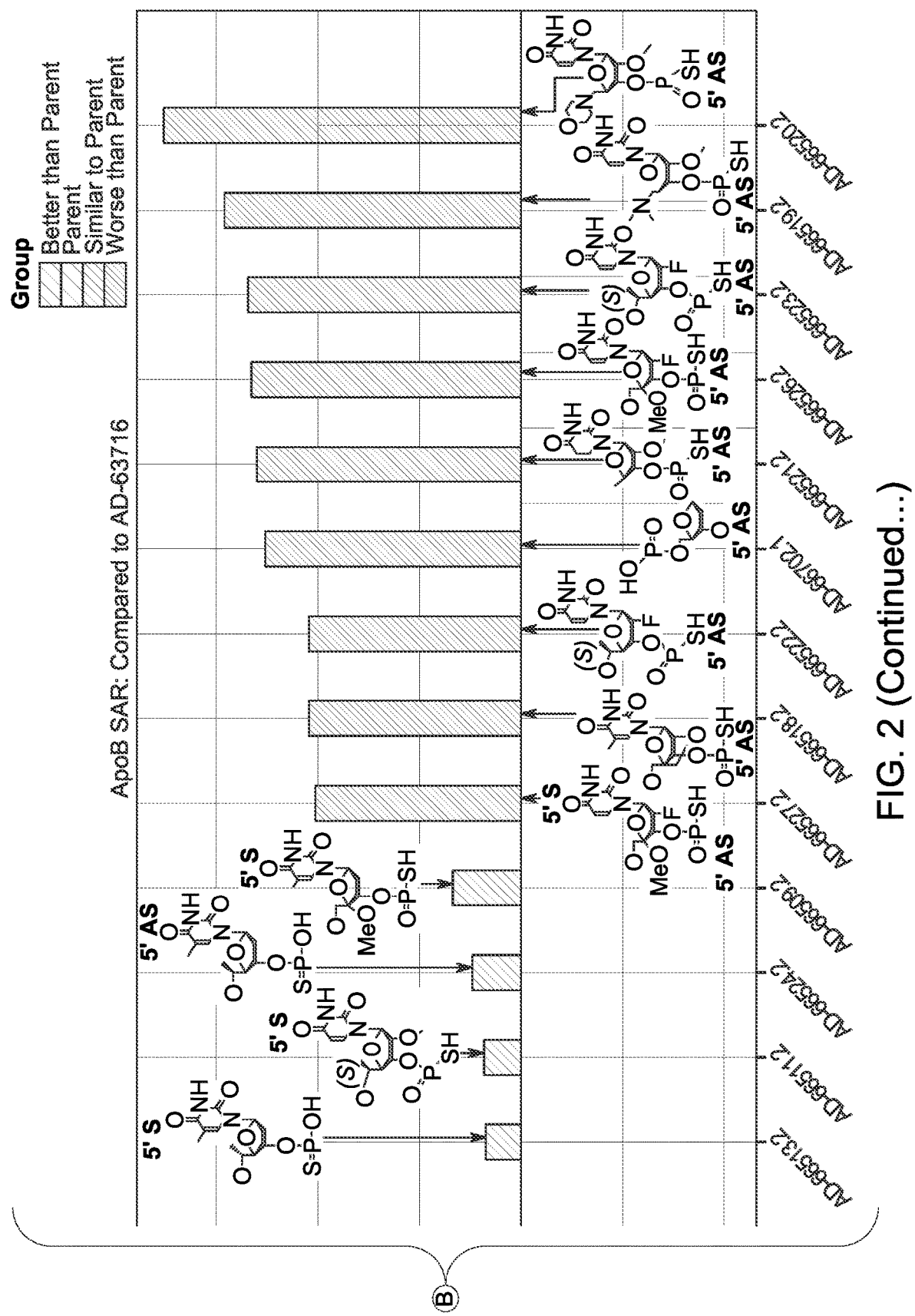
FIG. 2 (Continued...)

Compounds Evaluated
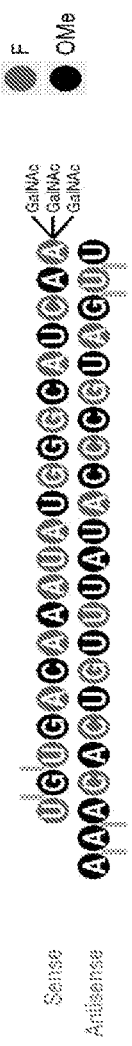
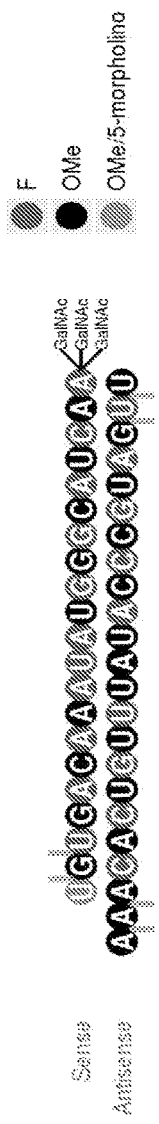
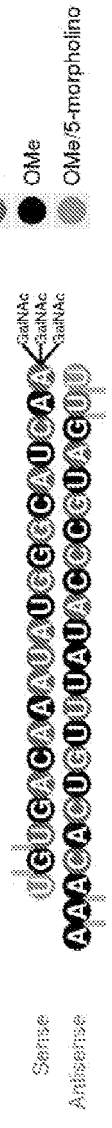
FIG. 6

*This animal is an outlier. No knockdown and No RISC loading indicate there was a dosing issue with this animal.*

*Animal 1 removed from group average

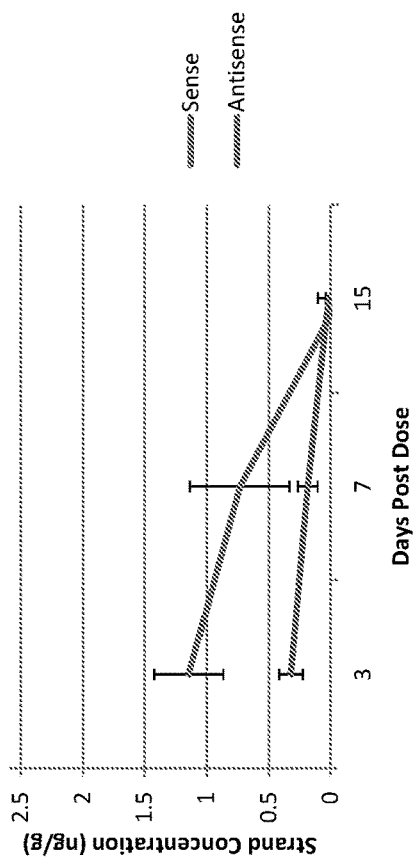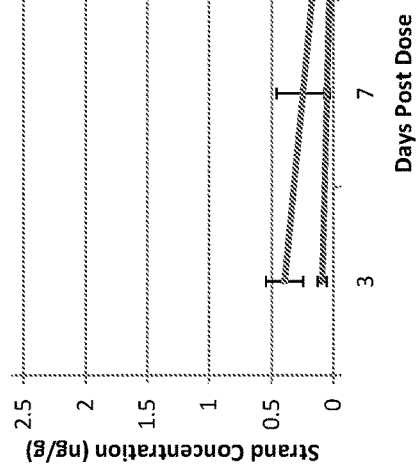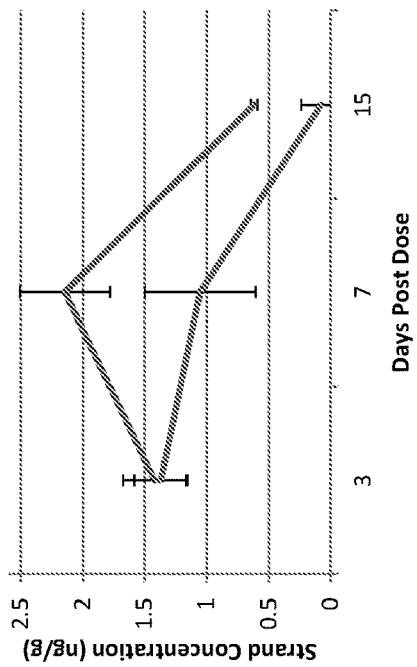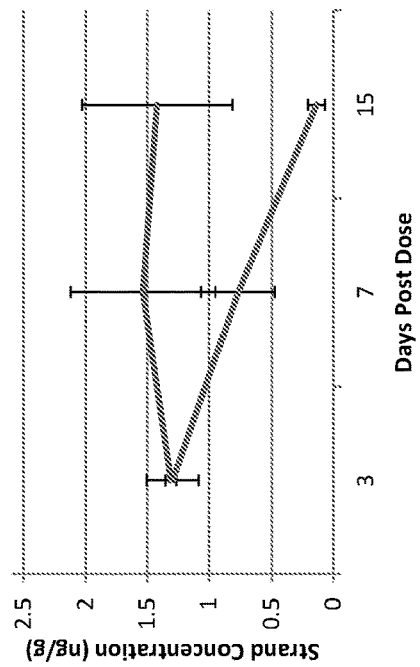
FIG. 10

| Group | Test/Control Article | Dose (mg/kg) | Concentration (mg/mL) | Dose Volume (mL/kg) | No. of Animals | SC Dose Regimen | Day of Necropsy |
|---|---|---|---|---|---|---|---|
| 1 | 0.9% NaCl | 0 | 0 | | 3 | | |
| 2 | AD-58641 (bad C5) | | | | 3 | | |
| 3 | AD-69962 (iB bad C5) | | | | 3 | | |
| 4 | AD-58643 (good C5) | | | | 3 | | |
| 5 | AD-69963 (iB good C5) | 30.0 | 6.0 | 5 | 3 | Days 1, 3, 5, 8, 10, 12 | Day 15 |
| 6 | AD-69964 (Mo good C5) | | | | 3 | | |
| 7 | AD-65421 (bad HBV) | | | | 3 | | |
| 8 | AD-69965 (iB bad HBV) | | | | 3 | | |

- Endpoints
  - Clinical chemistry, hematology, coagulation } Tox
  - Liver and kidney weights
  - Liver and kidney H&E
  - Liver Adipophilin IHC
  - siRNA liver concentration } Molecular
  - Hemolysis assay (C5 activity)
  - C5 liver knockdown
  - RISC loading

FIG. 15

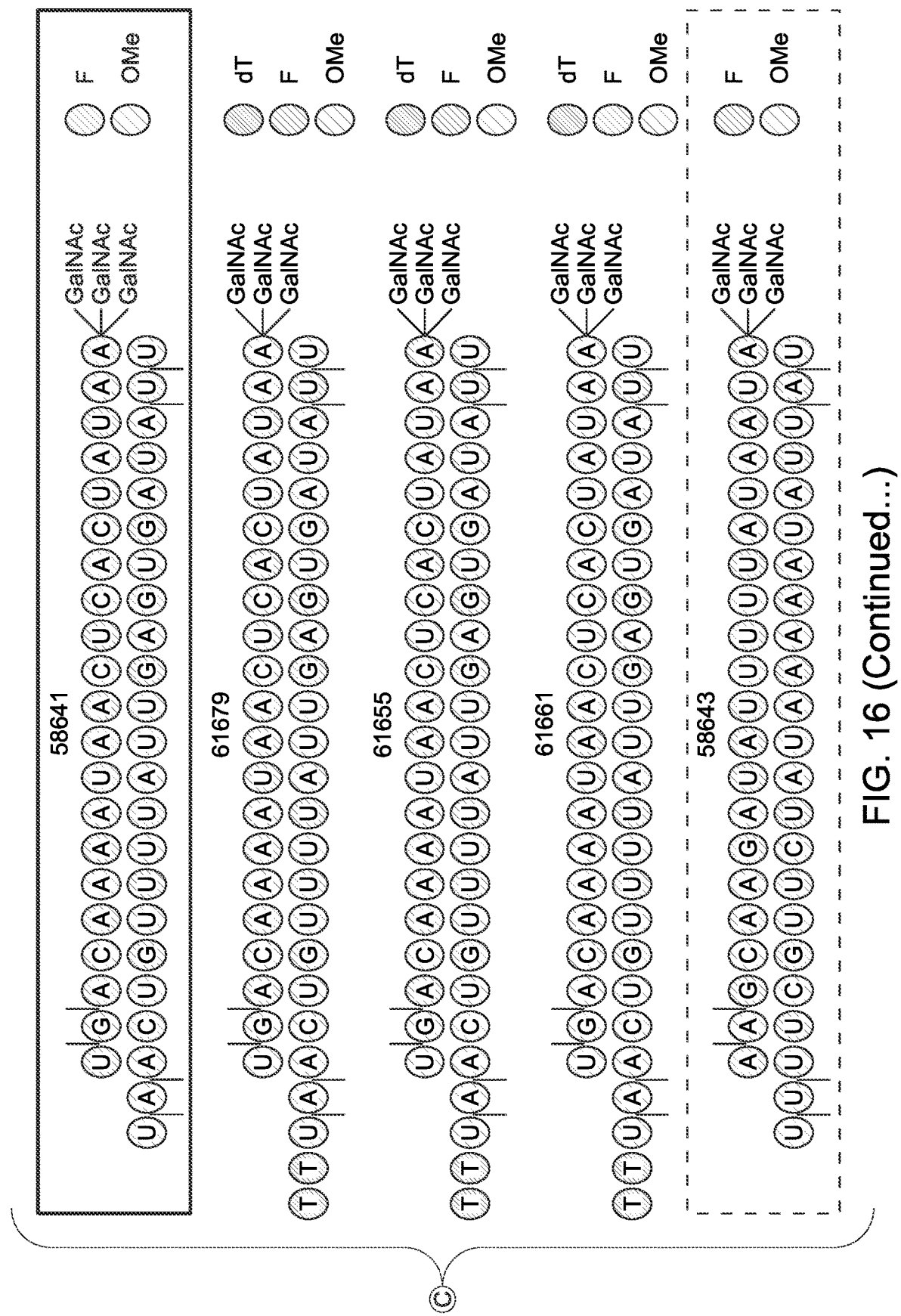
FIG. 16 (Continued...)

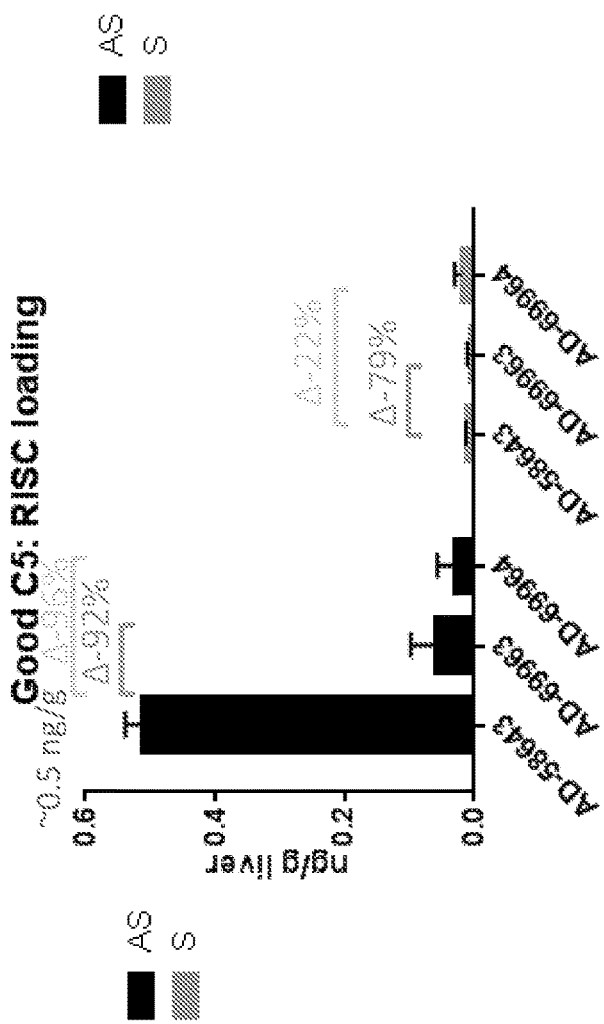
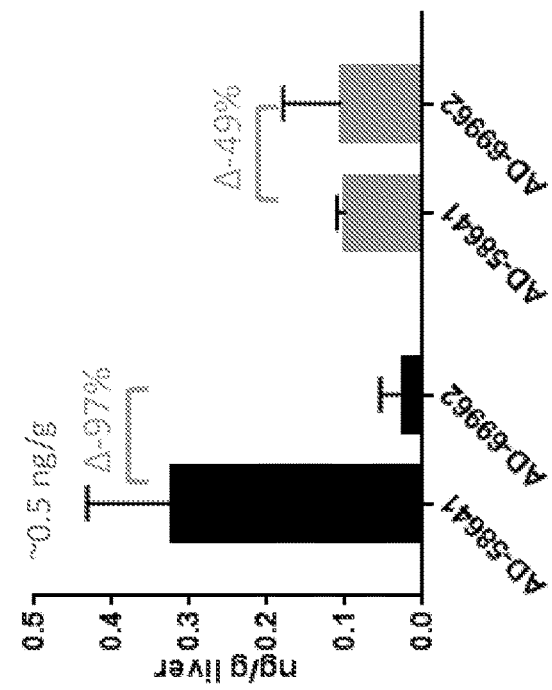
FIG. 23

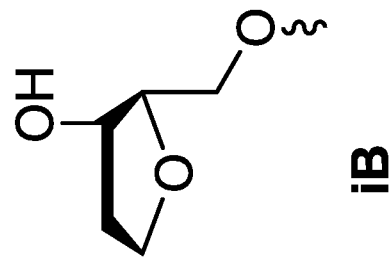
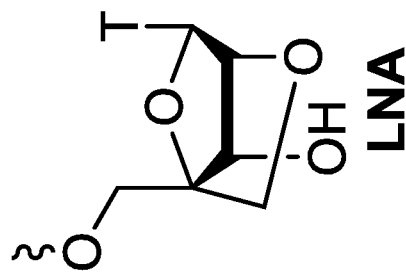
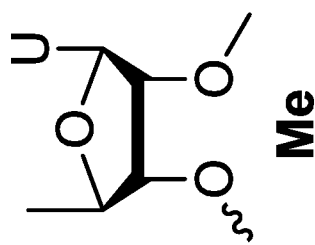
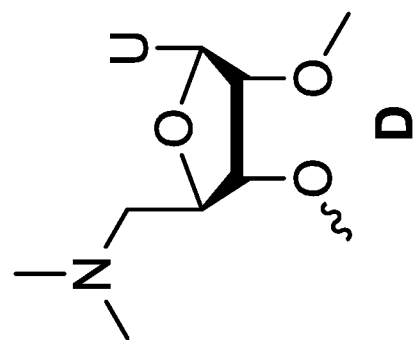
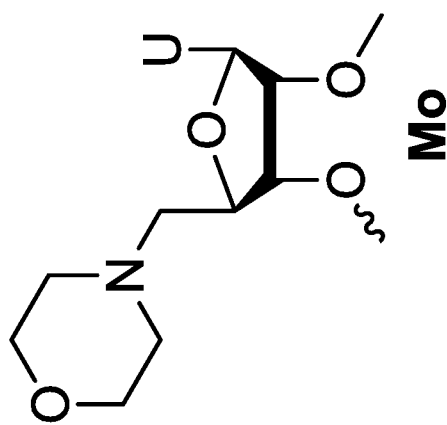
FIG. 32

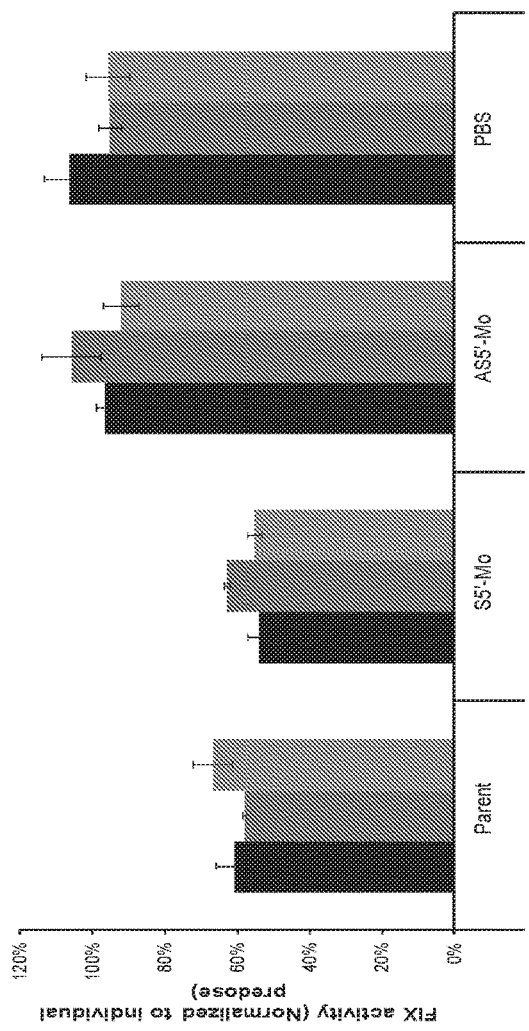
FIG. 34
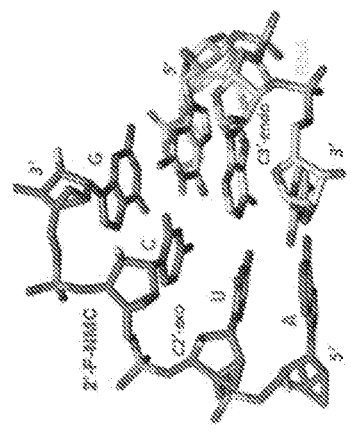
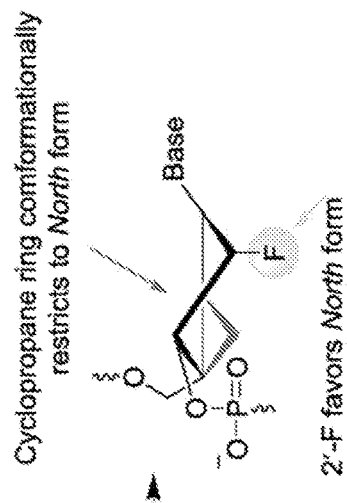
FIG. 35
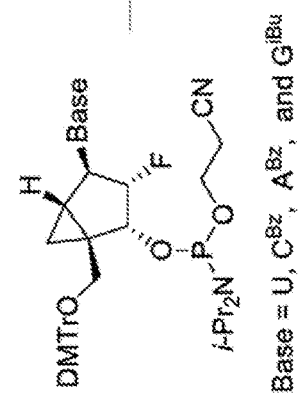

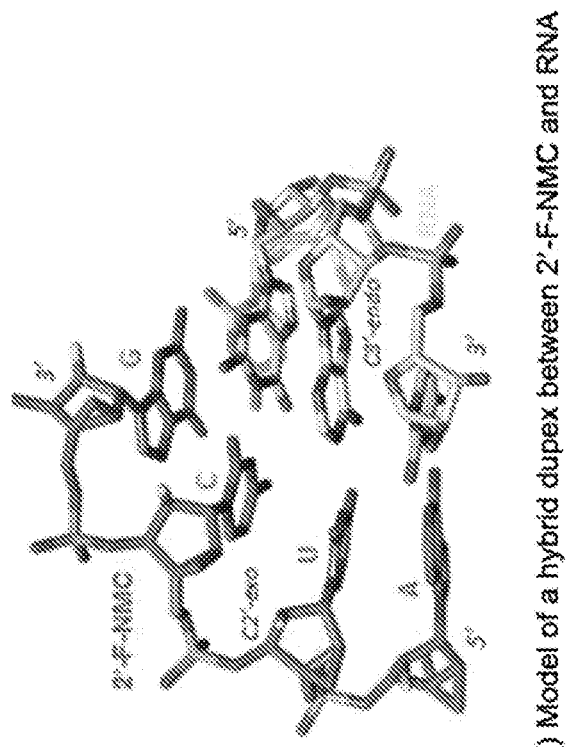
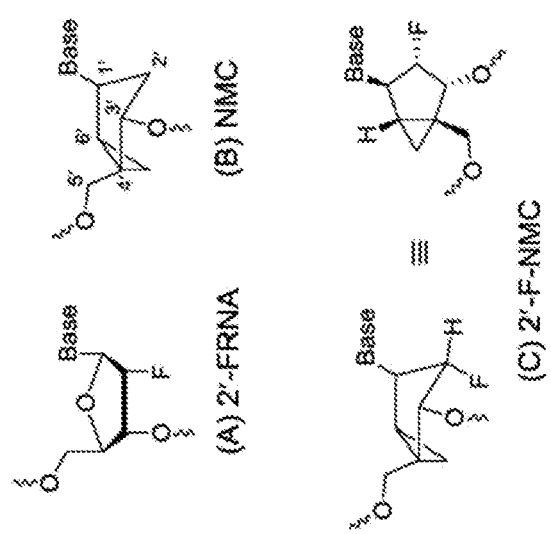
FIG. 36A-36D

SEQUENCE LISTING

```
<160> NUMBER OF SEQ ID NOS: 162

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ugugacaaau augggcauca a                                            21

<210> SEQ ID NO 2
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uugaugccca uauuugcac aaa                                           23

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
```
ugugacaaau augggcauca a          21

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
augugacaaa uaugggcauc aa         22

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ugugacaaau augggcauca a          21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgugacaaau augggcauca a          21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any inverted abasic nucleotide

<400> SEQUENCE: 7
ngugacaaau augggcauca a          21

<210> SEQ ID NO 8
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uugaugccca uauuugucac aaa        23

<210> SEQ ID NO 9
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 9
uugaugccca uauuugucac aaa                                                23

<210> SEQ ID NO 10
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uugaugccca uauuugucac aaa                                                23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tugaugccca uauuugucac aaa                                                23

<210> SEQ ID NO 12
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any inverted abasic nucleotide

<400> SEQUENCE: 12
nugaugccca uauuugucac aaa                                                23

<210> SEQ ID NO 13
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtcgtatcca gtgcagggtc cgaggtattc gcactggata cgactgatgc ccat              54

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gccgcgctgt gacaaatatg                                                    20

<210> SEQ ID NO 15
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 15
ctggatacga ctgatgccc                                                      19

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtcgtatcca gtgcagggtc cgaggtattc gcactggata cgactttgtg acaa               54

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gccgcgcttg atgcccata                                                      19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
ctggatacga ctttgtgac                                                      19

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtgcagggtc cgaggt                                                         16

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uggaagcagu auguugaugg a                                                   21

<210> SEQ ID NO 21
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 21
uccaucaaca uacugcuucc aaa                                           23

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uggaagcagu auguugaugg a                                             21

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
uccaucaaca uacugcuucc aaa                                           23

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ugugacaaau augggcauca a                                             21

<210> SEQ ID NO 25
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uugaugccca uauuugucac aaa                                           23

<210> SEQ ID NO 26

<400> SEQUENCE: 26

000

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ugugacaaau augggcauca a                                             21
```

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
uugaugccca uauuugucac aaa                                           23

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ugugacaaau augggcauca a                                             21

<210> SEQ ID NO 30
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uugaugccca uauuugucac aaa                                           23

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ugugacaaau augggcauca a                                             21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ugugacaaau augggcauca a                                             21

<210> SEQ ID NO 33
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uugaugccca uauuugucac aaa                                           23

```
<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tgugacaaau augggcauca a                                              21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ugugacaaau augggcauca a                                              21

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tugaugccca uauuugucac aaa                                            23

<210> SEQ ID NO 37
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any inverted abasic nucleotide

<400> SEQUENCE: 37
nugugacaaa uaugggcauc aa                                             22

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ugugacaaau augggcauca a                                              21

<210> SEQ ID NO 39
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
```

```
<223> OTHER INFORMATION: Any inverted abasic nucleotide

<400> SEQUENCE: 39
nuugaugccc auauuuguca caaa                                          24

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
uggaagcagu auguugaugg a                                             21

<210> SEQ ID NO 41
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
uccaucaaca uacugcuucc aaa                                           23

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uggaagcagu auguugaugg a                                             21

<210> SEQ ID NO 43
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
uccaucaaca uacugcuucc aaa                                           23

<210> SEQ ID NO 44
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uccaucaaca uacugcuucc aaa                                           23

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 45
uggaagcagu auguugaugg a                                               21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uggaagcagu auguugaugg a                                               21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uggaagcagu auguugaugg a                                               21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uggaagcagu auguugaugg a                                               21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any inverted abasic nucleotide

<400> SEQUENCE: 49
nggaagcagu auguugaugg a                                               21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ugugcaauga aaggcaaaua a                                               21

<210> SEQ ID NO 51
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 51
uuauuugccu uucauugcac acu                                                23

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ugugcaauga aaggcaaaua a                                                  21

<210> SEQ ID NO 53
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uuauuugccu uucauugcac acu                                                23

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ugugcaauga aaggcaaaua a                                                  21

<210> SEQ ID NO 55
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uuauuugccu uucauugcac acu                                                23

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ugugcaauga aaggcaaaua a                                                  21

<210> SEQ ID NO 57
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 57
caguaccuua gaguuccacu a                                              21

<210> SEQ ID NO 58
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
uaguggaacu cuaagguacu gaa                                            23

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
caguaccuua gaguuccacu a                                              21

<210> SEQ ID NO 60
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uaguggaacu cuaagguacu gaa                                            23

<210> SEQ ID NO 61
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uaguggaacu cuaagguacu gaa                                            23

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
caguaccuua gaguuccacu a                                              21

<210> SEQ ID NO 63
<211> LENGTH: 12
<212> TYPE: RNA
<213> ORGANISM: Artificial Sequence
<220> FEATURE:
<223> OTHER INFORMATION: Description of Artificial Sequence: Synthetic
```

```
<210> SEQ ID NO 63
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
uacagucuau gu                                                           12

<210> SEQ ID NO 64
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
acauagacug ua                                                           12

<210> SEQ ID NO 65
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
uacagucuau gu                                                           12

<210> SEQ ID NO 66
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
acauagacug ua                                                           12

<210> SEQ ID NO 67
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uacagucuau gu                                                           12

<210> SEQ ID NO 68
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
acauagacug ua                                                           12

<210> SEQ ID NO 69
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 69
gcgaucucac                                                                    10

<210> SEQ ID NO 70
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
gugagaucgc                                                                    10

<210> SEQ ID NO 71
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
acauagacug ua                                                                 12

<210> SEQ ID NO 72
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
acauagacug ua                                                                 12

<210> SEQ ID NO 73
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
gcgaucucac                                                                    10

<210> SEQ ID NO 74
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
gcgaucucac                                                                    10

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tttttttttt ttttttttc                                                20

<210> SEQ ID NO 76

<400> SEQUENCE: 76

000

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tttttttttt tttttttct                                                20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78 ctttttttt tttttttttt                                                20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79 tcttttttt tttttttttt                                                20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tttttttttt ttttttttc                                                20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tttttttttt tttttttct                                                20

<210> SEQ ID NO 82
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cttttttttt tttttttttt                                              20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83 tcttttttttt tttttttttt                                             20

<210> SEQ ID NO 84
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
uacagucuau gu                                                      12

<210> SEQ ID NO 85
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
uacagucuau gu                                                      12

<210> SEQ ID NO 86
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
uacagucuau gu                                                      12

<210> SEQ ID NO 87
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
uacagucuau gu                                                      12

<210> SEQ ID NO 88
<211> LENGTH: 12
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 88
acauagacug ua                                                              12

<210> SEQ ID NO 89
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
acauagacug ua                                                              12

<210> SEQ ID NO 90
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
gcgaucucac                                                                 10

<210> SEQ ID NO 91
<211> LENGTH: 16
<212> TYPE: PRT
<213> ORGANISM: Unknown
<220> FEATURE:
<223> OTHER INFORMATION: Description of Unknown:
      RFGF peptide

<400> SEQUENCE: 91

Ala Ala Val Ala Leu Leu Pro Ala Val Leu Leu Ala Leu Leu Ala Pro
1               5                   10                  15

<210> SEQ ID NO 92
<211> LENGTH: 11
<212> TYPE: PRT
<213> ORGANISM: Unknown
<220> FEATURE:
<223> OTHER INFORMATION: Description of Unknown:
      RFGF analogue peptide

<400> SEQUENCE: 92

Ala Ala Leu Leu Pro Val Leu Leu Ala Ala Pro
1               5                   10

<210> SEQ ID NO 93
<211> LENGTH: 13
<212> TYPE: PRT
<213> ORGANISM: Human immunodeficiency virus

<400> SEQUENCE: 93

Gly Arg Lys Lys Arg Arg Gln Arg Arg Arg Pro Pro Gln
1               5                   10

<210> SEQ ID NO 94
<211> LENGTH: 16
<212> TYPE: PRT
<213> ORGANISM: Drosophila sp.
```

<400> SEQUENCE: 94

Arg Gln Ile Lys Ile Trp Phe Gln Asn Arg Arg Met Lys Trp Lys Lys
1               5                   10                  15

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tttttttttt tttttttc                                                    19

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tttttttttt tttttttttt                                                  20

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ugacaaauau gggcaucaau u                                                21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
uugaugccca uauuugucau u                                                21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
ugugacaaau augggcauca a                                                21

<210> SEQ ID NO 100
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uugaugccca uauuugucac aaa                                              23

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
caguaccuua gaguuccacu a                                                21

<210> SEQ ID NO 102
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
uaguggaacu cuaagguacu gaa                                              23

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
uggaagcagu auguugaugg a                                                21

<210> SEQ ID NO 104
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
uccaucaaca uacugcuucc aaa                                              23

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
caguaccuua gaguuccacu a                                                21

<210> SEQ ID NO 106
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
uaguggaacu cuaagguacu gaa                                              23

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
uggaagcagu auguugaugg a                                                21

<210> SEQ ID NO 108
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
uccaucaaca uacugcuucc aaa                                              23

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
caguaccuua gaguuccacu a                                                21

<210> SEQ ID NO 110
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
uaguggaacu cuaagguacu gaa                                              23

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
uggaagcagu auguugaugg a                                                21

<210> SEQ ID NO 112
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
uccaucaaca uacugcuucc aaa                                                23

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
ugugacaaau augggcauca a                                                  21

<210> SEQ ID NO 114
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
uugaugccca uauuugucac aaa                                                23

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
ugugacaaau augggcauca a                                                  21

<210> SEQ ID NO 116
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
uugaugccca uauuugucac aaa                                                23

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
ugugacaaau augggcauca a                                                  21

<210> SEQ ID NO 118
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
uugaugccca uauuugucac aaa 23

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 119
ugugacaaau augggcauca a 21

<210> SEQ ID NO 120
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 120
uugaugccca uauuugucac aaa 23

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 121
ugugacaaau augggcauca a 21

<210> SEQ ID NO 122
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 122
uugaugccca uauuugucac aaa 23

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 123
ugugacaaau augggcauca a 21

<210> SEQ ID NO 124
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 124
uugaugccca uauuugucac aaa 23

```
<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
ugugacaaau augggcauca a                                                 21

<210> SEQ ID NO 126
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
uugaugccca uauuugucac aaa                                               23

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ugacaaaaua acucacuaua a                                                 21

<210> SEQ ID NO 128
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
uuauagugag uuauuuuguc aau                                               23

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
aagcaagaua uuuuuauaau a                                                 21

<210> SEQ ID NO 130
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
uauuauaaaa auaucuugcu uuu                                               23
```

```
<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
gugcacuucg cuucaccucu a                                                 21

<210> SEQ ID NO 132
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
uagaggugaa gcgaagugca cuu                                               23

<210> SEQ ID NO 133
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any inverted abasic nucleotide

<400> SEQUENCE: 133
nugacaaaau aacucacuau aa                                                22

<210> SEQ ID NO 134
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any inverted abasic nucleotide

<400> SEQUENCE: 134
nuuauaguga guuauuuugu caau                                              24

<210> SEQ ID NO 135
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any inverted abasic nucleotide

<400> SEQUENCE: 135
naagcaagau auuuuuauaa ua                                                22

<210> SEQ ID NO 136
```

```
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any inverted abasic nucleotide

<400> SEQUENCE: 136
nuauuauaaa aauaucuugc uuuu                                              24

<210> SEQ ID NO 137
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any inverted abasic nucleotide

<400> SEQUENCE: 137
ngugcacuuc gcuucaccuc ua                                                22

<210> SEQ ID NO 138
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Any inverted abasic nucleotide

<400> SEQUENCE: 138
nuagagguga agcgaagugc acuu                                              24

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
uagcaagaua uuuuuauaau a                                                 21

<210> SEQ ID NO 140
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
uauuauaaaa auaucuugcu auu                                               23

<210> SEQ ID NO 141
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 141
ugacaaaaua acucacuaua a                                              21

<210> SEQ ID NO 142
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
uuauagugag uuauuuuguc aau                                            23

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
ugacaaaaua acucacuaua a                                              21

<210> SEQ ID NO 144
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
uuauagugag uuauuuuguc aautt                                          25

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
ugacaaaaua acucacuaua a                                              21

<210> SEQ ID NO 146
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
uuauagugag uuauuuuguc aautt                                          25

<210> SEQ ID NO 147
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 147
ugacaaaaua acucacuaua a                                              21

<210> SEQ ID NO 148
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
uuauagugag uuauuuuguc aautt                                          25

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
aagcaagaua uuuuuauaau a                                              21

<210> SEQ ID NO 150
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
uauuauaaaa auaucuugcu uuu                                            23

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gugcacuucg cuucaccucu a                                              21

<210> SEQ ID NO 152
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
uagaggugaa gcgaagugca cuu                                            23

<210> SEQ ID NO 153
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 153
gugcacuucg cuucaccucu a                                              21

<210> SEQ ID NO 154
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
uagaggugaa gcgaagugca cuu                                            23

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
gguggacuuc ucucaauuuu a                                              21

<210> SEQ ID NO 156
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
uaaaauugag agaaguccac cac                                            23

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
gguggacuuc ucucaauuuu a                                              21

<210> SEQ ID NO 158
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
uaaaauugag agaaguccac cac                                            23

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
oligonucleotide

<400> SEQUENCE: 159
aagcaagaua uuuuuauaau a                                              21

<210> SEQ ID NO 160
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
uauuauaaaa auaucuugcu uuu                                            23

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
uagcaagaua uuuuuauaau a                                              21

<210> SEQ ID NO 162
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
uauuauaaaa auaucuugcu auu                                            23
```

COMPOSITIONS AND METHODS FOR IMPROVING STRAND BIASED

CROSS-REFERENCE TO RELATED APPLICATIONS

This application is a 35 U.S.C. § 371 National Phase Entry Application of International Application No. PCT/US2019/031083 filed May 7, 2019, which designates the U.S. and claims benefit under 35 U.S.C. § 119(e) of U.S. Provisional Application No. 62/667,972 filed May 7, 2018 and U.S. Provisional Application No. 62/811,870 filed on Feb. 28, 2019, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jul. 15, 2019, is named 051058-092220WOPT_SL.txt and is 38,929 bytes in size.

FIELD OF THE INVENTION

The invention relates to compositions and methods for reducing or inhibiting sense strand of RNAi duplex agents loading into RISC complex of RNA interference that is advantageous for inhibition of target gene expression by reducing the undesired off-target effects, as well as RNAi compositions suitable for therapeutic use. Additionally, the invention provides methods of inhibiting the expression of a target gene by administering these RNAi duplex agents, e.g., for the treatment of various diseases.

BACKGROUND

RNA interference or "RNAi" is a term initially coined by Fire and co-workers to describe the observation that double-stranded RNAi (dsRNA) can block gene expression (Fire et al. (1998) Nature 391, 806-811; Elbashir et al. (2001) Genes Dev. 15, 188-200). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown. One of the off-target effects of siRNA is the RNAi due to loading of the sense strand into the RISC complex.

There is thus an ongoing effort to eliminate or reduce loading of the sense strand into the RISC complex to reduce or inhibit off-target effects of siRNAs. This invention is directed to that effort.

SUMMARY

This invention provides effective nucleotide or chemical motifs for dsRNA molecules, which are advantageous for inhibition of target gene expression, while having reduced off-target gene silencing effects, as well as RNAi compositions suitable for therapeutic use.

The inventors have discovered inter alia that dsRNA molecules, e.g., siRNAs that comprise certain modifications at 5'-end of the sense strand show little or no loading of sense strand into the RISC complex. Without wishing to be bound by a theory, this can reduce off-target effects of dsRNA molecules lacking such modifications. Thus, in one aspect the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference, and wherein the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2.

The inventors have discovered inter alia that activity of dsRNA molecules, e.g., siRNAs that comprise modifications at 5'-end of the antisense strand, which lead to inhibition or reduction in activity, can be rescued by modifying the 5'-end of the antisense strand with 5'-E-vinylphosphonate. Accordingly, the invention also provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference, and wherein the antisense strand comprises 5'-E-vinylphosphonate. In some embodiments, the antisense comprises a nucleoside at position N-1 that reduces or inhibits activity of siRNA relative to a siRNA having the same antisense strand sequence but unmodified N-1 position.

In various embodiments of the invention, the dsRNA comprises a sense strand and an antisense strand, each strand having 14 to 40 nucleotides, wherein the antisense strand has sufficient complementarity to the target sequence to mediate RNA interference, and wherein the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2, and the antisense strand comprises 5'-E-vinylphosphonate.

In various embodiments of the invention, the dsRNA comprises a sense strand and an antisense strand, each strand having 14 to 40 nucleotides, wherein the antisense strand has sufficient complementarity to the target sequence to mediate RNA interference, and wherein the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2, and the antisense strand comprises 5'-E-vinylphosphonate and the antisense the antisense comprises a nucleoside at position N-1 that reduces or inhibits activity of siRNA relative to a siRNA having the same antisense strand sequence but unmodified N-1 position.

In some embodiments, the dsRNA molecule capable of inhibiting the expression of a target gene comprises a sense strand and an antisense strand, each strand having 14 to 40 nucleotides, wherein the antisense strand has sufficient complementarity to the target sequence to mediate RNA interference, wherein the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2, and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven, eight or all nine) of the following characteristics: (i) a melting temperature (Tm) of from about 40° C. to about 80° C.; (ii) the antisense comprises 2, 3, 4, 5 or 6 2'-fluoro modifications; (iii) the antisense comprises 1, 2, 3 or 4 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3 or 4 phosphorothioate internucleotide linkages; (vii) the dsRNA comprises at least four 2'-fluoro modifications; (viii) the dsRNA comprises a duplex region of 12-40 nucleotide pairs in length; and (ix) a blunt end at 5' end of the antisense strand.

In some embodiments, the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference, wherein the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2, and wherein the antisense strand comprises at least one thermally destabilizing modification of the duplex within the seed region (i.e., at position 2-9, preferably 3-8, of the 5'-end of the antisense strand, counting from the 5'-end), and the dsRNA further has at least one (e.g., one, two, three, four, five, six seven, eight or all nine) of the following characteristics: (i) a melting temperature (Tm) of from about 40° C. to about 80° C.; (ii) the antisense comprises 6, 7, 8, 9, 10, 11 or 12 2'-OMe modifications; (iii) the antisense comprises 1, 2, 3 or 4 phosphorothioate internucleotide linkages; (iv) the sense strand is conjugated with a ligand; (v) the sense strand comprises 6, 7, 8, 9, 10, 11 or 12 2'-OMe modifications; (vi) the sense strand comprises 1, 2, 3 or 4 phosphorothioate internucleotide linkages; (vii) the dsRNA comprises at least 1, 2, 3, 4 or 5 2'-deoxy modification(s); (viii) the dsRNA comprises a duplex region of 12-40 nucleotide pairs in length; and (ix) a blunt end at 5' end of the antisense strand.

In some embodiments, the dsRNA molecule capable of inhibiting the expression of a target gene comprises a sense strand and an antisense strand, each strand having 14 to 40 nucleotides, wherein the antisense strand has sufficient complementarity to the target sequence to mediate RNA interference, wherein the antisense strand comprises 5'-E-vinylphosphonate, and wherein the antisense strand comprises at least one thermally destabilizing modification of the duplex within the seed region (i.e., at position 2-9, preferably 3-8, of the 5'-end of the antisense strand, counting from the 5'-end), and the dsRNA further has at least one (e.g., one, two, three, four, five, six seven, eight or all nine) of the following characteristics: (i) a melting temperature (Tm) of from about 40° C. to about 80° C.; (ii) the antisense comprises 2, 3, 4, 5 or 6 2'-fluoro modifications; (iii) the antisense comprises 1, 2, 3 or 4 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3 or 4 phosphorothioate internucleotide linkages; (vii) the dsRNA comprises at least four 2'-fluoro modifications; (viii) the dsRNA comprises a duplex region of 12-40 nucleotide pairs in length; and (ix) a blunt end at 5' end of the antisense strand.

In some embodiments, the dsRNA molecule capable of inhibiting the expression of a target gene comprises a sense strand and an antisense strand, each strand having 14 to 40 nucleotides, wherein the antisense strand has sufficient complementarity to the target sequence to mediate RNA interference, wherein the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2, and the antisense strand comprises 5'-E-vinylphosphonate, and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven, eight or all nine) of the following characteristics: (i) a melting temperature (Tm) of from about 40° C. to about 80° C.; (ii) the antisense comprises 2, 3, 4, 5 or 6 2'-fluoro modifications; (iii) the antisense comprises 1, 2, 3 or 4 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3 or 4 phosphorothioate internucleotide linkages; (vii) the dsRNA comprises at least four 2'-fluoro modifications; (viii) the dsRNA comprises a duplex region of 12-40 nucleotide pairs in length; and (ix) a blunt end at 5' end of the antisense strand.

In some embodiments, the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference, wherein the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2, and the antisense strand comprises 5'-E-vinylphosphonate, and wherein the antisense strand comprises at least one thermally destabilizing modification of the duplex within the seed region (i.e., at position 2-9, preferably 3-8, of the 5'-end of the antisense strand, counting from the 5'-end), and the dsRNA further has at least one (e.g., one, two, three, four, five, six seven, eight or all nine) of the following characteristics: (i) a melting temperature (Tm) of from about 40° C. to about 80° C.; (ii) the antisense comprises 6, 7, 8, 9, 10, 11 or 12 2'-OMe modifications; (iii) the antisense comprises 1, 2, 3 or 4 phosphorothioate internucleotide linkages; (iv) the sense strand is conjugated with a ligand; (v) the sense strand comprises 6, 7, 8, 9, 10, 11 or 12 2'-OMe modifications; (vi) the sense strand comprises 1, 2, 3 or 4 phosphorothioate internucleotide linkages; (vii) the dsRNA comprises at least 1, 2, 3, 4 or 5 2'-deoxy modification(s); (viii) the dsRNA comprises a duplex region of 12-40 nucleotide pairs in length; and (ix) a blunt end at 5' end of the antisense strand.

In some embodiments, the dsRNA molecule capable of inhibiting the expression of a target gene comprises a sense strand and an antisense strand, each strand having 14 to 40 nucleotides, wherein the antisense strand has sufficient complementarity to the target sequence to mediate RNA interference, wherein the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2, and the antisense strand comprises 5'-E-vinylphosphonate and a nucleoside at position N-1 that reduces or inhibits activity of siRNA relative to a siRNA having the same antisense strand sequence but unmodified N-1 position, and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven, eight or all nine) of the following characteristics: (i) a melting temperature (Tm) of from about 40° C. to about 80° C.; (ii) the antisense comprises 2, 3, 4, 5 or 6 2'-fluoro modifications; (iii) the antisense comprises 1, 2, 3 or 4 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3 or 4 phosphorothioate internucleotide linkages; (vii) the dsRNA comprises at least four 2'-fluoro modifications; (viii) the dsRNA comprises a duplex region of 12-40 nucleotide pairs in length; and (ix) a blunt end at 5' end of the antisense strand.

In some embodiments, the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference, wherein the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2, and the antisense strand comprises 5'-E-vinylphosphonate and a nucleoside at position N-1 that reduces or inhibits activity of siRNA relative to a siRNA having the same antisense strand sequence but unmodified N-1 position, and wherein the antisense strand comprises at least one thermally destabilizing modification of the duplex within the seed region (i.e., at position 2-9, preferably 3-8, of the 5'-end of the antisense strand, counting from the 5'-end), and the dsRNA further has at least one (e.g., one, two, three, four, five, six seven, eight or all nine) of the following characteristics: (i) a melting temperature (Tm) of from about 40° C. to about 80° C.; (ii) the antisense comprises 6, 7, 8, 9, 10, 11 or 12 2'-OMe modifications; (iii) the antisense comprises 1, 2, 3 or 4 phosphorothioate internucleotide linkages; (iv) the sense strand is conjugated with a ligand; (v) the sense strand comprises 6, 7, 8, 9, 10, 11 or 12 2'-OMe modifications; (vi) the sense strand comprises 1, 2, 3 or 4 phosphorothioate internucleotide linkages; (vii) the dsRNA comprises at least 1, 2, 3, 4 or 5 2'-deoxy modification(s); (viii) the dsRNA comprises a duplex region of 12-40 nucleotide pairs in length; and (ix) a blunt end at 5' end of the antisense strand.

In another aspect, the invention further provides a method for delivering the dsRNA molecule of the invention to a specific target in a subject by subcutaneous or intravenous administration. The invention further provides the dsRNA molecules of the invention for use in a method for delivering said agents to a specific target in a subject by subcutaneous or intravenous administration.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1 discloses SEQ ID NOS 97-98, respectively, in order of appearance. FIG. 2 discloses SEQ ID NOS 99-100, respectively, in order of appearance.

FIG. 4 discloses SEQ ID NOS 101, 103, 102, 104, 105, 107, 106, 108, 109, 111, 110 and 112, respectively, in order of appearance. FIG. 5 discloses SEQ ID NOS 113, 115, 114 and 116-118, respectively, in order of appearance.

FIG. 6 shows some exemplary RNAi agents evaluated. FIG. 6 discloses SEQ ID NOS 119-126, respectively, in order of appearance.

FIG. 7 shows results for individual animals and FIG. 8 shows group averages.

FIGS. 9 and 10 shows Ago2 IP measurements showing that 5'-morpholino modifications alter the RISC loading of and exemplary RNAi agent (ApoB) sense and antisense strands.

FIG. 14 discloses SEQ ID NOS 127, 129, 131, 128, 130, 132-133, 135, 137, 134, 136 and 138-140, respectively, in order of appearance.

FIG. 15 is a representation of study design and endpoints.

FIG. 16 discloses SEQ ID NOS 141-150, respectively, in order of appearance.

FIG. 17 discloses SEQ ID NOS 151-158, respectively, in order of appearance.

Organs not listed were observed to be within normal limits.

Figure 21:
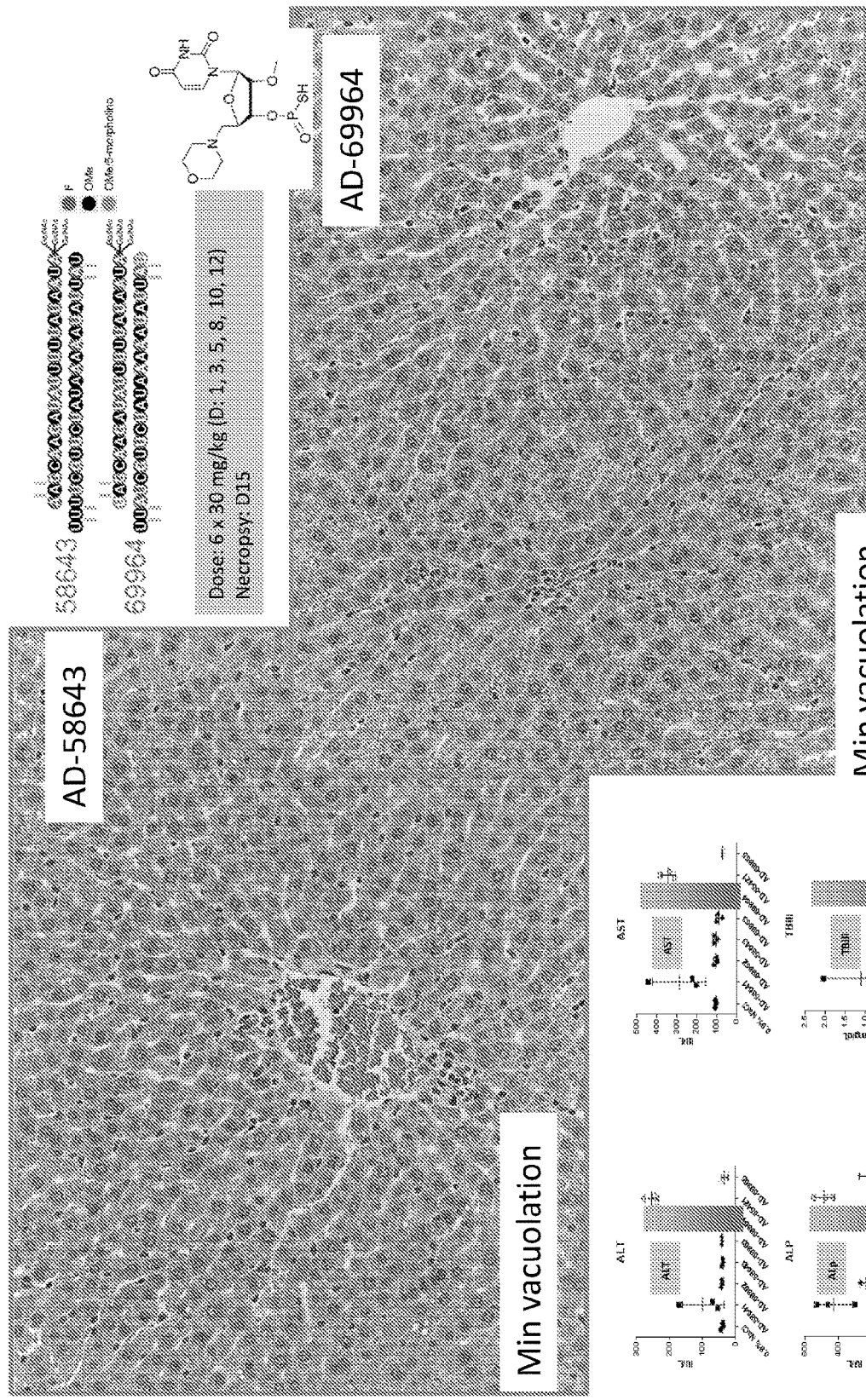

FIG. 21 shows comparison between parent (AD-58643, good C5) and 5'-morpholino modified (AD-69964) RNAi agents. FIG. 21 discloses SEQ ID NOS 159-162, respectively, in order of appearance.

Figure 22:
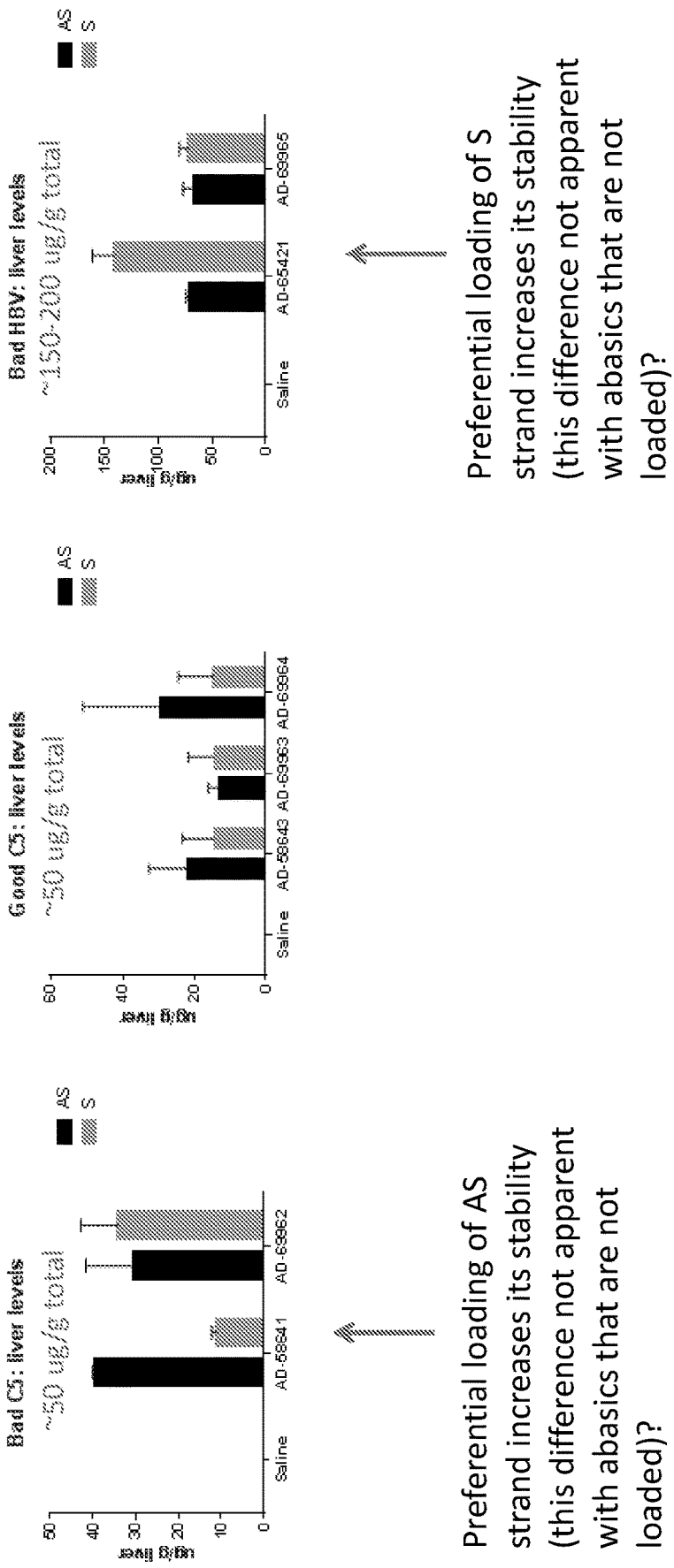

FIG. 22 shows blocking RISC loading did not decrease liver levels of siRNAs, but did alter antisense/sense ratio in some cases. It is noted that vast majority of the siRNA is not loaded into the RISC because loading does not destabilize siRNA.

FIG. 23 show RISC loading of some exemplary C5 siRNAs. As can be seen antisense strands had higher RISC loading and greater effect of inverted abasic and morpholino than on sense strand. This demonstrates stand bias on loading RISC. Equivalent RISC loading was seen for parent good and bad siRNAs (~1ng/g liver) indicating that RISC saturation does not cause toxicity.

Figure 24:
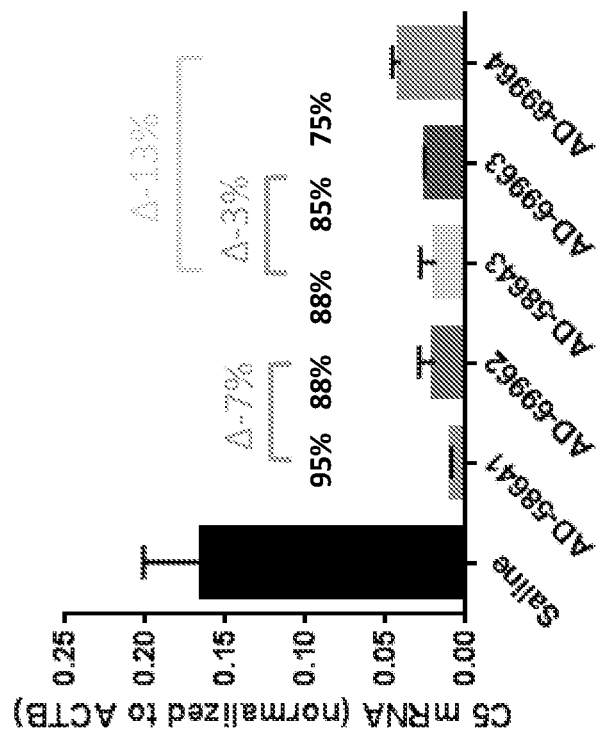

FIG. 24 shows that morpholino is more effective in blocking RISC loading.

Figure 25:
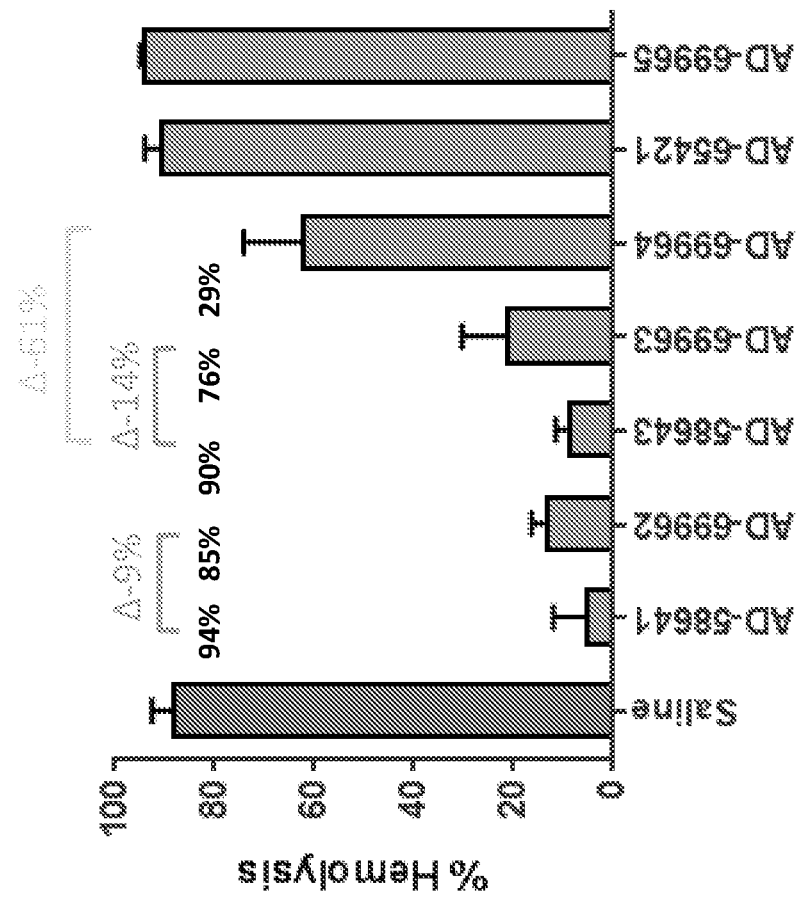

FIG. 25 shows hemolysis analysis of C5 knockdown with exemplary RNAi agents.

Figure 26:
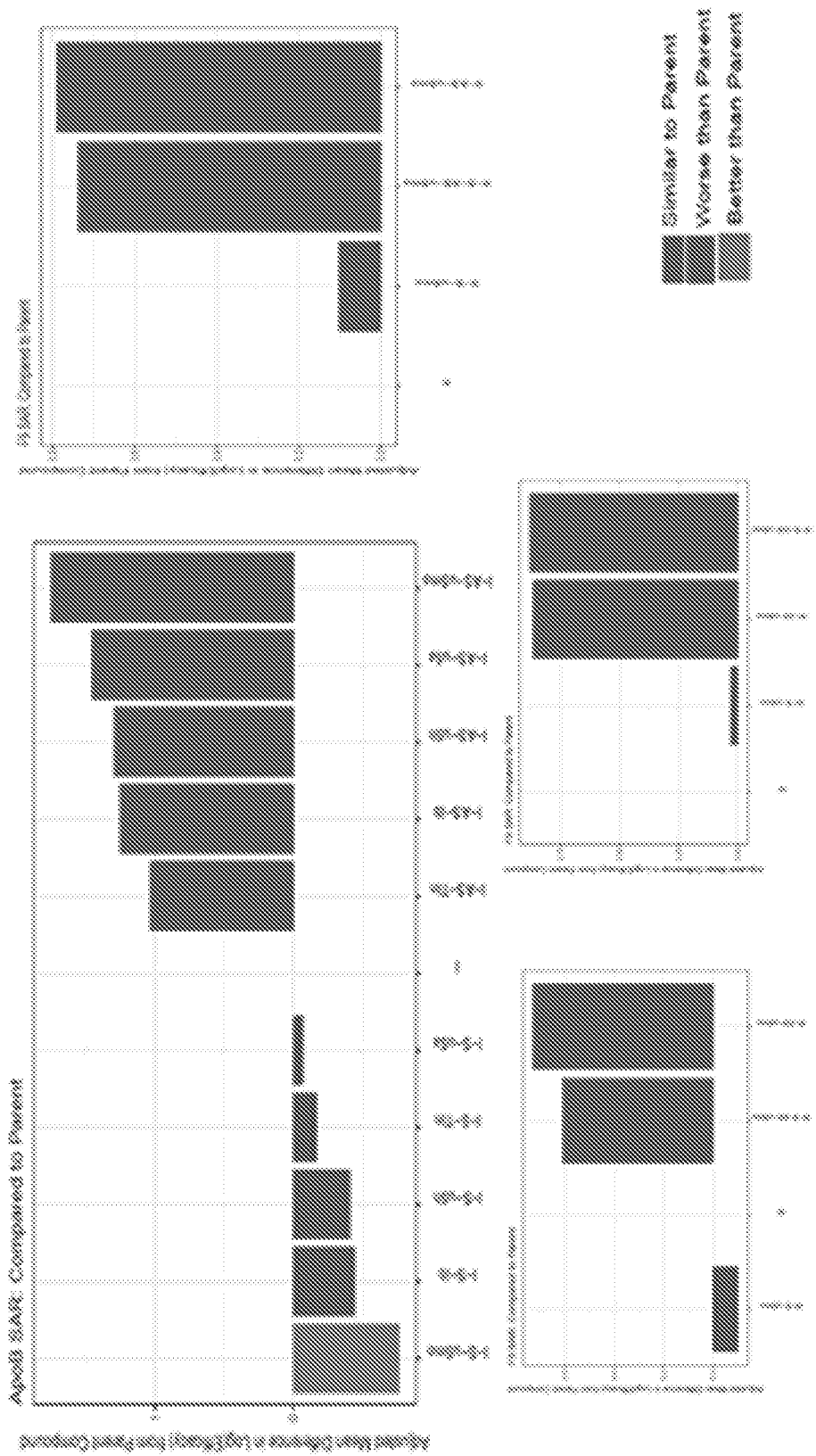

FIG. 26 shows effect of 5'-modification of sense strand. A) Apo B sequence I. The 5' morpholino on the sense strand enhances siRNA activity. In vitro RNAi activity of siRNA-GalNAc conjugates modified at the 5' end of the sense strand (S, green and blue) or antisense strand (AS, red) as indicated. Plotted is mean log difference in activity relative to the parent siRNA. B) FIX sequence II, C) FIX sequence III, and D) FIX sequence VI.

Figure 27:
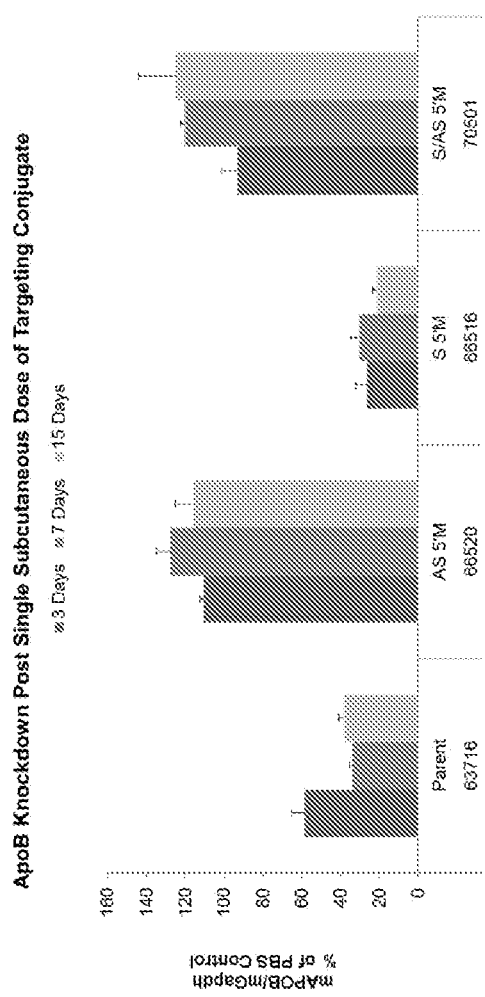

FIG. 27 shows ApoB knockdoen post single subcutaneous dose of exemplary targeting conjugate. The 5'-morpholino modification directs strand selection in vivo. Mice (n=3 per group) were treated with a single dose (3 mg/kg) of parent, AS5'-Mo, S5'-Mo, or S/AS5'-Mo siRNA targeting Apob. Cohorts of mice were sacrificed at 3, 7, and 15 days post-dose, and livers were processed for mRNA quantification using qPCR. Apob mRNA levels were normalized to Gapdh mRNA. Data are expressed as percent of the PBS-treated control animals.

Figure 28:
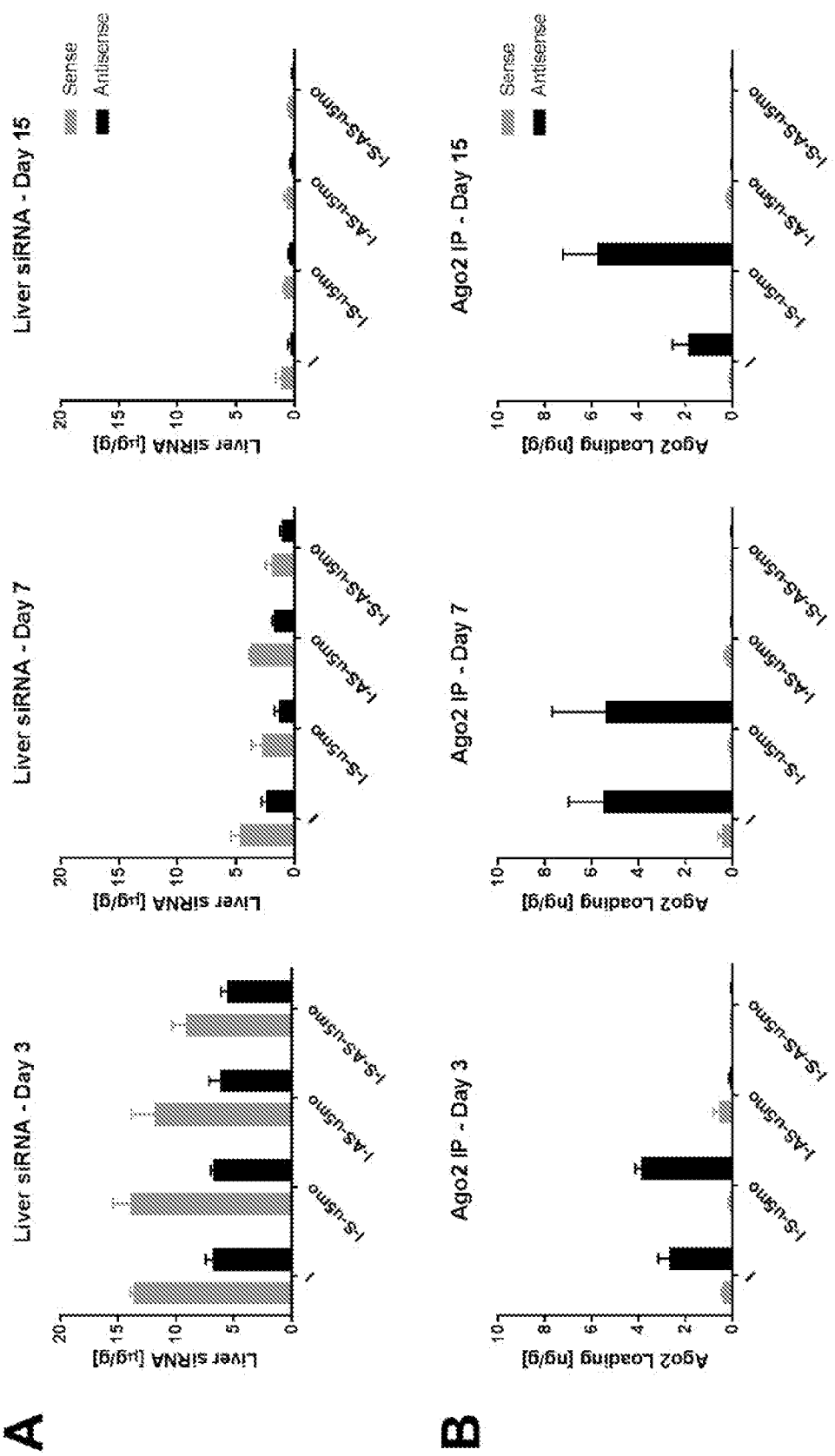

FIG. 28 shows liver levels and Ago3 IP at day 3, 7 and 15. 5'-Morpholino modification of the sense strand increases RISC loading of paired antisense strand. Mice (n=3 per group) were treated with a single dose of 3 mg/kg parent, AS5'-Mo, S5'-Mo, or S/AS5'-Mo siRNA targeting Apob. Cohorts of mice were sacrificed at 3, 7, and 15 days post-dose, and liver lysates were generated. (A) Liver levels of the antisense and sense strand of siRNA-GalNAc conjugates quantified by RT-qPCR. (B) Ago-2 was immunoprecipiated and Ago2-bound antisense and sense strand levels were quantified by RT-qPCR.

Figure 29:
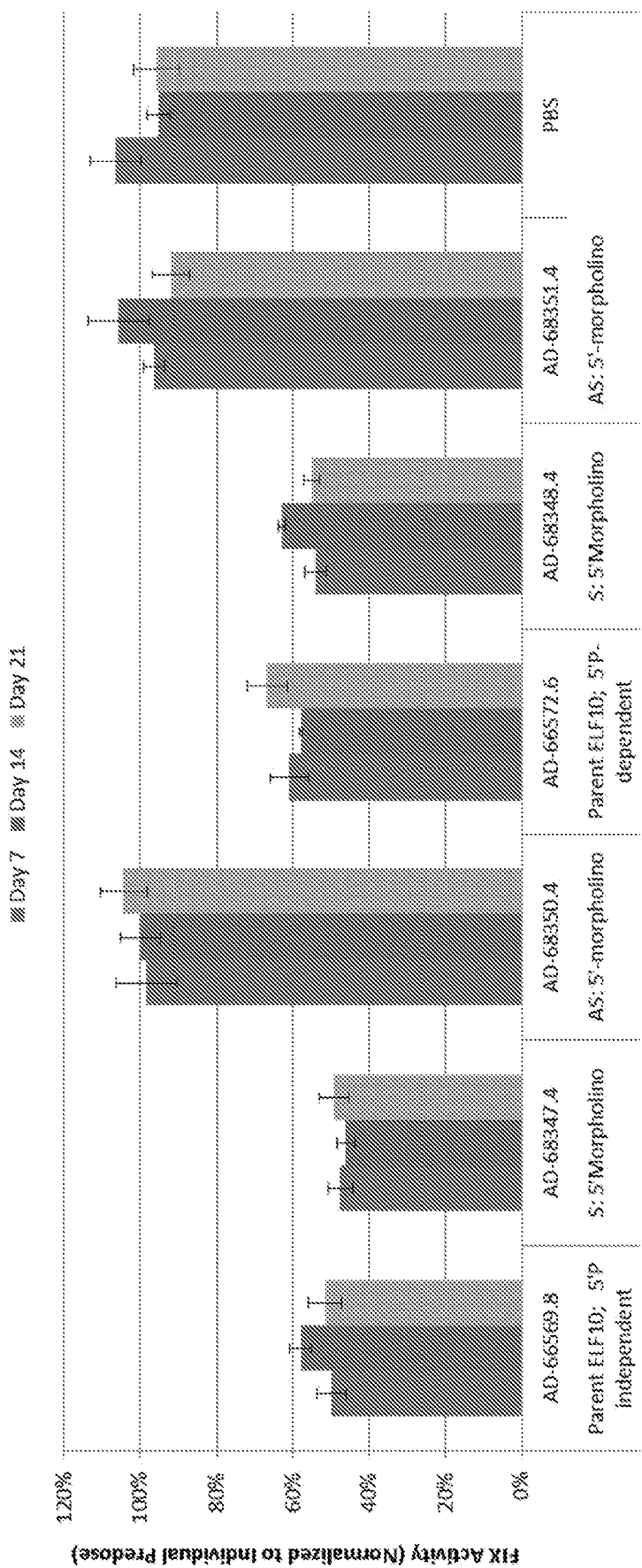

FIG. 29 shows strand specific RISC loading of exemplary siRNAs.

Figure 30:
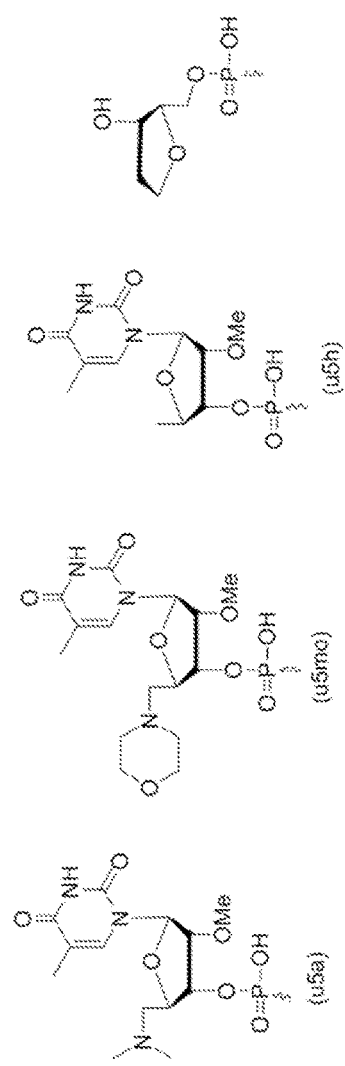

FIG. 30 shows structures of exemplary modifications.

Figure 31:
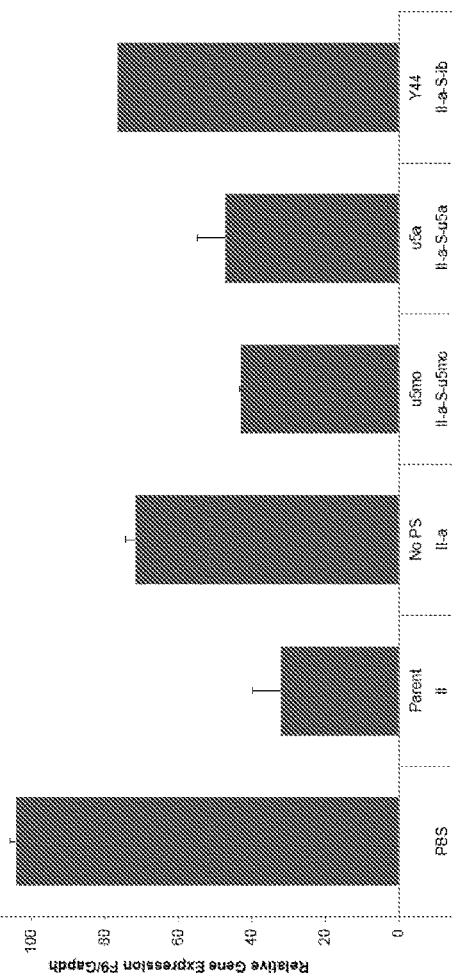

FIG. 31 relative Factor IX (F9) gene expression in mice day 10 post dosing of exemplary siRNAs.

FIG. 32 shows Modifications tested: 5'-deoxy-5'-morpholino-2'-O-methyl uridine (Mo), 5'-deoxy-5'-dimethylamino-2'-O-methyl uridine (D), 5'-deoxy-2'-O-methyl uridine (Me), locked nucleic acid (LNA), and inverted abasic site (iB).

Figure 33:
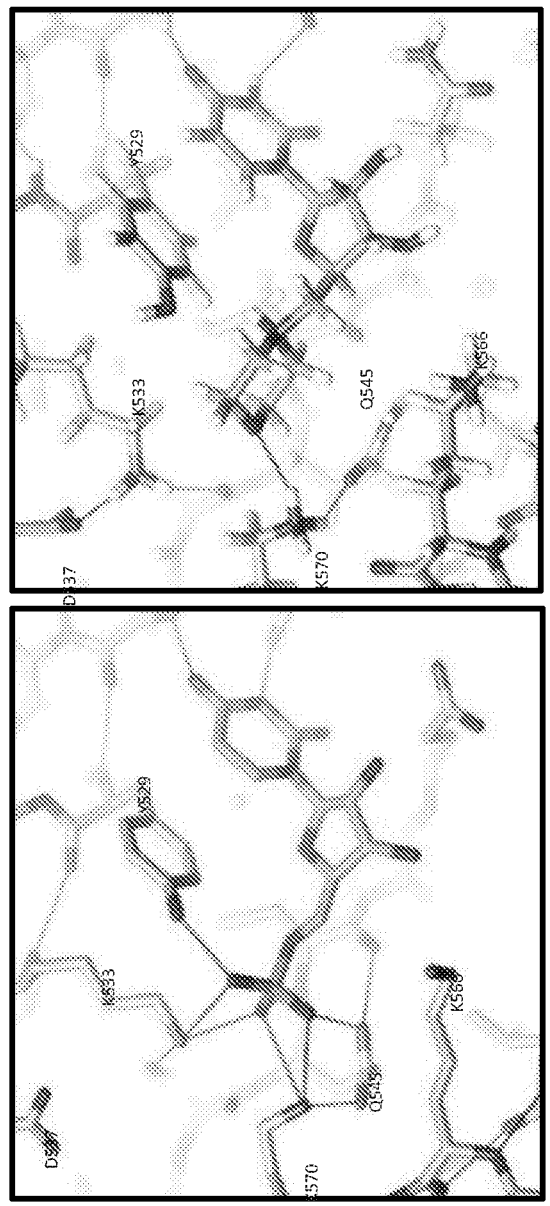

FIG. 33 shows illustrations of the binding modes of (Left) UMP and (Right) 5'-morpholino-U to Ago2 MID. Hydrogen bonds are thin solid lines in black, and selected Ago2 residues are labeled.

FIG. 34 shows serum FIX levels in mice on days 7 (left), 14 (middle), and 21 (right) following a single subcutaneous 1 mg/kg dose of indicated siRNAs. FIX levels were normalized to the individual pre-dose values.

FIG. 35 is a reaction scheme showing synthesis of 2'-fluorinated Northern methanocarbacyclic (2'-F-NMC) nucleosides and phosphoramidites bearing all four natural nucleobases (U, C, A, and G). The 2'-F-NMC is related to 2'-deoxy-2'-fluororibonucleotides(2'-F-RNA) in RNA mimics being used for therapeutic applications.

FIG. 36A-36C show Structures of (A) 2'-F-RNA, (B) NMC, (C) 2'-F-NMC. FIG. 36D is a model of a hybrid duplex between 2'-F-NMC and RNA constructed using the program UCSF Chimera, 2'-F-NMC residues have an idealized C2'-exo pucker with an axial 2'-fluorine.

Figure 37:
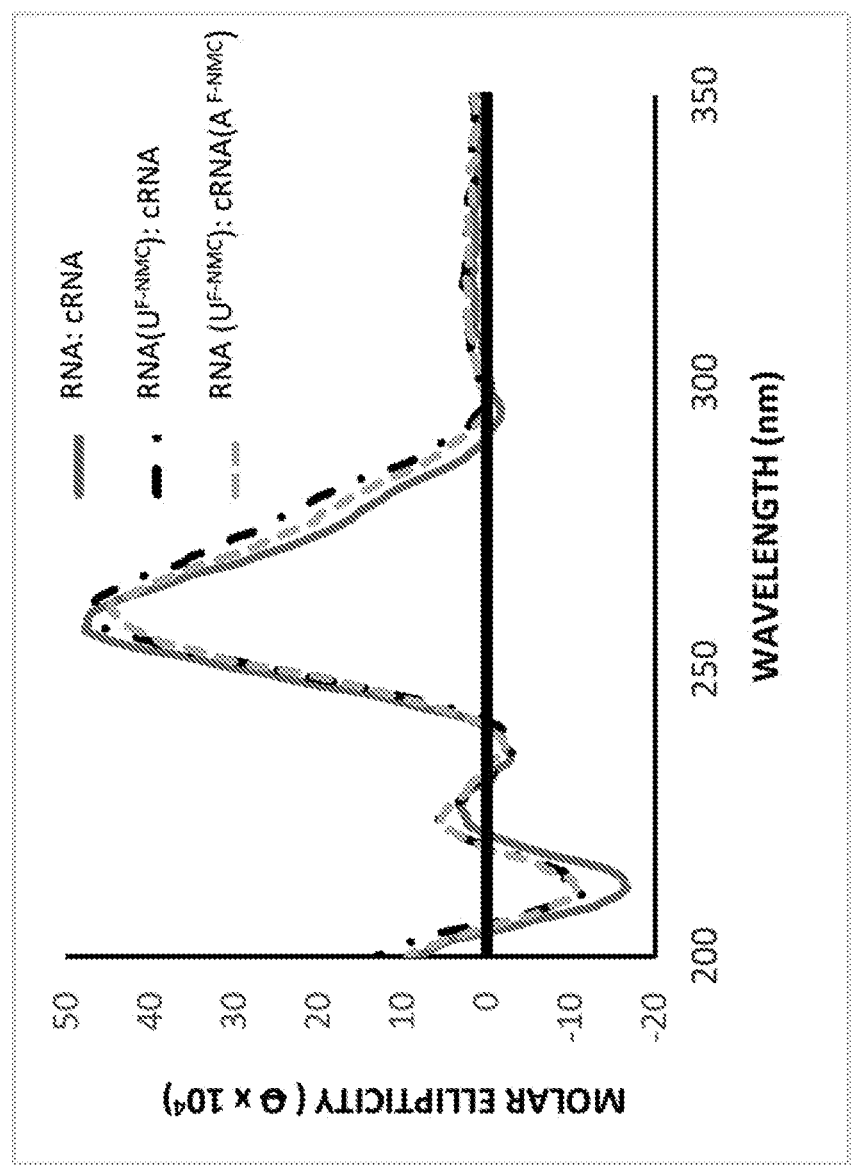

FIG. 37 is a CD spectra of 2'-F-NMC-modified RNA duplexes and an unmodified RNA duplex at 15° C. in PBS (pH 7.4).

Figures 38A, 38B:
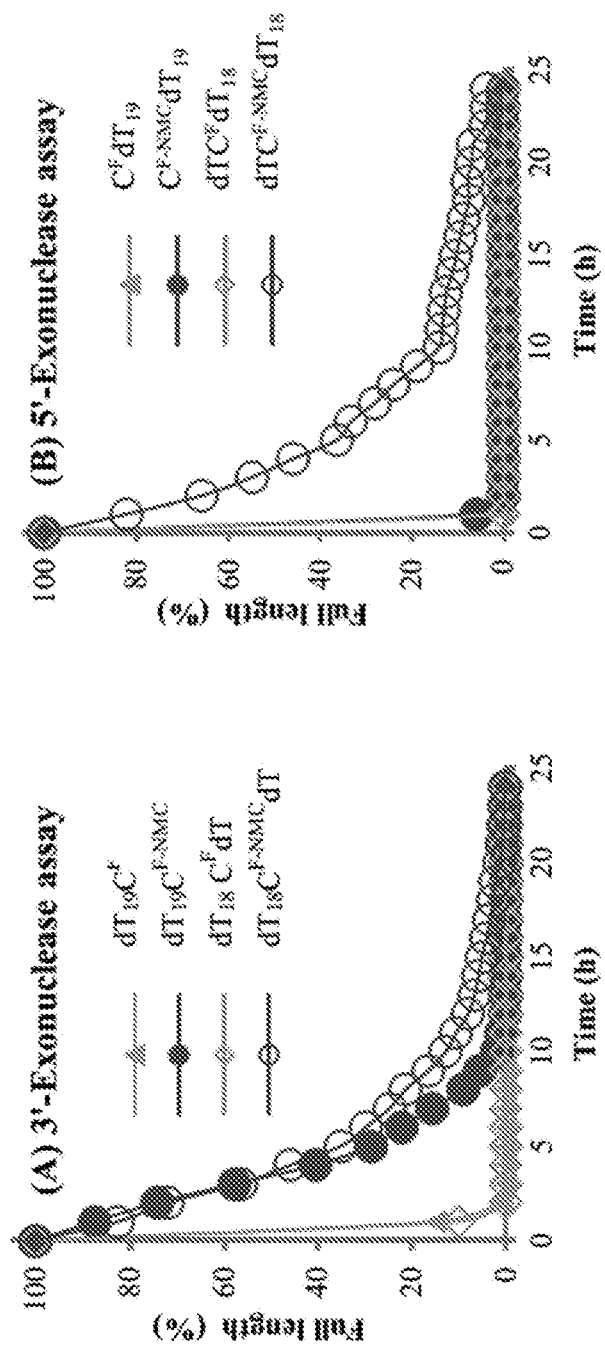
Figure 39:
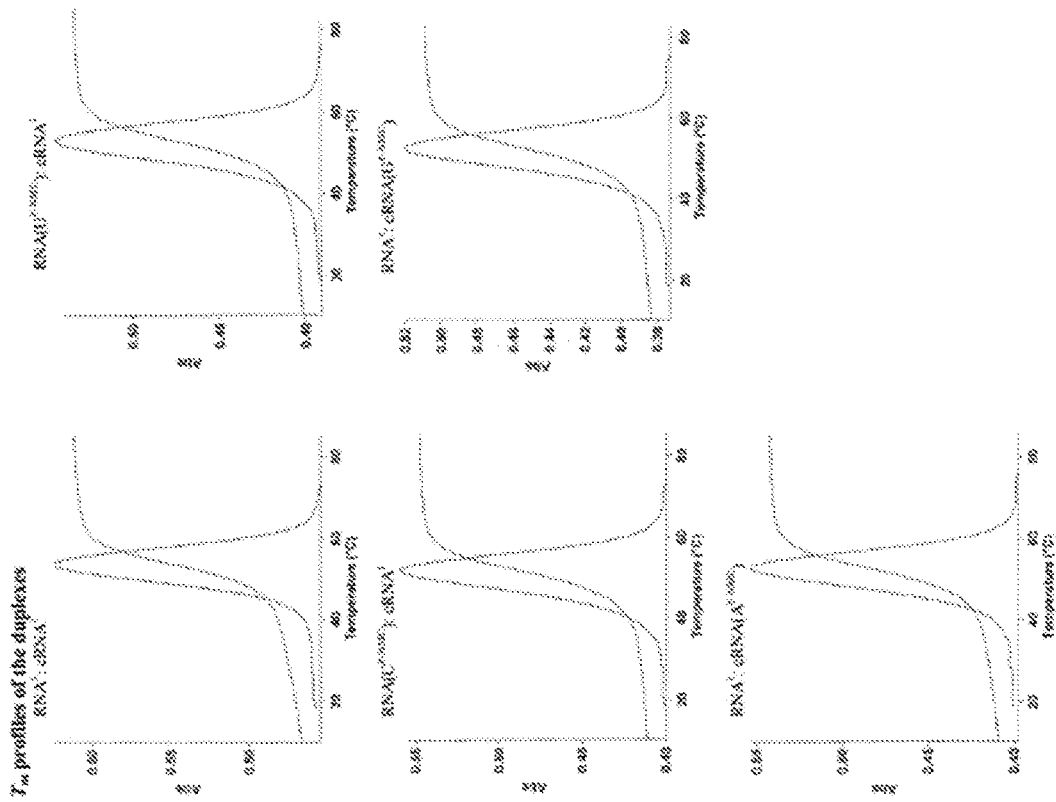
Figure 40:
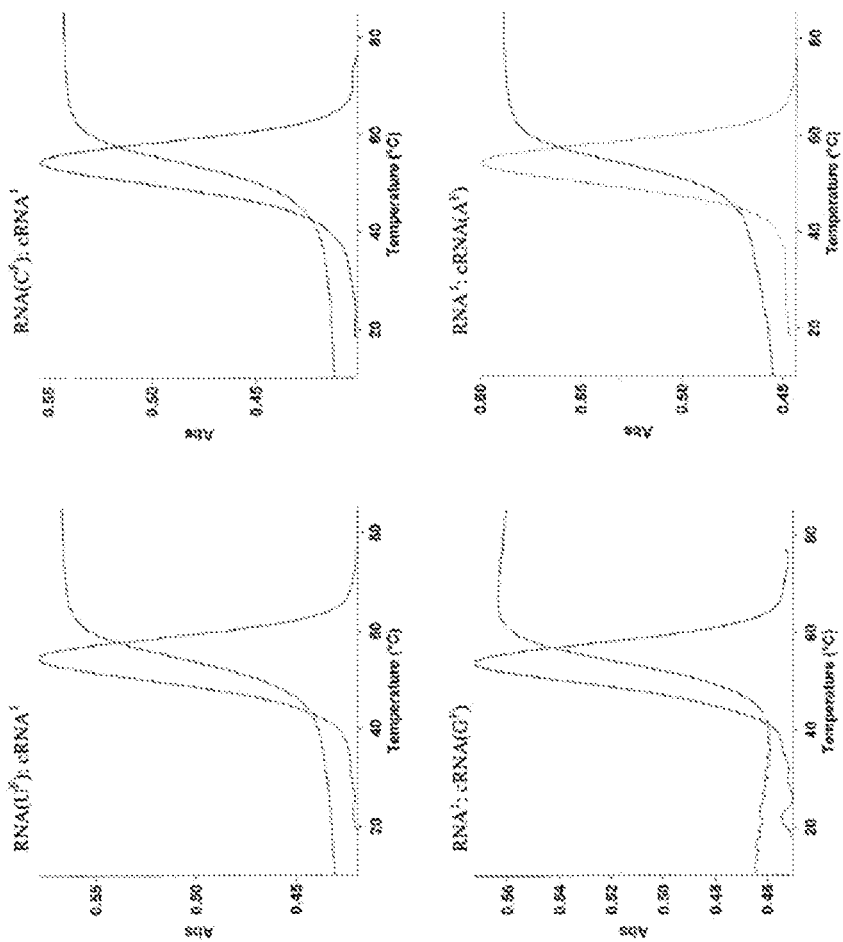
Figure 41:
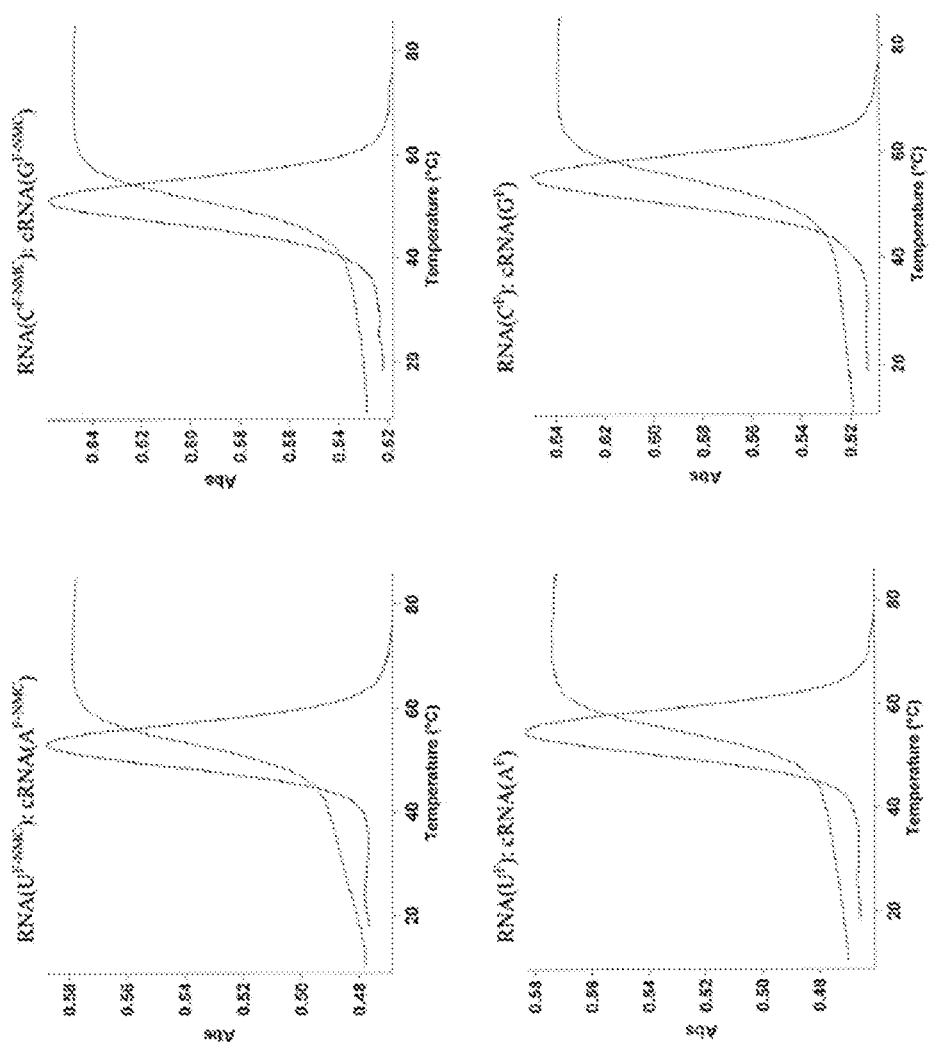
Figure 42:
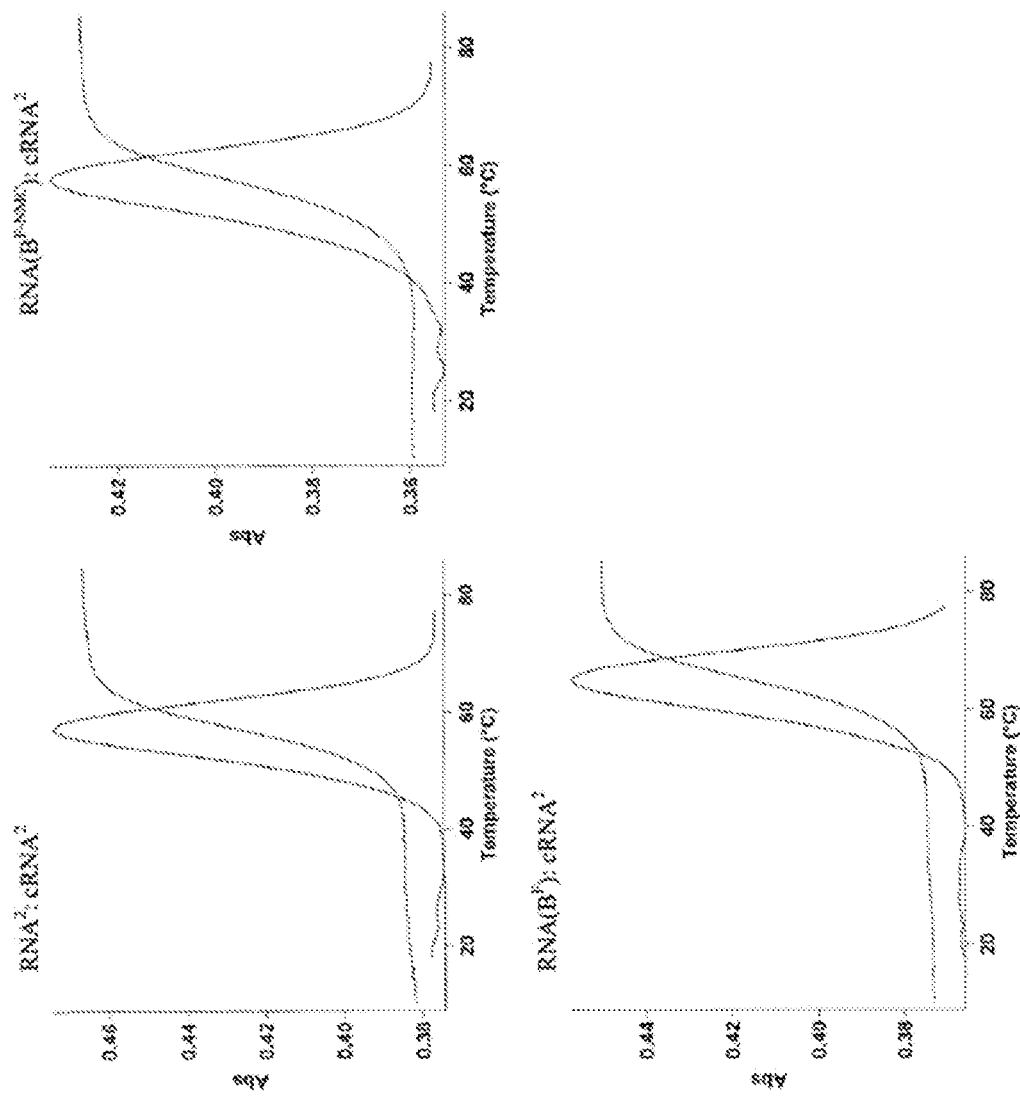

FIG. 38A-38B show HPLC quantification of indicated full-length oligonucleotide after incubation with (A) SVPD and (B) PDE-II as a function of time. For $dT_{18}C^{F-NMC}dT$ (SEQ ID NO: 77), the percentage of 19-mer $dT_{18}C^{F-NMC}$ (SEQ ID NO: 95) remaining is plotted. FIG. 38A discloses SEQ ID NOS 80, 75, 81 and 77, respectively, in order of appearance. FIG. 38B discloses SEQ ID NOS 82, 78, 83 and 79, respectively, in order of appearance.

FIGS. 39-42 show $T_m$ profiles of duplexes.

Figure 43:
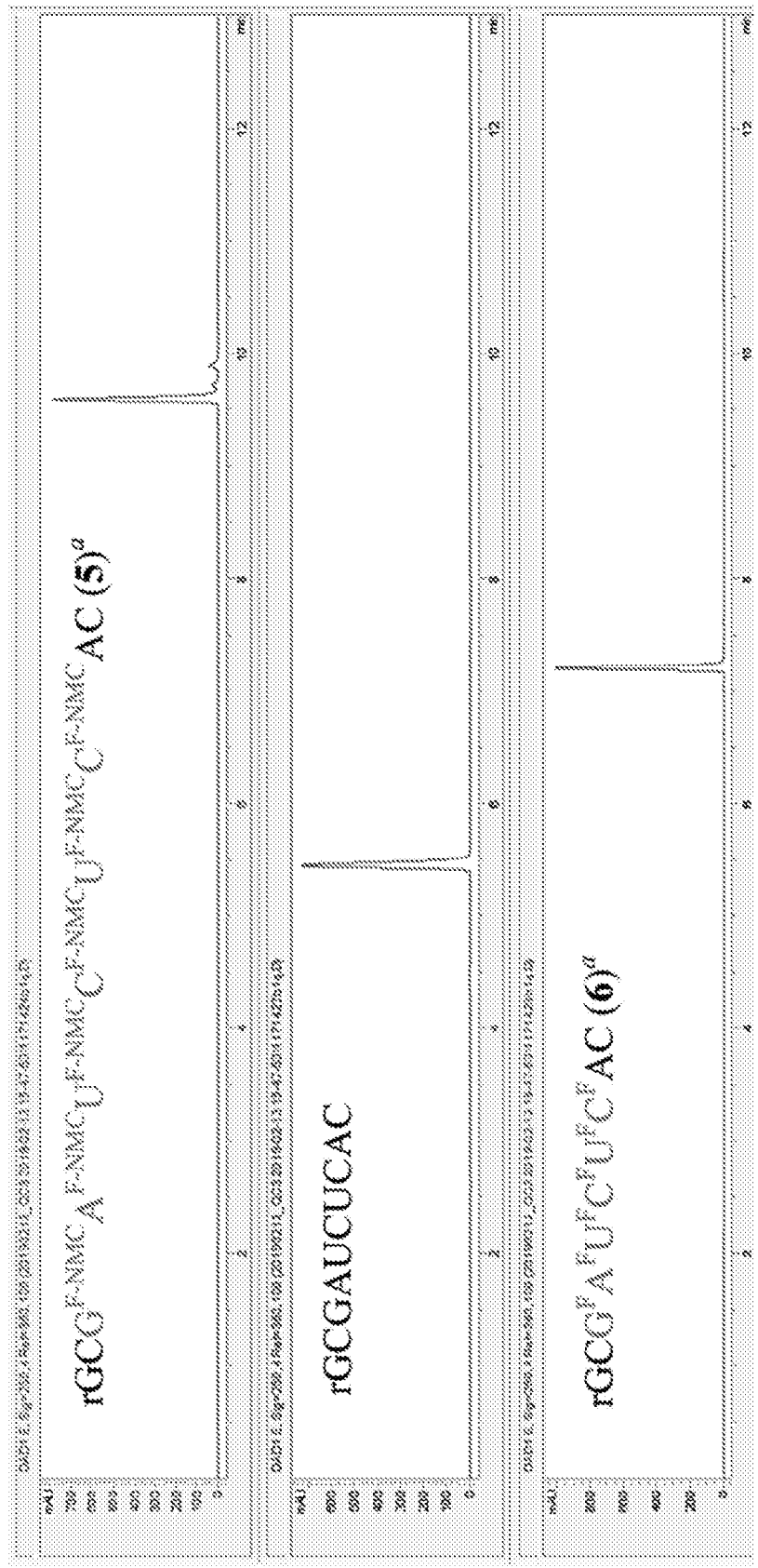

FIG. 43 shows HPLC profiles of oligonucleotides for comparison of lipophilicity. FIG. 43 discloses SEQ ID NOS 73, 69 and 74, respectively, in order of appearance.

Figure 44:
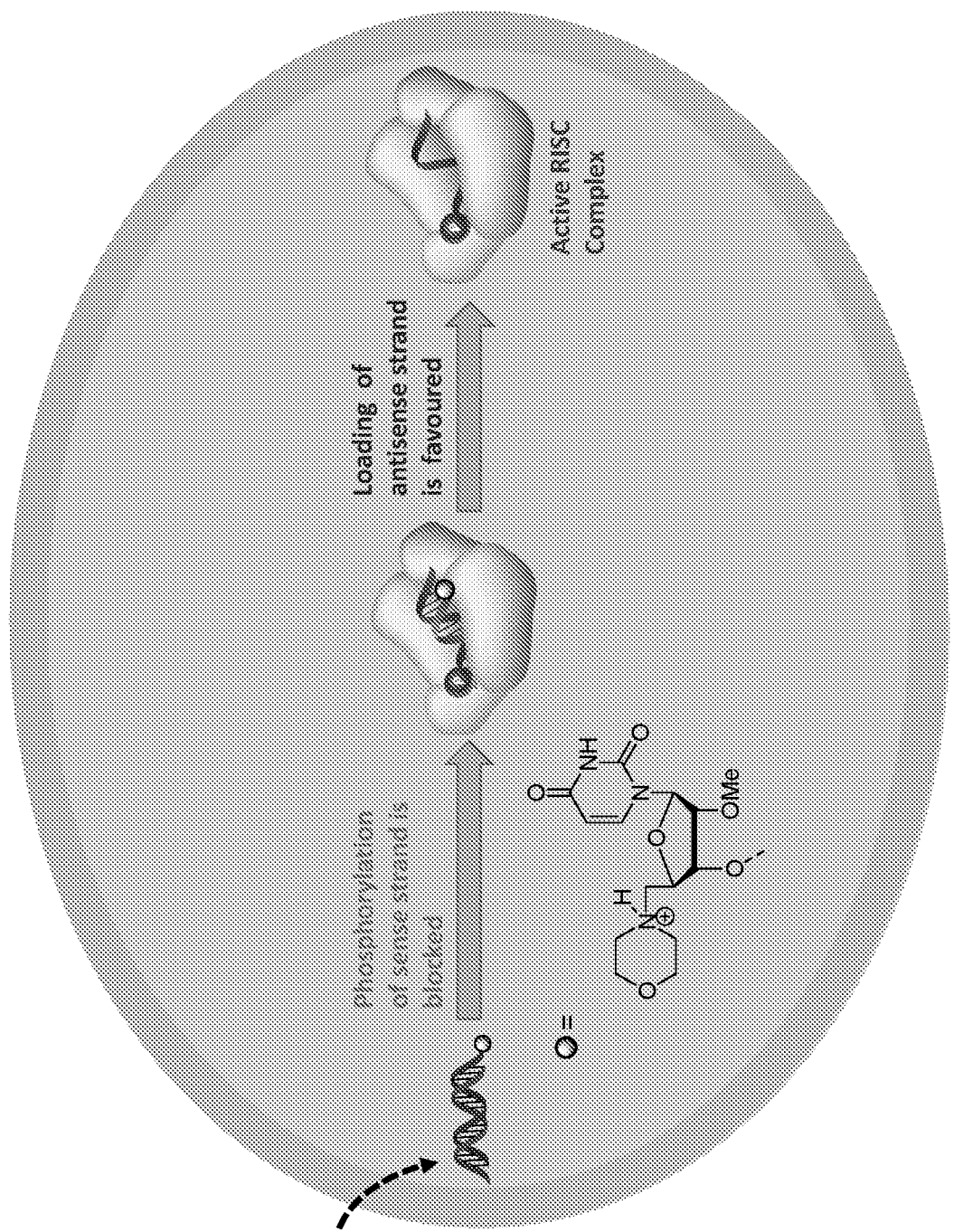

FIG. 44 shows that blocking 5'-phosphorylation of the sense strand favors selective loading of the antisense strand into RISC complex.

DETAILED DESCRIPTION

Inventors have discovered inter alia that off-target effects of dsRNA molecules can be reduced or inhibited by inhibiting, reducing or eliminating loading of sense strand into the RISC complex. As such, in one aspect, the invention provides a double-stranded RNAi (dsRNA) agent capable of inhibiting expression of a target gene. Generally, the dsRNA molecules of the invention show high on-target gene silencing while reducing or minimizing off-target gene silencing and/or toxicity. Without limitations, the dsRNA molecules of the invention can be substituted for the dsRNA molecules and can be used for in RNA interference based gene silencing techniques, including, but not limited to, in vitro or in vivo applications.

Generally, the dsRNA molecule comprises a sense strand (also referred to as passenger strand) and an antisense strand (also referred to as guide strand). Each strand of the dsRNA molecule can range from 12-40 nucleotides in length. For example, each strand can be between 14-40 nucleotides in length, 17-37 nucleotides in length, 25-37 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length. Without limitations, the sense and antisense strands can be equal length or unequal length.

In some embodiments, the antisense strand is of length 18 to 35 nucleotides. In some embodiments, the antisense strand is 21-25, 19-25, 19-21 or 21-23 nucleotides in length. In some particular embodiments, the antisense strand is 23 nucleotides in length. Similar to the antisense strand, the sense strand can be, in some embodiments, 18-35 nucleotides in length. In some embodiments, the sense strand is 21-25, 19-25, 19-21 or 21-23 nucleotides in length. In some particular embodiments, the antisense strand is 21 nucleotides in length.

The inventors also discovered that for the dsRNA molecules to be more effective in vivo, the antisense strand must have some metabolic stability. In other words, for the dsRNA molecules to be more effective in vivo, some amount of the antisense stand may need to be present in vivo after a period time after administration. Accordingly, in some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 5 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 6 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 7 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 8 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 9 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 10 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 11 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 12 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 13 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 14 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 15 after in vivo administration.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), the dsRNA has a melting temperature (Tm) of from about 40° C. to about 80° C., wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphonate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; (vii) the dsRNA comprises a duplex region of 12-40 nucleotide pairs in length; and (viii) a blunt end at 5' end of the antisense strand. In some embodiments, the $T_m$ of from about 40° C. to about 80° C. is optional.

In some embodiments, the dsRNA molecule has a duplex region of 12-40 nucleotide pairs in length, wherein the antisense strand comprises at least one thermally destabilizing modification of the duplex within the seed region (i.e., at position 2-9 of the 5'-end of the antisense strand, counting from the 5'-end), and the dsRNA has a $T_m$ of from about 40° C. to about 80° C., wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; and vii) a blunt end at 5' end of the antisense strand. In some embodiments, the $T_m$ of from about 40° C. to about 80° C. is optional.

In some embodiments, the dsRNA molecule has a duplex region of 19, 20, 21, 22 or 23 nucleotide base pairs in length, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the $T_m$ of from about 40° C. to about 80° C. is optional.

In some embodiments, the dsRNA molecule has a duplex region of 19, 20, 21, 22 or 23 nucleotide base pairs in length, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C. (e.g., 40° C., 50° C., 60° C., 70° C. or 80° C.), and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the $T_m$ of from about 40° C. to about 80° C. is optional.

In some particular embodiments, the thermally destabilizing modification of the duplex is at position 5, 6, 7, or 8 of the antisense strand, counting from 5'-end of the antisense strand.

In some particular embodiments, the thermally destabilizing modification of the duplex is at position 5 of the antisense strand, counting from 5'-end of the antisense strand.

In some particular embodiments, the thermally destabilizing modification of the duplex is at position 6 of the antisense strand, counting from 5'-end of the antisense strand.

In some particular embodiments, the thermally destabilizing modification of the duplex is at position 7 of the antisense strand, counting from 5'-end of the antisense strand.

In some particular embodiments, the thermally destabilizing modification of the duplex is at position 8 of the antisense strand, counting from 5'-end of the antisense strand.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C.), and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the antisense strand further comprises one or both of the following characteristics:
   (i) 2, 3, 4, 5 or 6 2'-fluoro modifications; and
   (ii) 1, 2, 3 or 4 phosphorothioate internucleotide linkages; and the sense strand comprises one, two or three of the following characteristics:
   (i) a ligand conjugated with the sense strand;
   (ii) 2, 3, 4 or 5 2'-fluoro modifications; and
   (iii) 1, 2, 3 or 4 phosphorothioate internucleotide linkages.

In some embodiments of this, the Tw of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, and a ligand is conjugated with the sense strand, wherein the dsRNA has a melting temperature of about 40° C. to about 80° C.), and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications,), and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, said sense strand comprises a ligand, and wherein the dsRNA has a melting temperature of about 40° C. to about 80° C.,), and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some further embodiments of this, the ligand is an ASGPR ligand. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, wherein each of the sense and antisense strands comprise at least two 2'-fluoro modifications, and wherein the dsRNA has a melting temperature of about 40° C. to about 80° C. In some further embodiments of this, the ligand is an ASGPR ligand,), and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the antisense further comprises at least two of the following characteristics: (i) the thermally destabilizing modification of the duplex is located in position 4 to 8 of the antisense strand; (ii) at least two 2'-fluoro modifications; (iii) phosphorothioate internucleotide linkages between nucleotide positions 1 and 2 (counting from the 5' end); and antisense strand has a length of 18 to 35 nucleotides; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some further embodiments the ligand is an ASGPR ligand. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and the sense strand has at least one of the following characteristics: (i) the ligand is attached to either end of the sense strand; (ii) sense strand comprises at least two 2'-fluoro modifications; and (iii) the sense strand and the antisense strand show sufficient complementarity to form a double stranded region spanning at least 19 nucleotide positions and wherein the thermally destabilizing modification of the duplex is located within said double-stranded region, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the thermally destabilizing modification of the duplex is selected from the group consisting of:

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, wherein the dsRNA has a melting temperature of about 40° C. to about 80° C., and wherein the thermally destabilizing modification of the duplex is selected from the group consisting of:

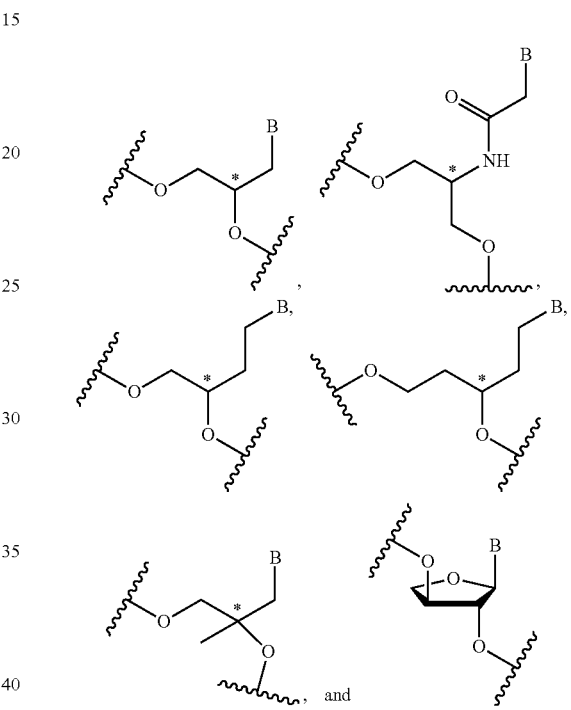

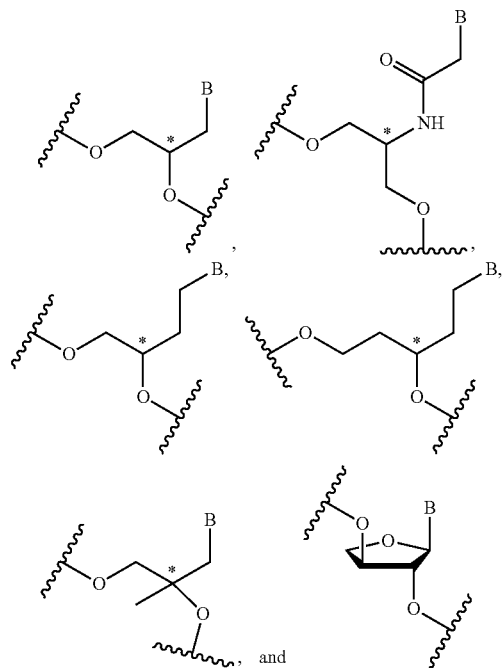

wherein B is a modified or unmodified nucleobase and the asterisk on each structure represents either R, S or racemic, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the $T_m$ of from about 40° C. to about 80° C. is optional.

wherein B is a modified or unmodified nucleobase and the asterisk on each structure represents either R, S or racemic, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the Tw of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex located at position 7, counting from the 5'-end of the antisense strand, wherein said sense strand comprises a ligand, and wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located at position 7, counting from the 5'-end, wherein said sense strand comprises a ligand, and wherein each of the sense and antisense strands comprise at least two 2'-fluoro modifications, wherein the dsRNA has a melting temperature of about 40° C. to about 80° C., and wherein the thermally destabilizing modification of the duplex is selected from the group consisting of:

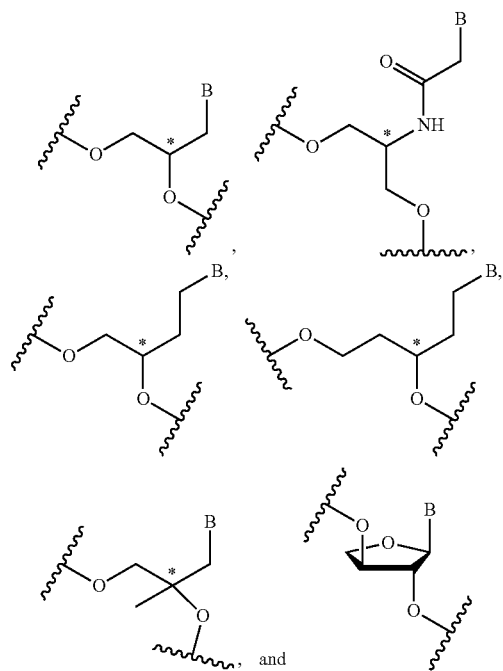

wherein B is a modified or unmodified nucleobase and the asterisk on each structure represents either R, S or racemic, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, wherein said sense strand comprises a ligand, wherein the dsRNA has a melting temperature of about 40° C. to about 80° C., and wherein the ligand comprises one or more GalNAc derivatives attached through a bivalent or trivalent branched linker, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA optionally has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the ligand is an ASGPR ligand of structure:

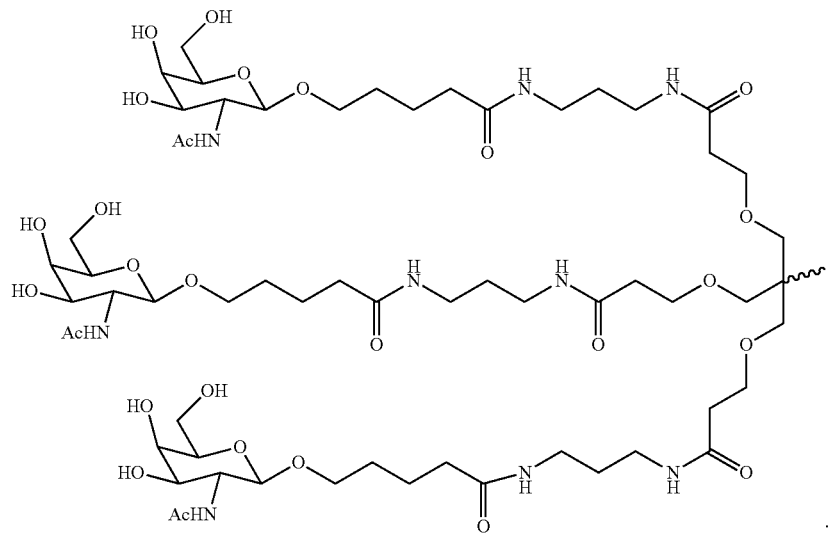 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, the Tw of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3phosphorothioate internucleotide linkages; wherein the antisense strand comprises 3, 4, 5 or 6 2'-fluoro modifications, and comprises 2, 3, 4 or 5 phosphorothioate internucleotide linkages; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the I'm of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 3, 4, 5 or 6 2'-fluoro modifications, comprises 2, 3, 4 or 5 phosphorothioate internucleotide linkages; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the Tw of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the TW of from about 40° C. to about 80° C. is optional.

In some embodiments, the sense and antisense strands are independently 19, 20, 21, 22, 23, 24 or 25 nucleotides in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3. 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 18, 19, 20, 21, 22, 23, 24 or 24 nucleotide pairs in length; and (viii) the dsRNA comprises a blunt end at 5'-end of the sense strand. In some particular embodiments, sense strand is 19, 20 or 21 or 22 nucleotides in length and the antisense strand is 20, 21 or 22 nucleotides in length. In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C., and wherein the dsRNA has at least one (e.g., one, two or all three) of the following characteristics: (i) the sense strand comprises a 5'-morpholino, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the I'm of from about 40° C. to about 80° C. is optional.

In some embodiments, one end of the dsRNA is a blunt end and the other end has an overhang, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) and the dsRNA comprises a duplex region of 12-40 nucleotide pairs in length. In some embodiments, the overhang is on the 3'-end of the antisense strand and the blunt end is at the 5'-end of the antisense strand. In some particular embodiments, the overhang is 2, 3 or 4-nucleotides in length. In some embodiments, the Tw of from about 40° C. to about 80° C. is optional.

In some embodiments, the dsRNA molecule has a duplex region of 19, 20, 21, 22 or 23 nucleotide base pairs in length, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications, and optionally the 2 nucleotide overhang is on the 3'-end of the antisense strand and the blunt end is at the 5'-end of the antisense strand. In some embodiments, the overhang is on the 3'-end of the antisense strand and the blunt end is at the 5'-end of the antisense strand. In some embodiments, the $T_m$ of from about 40° C. to about 80° C. is optional.

In some embodiments, the dsRNA molecule of the invention may also have two blunt ends, at both ends of the dsRNA duplex.

In some embodiments, the dsRNA has a blunt end at both ends of the duplex, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a duplex region of 12-40 nucleotide pairs in length. In some embodiments, the $T_m$ of from about 40° C. to about 80° C. is optional.

In some embodiments, the dsRNA molecule has a duplex region of 19, 20, 21, 22 or 23 nucleotide base pairs in length and has a blunt end at both ends of the duplex, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications. In some embodiments, the I'm of from about 40° C. to about 80° C. is optional.

In some embodiments, the dsRNA molecule of the invention comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a blunt end at 5'-end of the antisense strand. Preferably, the 2 nt overhang is at the 3'-end of the antisense. In some embodiments, the $T_m$ of from about 40° C. to about 80° C. is optional.

In some embodiments, the dsRNA molecule of the invention comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3 ' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand), and wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. For example, the thermally destabilizing nucleotide occurs between positions opposite or complimentary to positions 14-17 of the 5'-end of the sense strand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA comprises a duplex region of 12-30 nucleotide pairs in length. In some embodiments, the $T_m$ of from about 40° C. to about 80° C. is optional.

In some embodiments, the dsRNA molecule of the invention comprises a sense and antisense strands, wherein said dsRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5' end, wherein the 3' end of said sense strand and the 5' end of said antisense strand form a blunt end and said antisense strand is 1~4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA has a duplex region of 12-29 nucleotide pairs in length. In some embodiments, the $T_m$ of from about 40° C. to about 80° C. is optional.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand. In some embodiments, the Tw of from about 40° C. to about 80° C. is optional.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics:

(i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; and (viii) the dsRNA has a blunt end at 5'-end of the antisense strand. In some embodiments, the I'm of from about 40° C. to about 80° C. is optional.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand. In some embodiments, the $T_m$ of from about 40° C. to about 80° C. is optional.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 3, 4 or 5 phosphorothioate internucleotide linkages; (v) the dsRNA comprises at least four 2'-fluoro modifications; (vi) the dsRNA comprises a duplex region of 12-40 nucleotide pairs in length; and (vii) the dsRNA has a blunt end at 5'-end of the antisense strand. In some embodiments, the $T_m$ of from about 40° C. to about 80° C. is optional.

In one aspect the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and the dsRNA further has at least one (e.g., one, two, three, four, five, six seven or all eight) of the following characteristics:

(i) the antisense comprises 2, 3, 4, 5 or 6 2'-fluoro modifications;
(ii) the antisense comprises 1, 2, 3, 4 or 5 phosphorothioate internucleotide linkages;
(iii) the sense strand is conjugated with a ligand;
(iv) the sense strand comprises 2, 3, 4 or 5 2'-fluoro modifications;
(v) the sense strand comprises 1, 2, 3, 4 or 5 phosphorothioate internucleotide linkages;

(vi) the dsRNA comprises at least four 2'-fluoro modifications;

(vii) the dsRNA comprises a duplex region of 12-40 nucleotide pairs in length; and (viii) a blunt end at 5' end of the antisense strand.

In some particular embodiments, the thermally destabilizing modification of the duplex is at position 7 of the antisense strand, counting from 5'-end of the antisense strand.

In some embodiments, the thermally destabilizing modification of the duplex is at position 2, 3, 4, 5, 6, 8 or 9 of the antisense strand, counting from 5'-end of the antisense strand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the antisense strand comprises at least one thermally destabilizing modification of the duplex within the seed region (i.e., at position 2-9 of the 5'-end of the antisense strand, counting from the 5'-end), and the antisense strand further comprises one or both of the following characteristics:

(i) 2, 3, 4, 5 or 6 2'-fluoro modifications; and (ii) 1, 2, 3, 4 or 5 phosphorothioate internucleotide linkages; and the sense strand comprises one, two or three of the following characteristics:

(i) a ligand conjugated with the sense strand;

(ii) 2, 3, 4 or 5 2'-fluoro modifications; and (iii) 1, 2, 3, 4 or 5 phosphorothioate internucleotide linkages.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, and a ligand is conjugated with the sense strand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand. In some further embodiments of this, the ligand is an ASGPR ligand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications. In some further embodiments of this, the ligand is an ASGPR ligand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the antisense further comprises at least two of the following characteristics: (i) the thermally destabilizing modification of the duplex is located in position 4 to 8 of the antisense strand; (ii) at least two 2'-fluoro modifications; (iii) phosphorothioate internucleotide linkages between nucleotide positions 1 and 2 (counting from the 5' end); and antisense strand has a length of 18 to 35 nucleotides. In some further embodiments the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein said sense strand comprises a ligand, and the sense strand has at least one of the following characteristics: (i) the ligand is attached to either end of the sense strand; (ii) sense strand comprises at least two 2'-fluoro modifications; and (iii) the sense strand and the antisense strand show sufficient complementarity to form a double stranded region spanning at least 19 nucleotide positions and wherein the thermally destabilizing modification of the duplex is located within said double-stranded region.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein the thermally destabilizing modification of the duplex is selected from the group consisting of:

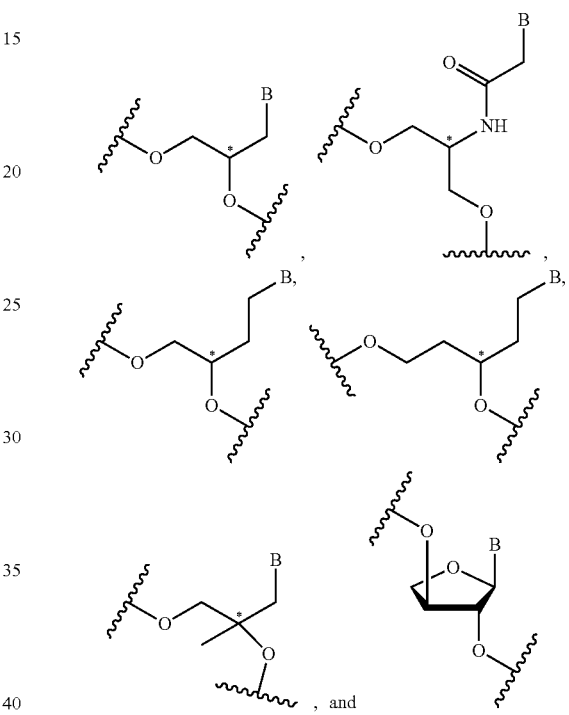

wherein B is a modified or unmodified nucleobase and the asterisk on each structure represents either R, S or racemic, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, and wherein the thermally destabilizing modification of the duplex is selected from the group consisting of:

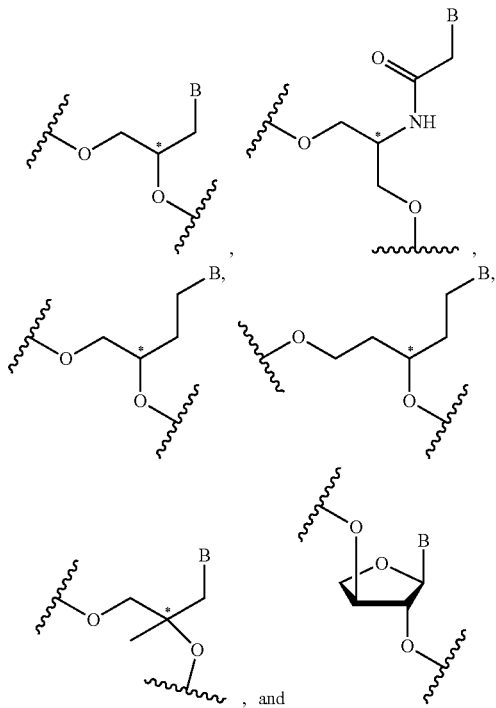

wherein B is a modified or unmodified nucleobase and the asterisk on each structure represents either R, S or racemic, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex located at position 7, counting from the 5'-end of the antisense strand, and wherein said sense strand comprises a ligand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located at position 7, counting from the 5'-end, wherein said sense strand comprises a ligand, and wherein each of the sense and antisense strands comprise at least two 2'-fluoro modifications, and wherein the thermally destabilizing modification of the duplex is selected from the group consisting of:

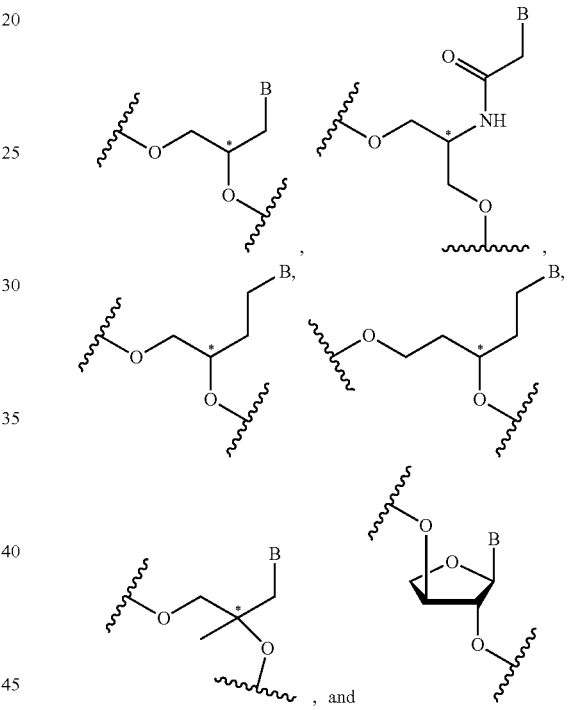

wherein B is a modified or unmodified nucleobase and the asterisk on each structure represents either R, S or racemic, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex relative to a siRNA having the same antisense strand sequence but unmodified N-1 position, and wherein the ligand is an ASGPR ligand of structure:

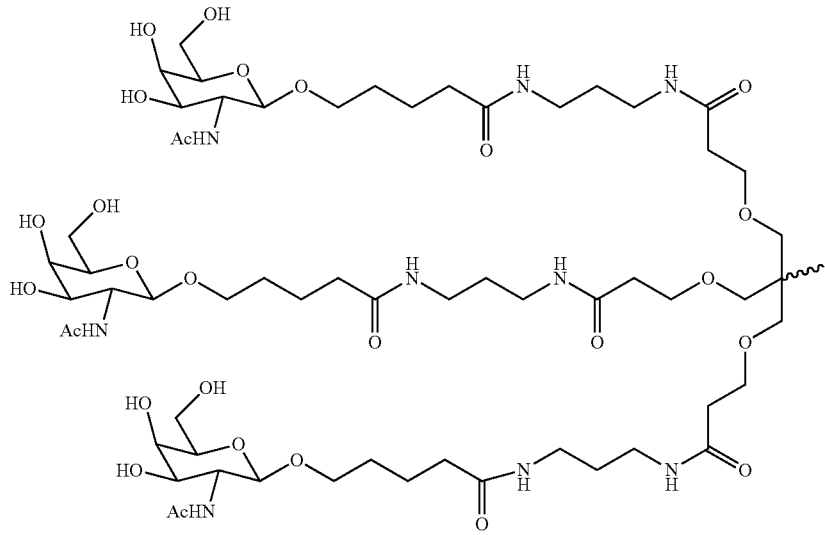 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

within the first 9 nucleotide positions, counting from the 5'-end, and wherein said sense strand comprises a ligand, wherein the ligand comprises one or more GalNAc derivatives attached through a bivalent or trivalent branched linker, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 3, 4, 5 or 6 2'-fluoro modifications, comprises 2, 3, 4 or 5 phosphorothioate internucleotide linkages, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 3, 4, 5 or 6 2'-fluoro modifications, comprises 2, 3, 4 or 5 phosphorothioate internucleotide linkages, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In a particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker; and
  (iii) 2'-F modifications at positions 7, 10, and 11 (counting from the 5' end);
and
(b) an antisense strand having:
  (i) a length of 23 nucleotides;
  (ii) 2'-F modifications at positions 2, 6 to 8, 9, 14, and 16 (counting from the 5' end);
  (iii) phosphorothioate internucleotide linkages between nucleotide positions 21 and 22, and between nucleotide positions 22 and 23 (counting from the 5' end); and
  (iv) a thermally destabilizing modification of the duplex at position 7 (counting from the 5' end);
wherein the dsRNA molecules have a two nucleotide overhang at the 3'-end of the antisense strand, and a blunt end at the 5'-end of the antisense strand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);
and
(b) an antisense strand having:
  (i) a length of 23 nucleotides;
  (ii) 2'-F modifications at positions 2, 6, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 7 (counting from the 5' end);
wherein the dsRNA molecules have a two nucleotide overhang at the 3'-end of the antisense strand, and a blunt end at the 5'-end of the antisense strand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);
and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and (iv) a thermally destabilizing modification of the duplex at position 6 or 7 (counting from the 5' end);

wherein the dsRNA molecules have a two nucleotide overhang at the 3'-end of the antisense strand, and a blunt end at the 5'-end of the antisense strand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In another particular embodiment, the dsRNA molecules of the present invention comprise:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 7, 9, 10, and 11 (counting from the 5' end); and
(iv) phosphorothioate internucleotide linkages between nucleotide positions 1 and 2, and between nucleotide positions 2 and 3 (counting from the 5' end); and (b) an antisense strand having:
(i) a length of 23 nucleotides;
(ii) 2'-F modifications at positions 2, 6, 8, 9, 14, and 16 (counting from the 5' end);
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
(iv) a thermally destabilizing modification of the duplex at position 7 (counting from the 5' end);
wherein the dsRNA molecules have a two nucleotide overhang at the 3'-end of the antisense strand, and a blunt end at the 5'-end of the antisense strand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In another particular embodiment, the dsRNA molecules of the present invention comprising an antisense strand having:

(i) 2'-F modifications at positions 2, 14, and 16 (counting from the 5' end); and
(2) a thermally destabilizing modification of the duplex at position 6 or 7 (counting from the 5' end);
and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In another particular embodiment, the dsRNA molecules of the present invention comprise:

(a) a sense strand having:
(i) an ASGPR ligand, wherein said ASGPR ligand comprises three GalNAc derivatives attached through a trivalent branched linker;
(ii) phosphorothioate internucleotide linkages between nucleotide positions 1 and 2, and between nucleotide positions 2 and 3 (counting from the 5' end); and (b) an antisense strand having:
(i) 2'-F modifications at positions 2, 14, and 16 (counting from the 5' end);
(ii) a thermally destabilizing modification of the duplex at position 6 or 7 (counting from the 5' end);
and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position In another particular embodiment, the dsRNA molecules of the present invention comprise:

(a) a sense strand having:
(i) an ASGPR ligand attached to the 3'-end, wherein said ASGPR ligand comprises three GalNAc derivatives attached through a trivalent branched linker;
(ii) phosphorothioate internucleotide linkages between nucleotide positions 1 and 2, and between nucleotide positions 2 and 3 (counting from the 5' end); and (b) an antisense strand having:
(ii) 2'-F modifications at positions 2, 14, and 16 (counting from the 5' end);
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and (iv) a thermally destabilizing modification of the duplex at position 6 or 7 (counting from the 5' end);
wherein the dsRNA molecules have a two nucleotide overhang at the 3'-end of the antisense strand, and a blunt end at the 5'-end of the antisense strand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule further comprises at least one ASGPR ligand. For example, the ASGPR ligand is one or more GalNAc derivatives attached through a bivalent or trivalent branched linker, such as:

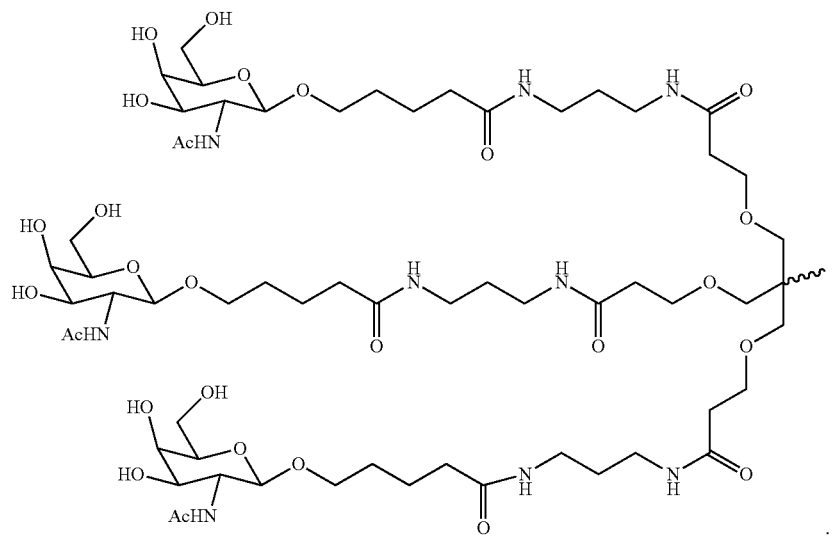 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one example, the ASGPR ligand is attached to the 3' end of the sense strand.

In some cases 2'-fluoro modifications in the seed region of the antisense strand, e.g., positions 2-9, particularly positions 3-9, can adversely affect the in vivo activity of the dsRNA while having minimal effect on in vitro potency of the dsRNA. Inventors have discovered inter alia that in vivo activity of such dsRNAs can be restored to comparable levels relative to the parent dsRNA by removing some or all of 2'-fluoro modifications from the seed region of the antisense strand, i.e., position 2-9, particularly position 3-9 counting from the 5'-end.

Accordingly, in some embodiments, the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and the dsRNA further has at least one (e.g., one, two, three, four, five, six seven, eight, nine or all ten) of the following characteristics: (i) a melting temperature (Tm) of from about 40° C. to about 80° C.; (ii) the antisense comprises 2, 3, 4, 5, 6, 7, 8, 9, or 10 2'-fluoro modifications; (iii) the antisense comprises 1, 2, 3, 4 or 5 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3, 4 or 5 phosphorothioate internucleotide linkages; (vii) the dsRNA comprises at least four 2'-fluoro modifications; (viii) the dsRNA comprises a duplex region of 12-40 nucleotide pairs in length; (ix) a blunt end at 5' end of the antisense strand; (x) the sense strand comprises 1, 2, 3, 4, 5, 6, 7, 8, 9 or 10 LNA modifications.

In some embodiments, the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and the dsRNA further has at least one (e.g., one, two, three, four, five, six seven, eight, nine or all ten) of the following characteristics: (i) a melting temperature (Tm) of from about 40° C. to about 80° C.; (ii) the antisense comprises 2, 3, 4, 5, 6, 7, 8, 9, or 10 2'-fluoro modifications; (iii) the antisense comprises 1, 2, 3, 4 or 5 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3, 4 or 5 phosphorothioate internucleotide linkages; (vii) the dsRNA comprises at least four 2'-fluoro modifications; (viii) the dsRNA comprises a duplex region of 12-40 nucleotide pairs in length; (ix) a blunt end at 5' end of the antisense strand; and (x) the sense strand comprises 1, 2, 3, 4, 5, 6, 7, 8, 9 or 10 LNA modifications, and wherein no 2'-fluoro modification is present at positions 3-9 (counting from 5'-end) of the antisense strand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises one or both of the following characteristics: (i) 2, 3, 4, 5, 6, 7, 8, 9 or 10 2'-fluoro modifications, wherein the antisense does not have a 2'-fluoro modification at positions 3-9 (counting from 5'-end); and (ii) 1, 2, 3, 4 or 5 phosphorothioate internucleotide linkages; and the sense strand comprises one, two, three of four of the following characteristics: (i) a ligand conjugated with the sense strand; (ii) 2, 3, 4 or 5 2'-fluoro modifications; (iii) 1, 2, 3, 4 or 5 phosphorothioate internucleotide linkages; and (iv) 1, 2, 3, 4, 5, 6, 7, 8, 9 or 10 LNA modifications. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises: (i) 2, 3, 4, 5, 6, 7, 8, 9 or 10 2'-fluoro modifications; and (ii) 1, 2, 3, 4 or 5 phosphorothioate internucleotide linkages; and the sense strand comprises: 1, 2, 3, 4, 5, 6, 7, 8, 9 or 10 LNA modifications, and wherein the sense strand optionally comprises one, two or three of the following characteristics: (i) a ligand conjugated with the sense strand; (ii) 2, 3, 4 or 5 2'-fluoro modifications; (iii) 1, 2, 3, 4 or 5 phosphorothioate internucleotide linkages; and (iv) 1, 2, 3, 4, 5, 6, 7, 8, 9 or 10 LNA modifications. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises 1, 2, 3 or 4 phosphorothioate internucleotide linkages, wherein the antisense strand optionally comprises 2, 3, 4, 5, 6, 7, 8, 9 or 10 2'-fluoro modifications; and the sense strand comprises 1, 2, 3, 4, 5, 6, 7, 8, 9 or 10 LNA modifications, and wherein the sense strand optionally comprises a ligand conjugated with the sense strand, 2, 3, 4 or 5 2'-fluoro modifications; and/or 1, 2, 3, 4 or 5 phosphorothioate internucleotide linkages. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises 1, 2, 3 or 4 phosphorothioate internucleotide linkages, wherein the antisense strand optionally comprises 2, 3, 4, 5, 6, 7, 8, 9 or 10 2'-fluoro modifications, provided that no 2'-fluoro modification is present at positions 3-9 (counting from 5'-end); and the sense strand comprises 1, 2, 3, 4, 5, 6, 7, 8, 9 or 10 LNA modifications, and wherein the sense strand optionally comprises a ligand conjugated with the sense strand, 2, 3, 4 or 5 2'-fluoro modifications; and/or 1, 2, 3, 4 or 5phosphorothioate internucleotide linkages. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications, and wherein no 2'-fluoro modification is present at positions 3-9 of the antisense strand (counting from 5'-end).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, said sense strand comprises a ligand, wherein the dsRNA has a melting temperature of about 40° C. to about 80° C., and wherein no 2'-fluoro modification is present at positions 3-9 of the antisense strand (counting from 5'-end), and. In some further embodiments of this, the ligand is an ASGPR ligand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, wherein each of the sense and antisense strands comprise at least two 2'-fluoro modifications, wherein the dsRNA has a melting temperature of about 40° C. to about 80° C., and wherein no 2'-fluoro modification is present at positions 3-9 of the antisense strand (counting from 5'-end), and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some further embodiments of this, the ligand is an ASGPR ligand. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the antisense further comprises at least two of the following characteristics: (i) the thermally destabilizing modification of the duplex is located in position 4 to 8 of the antisense strand; (ii) at least two 2'-fluoro modifications; (iii) phosphorothioate internucleotide linkages between nucleotide positions 1 and 2 (counting from the 5' end); and (iv) antisense strand has a length of 18 to 35 nucleotides, and wherein no 2'-fluoro modification is present at positions 3-9 of the antisense strand (counting from 5'-end). In some further embodiments the ligand is an ASGPR ligand. In some embodiments, the melting temperature of about 40° C. to about 80° C. is optional In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the sense strand has at least one of the following characteristics: (i) the ligand is attached to either end of the sense strand; (ii) sense strand comprises at least two 2'-fluoro modifications; (iii) sense strand comprises 1, 2, 3, 4, 5, 6, 78, 9 or 10 LNA modifications; and (iv) the sense strand and the antisense strand show sufficient complementarity to form a double stranded region spanning at least 19 nucleotide positions, wherein the thermally destabilizing modification of the duplex is located within said double-stranded region, and wherein no 2'-fluoro modification is present at positions 3-9 of the antisense strand (counting from 5'-end). In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand and optionally at least one LNA modification, and wherein each of the sense and antisense strands comprise at least two 2'-fluoro modifications, wherein no 2'-fluoro modification is present at positions 3-9 of the antisense strand (counting from 5'-end), wherein the dsRNA has a melting temperature of about 40° C. to about 80° C., and wherein the thermally destabilizing modification of the duplex is selected from the group consisting of:

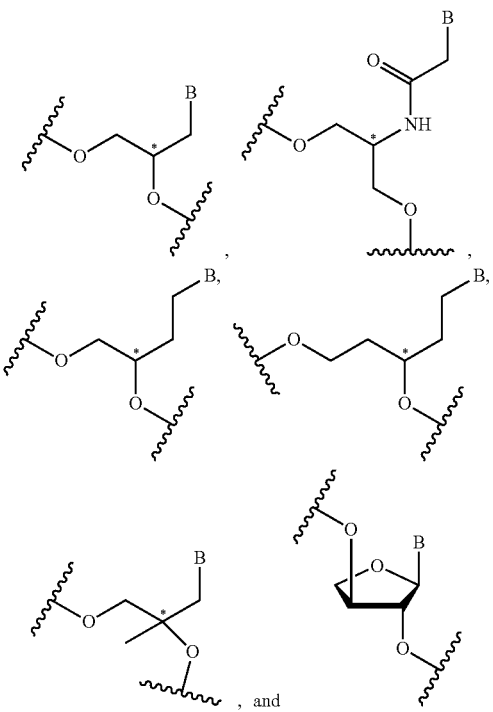

wherein B is a modified or unmodified nucleobase and the asterisk on each structure represents either R, S or racemic, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex located at position 5, 6 or 7, counting from the 5'-end of the antisense strand, wherein no 2'-fluoro modification is present at positions 3-9 of the antisense strand (counting from 5'-end), wherein said sense strand comprises a ligand and optionally at least one LNA modification, and wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located at position 5, 6 or 7, counting from the 5'-end, wherein said sense strand comprises a ligand and optionally at least one LNA modification, and wherein each of the sense and antisense strands comprise at least two 2'-fluoro modifications, wherein no 2'-fluoro modification is present at positions 3-9 of the antisense strand (counting from 5'-end), wherein the dsRNA has a melting temperature of about 40° C. to about 80° C., and wherein the thermally destabilizing modification of the duplex is selected from the group consisting of:

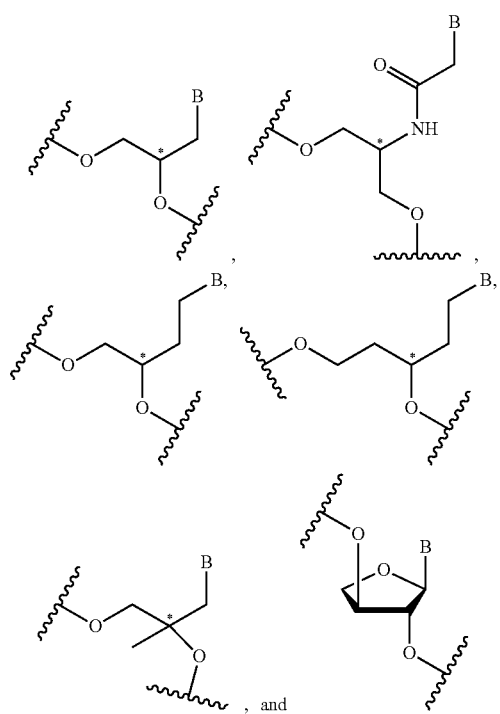

wherein B is a modified or unmodified nucleobase and the asterisk on each structure represents either R, S or racemic, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, wherein said sense strand comprises a ligand and optionally at least one LNA modification, wherein no 2'-fluoro modification is present at positions 3-9 of the antisense strand (counting from 5'-end), wherein the dsRNA has a melting temperature of about 40° C. to about 80° C., and wherein the ligand comprises one or more GalNAc derivatives attached through a bivalent or trivalent branched linker, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand and optionally at least one LNA modification, wherein no 2'-fluoro modification is present at positions 3-9 of the antisense strand (counting from 5'-end), wherein the dsRNA has a melting temperature of about 40° C. to about 80° C., and wherein the ligand is an ASGPR ligand of structure:

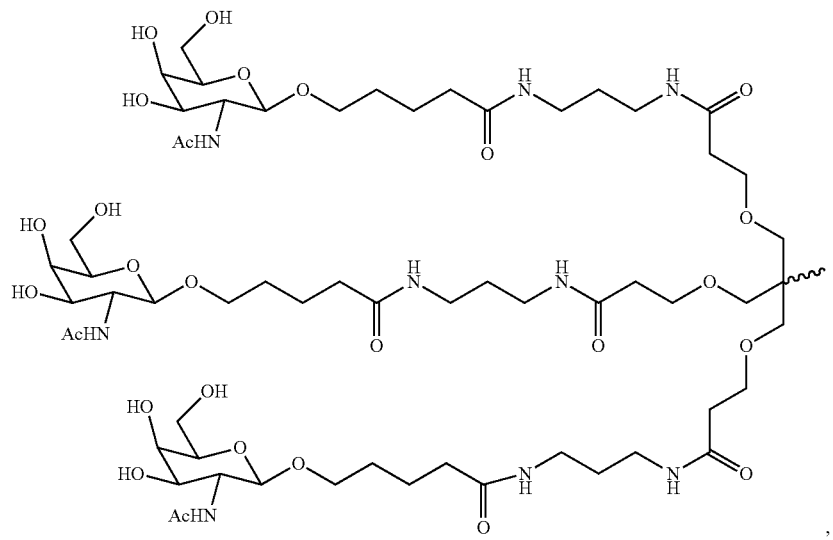 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand and optionally comprises at least one LNA modification, comprises 3 or 4 2'-fluoro modifications, and comprises 0, 1, 2 or 3 phosphorothioate internucleotide linkages; wherein the antisense strand comprises 3, 4, 5 or 6 2'-fluoro modifications, provided that no 2'-modification is present at positions 3-9 of the antisense strand (counting from 5'-end), comprises 2, 3, 4 or 5 phosphorothioate internucleotide linkages; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3, and optionally comprises at least one LNA modification; wherein the antisense strand comprises 3, 4, 5 or 6 2'-fluoro modifications, provided that no 2'-modification is present at positions 3-9 of the antisense strand (counting from 5'-end), comprises 2, 3, 4 or 5 phosphorothioate internucleotide linkages; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 0, 1, 2 or 3 phosphorothioate internucleotide linkages, and optionally comprises at least one LNA modification; wherein the antisense strand comprises 2'-fluoro modifications at positions 2, 14 or 16; and the antisense comprises phosphorothioate internucleotide linkages between nucleotide positions 21 and 22, and between nucleotide positions 22 and 23; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises at least one LNA modification, and optionally comprises 0, 1, 2 or 3 phosphorothioate internucleotide linkages; wherein the antisense strand comprises 2'-fluoro modifications at positions 2, 14 or 16; and the antisense comprises phosphorothioate internucleotide linkages between nucleotide positions 21 and 22, and between nucleotide positions 22 and 23; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2, or 3 phosphorothioate internucleotide linkages, and optionally comprises at least one LNA modification; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 0, 1, 2, or 3 phosphorothioate internucleotide linkages, and comprises at least one LNA modification; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40°

C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises phosphorothioate internucleotide linkages between nucleotide positions 1 and 2, and between nucleotide positions 2 and 3, and optionally comprises at least one LNA modification; wherein the antisense strand comprises 2'-fluoro modifications at positions 2, 14 or 16; and the antisense comprises phosphorothioate internucleotide linkages between nucleotide positions 21 and 22, and between nucleotide positions 22 and 23; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises at least one LNA modification, and optionally comprises phosphorothioate internucleotide linkages between nucleotide positions 1 and 2, and between nucleotide positions 2 and 3; wherein the antisense strand comprises 2'-fluoro modifications at positions 2, 14 or 16; and the antisense comprises phosphorothioate internucleotide linkages between nucleotide positions 21 and 22, and between nucleotide positions 22 and 23; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven, eight or all nine) of the following characteristics: (i) the antisense comprises 2, 3, 4, 5 or 6 2'-fluoro modifications, provided that no 2'-modification is present at positions 3-9 of the antisense strand (counting from 5'-end); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 18, 19, 20, 21, 22, 23, 24 or 24 nucleotide pairs in length; (viii) the dsRNA comprises a blunt end at 5'-end of the sense strand; and (ix) the sense strand comprises 1, 2, 3, 4, 5, 6, 7, 8, 9 lor 10 LNA modifications. In some particular embodiments, sense strand is 19, 20 or 21 or 22 nucleotides in length and the antisense strand is 20, 21 or 22 nucleotides in length. In some embodiments, the melting temperature of about 40° C. to about 80° C. is optional.

In some embodiments, the sense and antisense strands are independently 19, 20, 21, 22, 23, 24 or 25 nucleotides in length, wherein the antisense strand contains at least one thermally destabilizing nucleotide and 1, 2, 3 or 4 phosphorothioate internucleotide linkages, and where the at least one thermally destabilizing nucleotide is in the seed region of the antisense strand (i.e., at position 2-9 of the 5'-end of the antisense strand), the sense strand comprises 1, 2, 3, 4, 5, 6, 7, 8, 9 or 10 LNA modifications, wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six or all seven) of the following characteristics: (i) the antisense comprises 2, 3, 4, 5 or 6 2'-fluoro modifications, provided that no 2'-modification is present at positions 3-9 of the antisense strand (counting from 5'-end); (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 18, 19, 20, 21, 22, 23, 24 or 24 nucleotide pairs in length; and (vii) the dsRNA comprises a blunt end at 5'-end of the sense strand. In some particular embodiments, sense strand is 19, 20 or 21 or 22 nucleotides in length and the antisense strand is 20, 21 or 22 nucleotides in length. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises 1, 2, 3, 4, 5, 6, 7, 8, 9 or 10 LNA modifications, and optionally comprises phosphorothioate internucleotide linkages between nucleotide positions 1 and 2, and between nucleotide positions 2 and 3; wherein the antisense strand comprises 2'-fluoro modifications at positions 2, 9, 14 or 16, or at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises 1, 2, 3, 4, 5, 6, 7, 8, 9 or 10 LAN modifications, and optionally comprises phosphorothioate internucleotide linkages between nucleotide positions 1 and 2, and between nucleotide positions 2 and 3; wherein the antisense strand comprises 2'-fluoro modifications at positions 2, 9, 14 or 16, or at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, one end of the dsRNA is a blunt end and the other end has an overhang, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present in positions 3-9 (counting from the 5'-end); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (vii) the sense strand comprises 1, 2, 3, 4, 5, 6, 7, 8, 9 or 10 LNA modifications. In some embodiments, the overhang is on the 3'-end of the antisense strand and the blunt end is at the 5'-end of the antisense strand. In some particular embodiments, the overhang is 2, 3 or 4-nucleotides in length. In some embodiments, the melting temperature of about 40° C. to about 80° C. is optional.

In some embodiments, the dsRNA molecule has a duplex region of 19, 20, 21, 22 or 23 nucleotide base pairs in length, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, five, six or all seven) of the following characteristics: (i) the antisense comprises 2, 3, 4, 5 or 6 2'-fluoro modifications, wherein no 2'-fluoro modification is present at positions 3-9 (counting from 5'-end of the antisense strand); (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the sense strand comprises 1, 2, 3, 4, 5, 6, 7, 8, 9 or 10 LNA modifications, and optionally the 2 nucleotide overhang is on the 3'-end of the antisense strand and the blunt end is at the 5'-end of the antisense strand. In some embodiments, the overhang is on the 3'-end of the antisense strand and the blunt end is at the 5'-end of the antisense strand. In some embodiments, the melting temperature of about 40° C. to about 80° C. is optional.

In some embodiments, the dsRNA molecule of the invention may also have two blunt ends, at both ends of the dsRNA duplex.

In some embodiments, the dsRNA has a blunt end at both ends of the duplex, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present at positions 3-9 (counting from the 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the sense strand comprises at least 1, 2, 3, 4, 5, 6, 7, 8, 9 or 10 LNA modifications. In some embodiments, the melting temperature of about 40° C. to about 80° C. is optional.

In some embodiments, the dsRNA molecule has a duplex region of 19, 20, 21, 22 or 23 nucleotide base pairs in length and has a blunt end at both ends of the duplex, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, five, six or all seven) of the following characteristics: (i) the antisense comprises 2, 3, 4, 5 or 6 2'-fluoro modifications, wherein no 2'-fluoro modification is present at positions 3-9 (counting from the 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the sense strand comprises at least 1, 2, 3, 4, 5, 6, 7, 8, 9 or 10 LNA modifications. In some embodiments, the melting temperature of about 40° C. to about 80° C. is optional.

In some embodiments, the dsRNA molecule of the invention comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present at positions 3-9 (counting from the 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a blunt end at 5'-end of the antisense strand. Preferably, the 2 nt overhang is at the 3'-end of the antisense; and (viii) the sense strand comprises at least 1, 2, 3, 4, 5, 6, 7, 8, 9 or 10 LNA modifications. In some embodiments, the melting temperature of about 40° C. to about 80° C. is optional.

In some embodiments, the dsRNA molecule of the invention comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3 ' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand), and wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. For example, the thermally destabilizing nucleotide occurs between positions opposite or complimentary to positions 14-17 of the 5'-end of the sense strand, and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present at positions 3-9 (counting from 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; (vii) the dsRNA comprises a duplex region of 12-30 nucleotide pairs in length; and the sense strand comprises 1, 2, 3, 4, 5, 6, 7, 8, 9 or 10 LNA modifications. In some embodiments, the melting temperature of about 40° C. to about 80° C. is optional.

In some embodiments, the dsRNA molecule of the invention comprises a sense and antisense strands, wherein said dsRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5' end, wherein the 3' end of said sense strand and the 5' end of said antisense strand form a blunt end and said antisense strand is 1~4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present at positions 3-9 (counting from 5'-end of antisense strand); (ii) the antisense comprises 1, 2, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; (vii) the dsRNA has a duplex region of 12-29 nucleotide pairs in length; (viii) and the sense strand comprises 1, 2, 3, 4, 5, 7, 8, 9 or 10 LNA modifications. In some embodiments, the melting temperature of about 40° C. to about 80° C. is optional.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven, eight or all nine) of the following characteristics: (i) the antisense comprises 2, 3, 4, 5 or 6 2'-fluoro modifications, wherein no 2'-fluoro modification is present at positions 3-9 (counting from 5'-end of antisense strand); (ii) the antisense comprises 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; (viii) the dsRNA has a blunt end at 5'-end of the antisense strand; (ix) and the sense strand comprises 1, 2, 3, 4, 5, 6, 7, 8, 9 or 10 LNA modifications. In some embodiments, the melting temperature of about 40° C. to about 80° C. is optional.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven, eight or all nine) of the following characteristics: (i) the antisense comprises 2, 3, 4, 5 or 6 2'-fluoro modifications, wherein no 2'-fluoro modification is present at positions 3-9 (counting from 5'-end of the antisense strand); (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; (viii) the dsRNA has a blunt end at 5'-end of the antisense strand; and (ix) and the sense strand comprises 1, 2, 3, 4, 5, 6, 7, 8, 9 or 10 LNA modifications. In some embodiments, the melting temperature of about 40° C. to about 80° C. is optional.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven, eight or all nine) of the following characteristics: (i) the antisense comprises 2, 3, 4, 5 or 6 2'-fluoro modifications, wherein no 2'-fluoro modification is present at positions 3-9 (counting from 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; (viii) the dsRNA has a blunt end at 5'-end of the antisense strand; and (ix) the sense strand comprises 1, 2, 3, 4, 5, 6, 7, 8, 9 or 10 LNA modifications. In some embodiments, the melting temperature of about 40° C. to about 80° C. is optional.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications, wherein no 2'-fluoro modification is present at positions 3-9 (counting from 5'-end of the antisense strand); (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA has a blunt end at 5'-end of the antisense strand; and (viii) the sense strand comprises 1, 2, 3, 4, 5, 6, 7, 8, 9 or 10 LNA modifications. In some embodiments, the melting temperature of about 40° C. to about 80° C. is optional.

In one aspect the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position, and the dsRNA further has at least one (e.g., one, two, three, four, five, six seven, eight or all nine) of the following characteristics: (i) the antisense comprises 2, 3, 4, 5 or 6 2'-fluoro modifications, wherein no 2'-fluoro modification is present at positions 3-9 (counting from 5'-end); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; (viii) a blunt end at 5' end of the antisense strand; and (ix) the sense strand comprises 1, 2, 3, 4, 5, 6, 7, 8, 9 or 10 LNA modifications. In some embodiments, the melting temperature of about 40° C. to about 80° C. is optional.

In some particular embodiments, the thermally destabilizing modification of the duplex is at position 5, 6 or 7 of the antisense strand, counting from 5'-end of the antisense strand. In some embodiments, the thermally destabilizing modification of the duplex is at position 2, 3, 4, 8 or 9 of the antisense strand, counting from 5'-end of the antisense strand.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the antisense strand further comprises one or both of the following characteristics: (i) 2, 3, 4, 5 or 6 2'-fluoro modifications, wherein no 2'-modification is present at positions 3-9 (counting from 5'-end of the antisense strand); and (ii) 1, 2, 3, 4 or 5 phosphorothioate internucleotide linkages; and the sense strand comprises one, two, three or four of the following characteristics: (i) a ligand conjugated with the sense strand; (ii) 2, 3, 4 or 5 2'-fluoro modifications; (iii) 1, 2, 3, 4 or 5 phosphorothioate internucleotide linkages; and (iv) 1, 2, 3, 4, 5, 6, 7, 8, 9 or 10 LNA modifications; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications, and wherein no 2'-modification is present at positions 3-9 of the antisense strand (counting from 5'-end of the antisense strand); and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein no 2'-modification is present at positions 3-9 of the antisense strand (counting from 5'-end of the antisense strand); and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some further embodiments of this, the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, and wherein no 2'-modification is present at positions 3-9 of the antisense strand (counting from 5'-end of the antisense strand); and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some further embodiments of this, the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein the antisense further comprises at least two of the following characteristics: (i) the thermally destabilizing modification of the duplex is located in position 4 to 8 of the antisense strand; (ii) at least two 2'-fluoro modifications, and wherein no 2'-modification is present at positions 3-9 of the antisense strand (counting from 5'-end of the antisense strand); (iii) phosphorothioate internucleotide linkages between nucleotide positions 1 and 2 (counting from the 5' end); and antisense strand has a length of 18 to 35 nucleotides; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some further embodiments the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and the sense strand has at least one of the following characteristics: (i) the ligand is attached to either end of the sense strand; (ii) sense strand comprises at least two 2'-fluoro modifications; (iii) the sense strand and the antisense strand show sufficient complementarity to form a double stranded region spanning at least 19 nucleotide positions; (iv) the sense strand comprises at least 1, 2, 3, 4, 5, 6, 7, 8, 9 or 10 LNA modifications, and wherein the thermally destabilizing modification of the duplex is located within said double-stranded region, and wherein no 2'-modification is present at positions 3-9 of the antisense strand (counting from 5'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, where no 2'-modification is present at positions 3-9 of the antisense strand (counting from 5'-end of the antisense strand), wherein said antisense strand comprises at least one thermally destabilizing modification of the duplex within the first 9 nucleotide positions, counting from the 5'-end, and wherein said sense strand comprises a ligand, and wherein the thermally destabilizing modification of the duplex is selected from the group consisting of:

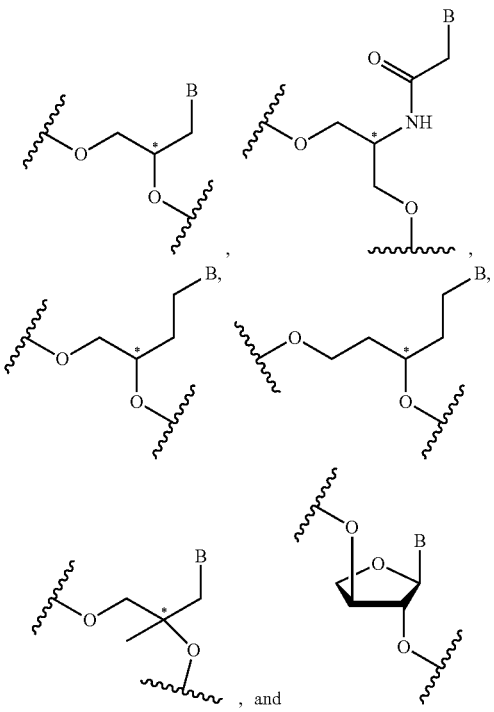

wherein B is a modified or unmodified nucleobase and the asterisk on each structure represents either R, S or racemic; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, wherein no 2'-modification is present at positions 3-9 of the antisense strand (counting from 5'-end of the antisense strand), and wherein the thermally destabilizing modification of the duplex is selected from the group consisting of:

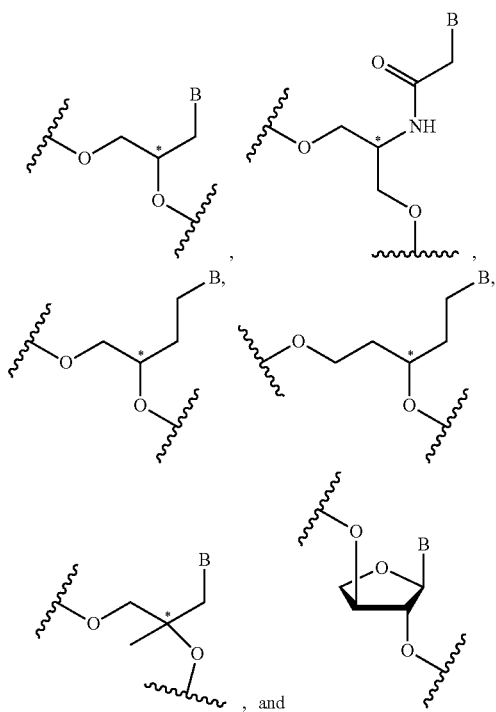

wherein B is a modified or unmodified nucleobase and the asterisk on each structure represents either R, S or racemic; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein no 2'-modification is present at positions 3-9 of the antisense strand (counting from 5'-end of the antisense strand), wherein said antisense strand comprises at least one thermally destabilizing modification of the duplex located at position 5, 6 or 7, counting from the 5'-end of the antisense strand, and wherein said sense strand comprises a ligand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located at position 5, 6 or 7, counting from the 5'-end, wherein said sense strand comprises a ligand, and wherein each of the sense and antisense strands comprise at least two 2'-fluoro modifications, wherein no 2'-modification is present at positions 3-9 of the antisense strand (counting from 5'-end of the antisense strand) and wherein the thermally destabilizing modification of the duplex is selected from the group consisting of:

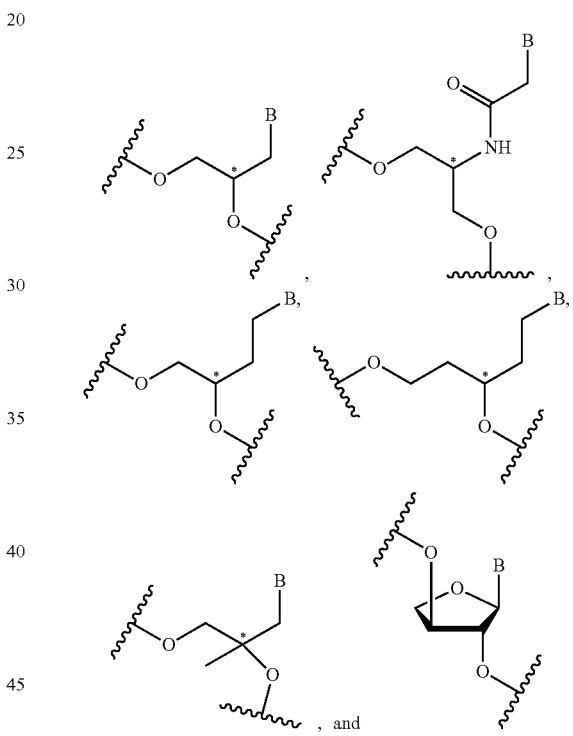

wherein B is a modified or unmodified nucleobase and the asterisk on each structure represents either R, S or racemic; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein no 2'-modification is present at positions 3-9 of the antisense strand (counting from 5'-end of the antisense strand), wherein said antisense strand comprises at least one thermally destabilizing modification of the duplex within the first 9 nucleotide positions, counting from the 5'-end, and wherein said sense strand comprises a ligand, wherein the ligand comprises one or more GalNAc derivatives attached through a bivalent or trivalent branched linker; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein no 2'-modification is present at positions 3-9 of the antisense strand (counting from 5'-end of the antisense strand), wherein said antisense strand comprises at least one thermally destabilizing modification of the duplex within the first 9 nucleotide positions, counting from the 5'-end, and wherein said sense strand comprises a ligand, wherein the ligand is an ASGPR ligand of structure:

strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 3, 4, 5 or 6 2'-fluoro modifications, comprises 2, 3, 4 or 5 phosphorothioate internucleotide linkages; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity

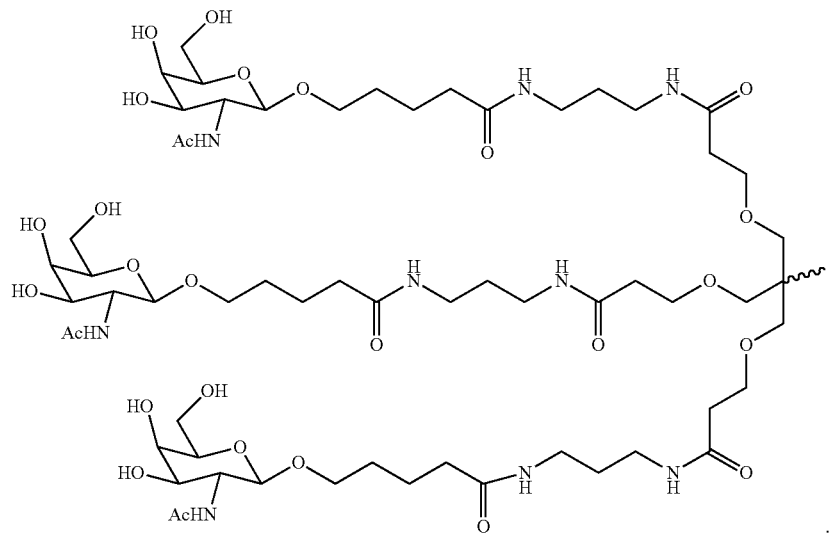 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 3, 4, 5 or 6 2'-fluoro modifications, where no 2'-fluoro modification is present at positions 3-9 of the antisense strand, comprises 2, 3 or 4 phosphorothioate internucleotide linkages; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 0 or 2 phosphorothioate internucleotide linkages, and optionally comprises 1, 2, 3, 4, 5, 6, 7, 8, 9 or 10 LNA modifications; wherein the antisense strand comprises 2'-fluoro modifications at positions 2, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 1, 2, 3, 4, 5, 6, 7, 8, 9 or 10 LNA modifications, and optionally comprises 0 or 2 phosphorothioate internucleotide linkages; wherein the antisense strand comprises 2'-fluoro modifications at positions 2, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 1, 2, 3, 4, 5, 6, 7, 8, 9 or 10 LNA modifications, and comprises 0, 1, 2 or 3 phosphorothioate internucleotide linkages; wherein the antisense strand comprises 2'-fluoro modifications at positions 2, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 0, 1, 2 or 3 phosphorothioate internucleotide linkages, and optionally comprises 1, 2, 3, 4, 5, 6, 7, 8, 9 or 10 LNA modifications; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 1, 2, 3, 4, 5, 6, 7, 8, 9 or 10 LNA modifications, and optionally comprises 0, 1, 2 or 3 phosphorothioate internucleotide linkages; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 1, 2, 3, 4, 5, 6, 7, 8, 9 or 10 LNA modifications, and optionally comprises 0, 1, 2 or 3 phosphorothioate internucleotide linkages; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 2'-fluoro modifications at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 2'-fluoro modifications at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises 1, 2, 3, 4, 5, 6, 7, 8, 9 or 10 LNA modifications and optionally comprises phosphorothioate internucleotide linkages between nucleotide positions 1 and 2, and between nucleotide positions 2 and 3; wherein the antisense strand comprises 2'-fluoro modifications at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises 1, 2, 3, 4, 5, 6, 7, 8, 9 or 10 LNA modifications, and comprises phosphorothioate internucleotide linkages between nucleotide positions 1 and 2, and between nucleotide positions 2 and 3; wherein the antisense strand comprises 2'-fluoro modifications at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises 1, 2, 3, 4, 5, 6, 7, 8, 9 or 10 LNA modifications, and optionally comprises phosphorothioate internucleotide linkages between nucleotide positions 1 and 2, and between nucleotide positions 2 and 3; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), the dsRNA has a melting temperature (Tm) of from about 40° C. to about 80° C., and the dsRNA optionally further has at least one (e.g., one, two, three, four, five, six, seven, eight or all nine) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; (viii) a blunt end at 5' end of the antisense strand; (ix) provided that no 2'-fluoro modification is present at positions 3-9 (counting from 5'-end) of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the melting temperature of about 40° C. to about 80° C. is optional.

In some embodiments, the dsRNA molecule has a duplex region of 12-40 nucleotide pairs in length, wherein the antisense strand comprises at least one thermally destabilizing modification of the duplex within the seed region (i.e., at position 2-9 of the 5'-end of the antisense strand, counting from the 5'-end), and the dsRNA has a $T_m$ of from about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and vii) a blunt end at 5' end of the antisense strand, provided that no 2'-fluoro modification is present at positions 3-9 (counting from 5'-end) of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the melting temperature of about 40° C. to about 80° C. is optional.

In some embodiments, the dsRNA molecule has a duplex region of 19, 20, 21, 22 or 23 nucleotide base pairs in length, wherein the antisense strand contains at least one thermally destabilizing modification of the duplex located in the seed region of the antisense strand (i.e., at position 2-9 of the 5'-end of the antisense strand), and wherein the dsRNA has a melting temperature of about 40° C. to about 80° C., provided that no 2'-fluoro modification is present at positions 3-9 (counting from 5'-end) of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some embodiments, the melting temperature of about 40° C. to about 80° C. is optional.

In a particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker; and
  (iii) 2'-F modifications at positions 7, 10, and 11 (counting from the 5' end);
and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 21 and 22, and between nucleotide positions 22 and 23 (counting from the 5' end); and
  (iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);
and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 5, 6 or 7 (counting from the 5' end);
  wherein the dsRNA molecules have a two nucleotide overhang at the 3'-end of the antisense strand, and a blunt end at the 5'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);
and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) at least one (e.g., one, two, three, four, five, six, seven, eight, nine, ten or more) LNA modification;
and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) at least one (e.g., one, two or three) LNA modifications at positions 1, 2 and 3 (counting from the 5' end);
and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end);
  (iv) at least one (e.g., one, two, three, four, five, six, seven, eight, nine, ten or more) LNA modification; and
  (iv) phosphorothioate internucleotide linkages between nucleotide positions 1 and 2, and between nucleotide positions 2 and 3 (counting from the 5' end); and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) at least one (e.g., one, two or three) LNA modifications at positions 1, 2 and 3 (counting from the 5' end); and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end);
  (iv) at least one (e.g., one, two or three) LNA modifications at positions 1, 2 and 3 (counting from the 5' end); and
  (iv) phosphorothioate internucleotide linkages between nucleotide positions 1 and 2, and between nucleotide positions 2 and 3 (counting from the 5' end); and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position.

In some embodiments, the sense and antisense strands are independently 19, 20, 21, 22, 23, 24 or 25 nucleotides in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 18, 19, 20, 21, 22, 23, 24 or 24 nucleotide pairs in length; and (viii) the dsRNA comprises a blunt end at 5'-end of the sense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some particular embodiments, sense strand is 19, 20 or 21 or 22 nucleotides in length and the antisense strand is 20, 21 or 22 nucleotides in length.

The sense strand and antisense strand typically form a duplex dsRNA. The duplex region of a dsRNA molecule may be 12-40 nucleotide pairs in length. For example, the duplex region can be between 14-40 nucleotide pairs in length, 17-30 nucleotide pairs in length, 25-35 nucleotides in length, 27-35 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotide pairs in length.

In some embodiments, the dsRNA molecule of the invention has a duplex region of 12-40 nucleotides pairs in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA comprises a blunt end at 5'-end of the antisense strand; and wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position. In some particular embodiments, the duplex region is 18, 19, 20, 21, 22 or 23 nucleotides pairs in length. In a particular embodiment, the duplex region is 21 nucleotide pairs in length.

In some embodiments, the dsRNA molecule of the invention comprises one or more overhang regions and/or capping groups of dsRNA molecule at the 3'-end, or 5'-end or both ends of a strand. The overhang can be 1-10 nucleotides in length, 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be other sequence. The first and second strands can also be joined, e.g., by additional bases to form a hairpin, or by other non-base linkers.

In some embodiments, the nucleotides in the overhang region of the dsRNA molecule of the invention can each independently be a modified or unmodified nucleotide including, but not limited to 2'-sugar modified, such as, 2'-Fluoro 2'-O-methyl, thymidine (T), 2'-O-methoxyethyl-5-methyluridine, 2'-O-methoxyethyladenosine, 2'-O-methoxyethyl-5-methylcytidine, GNA, SNA, hGNA, hhGNA, mGNA, TNA, h'GNA, and any combinations thereof. For example, TT can be an overhang sequence for either end on either strand. The overhang can form a mismatch with the target mRNA or it can be complementary to the gene sequences being targeted or can be other sequence.

The 5'- or 3'-overhangs at the sense strand, antisense strand or both strands of the dsRNA molecule of the invention may be phosphorylated. In some embodiments, the overhang region contains two nucleotides having a phosphorothioate between the two nucleotides, where the two nucleotides can be the same or different. In some embodiments, the overhang is present at the 3'-end of the sense strand, antisense strand or both strands. In some embodiments, this 3'-overhang is present in the antisense strand. In some embodiments, this 3'-overhang is present in the sense strand.

The dsRNA molecule of the invention may comprise only a single overhang, which can strengthen the interference activity of the dsRNA, without affecting its overall stability. For example, the single-stranded overhang is located at the 3'-terminal end of the sense strand or, alternatively, at the 3'-terminal end of the antisense strand. The dsRNA may also have a blunt end, located at the 5'-end of the antisense strand (or the 3'-end of the sense strand) or vice versa. Generally, the antisense strand of the dsRNA has a nucleotide overhang at the 3'-end, and the 5'-end is blunt. While not bound by theory, the asymmetric blunt end at the 5'-end of the antisense strand and 3'-end overhang of the antisense strand favor the guide strand loading into RISC process. For example the single overhang comprises at least two, three, four, five, six, seven, eight, nine, or ten nucleotides in length. In some embodiments, the dsRNA has a 2 nucleotide overhang on the 3'-end of the antisense strand and a blunt end at the 5'-end of the antisense strand.

In some embodiments, one end of the dsRNA is a blunt end and the other end has an overhang, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) and the dsRNA comprises a duplex region of 12-40 nucleotide pairs in length. In some embodiments, the overhang is on the 3'-end of the antisense strand and the blunt end is at the 5'-end of the antisense strand. In some particular embodiments, the overhang is 2, 3 or 4-nucleotides in length.

In some embodiments, the dsRNA molecule has a duplex region of 19, 20, 21, 22 or 23 nucleotide base pairs in length, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications, and optionally the 2 nucleotide overhang is on the 3'-end of the antisense strand and the blunt end is at the 5'-end of the antisense strand. In some embodiments, the overhang is on the 3'-end of the antisense strand and the blunt end is at the 5'-end of the antisense strand.

In some embodiments, the dsRNA molecule of the invention may also have two blunt ends, at both ends of the dsRNA duplex.

In some embodiments, the dsRNA has a blunt end at both ends of the duplex, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a duplex region of 12-40 nucleotide pairs in length.

In some embodiments, the dsRNA molecule has a duplex region of 19, 20, 21, 22 or 23 nucleotide base pairs in length and has a blunt end at both ends of the duplex, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has at least one (e.g., one, two or all three) of the following characteristics: (i) the sense strand comprises a 5'-morpholinno, 5'-dimethylamino, inverted abasic, L-sugar, a 5'-deoxy, or an inverted abasic locked nucleic acid modification at the 5'-end, or a 2'-5'-linkage between positions N-1 and N-2; (ii) the antisense strand comprises 5'-E-vinylphosphanate; and (iii) the antisense strand comprises 5'-E-vinylphosphanate and a nucleoside at position N-1 that reduces or inhibits activity of siRNA relative to a siRNA having the same antisense strand sequence but unmodified N-1 position and a nucleoside at position N-1 that reduces or inhibits activity of siRNA relative to a siRNA having the same antisense strand sequence but unmodified N-1 position; and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications.

Thermally Destabilizing Modifications.

As noted above, dsRNA molecule can be optimized for RNA interference by incorporating thermally destabilizing modifications in the seed region of the antisense strand (i.e., at positions 2-9 of the 5'-end of the antisense strand) to reduce or inhibit off-target gene silencing. Inventors have discovered that dsRNAs with an antisense strand comprising at least one thermally destabilizing modification of the duplex within the first 9 nucleotide positions, counting from the 5' end, of the antisense strand have reduced off-target gene silencing activity. Accordingly, in some embodiments, the antisense strand comprises at least one (e.g., one, two, three, four, five or more) thermally destabilizing modification of the duplex within the first 9 nucleotide positions of the 5' region of the antisense strand. In some embodiments, thermally destabilizing modification of the duplex is located in positions 2-9, or preferably positions 4-8, from the 5'-end of the antisense strand. In some further embodiments, the thermally destabilizing modification of the duplex is located at position 6, 7 or 8 from the 5'-end of the antisense strand. In still some further embodiments, the thermally destabilizing modification of the duplex is located at position 7 from the 5'-end of the antisense strand. The term "thermally destabilizing modification(s)" includes modification(s) that would result with a dsRNA with a lower overall melting temperature (Tm) (preferably a Tm with one, two, three or four degrees lower than the Tm of the dsRNA without having such modification(s). In some embodiments, the thermally destabilizing modification of the duplex is located at position 2, 3, 4, 5 or 9 from the 5'-end of the antisense strand.

The thermally destabilizing modifications can include, but are not limited to, abasic modification; mismatch with the opposing nucleotide in the opposing strand; and sugar modification such as 2'-deoxy modification or acyclic nucleotide, e.g., unlocked nucleic acids (UNA) or glycol nucleic acid (GNA).

Exemplified abasic modifications include, but are not limited to the following:

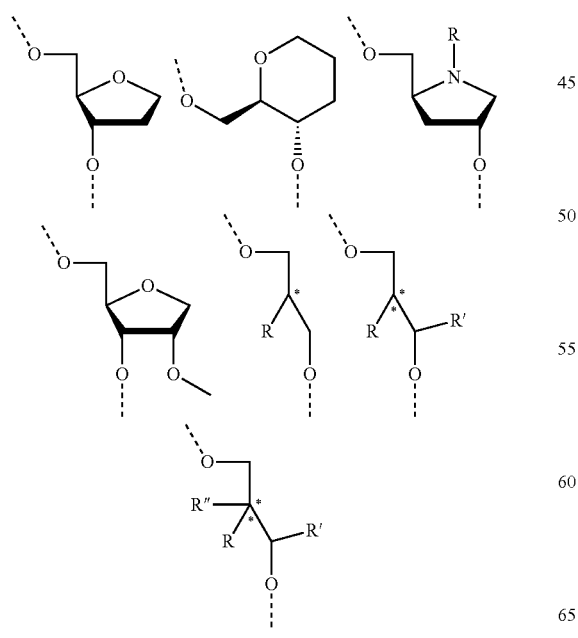

Wherein R=H, Me, Et or OMe; R'=H, Me, Et or OMe; R"=H, Me, Et or OMe

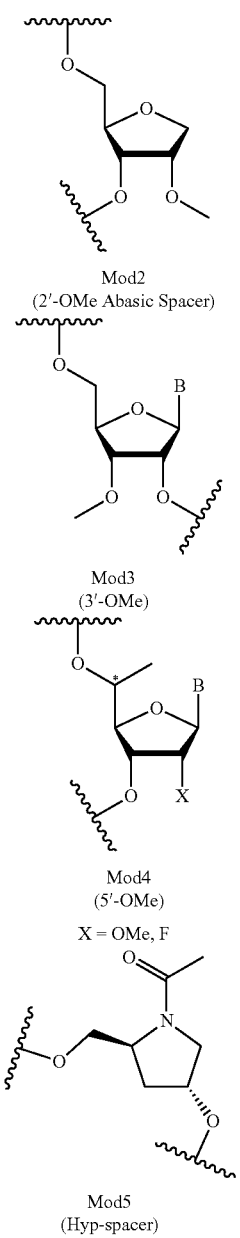

wherein B is a modified or unmodified nucleobase.

Exemplified sugar modifications include, but are not limited to the following:

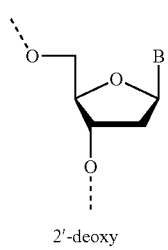

2'-deoxy

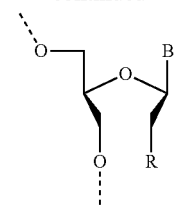

unlocked nucleic acid
R = H, OH, O-alkyl

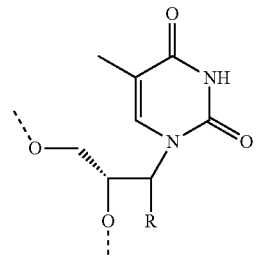

glycol nucleic acid
R = H, OH, O-alkyl

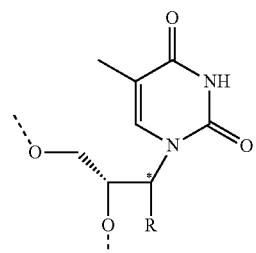

glycol nucleic acid
R = H, OH, O-alkyl

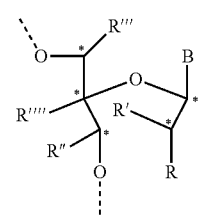

unlocked nucleic acid
R = H, OH, CH$_3$, CH$_2$CH$_3$, O-alkyl, NH$_2$, NHMe, NMe$_2$
R' = H, OH, CH$_3$, CH$_2$CH$_3$, O-alkyl, NH$_2$, NHMe, NMe$_2$
R'' = H, OH, CH$_3$, CH$_2$CH$_3$, O-alkyl, NH$_2$, NHMe, NMe$_2$
R''' = H, OH, CH$_3$, CH$_2$CH$_3$, O-alkyl, NH$_2$, NHMe, NMe$_2$
R'''' = H, OH, CH$_3$, CH$_2$CH$_3$, O-alkyl, NH$_2$, NHMe, NMe$_2$

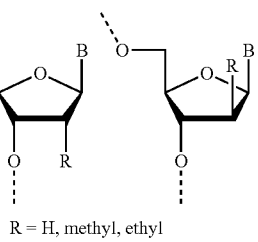

R = H, methyl, ethyl wherein B is a modified or unmodified nucleobase.

In some embodiments the thermally destabilizing modification of the duplex is selected from the group consisting of:

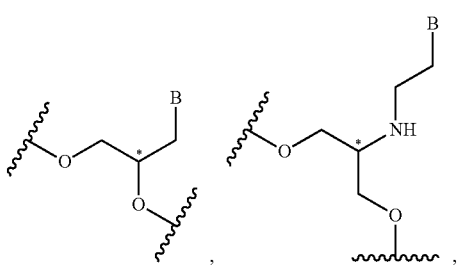

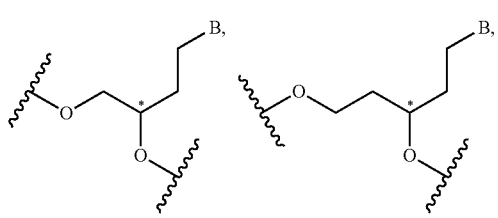

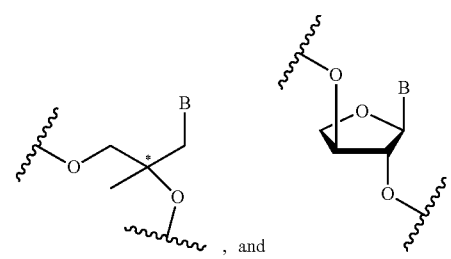

, and wherein B is a modified or unmodified nucleobase and the asterisk on each structure represents either R, S or racemic.

The term "acyclic nucleotide" refers to any nucleotide having an acyclic ribose sugar, for example, where any of bonds between the ribose carbons (e.g., C1'-C2', C2'-C3', C3'-C4', C4'-O4', or C1'-O4') is absent and/or at least one of ribose carbons or oxygen (e.g., C1', C2', C3', C4' or O4') are independently or in combination absent from the nucleotide. In some embodiments, acyclic nucleotide is

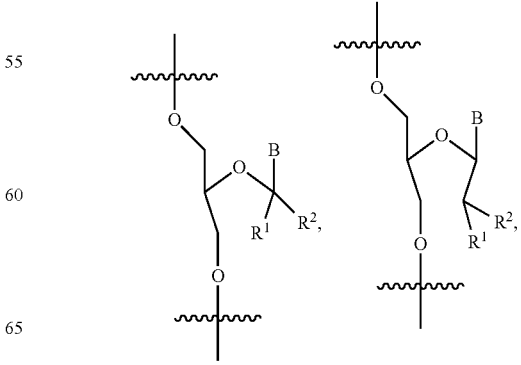

-continued

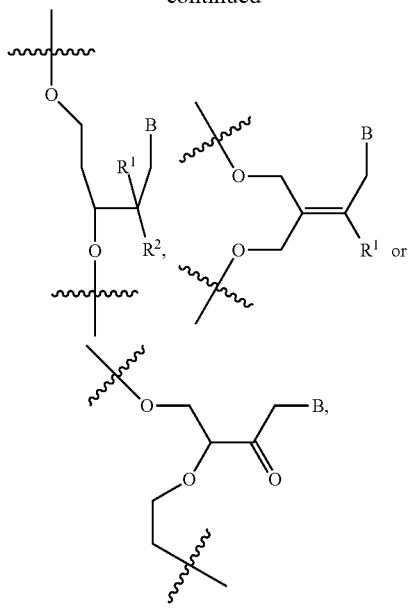

wherein B is a modified or unmodified nucleobase, $R^1$ and $R^2$ independently are H, halogen, $OR_3$, or alkyl; and $R^3$ is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'-C4' being removed (i.e. the covalent carbon-oxygen-carbon bond between the C1' and C4' carbons). In another example, the C2'-C3' bond (i.e. the covalent carbon-carbon bond between the C2' and C3' carbons) of the sugar is removed (see Mikhailov et. al., Tetrahedron Letters, 26 (17): 2059 (1985); and Fluiter et al., Mol. Biosyst., 10: 1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

(R)-OXA

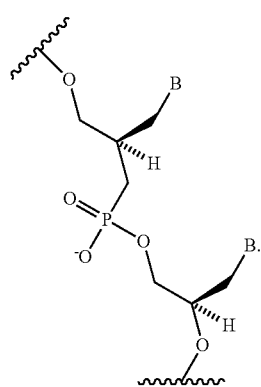

The thermally destabilizing modification of the duplex can be mismatches (i.e., noncomplementary base pairs) between the thermally destabilizing nucleotide and the opposing nucleotide in the opposite strand within the dsRNA duplex. Exemplary mismatch base pairs include G:G, G:A, G:U, G:T, A:A, A:C, C:C, C:U, C:T, U:U, T:T, U:T, or a combination thereof. Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the dsRNA molecule contains at least one nucleobase in the mismatch pairing that is a 2'-deoxy nucleobase; e.g., the 2'-deoxy nucleobase is in the sense strand.

In some embodiments, the thermally destabilizing modification of the duplex in the seed region of the antisense strand includes nucleotides with impaired W-C H-bonding to complementary base on the target mRNA, such as:

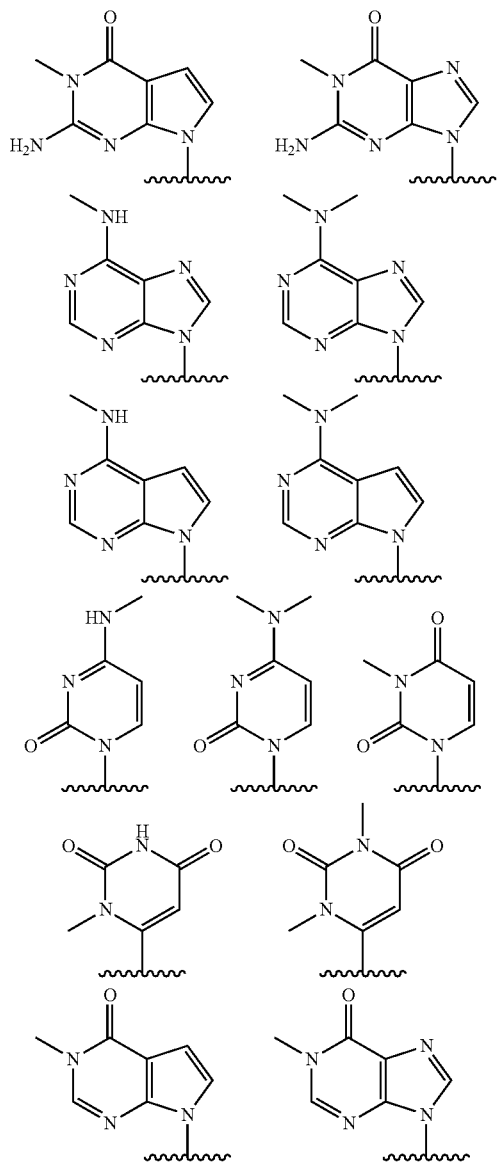

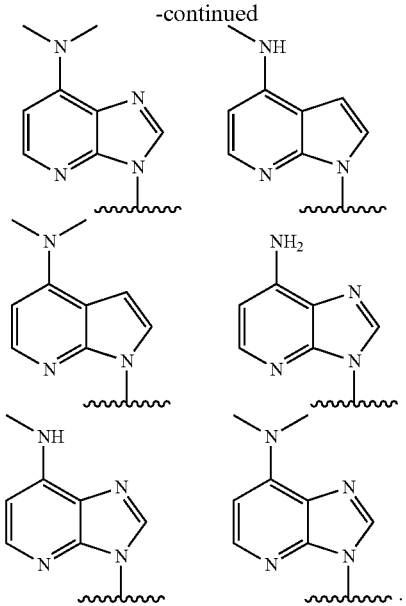

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

In some embodiments, the thermally destabilizing modification of the duplex includes nucleotides with non-canonical bases such as, but not limited to, nucleobase modifications with impaired or completely abolished capability to form hydrogen bonds with bases in the opposite strand. These nucleobase modifications have been evaluated for destabilization of the central region of the dsRNA duplex as described in WO 2010/0011895, which is herein incorporated by reference in its entirety. Exemplary nucleobase modifications are:

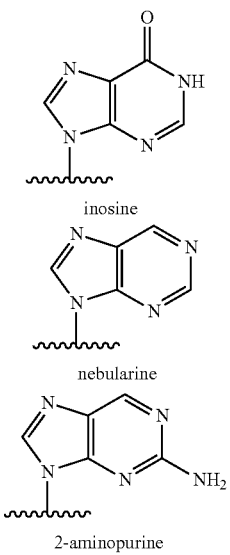

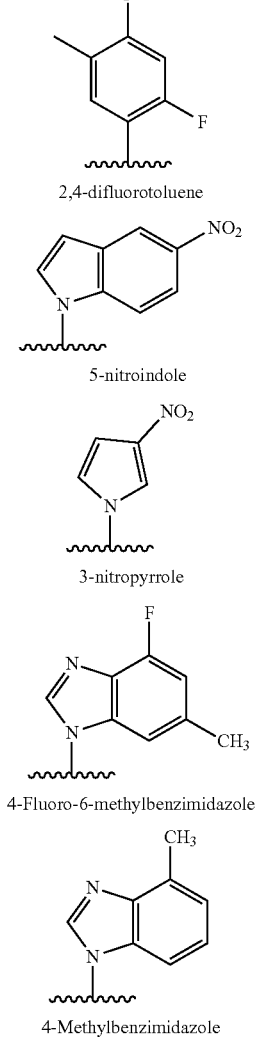

In some embodiments, the thermally destabilizing modification of the duplex in the seed region of the antisense strand includes one or more α-nucleotide complementary to the base on the target mRNA, such as:

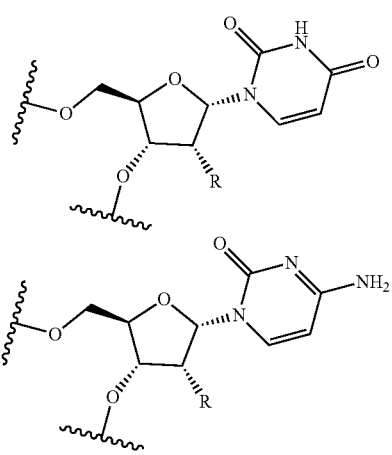

-continued

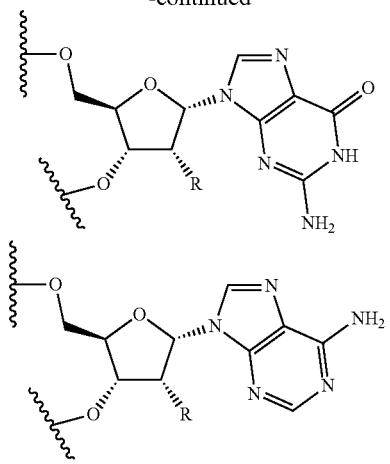

Wherein R is H, OH, OCH$_3$, F, NH$_2$, NHMe, NMe$_2$ or O-alkyl

Exemplary phosphate modifications known to decrease the thermal stability of dsRNA duplexes compared to natural phosphodiester linkages are:

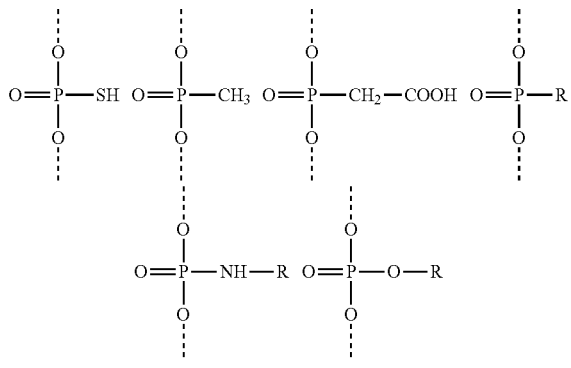

R = alkyl

The alkyl for the R group can be a C$_1$-C$_6$alkyl. Specific alkyls for the R group include, but are not limited to methyl, ethyl, propyl, isopropyl, butyl, pentyl and hexyl.

Figure 1:
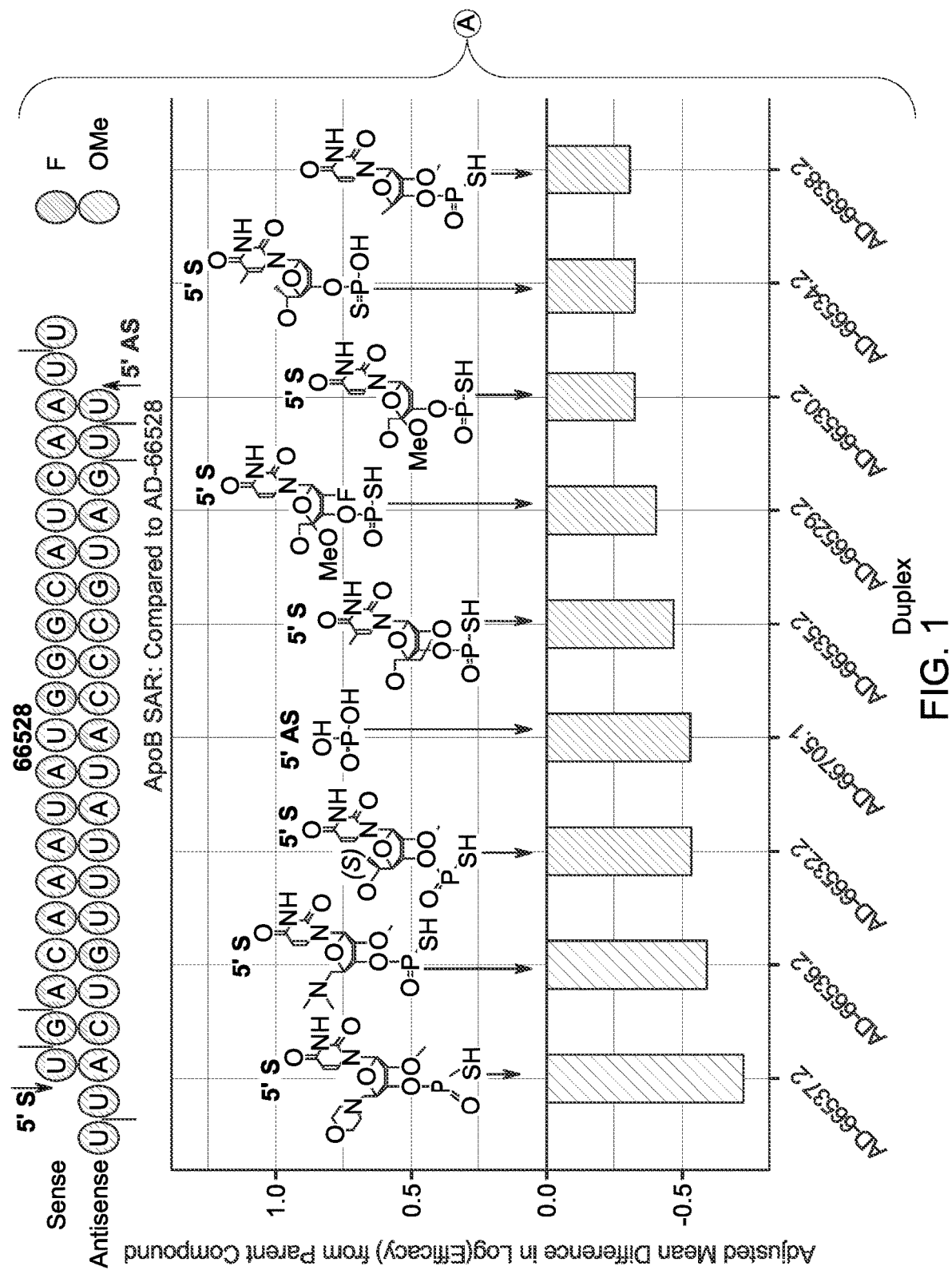
FIGS. 1 and 2 show effect of some exemplary 5'-modifications of sense and antisense strands of two different RNAi agent designs.
Figure 2:
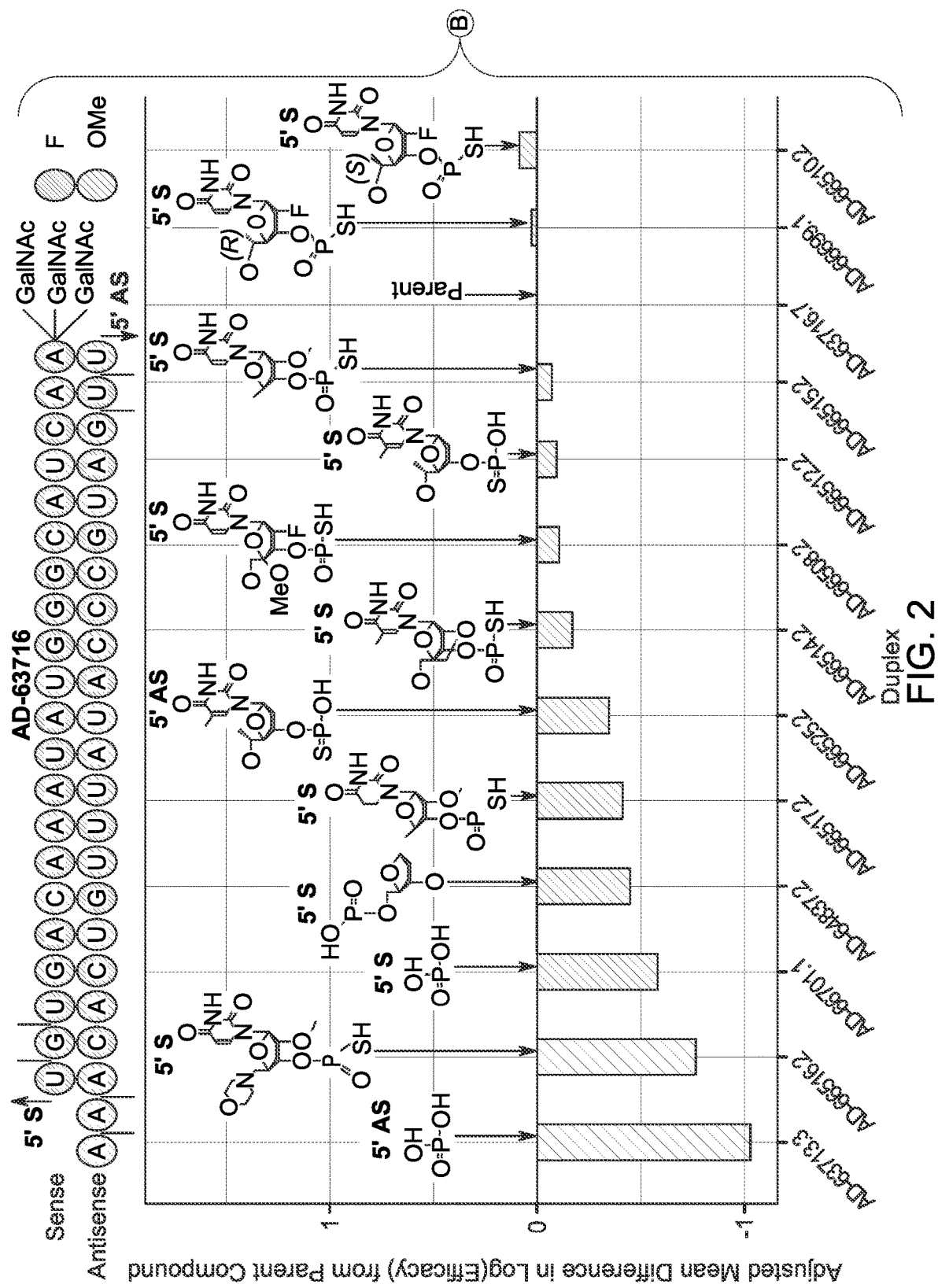
Figure 3:
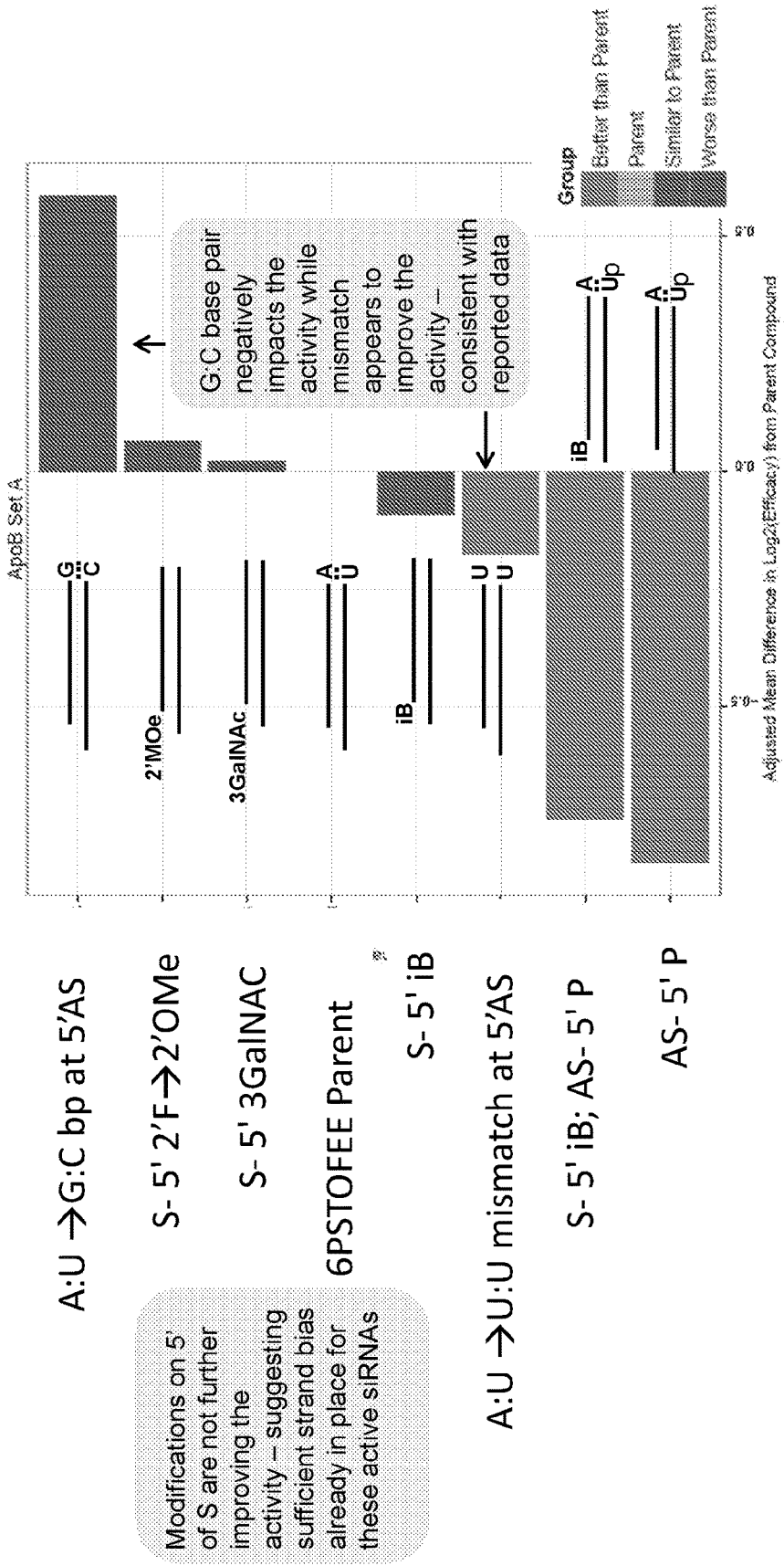
FIG. 3 is a schematic representation showing improving the strand bias by end modifications.
Figure 4:
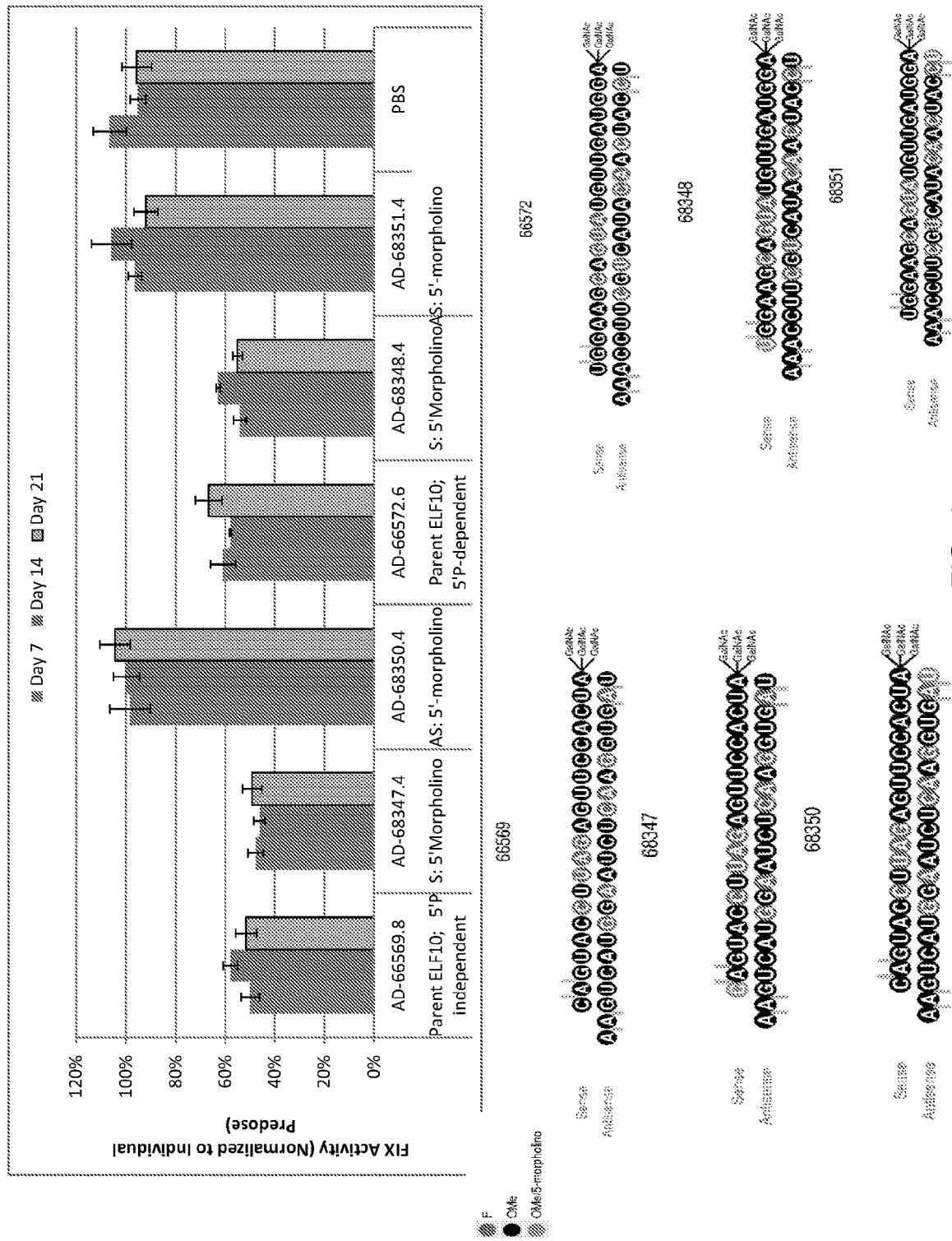
FIGS. 4 and 5 show strand specific RISC loading of an exemplary RNAi agent against Factor IX (FIG. 4, single subcutaneous administration at 1 mg/kg) and ApoB (FIG. 5, single subcutaneous administration at 1 mg/kg).

In some embodiments, exemplary destabilizing modifications shown in FIG. 1.

In addition to the antisense strand comprising a thermally destabilizing modification, the dsRNA can also comprise one or more stabilizing modifications. For example, the dsRNA can comprise at least two (e.g., two, three, four, five, six, seven, eight, nine, ten or more) stabilizing modifications. Without limitations, the stabilizing modifications all can be present in one strand. In some embodiments, both the sense and the antisense strands comprise at least two stabilizing modifications. The stabilizing modification can occur on any nucleotide of the sense strand or antisense strand. For instance, the stabilizing modification can occur on every nucleotide on the sense strand and/or antisense strand; each stabilizing modification can occur in an alternating pattern on the sense strand or antisense strand; or the sense strand or antisense strand comprises both stabilizing modification in an alternating pattern. The alternating pattern of the stabilizing modifications on the sense strand may be the same or different from the antisense strand, and the alternating pattern of the stabilizing modifications on the sense strand can have a shift relative to the alternating pattern of the stabilizing modifications on the antisense strand.

In some embodiments, the antisense strand comprises at least two (e.g., two, three, four, five, six, seven, eight, nine, ten or more) stabilizing modifications. Without limitations, a stabilizing modification in the antisense strand can be present at any positions. In some embodiments, the antisense comprises stabilizing modifications at positions 2, 6, 8, 9, 14 and 16 from the 5'-end. In some other embodiments, the antisense comprises stabilizing modifications at positions 2, 6, 14 and 16 from the 5'-end. In still some other embodiments, the antisense comprises stabilizing modifications at positions 2, 14 and 16 from the 5'-end.

In some embodiments, the antisense strand comprises at least one stabilizing modification adjacent to the destabilizing modification. For example, the stabilizing modification can be the nucleotide at the 5'-end or the 3'-end of the destabilizing modification, i.e., at position −1 or +1 from the position of the destabilizing modification. In some embodiments, the antisense strand comprises a stabilizing modification at each of the 5'-end and the 3'-end of the destabilizing modification, i.e., positions-1 and +1 from the position of the destabilizing modification.

In some embodiments, the antisense strand comprises at least two stabilizing modifications at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) stabilizing modifications. Without limitations, a stabilizing modification in the sense strand can be present at any positions. In some embodiments, the sense strand comprises stabilizing modifications at positions 7, 10 and 11 from the 5'-end. In some other embodiments, the sense strand comprises stabilizing modifications at positions 7, 9, 10 and 11 from the 5'-end. In some embodiments, the sense strand comprises stabilizing modifications at positions opposite or complimentary to positions 11, 12 and 15 of the antisense strand, counting from the 5'-end of the antisense strand. In some other embodiments, the sense strand comprises stabilizing modifications at positions opposite or complimentary to positions 11, 12, 13 and 15 of the antisense strand, counting from the 5'-end of the antisense strand. In some embodiments, the sense strand comprises a block of two, three or four stabilizing modifications.

In some embodiments, the sense strand does not comprise a stabilizing modification in position opposite or complimentary to the thermally destabilizing modification of the duplex in the antisense strand.

Exemplary thermally stabilizing modifications include, but are not limited to 2'-fluoro modifications. Other thermally stabilizing modifications include, but are not limited to LNA.

In some embodiments, the dsRNA of the invention comprises at least four (e.g., four, five, six, seven, eight, nine, ten or more) 2'-fluoro nucleotides. Without limitations, the 2'-fluoro nucleotides all can be present in one strand. In some embodiments, both the sense and the antisense strands comprise at least two 2'-fluoro nucleotides. The 2'-fluoro modification can occur on any nucleotide of the sense strand or antisense strand. For instance, the 2'-fluoro modification can occur on every nucleotide on the sense strand and/or antisense strand; each 2'-fluoro modification can occur in an alternating pattern on the sense strand or antisense strand; or the sense strand or antisense strand comprises both 2'-fluoro modifications in an alternating pattern. The alternating pattern of the 2'-fluoro modifications on the sense strand may be the same or different from the antisense strand, and the alternating pattern of the 2'-fluoro modifications on the sense strand can have a shift relative to the alternating pattern of the 2'-fluoro modifications on the antisense strand.

In some embodiments, the antisense strand comprises at least two (e.g., two, three, four, five, six, seven, eight, nine, ten or more) 2'-fluoro nucleotides. Without limitations, a 2'-fluoro modification in the antisense strand can be present at any positions. In some embodiments, the antisense comprises 2'-fluoro nucleotides at positions 2, 6, 8, 9, 14 and 16 from the 5'-end. In some other embodiments, the antisense comprises 2'-fluoro nucleotides at positions 2, 6, 14 and 16 from the 5'-end. In still some other embodiments, the antisense comprises 2'-fluoro nucleotides at positions 2, 14 and 16 from the 5'-end.

In some embodiments, the antisense strand comprises at least one 2'-fluoro nucleotide adjacent to the destabilizing modification. For example, the 2'-fluoro nucleotide can be the nucleotide at the 5'-end or the 3'-end of the destabilizing modification, i.e., at position-1 or +1 from the position of the destabilizing modification. In some embodiments, the antisense strand comprises a 2'-fluoro nucleotide at each of the 5'-end and the 3'-end of the destabilizing modification, i.e., positions-1 and +1 from the position of the destabilizing modification.

In some embodiments, the antisense strand comprises at least two 2'-fluoro nucleotides at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) 2'-fluoro nucleotides. Without limitations, a 2'-fluoro modification in the sense strand can be present at any positions. In some embodiments, the antisense comprises 2'-fluoro nucleotides at positions 7, 10 and 11 from the 5'-end. In some other embodiments, the sense strand comprises 2'-fluoro nucleotides at positions 7, 9, 10 and 11 from the 5'-end. In some embodiments, the sense strand comprises 2'-fluoro nucleotides at positions opposite or complimentary to positions 11, 12 and 15 of the antisense strand, counting from the 5'-end of the antisense strand. In some other embodiments, the sense strand comprises 2'-fluoro nucleotides at positions opposite or complimentary to positions 11, 12, 13 and 15 of the antisense strand, counting from the 5'-end of the antisense strand. In some embodiments, the sense strand comprises a block of two, three or four 2'-fluoro nucleotides.

In some embodiments, the sense strand does not comprise a 2'-fluoro nucleotide in position opposite or complimentary to the thermally destabilizing modification of the duplex in the antisense strand.

In some embodiments, the dsRNA molecule of the invention comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a blunt end at 5'-end of the antisense strand. Preferably, the 2 nt overhang is at the 3'-end of the antisense.

In some embodiments, the dsRNA molecule of the invention comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3 ' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand), For example, the thermally destabilizing nucleotide occurs between positions opposite or complimentary to positions 14-17 of the 5'-end of the sense strand, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA comprises a duplex region of 12-30 nucleotide pairs in length.

In some embodiments, the dsRNA molecule of the invention comprises a sense and antisense strands, wherein said dsRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5' end, wherein the 3' end of said sense strand and the 5' end of said antisense strand form a blunt end and said antisense strand is 1~4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA has a duplex region of 12-29 nucleotide pairs in length.

In some embodiments, every nucleotide in the sense strand and antisense strand of the dsRNA molecule may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. E.g., a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, HNA, CeNA, 2'-methoxyethyl, 2'-O-methyl, 2'-O-allyl, 2'-C-allyl, 2'-deoxy, or 2'-fluoro. The strands can contain more than one modification. In some embodiments, each residue of the sense strand and antisense strand is independently modified with 2'-O-methyl or 2'-fluoro. It is to be understood that these modifications are in addition to the at least one thermally destabilizing modification of the duplex present in the antisense strand.

At least two different modifications are typically present on the sense strand and antisense strand. Those two modifications may be the 2'-deoxy, 2'-O-methyl or 2'-fluoro modifications, acyclic nucleotides or others. In some embodiments, the sense strand and antisense strand each comprises two differently modified nucleotides selected from 2'-O-methyl or 2'-deoxy. In some embodiments, each residue of the sense strand and antisense strand is independently modified with 2'-O-methyl nucleotide, 2'-deoxy nucleotide, 2'-deoxy-2'-fluoro nucleotide, 2'-O-N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, or 2'-ara-F nucleotide. Again, it is to be understood that these modifications are in addition to the at least one thermally destabilizing modification of the duplex present in the antisense strand.

In some embodiments, the dsRNA molecule of the invention comprises modifications of an alternating pattern, particular in the B1, B2, B3, B1', B2', B3', B4' regions. The term "alternating motif" or "alternative pattern" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAAB-BAABB . . . ," "AABAABAABAAB . . . " "AAABAAA-BAAAB . . . ," "AAABBBAAABBB . . . ," or "ABCAB-CABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In some embodiments, the dsRNA molecule of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 3'-5' of the strand within the duplex region. As another example, the alternating motif in the sense strand may start with "AABBAABB" from 5'-3' of the strand and the alternating motif in the antisense strand may start with "BBAABBAA" from 3'-5' of the strand within the duplex region, so that there is a complete or partial shift of the modification patterns between the sense strand and the antisense strand.

The dsRNA molecule of the invention may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand and/or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA molecule comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. Preferably, these terminal three nucleotides may be at the 3'-end of the antisense strand.

In some embodiments, the sense strand of the dsRNA molecule comprises 1-10 blocks of two to ten phosphorothioate or methylphosphonate internucleotide linkages separated by 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said sense strand is paired with an antisense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of two phosphorothioate or methylphosphonate internucleotide linkages separated by 1, 2, 3, 4, 5, 6, 7, 8, 9, 10, 11, 12, 13, 14, 15, 16, 17, or 18 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of three phosphorothioate or methylphosphonate internucleotide linkages separated by 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of four phosphorothioate or methylphosphonate internucleotide linkages separated by 1, 2, 3, 4, 5, 6, 7, 8, 9, 10, 11, 12, 13 or 14 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of five phosphorothioate or methylphosphonate internucleotide linkages separated by 1, 2, 3, 4, 5, 6, 7, 8, 9, 10, 11 or 12 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of six phosphorothioate or methylphosphonate internucleotide linkages separated by 1, 2, 3, 4, 5, 6, 7, 8, 9 or 10 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of seven phosphorothioate or methylphosphonate internucleotide linkages separated by 1, 2, 3, 4, 5, 6, 7 or 8 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of eight phosphorothioate or methylphosphonate internucleotide linkages separated by 1, 2, 3, 4, 5 or 6 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of nine phosphorothioate or methylphosphonate internucleotide linkages separated by 1, 2, 3 or 4 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the dsRNA molecule of the invention further comprises one or more phosphorothioate or methylphosphonate internucleotide linkage modification within 1-10 of the termini position(s) of the sense and/or antisense strand. For example, at least 2, 3, 4, 5, 6, 7, 8, 9 or 10 nucleotides may be linked through phosphorothioate or methylphosphonate internucleotide linkage at one end or both ends of the sense and/or antisense strand.

In some embodiments, the dsRNA molecule of the invention further comprises one or more phosphorothioate or methylphosphonate internucleotide linkage modification within 1-10 of the internal region of the duplex of each of the sense and/or antisense strand. For example, at least 2, 3, 4, 5, 6, 7, 8, 9 or 10 nucleotides may be linked through phosphorothioate methylphosphonate internucleotide linkage at position 8-16 of the duplex region counting from the 5'-end of the sense strand; the dsRNA molecule can optionally further comprise one or more phosphorothioate or methylphosphonate internucleotide linkage modification within 1-10 of the termini position(s).

In some embodiments, the dsRNA molecule of the invention further comprises one to five phosphorothioate or methylphosphonate internucleotide linkage modification(s) within position 1-5 and one to five phosphorothioate or methylphosphonate internucleotide linkage modification(s) within position 18-23 of the sense strand (counting from the 5'-end), and one to five phosphorothioate or methylphosphonate internucleotide linkage modification at positions 1 and 2 and one to five within positions 18-23 of the antisense strand (counting from the 5'-end).

In some embodiments, the dsRNA molecule of the invention further comprises one phosphorothioate internucleotide linkage modification within position 1-5 and one phosphorothioate or methylphosphonate internucleotide linkage modification within position 18-23 of the sense strand (counting from the 5'-end), and one phosphorothioate internucleotide linkage modification at positions 1 and 2 and two phosphorothioate or methylphosphonate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the invention further comprises one phosphorothioate internucleotide linkage modification within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the invention further comprises one phosphorothioate internucleotide linkage modification within position 1-5 and one within position 18-23 of the sense strand (counting from the 5'-end), and two phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the invention further comprises one phosphorothioate internucleotide linkage modification within position 1-5 (counting from the 5'-end) of the sense strand, and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the invention further comprises two phosphorothioate internucleotide linkage modifications within position 1-5 (counting from the 5'-end) of the sense strand, and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and one within position 18-23 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the invention further comprises two phosphorothioate internucleotide linkage modifications within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications at position 1 and 2, and two phosphorothioate internucleotide linkage modifications at position 20 and 21 of the sense strand (counting from the 5'-end), and one phosphorothioate internucleotide linkage modification at positions 1 and one at position 21 of the antisense strand (counting from the 5'-end).

In some embodiments, the dsRNA molecule of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 20 and 21 the antisense strand (counting from the 5'-end).

In some embodiments, the dsRNA molecule of the invention further comprises two phosphorothioate internucleotide linkage modifications at position 1 and 2, and two phosphorothioate internucleotide linkage modifications at position 21 and 22 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 21 and 22 the antisense strand (counting from the 5'-end).

In some embodiments, the dsRNA molecule of the invention further comprises two phosphorothioate internucleotide linkage modifications at position 1 and 2, and two phosphorothioate internucleotide linkage modifications at position 22 and 23 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 23 and 23 the antisense strand (counting from the 5'-end).

In some embodiments, compound of the invention comprises a pattern of backbone chiral centers. In some embodiments, a common pattern of backbone chiral centers comprises at least 5 internucleotidic linkages in the Sp configuration. In some embodiments, a common pattern of backbone chiral centers comprises at least 6 internucleotidic linkages in the Sp configuration. In some embodiments, a common pattern of backbone chiral centers comprises at least 7 internucleotidic linkages in the Sp configuration. In some embodiments, a common pattern of backbone chiral centers comprises at least 8 internucleotidic linkages in the Sp configuration. In some embodiments, a common pattern of backbone chiral centers comprises at least 9 internucleotidic linkages in the Sp configuration. In some embodiments, a common pattern of backbone chiral centers comprises at least 10 internucleotidic linkages in the Sp configuration. In some embodiments, a common pattern of backbone chiral centers comprises at least 11 internucleotidic linkages in the Sp configuration. In some embodiments, a common pattern of backbone chiral centers comprises at least 12 internucleotidic linkages in the Sp configuration. In some embodiments, a common pattern of backbone chiral centers comprises at least 13 internucleotidic linkages in the Sp configuration. In some embodiments, a common pattern of backbone chiral centers comprises at least 14 internucleotidic linkages in the Sp configuration. In some embodiments, a common pattern of backbone chiral centers comprises at least 15 internucleotidic linkages in the Sp configuration. In some embodiments, a common pattern of backbone chiral centers comprises at least 16 internucleotidic linkages in the Sp configuration. In some embodiments, a common pattern of backbone chiral centers comprises at least 17 internucleotidic linkages in the Sp configuration. In some embodiments, a common pattern of backbone chiral centers comprises at least 18 internucleotidic linkages in the Sp configuration. In some embodiments, a common pattern of backbone chiral centers comprises at least 19 internucleotidic linkages in the Sp configuration. In some embodiments, a common pattern of backbone chiral centers comprises no more than 8 internucleotidic linkages in the Rp configuration. In some embodiments, a common pattern of backbone chiral centers comprises no more than 7 internucleotidic linkages in the Rp configuration. In some embodiments, a common pattern of backbone chiral centers comprises no more than 6 internucleotidic linkages in the Rp configuration. In some embodiments, a common pattern of backbone chiral centers comprises no more than 5 internucleotidic linkages in the Rp configuration. In some embodiments, a common pattern of backbone chiral centers comprises no more than 4 internucleotidic linkages in the Rp configuration. In some embodiments, a common pattern of backbone chiral centers comprises no more than 3 internucleotidic linkages in the Rp configuration. In some embodiments, a common pattern of backbone chiral centers comprises no more than 2 internucleotidic linkages in the Rp configuration. In some embodiments, a common pattern of backbone chiral centers comprises no more than 1 internucleotidic linkages in the Rp configuration. In some embodiments, a common pattern of backbone chiral centers comprises no more than 8 internucleotidic linkages which are not chiral (as a non-limiting example, a phosphodiester). In some embodiments, a common pattern of backbone chiral centers comprises no more than 7 internucleotidic linkages which are not chiral. In some embodiments, a common pattern of backbone chiral centers comprises no more than 6 internucleotidic linkages which are not chiral. In some embodiments, a common pattern of backbone chiral centers comprises no more than 5 internucleotidic linkages which are not chiral. In some embodiments, a common pattern of backbone chiral centers comprises no more than 4 internucleotidic linkages which are not chiral. In some embodiments, a common pattern of backbone chiral centers comprises no more than 3 internucleotidic linkages which are not chiral. In some embodiments, a common pattern of backbone chiral centers comprises no more than 2 internucleotidic linkages which are not chiral. In some embodiments, a common pattern of backbone chiral centers comprises no more than 1 internucleotidic linkages which are not chiral. In some embodiments, a common pattern of backbone chiral centers comprises at least 10 internucleotidic linkages in the Sp configuration, and no more than 8 internucleotidic linkages which are not chiral. In some embodiments, a common pattern of backbone chiral centers comprises at least 11 internucleotidic linkages in the Sp configuration, and no more than 7 internucleotidic linkages which are not chiral. In some embodiments, a common pattern of backbone chiral centers comprises at least 12 internucleotidic linkages in the Sp configuration, and no more than 6 internucleotidic linkages which are not chiral. In some embodiments, a common pattern of backbone chiral centers comprises at least 13 internucleotidic linkages in the Sp configuration, and no more than 6 internucleotidic linkages which are not chiral. In some embodiments, a common pattern of backbone chiral centers comprises at least 14 internucleotidic linkages in the Sp configuration, and no more than 5 internucleotidic linkages which are not chiral. In some embodiments, a common pattern of backbone chiral centers comprises at least 15 internucleotidic linkages in the Sp configuration, and no more than 4 internucleotidic linkages which are not chiral. In some embodiments, the internucleotidic linkages in the Sp configuration are optionally contiguous or not contiguous. In some embodiments, the internucleotidic linkages in the Rp configuration are optionally contiguous or not contiguous. In some embodiments, the internucleotidic linkages which are not chiral are optionally contiguous or not contiguous.

In some embodiments, compound of the invention comprises a block is a stereochemistry block. In some embodiments, a block is an Rp block in that each internucleotidic linkage of the block is Rp. In some embodiments, a 5'-block is an Rp block. In some embodiments, a 3'-block is an Rp block. In some embodiments, a block is an Sp block in that each internucleotidic linkage of the block is Sp. In some embodiments, a 5'-block is an Sp block. In some embodiments, a 3'-block is an Sp block. In some embodiments, provided oligonucleotides comprise both Rp and Sp blocks. In some embodiments, provided oligonucleotides comprise one or more Rp but no Sp blocks. In some embodiments, provided oligonucleotides comprise one or more Sp but no Rp blocks. In some embodiments, provided oligonucleotides comprise one or more PO blocks wherein each internucleotidic linkage in a natural phosphate linkage.

In some embodiments, compound of the invention comprises a 5'-block is an Sp block wherein each sugar moiety comprises a 2'-F modification. In some embodiments, a 5'-block is an Sp block wherein each of internucleotidic linkage is a modified internucleotidic linkage and each sugar moiety comprises a 2'-F modification. In some embodiments, a 5'-block is an Sp block wherein each of internucleotidic linkage is a phosphorothioate linkage and each sugar moiety comprises a 2'-F modification. In some embodiments, a 5'-block comprises 4 or more nucleoside units. In some embodiments, a 5'-block comprises 5 or more nucleoside units. In some embodiments, a 5'-block comprises 6 or more nucleoside units. In some embodiments, a 5'-block comprises 7 or more nucleoside units. In some embodiments, a 3'-block is an Sp block wherein each sugar moiety comprises a 2'-F modification. In some embodiments, a 3'-block is an Sp block wherein each of internucleotidic linkage is a modified internucleotidic linkage and each sugar moiety comprises a 2'-F modification. In some embodiments, a 3'-block is an Sp block wherein each of internucleotidic linkage is a phosphorothioate linkage and each sugar moiety comprises a 2'-F modification. In some embodiments, a 3'-block comprises 4 or more nucleoside units. In some embodiments, a 3'-block comprises 5 or more nucleoside units. In some embodiments, a 3'-block comprises 6 or more nucleoside units. In some embodiments, a 3'-block comprises 7 or more nucleoside units.

In some embodiments, compound of the invention comprises a type of nucleoside in a region or an oligonucleotide is followed by a specific type of internucleotidic linkage, e.g., natural phosphate linkage, modified internucleotidic linkage, Rp chiral internucleotidic linkage, Sp chiral internucleotidic linkage, etc. In some embodiments, A is followed by Sp. In some embodiments, A is followed by Rp. In some embodiments, A is followed by natural phosphate linkage (PO). In some embodiments, U is followed by Sp. In some embodiments, U is followed by Rp. In some embodiments, U is followed by natural phosphate linkage (PO). In some embodiments, C is followed by Sp. In some embodiments, C is followed by Rp. In some embodiments, C is followed by natural phosphate linkage (PO). In some embodiments, G is followed by Sp. In some embodiments, G is followed by Rp. In some embodiments, G is followed by natural phosphate linkage (PO). In some embodiments, C and U are followed by Sp. In some embodiments, C and U are followed by Rp. In some embodiments, C and U are followed by natural phosphate linkage (PO). In some embodiments, A and G are followed by Sp. In some embodiments, A and G are followed by Rp.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 3, 4 or 5 phosphorothioate internucleotide linkages; (v) the dsRNA comprises at least four 2'-fluoro modifications; (vi) the dsRNA comprises a duplex region of 12-40 nucleotide pairs in length; and (vii) the dsRNA has a blunt end at 5'-end of the antisense strand.

In some embodiments, the dsRNA molecule of the invention comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In some embodiments, the dsRNA molecule of the invention comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In some embodiments, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

The inventors found that introducing 4'-modified and/or 5'-modified nucleotide to the 3'-end of a phosphodiester (PO), phosphorothioate (PS), and/or phosphorodithioate (PS2) linkage of a dinucleotide at any position of single stranded or double stranded oligonucleotide can exert steric effect to the internucleotide linkage and, hence, protecting or stabilizing it against nucleases.

In some embodiments, 5'-modified nucleoside is introduced at the 3'-end of a dinucleotide at any position of single stranded or double stranded siRNA. For instance, a 5'-alkylated nucleoside may be introduced at the 3'-end of a dinucleotide at any position of single stranded or double stranded siRNA. The alkyl group at the 5' position of the ribose sugar can be racemic or chirally pure R or S isomer. An exemplary 5'-alkylated nucleoside is 5'-methyl nucleoside. The 5'-methyl can be either racemic or chirally pure R or S isomer.

In some embodiments, 4'-modified nucleoside is introduced at the 3'-end of a dinucleotide at any position of single stranded or double stranded siRNA. For instance, a 4'-alkylated nucleoside may be introduced at the 3'-end of a dinucleotide at any position of single stranded or double stranded siRNA. The alkyl group at the 4' position of the ribose sugar can be racemic or chirally pure R or S isomer. An exemplary 4'-alkylated nucleoside is 4'-methyl nucleoside. The 4'-methyl can be either racemic or chirally pure R or S isomer. Alternatively, a 4'-O-alkylated nucleoside may be introduced at the 3'-end of a dinucleotide at any position of single stranded or double stranded siRNA. The 4'-O-alkyl of the ribose sugar can be racemic or chirally pure R or S isomer. An exemplary 4'-O-alkylated nucleoside is 4'-O-methyl nucleoside. The 4'-O-methyl can be either racemic or chirally pure R or S isomer.

In some embodiments, 5'-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 5'-alkylated nucleoside is 5'-methyl nucleoside. The 5'-methyl can be either racemic or chirally pure R or S isomer.

In some embodiments, 4'-alkylated nucleoside is introduced at any position on the sense strand or antisense strand of a dsRNA, and such modification maintains or improves potency of the dsRNA. The 4'-alkyl can be either racemic or chirally pure R or S isomer. An exemplary 4'-alkylated nucleoside is 4'-methyl nucleoside. The 4'-methyl can be either racemic or chirally pure R or S isomer.

In some embodiments, 4'-O-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 4'-O-alkylated nucleoside is 4'-O-methyl nucleoside. The 4'-O-methyl can be either racemic or chirally pure R or S isomer.

In some embodiments, the dsRNA molecule of the invention can comprise 2'-5' linkages (with 2'-H, 2'-OH and 2'-OMe and with P=O or P=S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, the dsRNA molecule of the invention can comprise L sugars (e.g., L ribose, L-arabinose with 2'-H, 2'-OH and 2'-OMe). For example, these L sugars modifications can be used to promote nuclease resistance or to inhibit binding of the sense to the antisense strand, or can be used at the 5' end of the sense strand to avoid sense strand activation by RISC.

Various publications describe multimeric siRNA which can all be used with the dsRNA of the invention. Such publications include WO2007/091269, U.S. Pat. No. 7,858,769, WO2010/141511, WO2007/117686, WO2009/014887 and WO2011/031520 which are hereby incorporated by their entirely.

The dsRNA molecule that contains conjugations of one or more carbohydrate moieties to a dsRNA molecule can optimize one or more properties of the dsRNA molecule. In many cases, the carbohydrate moiety will be attached to a modified subunit of the dsRNA molecule. E.g., the ribose sugar of one or more ribonucleotide subunits of a dsRNA molecule can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In one embodiment the dsRNA molecule of the invention is conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3] dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

The double-stranded RNA (dsRNA) agent of the invention may optionally be conjugated to one or more ligands. The ligand can be attached to the sense strand, antisense strand or both strands, at the 3'-end, 5'-end or both ends. For instance, the ligand may be conjugated to the sense strand, in particular, the 3'-end of the sense strand.

In some embodiments dsRNA molecules of the invention are 5' phosphorylated or include a phosphoryl analog at the 5' prime terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N-O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)2(O)P-S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P-NH-5', (HO)(NH$_2$)(O)P—O-5'), 5'-alkylphosphonates (R=alkyl-methyl, ethyl, isopropyl, propyl, etc., e.g. RP(OH)(O)—O-5'-, 5'-alkenylphosphonates (i.e. vinyl, substituted vinyl), (OH)$_2$(O)P-5'-CH2—), 5'-alkyletherphosphonates (R=alkylether-methoxymethyl (MeOCH2—), ethoxymethyl, etc., e.g. RP(OH)(O)—O-5'-). In one example, the modification can in placed in the antisense strand of a dsRNA molecule.

Ligands

A wide variety of entities can be coupled to the oligonucleotides of the present invention. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, receptor e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In some embodiments, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972, which is incorporated by reference in its entirety), the EALA peptide (Vogel et al., J. Am. Chem. Soc., 1996, 118: 1581-1586, which is incorporated by reference in its entirety), and their derivatives (Turk et al., Biochem. Biophys. Acta, 2002, 1559: 56-68, which is incorporated by reference in its entirety). In some embodiments, the endosomolytic component may contain a chemical group (e.g., an amino acid) which will undergo a change in charge or protonation in response to a change in pH. The endosomolytic component may be linear or branched.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyamino acids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 2 shows some examples of targeting ligands and their associated receptors.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases or a chelating agent (e.g. EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptide species, such as lipids, lectins, carbohydrates, vitamins, cofactors, multivalent lactose, multivalent galactose, N-acetyl-galactosamine, N-acetyl-glucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by activating an inflammatory response, for example. Exemplary ligands that would have such an effect include tumor necrosis factor alpha (TNF-alpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or cross-linked peptide. In another alternative, the peptide moiety can include a hydrophobic membrane translocation sequence (MTS). An exemplary hydrophobic MTS-containing peptide is RFGF having the amino acid sequence AAVALLPAVL-LALLAP (SEQ ID NO: 91). An RFGF analogue (e.g., amino acid sequence AALLPVLLAAP (SEQ ID NO: 92)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 93)) and the *Drosophila* Antennapedia protein (RQIKIWFQNRRMKWKK (SEQ ID NO: 94)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-94, 1991, which is incorporated by reference in its entirety). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et al., Cancer Res., 62:5139-43, 2002, which is incorporated by reference in its entirety). An RGD peptide can facilitate targeting of an iRNA agent to tumors of a variety of other tissues, including the lung, kidney, spleen, or liver (Aoki et al., Cancer Gene Therapy 8:783-787, 2001, which is incorporated by reference in its entirety). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha v \beta_3$ (Haubner et al., Jour. Nucl. Med., 42:326-336, 2001, which is incorporated by reference in its entirety). Peptides that target markers enriched in proliferating cells can be used. E.g., RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogenesis. Preferred conjugates of this type ligands that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin PI), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003, which is incorporated by reference in its entirety).

In some embodiments, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, *Xenopus* peptides, esculentinis-1, and caerins.

A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; a, B, or y peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an aptamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polycations, masked oligo or poly cations or anions, acetals, polyacetals, ketals/polyketals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Exemplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as ligands (e.g. as PK modulating ligands).

In addition, aptamers that bind serum components (e.g. serum proteins) are also amenable to the present invention as PK modulating ligands.

Other ligand conjugates amenable to the invention are described in U.S. patent application Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g. a carrier described herein. The ligand or tethered ligand may be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., TAP-$(CH_2)_n NH_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

In some embodiments, the ligand is conjugated to the sense strand. As described herein, the ligand can be conjugated at the 3'-end, 5'-end or at an internal position of the sense strand. In some embodiments, the ligand is conjugated to the 3'-end of the sense strand. Further, the ligand can be conjugated to a nucleobase, sugar moiety or internucleotide linkage of the sense strand.

Any suitable ligand in the field of RNA interference may be used, although the ligand is typically a carbohydrate e.g. monosaccharide (such as GalNAc), disaccharide, trisaccharide, tetrasaccharide, polysaccharide.

Linkers that conjugate the ligand to the nucleic acid include those discussed above. For example, the ligand can be one or more GalNAc (N-acetylgalactosamine) derivatives attached through a monovalent, bivalent or trivalent branched linker.

In some embodiments, the dsRNA of the invention is conjugated to a bivalent and trivalent branched linkers include the structures shown in any of formula (IV)-(VII):

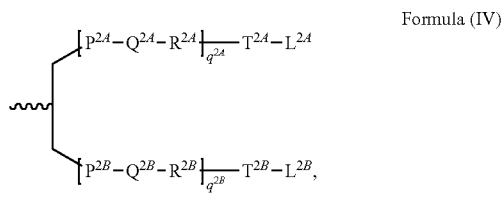

Formula (IV)

-continued

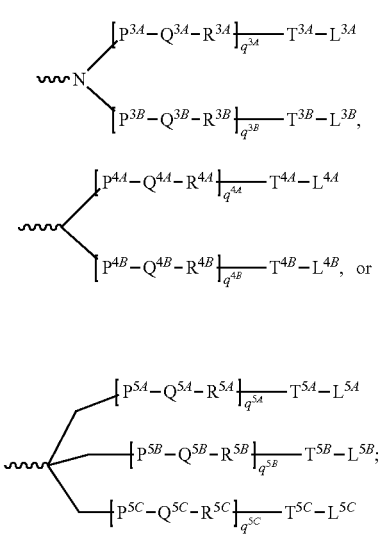

Formula (V)

Formula (VI)

Formula (VII)

wherein:

$q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20 and wherein the repeating unit can be the same or different;

$P^{2A}$, $P^{2B}$, $P^{3A}$, $P^{3B}$, $P^{4A}$, $P^{4B}$, Pf, $P^{5B}$, $P^{5C}$, $T^{2A}$, $T^{2B}$, $T^{3A}$, $T^{3B}$, $T^{4A}$, $T^{4B}$, $T^{5A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R''), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH($R^a$)—NH—, CO, CH=N—O,

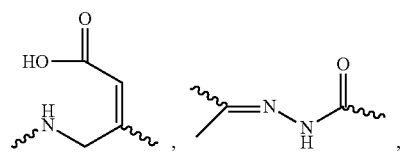

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain.

Trivalent conjugating GalNAc derivatives are particularly useful for use with RNAi agents for inhibiting the expression of a target gene, such as those of formula (VII):

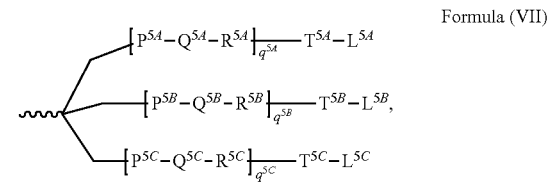

Formula (VII)

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the following compounds:

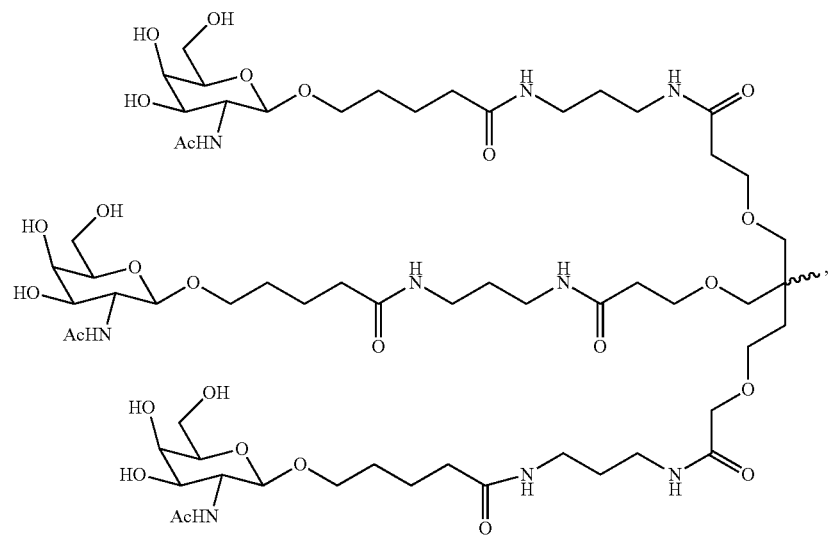

131
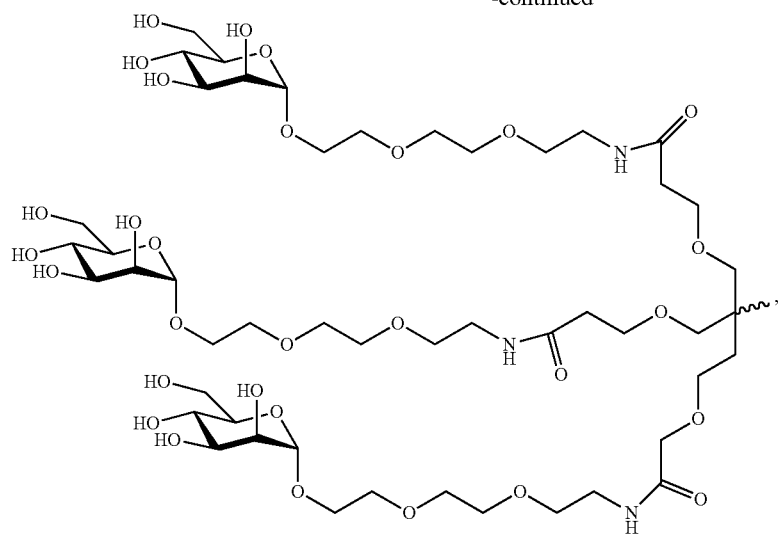
132
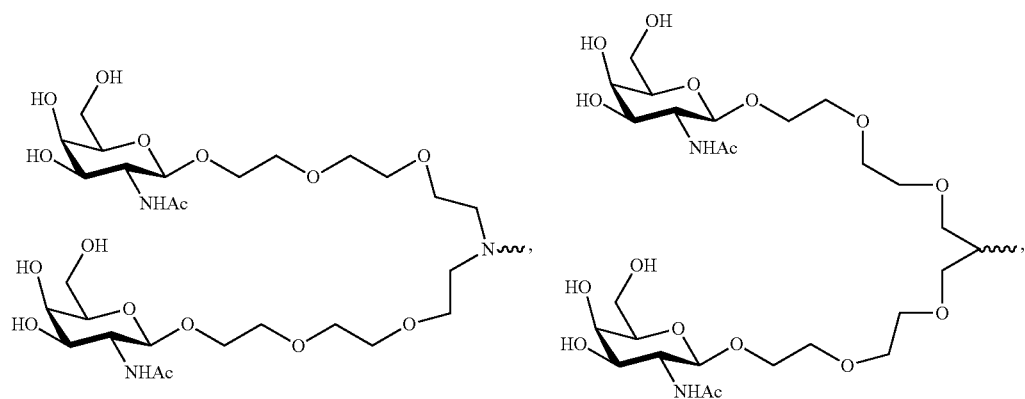
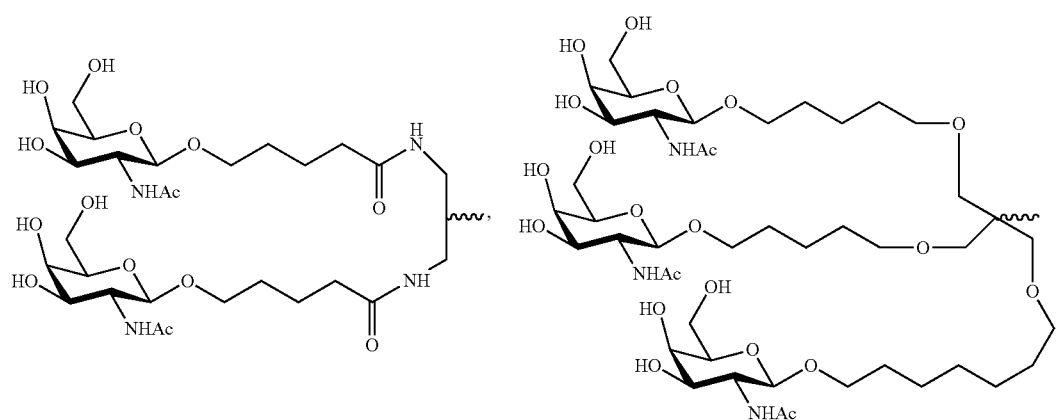

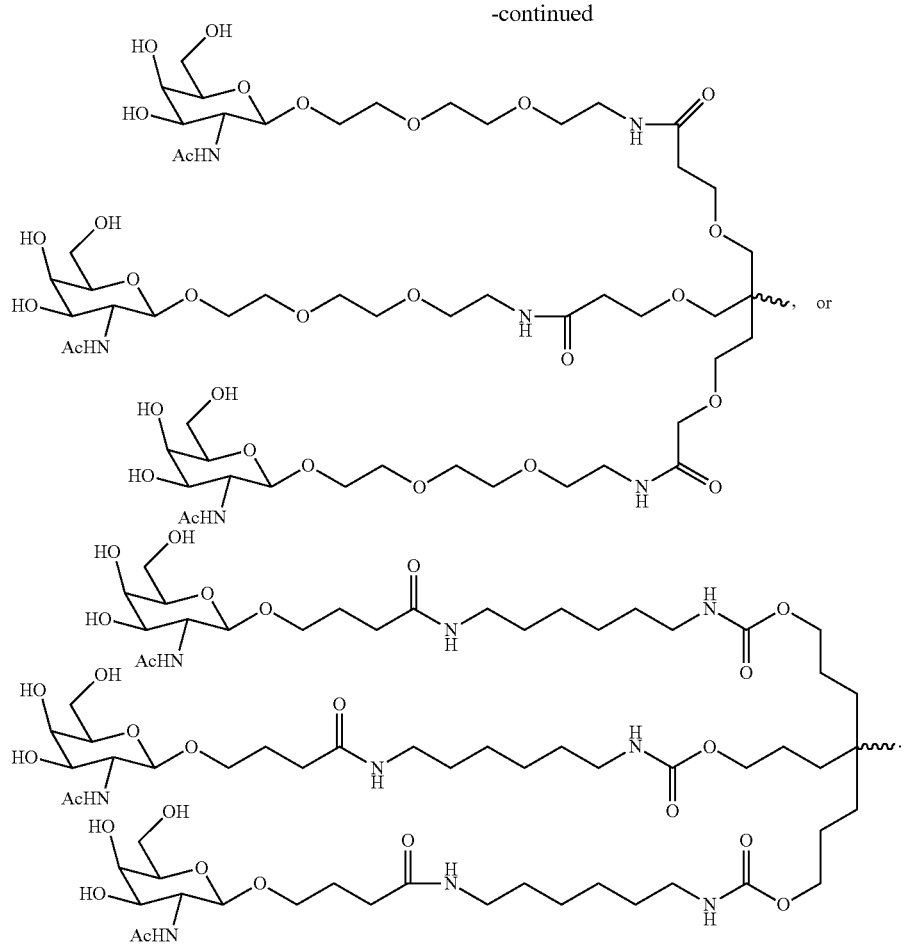

Definitions

As used herein, the terms "dsRNA", "siRNA", and "iRNA agent" are used interchangeably to agents that can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent of 21 to 23 nucleotides.

As used herein, "specifically hybridizable" and "complementary" are terms which are used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, i.e., under physiological conditions in the case of assays or therapeutic treatment, or in the case of in vitro assays, under conditions in which the assays are performed. The non-target sequences typically differ by at least 5 nucleotides.

In some embodiments, a dsRNA molecule of the invention is "sufficiently complementary" to a target RNA, e.g., a target mRNA, such that the dsRNA molecule silences production of protein encoded by the target mRNA. In another embodiment, the dsRNA molecule of the invention is "exactly complementary" to a target RNA, e.g., the target RNA and the dsRNA duplex agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in some embodiments, the dsRNA molecule of the invention specifically discriminates a single-nucleotide difference. In this case, the dsRNA molecule only mediates RNAi if exact complementary is found in the region (e.g., within 7 nucleotides of) the single-nucleotide difference.

As used herein, the term "oligonucleotide" refers to a nucleic acid molecule (RNA or DNA) for example of length less than 100, 200, 300, or 400 nucleotides.

The term 'BNA' refers to bridged nucleic acid, and is often referred as constrained or inaccessible RNA. BNA can contain a 5-, 6-membered, or even a 7-membered bridged structure with a "fixed" $C_3'$-endo sugar puckering. The bridge is typically incorporated at the 2'-, 4'-position of the ribose to afford a 2', 4'-BNA nucleotide (e.g., LNA, or ENA). Examples of BNA nucleotides include the following nucleosides:

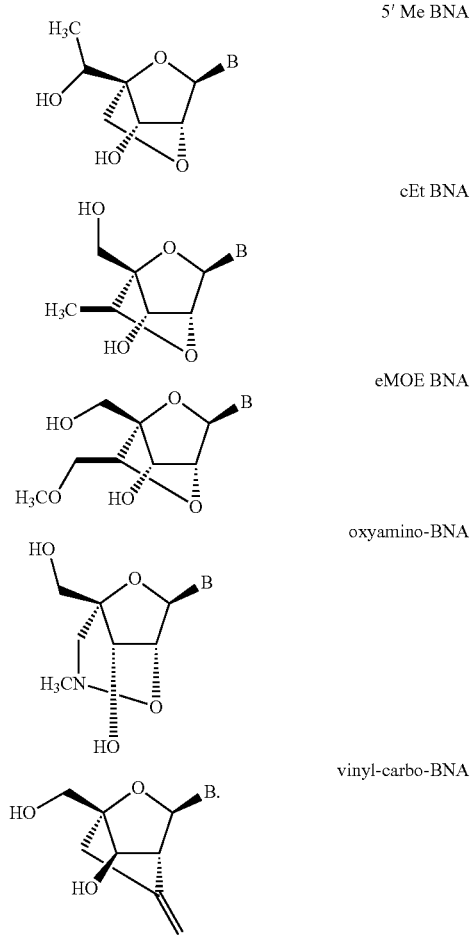

5' Me BNA cEt BNA eMOE BNA oxyamino-BNA vinyl-carbo-BNA

The term 'LNA' refers to locked nucleic acid, and is often referred as constrained or inaccessible RNA. LNA is a modified RNA nucleotide. The ribose moiety of an LNA nucleotide is modified with an extra bridge (e.g., a methylene bridge or an ethylene bridge) connecting the 2' hydroxyl to the 4' carbon of the same ribose sugar. For instance, the bridge can "lock" the ribose in the 3'-endo North) conformation:

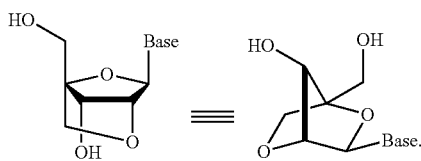

The term 'ENA' refers to ethylene-bridged nucleic acid, and is often referred as constrained or inaccessible RNA.

The "cleavage site" herein means the backbone linkage in the target gene or the sense strand that is cleaved by the RISC mechanism by utilizing the iRNA agent. And the target cleavage site region comprises at least one or at least two nucleotides on both side of the cleavage site. For the sense strand, the cleavage site is the backbone linkage in the sense strand that would get cleaved if the sense strand itself was the target to be cleaved by the RNAi mechanism. The cleavage site can be determined using methods known in the art, for example the 5'-RACE assay as detailed in Soutschek et al., Nature (2004) 432, 173-178, which is incorporated by reference in its entirety. As is well understood in the art, the cleavage site region for a conical double stranded RNAi agent comprising two 21-nucleotides long strands (wherein the strands form a double stranded region of 19 consecutive base pairs having 2-nucleotide single stranded overhangs at the 3'-ends), the cleavage site region corresponds to positions 9-12 from the 5'-end of the sense strand.

Cleavable Linking Groups

A cleavable linking group is one which is sufficiently stable outside the cell, but which upon entry into a target cell is cleaved to release the two parts the linker is holding together. In a preferred embodiment of the dsRNA molecule according to the present invention, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups is redox cleavable linking groups, which may be used in the dsRNA molecule according to the present invention that are cleaved upon reduction or oxidation. An example of reductively cleavable linking group is a disulfide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups, which may be used in the dsRNA molecule according to the present invention, are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is -O—P(O)(OH)—O—. These candidates can be evaluated using methods analogous to those described above.

Acid Cleavable Linking Groups

Acid cleavable linking groups, which may be used in the dsRNA molecule according to the present invention, are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups, which may be used in the dsRNA molecule according to the present invention, are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups, which may be used in the dsRNA molecule according to the present invention, are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynylene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where R$^A$ and R$^B$ are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

The present invention further relates to a use of a dsRNA molecule as defined herein for inhibiting expression of a target gene. In some embodiments, the present invention further relates to a use of a dsRNA molecule for inhibiting expression of a target gene in vitro.

The present invention further relates to a dsRNA molecule as defined herein for use in inhibiting expression of a target gene in a subject. The subject may be any animal, such as a mammal, e.g., a mouse, a rat, a sheep, a cattle, a dog, a cat, or a human In some embodiments, the dsRNA molecule of the invention is administered in buffer.

In some embodiments, siRNA compounds described herein can be formulated for administration to a subject. A formulated siRNA composition can assume a variety of states. In some examples, the composition is at least partially crystalline, uniformly crystalline, and/or anhydrous (e.g., less than 80, 50, 30, 20, or 10% water). In another example, the siRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the siRNA composition is formulated in a manner that is compatible with the intended method of administration, as described herein. For example, in particular embodiments the composition is prepared by at least one of the following methods: spray drying, lyophilization, vacuum drying, evaporation, fluid bed drying, or a combination of these techniques; or sonication with a lipid, freeze-drying, condensation and other self-assembly.

A siRNA preparation can be formulated in combination with another agent, e.g., another therapeutic agent or an agent that stabilizes a siRNA, e.g., a protein that complexes with siRNA to form an iRNP. Still other agents include chelating agents, e.g., EDTA (e.g., to remove divalent cations such as $Mg^{2+}$), salts, RNAse inhibitors (e.g., a broad specificity RNAse inhibitor such as RNAsin) and so forth.

In some embodiments, the siRNA preparation includes another siRNA compound, e.g., a second siRNA that can mediate RNAi with respect to a second gene, or with respect to the same gene. Still other preparation can include at least 3, 5, ten, twenty, fifty, or a hundred or more different siRNA species. Such siRNAs can mediate RNAi with respect to a similar number of different genes.

In some embodiments, the siRNA preparation includes at least a second therapeutic agent (e.g., an agent other than a RNA or a DNA). For example, a siRNA composition for the treatment of a viral disease, e.g., HIV, might include a known antiviral agent (e.g., a protease inhibitor or reverse transcriptase inhibitor). In another example, a siRNA composition for the treatment of a cancer might further comprise a chemotherapeutic agent.

Exemplary formulations which can be used for administering the dsRNA molecule according to the present invention are discussed below.

Liposomes. For ease of exposition the formulations, compositions and methods in this section are discussed largely with regard to unmodified siRNA compounds. It may be understood, however, that these formulations, compositions and methods can be practiced with other siRNA compounds, e.g., modified siRNAs, and such practice is within the invention. An siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparation can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the siRNA composition. The lipophilic material isolates the aqueous interior from an aqueous exterior, which typically does not include the siRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the siRNA are delivered into the cell where the siRNA can specifically bind to a target RNA and can mediate RNAi. In some cases the liposomes are also specifically targeted, e.g., to direct the siRNA to particular cell types.

A liposome containing a siRNA can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The siRNA preparation is then added to the micelles that include the lipid component. The cationic groups on the lipid interact with the siRNA and condense around the siRNA to form a liposome. After condensation, the detergent is removed, e.g., by dialysis, to yield a liposomal preparation of siRNA.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favor condensation.

Further description of methods for producing stable polynucleotide delivery vehicles, which incorporate a polynucleotide/cationic lipid complex as structural components of the delivery vehicle, are described in, e.g., WO 96/37194. Liposome formation can also include one or more aspects of exemplary methods described in Felgner, P. L. et al., *Proc. Natl. Acad. Sci.*, USA 8:7413-7417, 1987; U.S. Pat. Nos. 4,897,355; 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984, which are incorporated by reference in their entirety. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986, which is incorporated by reference in its entirety). Microfluidization can be used when consistently small (50 to 200 nm) and relatively uniform aggregates are desired (Mayhew, et al. *Biochim. Biophys. Acta* 775:169, 1984, which is incorporated by reference in its entirety). These methods are readily adapted to packaging siRNA preparations into liposomes.

Liposomes that are pH-sensitive or negatively-charged entrap nucleic acid molecules rather than complex with them. Since both the nucleic acid molecules and the lipid are similarly charged, repulsion rather than complex formation occurs. Nevertheless, some nucleic acid molecules are entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 19, (1992) 269-274, which is incorporated by reference in its entirety).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and include U.S. Pat. Nos. 5,283,185; 5,171, 678; WO 94/00569; WO 93/24640; WO 91/16024; Felgner, J. Biol. Chem. 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

In some embodiments, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver siRNAs to macrophages.

Further advantages of liposomes include: liposomes obtained from natural phospholipids are biocompatible and biodegradable; liposomes can incorporate a wide range of water and lipid soluble drugs; liposomes can protect encapsulated siRNAs in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of siRNA (see, e.g., Felgner, P. L. et al., Proc. Natl. Acad. Sci., USA 8:7413-7417, 1987 and U.S. Pat. No. 4,897,355 for a description of DOTMA and its use with DNA, which are incorporated by reference in their entirety).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Indiana) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wisconsin) and dipalmitoylphosphatidylethanolamine 5-carboxyspermylamide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991, which is incorporated by reference in its entirety). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, California) and Lipofectamine (DOSPA) (Life Technology, Inc., Gaithersburg, Maryland). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer siRNA, into the skin. In some implementations, liposomes are used for delivering siRNA to epidermal cells and also to enhance the penetration of siRNA into dermal tissues, e.g., into skin. For example, the liposomes can be applied topically. Topical delivery of drugs formulated as liposomes to the skin has been documented (see, e.g., Weiner et al., *Journal of Drug Targeting*, 1992, vol. 2,405-410 and du Plessis et al., *Antiviral Research*, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987, which are incorporated by reference in their entirety).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with siRNA are useful for treating a dermatological disorder.

Liposomes that include siRNA can be made highly deformable. Such deformability can enable the liposomes to penetrate through pore that are smaller than the average radius of the liposome. For example, transfersomes are a type of deformable liposomes. Transfersomes can be made by adding surface edge activators, usually surfactants, to a standard liposomal composition. Transfersomes that include siRNA can be delivered, for example, subcutaneously by infection in order to deliver siRNA to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transfersomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Surfactants. For ease of exposition the formulations, compositions and methods in this section are discussed largely with regard to unmodified siRNA compounds. It may be understood, however, that these formulations, compositions and methods can be practiced with other siRNA compounds, e.g., modified siRNA compounds, and such practice is within the scope of the invention. Surfactants find wide application in formulations such as emulsions (including microemulsions) and liposomes (see above). siRNA (or a precursor, e.g., a larger dsiRNA which can be processed into a siRNA, or a DNA which encodes a siRNA or precursor) compositions can include a surfactant. In some embodiments, the siRNA is formulated as an emulsion that includes a surfactant. The most common way of classifying and ranking the properties of the many different types of surfactants, both natural and synthetic, is by the use of the hydrophile/lipophile balance (HLB). The nature of the hydrophilic group provides the most useful means for categorizing the different surfactants used in formulations (Rieger, in "Pharmaceutical Dosage Forms," Marcel Dekker, Inc., New York, NY, 1988, p. 285).

If the surfactant molecule is not ionized, it is classified as a nonionic surfactant. Nonionic surfactants find wide application in pharmaceutical products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms," Marcel Dekker, Inc., New York, NY, 1988, p. 285).

Micelles and other Membranous Formulations. For ease of exposition the micelles and other formulations, compositions and methods in this section are discussed largely with regard to unmodified siRNA compounds. It may be understood, however, that these micelles and other formulations, compositions and methods can be practiced with other siRNA compounds, e.g., modified siRNA compounds, and such practice is within the invention. The siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof)) composition can be provided as a micellar formulation. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

Particles. For ease of exposition the particles, formulations, compositions and methods in this section are discussed largely with regard to modified siRNA compounds. It may be understood, however, that these particles, formulations, compositions and methods can be practiced with other siRNA compounds, e.g., unmodified siRNA compounds, and such practice is within the invention. In another embodiment, an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparations may be incorporated into a particle, e.g., a microparticle. Microparticles can be produced by spray-drying, but may also be produced by other methods including lyophilization, evaporation, fluid bed drying, vacuum drying, or a combination of these techniques.

Pharmaceutical Compositions

The iRNA agents of the invention may be formulated for pharmaceutical use. The present invention further relates to a pharmaceutical composition comprising the dsRNA molecule as defined herein. Pharmaceutically acceptable compositions comprise a therapeutically-effective amount of one or more of the dsRNA molecules in any of the preceding embodiments, taken alone or formulated together with one or more pharmaceutically acceptable carriers (additives), excipient and/or diluents.

The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. Delivery using subcutaneous or intravenous methods can be particularly advantageous.

The phrase "therapeutically-effective amount" as used herein means that amount of a compound, material, or composition comprising a compound of the invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

iRNA agent preparation can be formulated in combination with another agent, e.g., another therapeutic agent or an agent that stabilizes a iRNA, e.g., a protein that complexes with iRNA to form an iRNP. Still other agents include chelating agents, e.g., EDTA (e.g., to remove divalent cations such as $Mg^{2+}$), salts, RNAse inhibitors (e.g., a broad specificity RNAse inhibitor such as RNAsin) and so forth.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The compounds according to the invention may be formulated for administration in any convenient way for use in human or veterinary medicine, by analogy with other pharmaceuticals.

The term "treatment" is intended to encompass also prophylaxis, therapy and cure. The patient receiving this treatment is any animal in need, including primates, in particular humans, and other mammals such as equines, cattle, swine and sheep; and poultry and pets in general.

Double-stranded RNAi agents are produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470, which is incorporated by reference in its entirety), or by stereotactic injection (see, e.g., Chen et al. (1994) Proc. Natl. Acad. Sci. USA 91:3054-3057, which is incorporated by reference in its entirety). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of a dsRNA molecule and one that produces a transcript that includes the bottom strand of a dsRNA molecule. When the templates are transcribed, the dsRNA molecule is produced, and processed into siRNA agent fragments that mediate gene silencing.

Routes of Delivery

The dsRNA molecule as defined herein or a pharmaceutical composition comprising a dsRNA molecule as defined herein can be administered to a subject using different routes of delivery. A composition that includes an iRNA can be delivered to a subject by a variety of routes. Exemplary routes include: intravenous, subcutaneous, topical, rectal, anal, vaginal, nasal, pulmonary, ocular.

The iRNA molecules and/or the dsRNA molecule of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Dosage

In one aspect, the invention features a method of administering a dsRNA molecule, e.g., a siRNA agent, to a subject (e.g., a human subject). In another aspect, the present invention relates to a dsRNA molecule as defined herein for use in inhibiting expression of a target gene in a subject. The method or the medical use includes administering a unit dose of the dsRNA molecule, e.g., a siRNA agent, e.g., double stranded siRNA agent that (a) the double-stranded part is 14-40 nucleotides (nt) long, for example, 21-23 nt, (b) is complementary to a target RNA (e.g., an endogenous or pathogen target RNA), and, optionally, (c) includes at least one 3' overhang 1-5 nucleotide long. In some embodiments, the unit dose is less than 10 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight.

The defined amount can be an amount effective to treat or prevent a disease or disorder, e.g., a disease or disorder associated with the target RNA. The unit dose, for example, can be administered by injection (e.g., intravenous, subcutaneous or intramuscular), an inhaled dose, or a topical application. In some embodiments dosages may be less than 10, 5, 2, 1, or 0.1 mg/kg of body weight.

In some embodiments, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In some embodiments, the effective dose is administered with other traditional therapeutic modalities. In some embodiments, the subject has a viral infection and the modality is an antiviral agent other than a dsRNA molecule, e.g., other than a siRNA agent. In another embodiment, the subject has atherosclerosis and the effective dose of a dsRNA molecule, e.g., a siRNA agent, is administered in combination with, e.g., after surgical intervention, e.g., angioplasty.

In some embodiments, a subject is administered an initial dose and one or more maintenance doses of a dsRNA molecule, e.g., a siRNA agent, (e.g., a precursor, e.g., a larger dsRNA molecule which can be processed into a siRNA agent, or a DNA which encodes a dsRNA molecule, e.g., a siRNA agent, or precursor thereof). The maintenance dose or doses can be the same or lower than the initial dose, e.g., one-half less of the initial dose. A maintenance regimen can include treating the subject with a dose or doses ranging from 0.01 μg to 15 mg/kg of body weight per day, e.g., 10, 1, 0.1, 0.01, 0.001, or 0.00001 mg per kg of bodyweight per day. The maintenance doses are, for example, administered no more than once every 2, 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In some embodiments, the composition includes a plurality of dsRNA molecule species. In another embodiment, the dsRNA molecule species has sequences that are non-overlapping and non-adjacent to another species with respect to a naturally occurring target sequence. In another embodiment, the plurality of dsRNA molecule species is specific for different naturally occurring target genes. In another embodiment, the dsRNA molecule is allele specific.

The dsRNA molecules of the invention described herein can be administered to mammals, particularly large mammals such as nonhuman primates or humans in a number of ways.

In some embodiments, the administration of the dsRNA molecule, e.g., a siRNA agent, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The medication can be provided in measured doses or in a dispenser which delivers a metered dose. Selected modes of delivery are discussed in more detail below.

The invention provides methods, compositions, and kits, for rectal administration or delivery of dsRNA molecules described herein In particular embodiments, the present invention relates to the dsRNA molecules of the present invention for use in the methods described above.

Methods of Inhibiting Expression of the Target Gene

Embodiments of the invention also relate to methods for inhibiting the expression of a target gene. The method comprises the step of administering the dsRNA molecules in any of the preceding embodiments, in an amount sufficient to inhibit expression of the target gene. The present invention further relates to a use of a dsRNA molecule as defined herein for inhibiting expression of a target gene in a target cell. In a preferred embodiment, the present invention further relates to a use of a dsRNA molecule for inhibiting expression of a target gene in a target cell in vitro.

Another aspect the invention relates to a method of modulating the expression of a target gene in a cell, comprising providing to said cell a dsRNA molecule of this invention. In some embodiments, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, hepcidin, Activated Protein C, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPMID gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

In particular embodiments, the present invention relates to the dsRNA molecules of the present invention for use in the methods described above.

The invention is further illustrated by the following examples, which should not be construed as further limiting. The contents of all references, pending patent applications and published patents, cited throughout this application are hereby expressly incorporated by reference.

EXAMPLES

Example 1: 5'-Morpholino Modification of the Sense Strand of an siRNA Makes it a More Effective Passenger The 5'-monophosphate group plays an important role in strand selection during gene silencing mediated by small-interfering RNA. It is shown that blocking of 5' phosphorylation of the sense strand by introducing a 5'-morpholino modification improves antisense strand selection and RNAi activity. The 5'-morpholino modification of the antisense strand triggers complete loss of activity.

Small interfering RNAs (siRNAs) harness the natural RNA interference (RNAi) pathway to silence genes of interest and have shown tremendous potential as therapeutic agents (S. M. Elbashir, J. Harborth, W. Lendeckel, A. Yalcin, K. Weber and T. Tuschl, Nature, 2001, 411, 494; M. Manoharan, Curr. Opin. Chem. Biol., 2004, 8, 570-579; D. Bumcrot, M. Manoharan, V. Koteliansky and D. W. Y. Sah, Nat. Chem. Biol., 2006, 2, 711; J. Soutschek, A. Akinc, B. Bramlage, K. Charisse, R. Constien, M. Donoghue, et al., Nature, 2004, 432, 173; T. S. Zimmermann, A. C. H. Lee, A. Akinc, B. Bramlage, D. Bumcrot, M. N. Fedoruk, et al., Nature, 2006, 441, 111; J. K. Nair, J. L. S. Willoughby, A. Chan, K. Charisse, M. R. Alam, Q. Wang, et al., J. Am. Chem. Soc., 2014, 136, 16958-16961; K. Fitzgerald, S. White, A. Borodovsky, B. R. Bettencourt, A. Strahs, V. Clausen, et al., N. Eng. J. Med., 2017, 376, 41-51). The approval of patisiran (ONPATTRO) in the USA and in Europe for treatment of polyneuropathy of hereditary transthyretin-mediated amyloidosis marked the translation of siRNAs into a validated class of medicines (D. Adams, A. Gonzalez-Duarte, W. D. O'Riordan, C.-C. Yang, M. Ueda, A. V. Kristen, et al., N. Eng. J. Med., 2018, 379, 11-21).

Exogenous siRNAs are typically chemically modified, 21-23-nucleotide long double-stranded RNAs (S. M. Elbashir, J. Martinez, A. Patkaniowska, W. Lendeckel and T. Tuschl, EMBO J., 2001, 20, 6877-6888). Once inside target cells, the RNA duplex engages with the RNA-induced silencing complex (RISC), which separates the antisense (guide) strand from the sense (passenger) strand and retains the antisense strand (G. J. Hannon, Nature, 2002, 418, 244). RISC loaded with antisense strand (also called active RISC) then binds and cleaves target mRNA, thereby silencing expression of the gene.

Strand selection is a critical step in RNAi-mediated gene silencing, as loading of the incorrect sense strand into the RISC can lead to off-target effects through silencing of irrelevant genes (N. M. Snead, J. R. Escamilla-Powers, J. J. Rossi and A. P. McCaffrey, Mol. Ther. Nucleic Acids, 2013, 2, e103; N. Vaish, F. Chen, S. Seth, K. Fosnaugh, Y. Liu, R. Adami, et al., Nucleic Acids Res., 2011, 39, 1823-1832). The strand with its 5' terminus at the thermodynamically less stable end of the duplex is selected by RISC as the antisense strand (D. S. Schwarz, G. Hutvágner, T. Du, Z. Xu, N. Aronin and P. D. Zamore, Cell, 2003, 115, 199-208). With careful design, preferential loading of the intended antisense strand can be achieved in most cases. However, potential loading of the sense strand into RISC cannot be excluded, especially when the thermodynamic asymmetry between the two ends of siRNAs is not significant. It is known that the presence of the monophosphate group at the 5' end helps anchor the antisense strand in RISC, and there is an interaction between the 5' monophosphate of the antisense strand and MID domain of the Argonaute 2—the protein component of RISC responsible for target cleavage (E. Elkayam, C.-D. Kuhn, A. Tocilj, A. D. Haase, E. M. Greene, G. J. Hannon and L. Joshua-Tor, Cell, 2012, 150, 100-110; N. T. Schirle and I. J. MacRae, Science, 2012, 336, 1037; E. Elkayam, R. Parmar, C. R. Brown, J. L. Willoughby, C. S. Theile, M. Manoharan and L. Joshua-Tor, Nucleic Acids Res., 2017, 45, 3528-3536; R. G. Parmar, C. R. Brown, S. Matsuda, J. L. S. Willoughby, C. S. Theile, K. Charisse, et al., J Med Chem, 2018, 61, 734-744). Hence, it was hypothesized that loading of the sense strand into the RISC could be impeded by blocking the 5'-phosphorylation site. Indeed, 5'-O-methylation (5'-OMe) of one of the siRNA strands has been shown to affect strand selection (P. Y. Chen, L. Weinmann, D. Gaidatzis, Y. Pei, M. Zavolan, T. Tuschl and G. Meister, R N A, 2007, 14, 263-274). An unlocked nucleic acid (UNA), a monomer that features an acyclic backbone and that is not phosphorylated by natural kinases, has also been used to block the loading of the sense strand into RISC, leading to preferential selection of the desired antisense strand. Moreover, RISC loading and RNAi activity can partially be restored by incorporating a phosphate group at the UNA modification, further strengthening the hypothesis that the 5'-phosphate group directs RISC loading (D. M. Kenski, A. J. Cooper, J. J. Li, A. T. Willingham, H. J. Haringsma, T. A. Young, et al., Nucleic Acids Res., 2010, 38, 660-671).

In this communication, a synthesis of 5'-morpholino-bearing nucleoside phosphoramidites is reported and demonstrated that the presence of a morpholino moiety at the 5' end of the sense strand improves antisense strand selection and RNAi activity. It is also shown that the morpholino modification, when placed at the 5' end of the antisense strand, results in complete loss of RNAi activity. Among a set of 5' end modifications tested, morpholino modification had the largest influence on strand selection.

Scheme 1

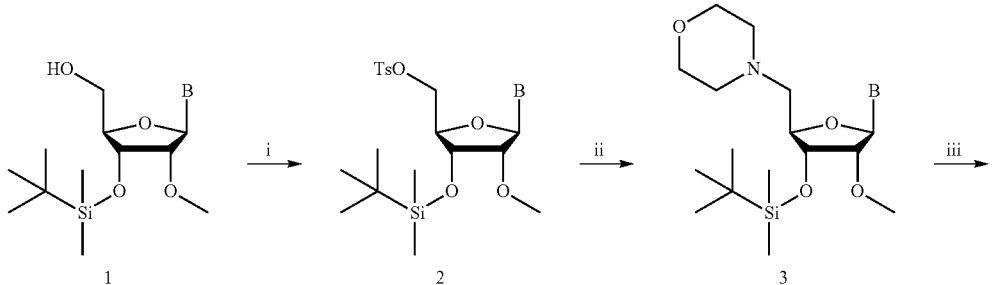

1,2 a: B = uracil-1-yl
1,2 b: B = N6-Benzoyl-adenin-9-yl
1,2 c: B = N4-Acetyl-cytosin-1-yl
1,2 d: B = N2-Isobutryl-guanin-9-yl 3 a: B = uracil-1-yl
3 b: B = Adenin-9-yl
3 c: B = N4-Benzoyl-cytosin-1-yl
3 d: B = N2-Dmf-guanin-9-yl

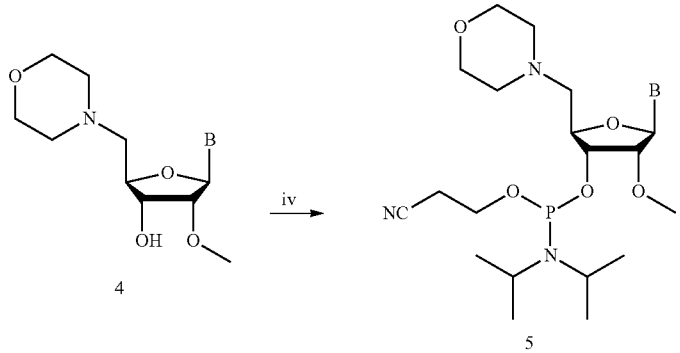

4,5 a: B = uracil-1-yl; b: B = N6-Dmf-adenin-9-yl;
c: B = N4-Benzoyl-cytosin-1-yl; d: B = N2-Dmf-guanin-9-yl Synthesis of 5'-morpholino 2'-OMe phosphoramidites. i) 2a-2d: 4-toluenesulfonyl chloride, 4-dimethylaminopyridine, CH$_2$Cl$_2$, 79%, 84%, 79%, and 56%, respectively; ii) 3a-3b: morpholine, 60° C., 66%, 78%; 3c: A) morpholine, 60° C.; B) benzoic anhydride, dimethylformamide (DMF), 66%; 3d: A) morpholine, 60° C., B) N, N-dimethylformamidedimethyl acetal, DMF, 62%; iii) 4a: tetra-n-butylammonium fluoride (TBAF), tetrahydrofuran (THF), 90%; 4b: A) N, N-dimethylformamidedimethyl acetal, DMF, B) TBAF, THF, 69%; 4c-4d: TBAF, THF, 79%, 88%, respectively; iv) 5a: 2-cyanoethyl N,N,N',N'-tetraisopropyl-phosphoriamidite, 5-(ethylthio)-1-H-tetrazole, CH$_3$CN, 65%; 5b, 5c, 5d: 2-cyanoethyl N, N-diisopropylchlorophosphordiamidite, N, N-diisopropylethylamine, CH$_2$Cl$_2$, 73%, 57%, 78%, repectively.

Initially, five different modifications that either lack the 5'-hydroxyl group or have a sterically hindered 5'-hydroxyl group with the aim of blocking 5' phosphorylation were evaluated and thus RISC loading. In order to study the impact on RNAi activity, each of these modifications was incorporated at the 5' end of the antisense or sense stand of an siRNA previously shown to silence expression of apolipoprotein B (Apob).4, 5 The tested modifications included 5'-deoxy-5'-morpholino-2'-O-methyl uridine (Mo), 5'-deoxy-5'-dimethylamino-2'-O-methyl uridine (D), 5'-deoxy-2'-O-methyl uridine (Me), locked nucleic acid (LNA), and inverted abasic site (iB) (FIG. 35).

The synthesis of 5'-morpholino-2'-OMe phosphoramidites (5a-d) was accomplished in 4 or 5 steps starting from the corresponding, 3'-O-protected nucleosides 1a-d (Scheme 1). The 5'-tosylation of 1a-d gave fully protected nucleosides 2a-d in good yields. Heating 2a-d with morpholine afforded 5'-morpholino nucleosides 3a-d. Interestingly, loss of the protecting group from the exocyclic amine of nucleobases C, A, and G was observed, probably due to the basic nature of morpholine. Therefore, protecting groups at exocyclic amines were re-installed and 3'-O-silyl protection was removed to yield the free alcohols 4a-d. 3'-Phosphitylation of 4a-d then gave the desired phosphoramidites 5a-d.

In an alternate simplified approach, 5'-morpholino-2'-O-methyl U (4a) was obtained from 2'-OMe U (6a) in two steps (Scheme 2). This route involved 5'-iodination of 6a followed by reaction of 5'-iodo-2'-OMe U (7a) with morpholine. Importantly, in the first approach, selective 5'-tosylation of unprotected 2'-OMe U could not be achieved. A similar 5'-iodination approach was extended to purine analogs, and 5'-morpholino-2'-OMe A (4b) was successfully obtained from fully unprotected 2'-OMe A (6b, Scheme 2).

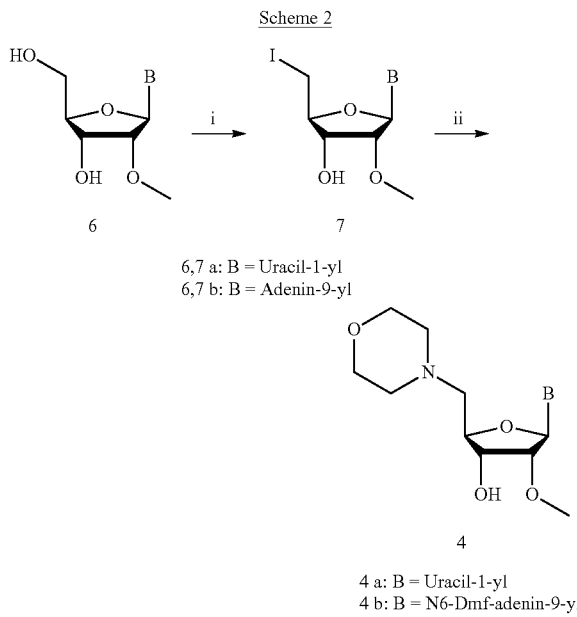

6,7 a: B = Uracil-1-yl
6,7 b: B = Adenin-9-yl 4 a: B = Uracil-1-yl
4 b: B = N6-Dmf-adenin-9-yl Simplified approach for synthesis of 5'-morpholino 2'-OMe phosphoramidites.
i) 2a, 2b: triphenylphosphine, imidazole, I$_2$, THF, 86%, 80; ii) 2a: morpholine, THF, room temperature, 62%; 2b: A) morpholine, THF, room temperature, B) N,N-dimethylformamidedimethyl acetal, MeOH, 40%.

TABLE 1 siRNAs targeting ApoB

| Entry | siRNA | siRNA duplex | SEQ ID NO: |
|---|---|---|---|
| 1 | Parent | 5'-U•g•UgAcAaAUAuGgGcAuCaA-GalNAc$_3$<br>5'-u•U•gAuGcCcAuauUuGuCaCa•a•a | 1<br>2 |
| 2 | S5'-Mo | 5'-Mou•g•UgAcAaAUAuGgGcAuCaA-GalNAc$_3$<br>5'-u•U•gAuGcCcAuauUuGuCaCa•a•a | 3<br>2 |
| 3 | S5'-D | 5'-DmAu•g•UgAcAaAUAuGgGcAuCaA-GalNAc$_3$<br>5'-u•U•gAuGcCcAuauUuGuCaCa•a•a | 4<br>2 |
| 4 | S5'-Me | 5'-Meu•g•UgAcAaAUAuGgGcAuCaA-GalNAc$_3$<br>5'-u•U•gAuGcCcAuauUuGuCaCa•a•a | 5<br>2 |
| 5 | S5'-LNA | 5'-LNAT•g•UgAcAaAUAuGgGcAuCaA-GalNAc$_3$<br>5'-u•U•gAuGcCcAuauUuGuCaCa•a•a | 6<br>2 |

TABLE 1-continued siRNAs targeting ApoB

| Entry | siRNA | siRNA duplex | SEQ ID NO: |
|---|---|---|---|
| 6 | S5'-iB | 5'-iB•g•UgAcAaAUAuGgGcAuCaA-GalNAc₃<br>5'-u•U•gAuGcCcAuauUuGuCaCa•a•a | 7<br>2 |
| 7 | AS5'-Mo | 5'-U•g•UgAcAaAUAuGgGcAuCaA-GalNAc₃<br>5'-Mou•U•gAuGcCcAuauUuGuCaCa•a•a | 1<br>8 |
| 8 | AS5'-D | 5'-U•g•UgAcAaAUAuGgGcAuCaA-GalNAc₃<br>5'-Du•U•gAuGcCcAuauUuGuCaCa•a•a | 1<br>9 |
| 9 | AS5'-Me | 5'-U•g•UgAcAaAUAuGgGcAuCaA-GalNAc₃<br>5'-Meu•U•gAuGcCcAuauUuGuCaCa•a•a | 1<br>10 |
| 10 | AS5'-LNA | 5'-U•g•UgAcAaAUAuGgGcAuCaA-GalNAc₃<br>5'-LNAT•U•gAuGcCcAuauUuGuCaCa•a•a | 1<br>11 |
| 11 | AS5'-IB | 5'-U•g•UgAcAaAUAuGgGcAuCaA-GalNAc₃<br>5'-iB•U•gAuGcCcAuauUuGuCaCa•a•a | 1<br>12 |

Conjugates of siRNA with the trivalent N-acetyl-galactosamine (GalNAc) ligand, which results in targeting of the siRNAs to hepatocytes, carrying modifications at the 5' end of the sense, antisense, or both strands (Table 1) were prepared following reported procedures. To evaluate silencing, siRNAs were transfected into primary mouse hepatocytes and Apob mRNA was quantified by RT-PCR. Gene silencing was normalized to levels of Apob in cells treated with the parent siRNA. Interestingly, siRNA conjugates with the morpholino moiety on the sense strand showed improved siRNA activity compared to the parent compound, whereas all other modifications showed activity comparable to the parent (FIG. 26). When placed at the 5' end of the antisense strand, all modifications resulted in loss of activity (FIG. 26); this is consistent with the notion that modifications that block 5' phosphorylation inhibit RISC loading. Consistent with the observation that the morpholino moiety showed the largest effect, the 5' morpholino modification on the antisense strand was the least effective of all modified siRNAs tested.

The 5'-morpholino modification was selected for in vivo studies. siRNAs with the 5'-morpholino modification on the sense strand, the antisense strand, or on both strands were compared to the siRNA without a 5' modification. Mice were treated subcutaneously with 3 mg/kg of siRNA, and cohorts were sacrificed on days 3, 7, and 15 for analysis of expression of Apob in liver. The siRNA with the 5'-morpholino on the sense strand had higher activity than the parent on day 3 (FIG. 27). These data suggest that blocking sense strand loading improves loading of antisense strand into the active RISC. The effect was less pronounced on days 7 and 15. siRNAs with the 5'-morpholino modification on the antisense strand or both strands were inactive (FIG. 27), consistent with the hypothesis that the 5'-morpholino blocks phosphorylation and impedes RISC loading.

To confirm that the loss of activity resulting from modification of the 5' end of the antisense strand with morpholino is due to impeded RISC loading, the levels of each siRNA conjugate were measured in liver as well as in RISC. The amount of siRNA in liver was not affected by the presence of 5'-morpholino modification on day 3 (FIG. 28). However, no Ago2 loading of the antisense strand with the 5'-morpholino modification was observed (FIG. 28). This demonstrates that the lack of activity of the siRNA with a 5'-modified antisense strand is due to its inability to load or remain loaded in the RISC. Furthermore, on day 3, for siRNA modified on the sense strand we observed slightly higher levels of antisense strand in the RISC than observed for the parent siRNA, consistent with improved RNAi activity. This higher level of loaded antisense strand was also seen on day 15 (FIG. 34).

To test whether the morpholino modification of the sense strand would improve activity of an siRNA targeting another gene, modified siRNAs targeting the FIX gene20 were synthesized (Table 2). Mice were treated with 1 mg/kg of siRNA subcutaneously, and circulating FIX levels were assayed on days 7, 14, and 21 post dose (FIG. 34). siRNA conjugates with the 5'-morpholino modification on the antisense strand showed complete loss of activity. siRNA conjugates with a 5'-morpholino moiety on the sense strand showed activity comparable to that of the parent compound. These results suggest generalizability of the 5'-morpholino modification.

Next, molecular modeling studies were performed. The crystal structure of the human Ago2 MID domain in complex with UMP21 (PDB ID 3LUJ) was used as a template (FIG. 33). The phosphate group was removed with the program UCSF Chimera (E. F. Pettersen, T. D. Goddard, C. C. Huang, G. S. Couch, D. M. Greenblatt, E. C. Meng and T. E. Ferrin, J. Comput. Chem., 2004, 25, 1605-1612) and replaced by a morpholino moiety. The initial model was refined using the Amber 14ff force field in combination with Gasteiger potentials as implemented in UCSF Chimera. The final model demonstrates that the morpholino modification fits well inside the MID domain binding site as indicated by only minor adjustments of adjacent amino acid side chains (FIG. 33). However, all of the interactions with the phosphate group observed in the structure with UMP are lost except for a single hydrogen bond between Lys-570 and the morpholino ring oxygen (N—H . . . . O distance of 2.35 Å). As the morpholino group is positively charged and the ether oxygen is not a potent acceptor, the stabilizing effect of this hydrogen bond is presumably negligible. Furthermore, the cationic morpholino may generate repulsive interactions with Lys-570 and Lys-533 through electronic field effects.

In summary, it is shown that by blocking phosphorylation using morpholino modification at the 5' end of the either strand of an siRNA duplex, loading and/or retention of the modified strand in the RISC was reduced. Importantly, RNAi activity and levels of the antisense strand loaded into RISC were improved by introducing a 5'-morpholino modification on the sense strand. Modification of the 5' end of the sense strand decreased its selection, making it a more efficient passenger. Our investigation confirms the earlier observations that the 5'-phosphate group plays an important role in RISC loading (S. M. Elbashir, W. Lendeckel and T. Tuschl, Genes & development, 2001, 15, 188-200; S. Weitzer and J. Martinez, Nature, 2007, 447, 222). Recently, various chemical modifications have been evaluated with the aim of mitigating potential off-target effects associated with siRNAs. These include base modifications, (S. R. Suter, A. Ball-Jones, M. M. Mumbleau, R. Valenzuela, J. Ibarra-Soza, H. Owens, et al., Org. Biomol. Chem., 2017, 15, 10029-10036) backbone modification (T. Hardcastle, I. Novosjolova, V. Kotikam, S. K. Cheruiyot, D. Mutisya, S. D. Kennedy, et al., ACS Chem. Biol., 2018, 13, 533-536) and thermally destabilizing modifications such as UNA12 and GNA (M. M. Janas, M. K. Schlegel, C. E. Harbison, V. O. Yilmaz, Y. Jiang, R. Parmar, et al., Nature Commun., 2018, 9). The 5'-morpholino modification reported here presents an alternative effective strategy to nullify the off-target effects originating from loading of sense strand into RISC complex.

General synthetic details: Commercially available starting materials, reagents, and solvents were used as received. All moisture-sensitive reactions were carried under anhydrous conditions under argon atmosphere. Flash chromatography was performed on a Teledyne ISCO Combi Flash system using pre-packed ReadySep Teledyne ISCO silica gel columns. TLC was performed on Merck silica-coated plates 60 F254. Compounds were visualized under UV light (254 nm) or after spraying with the p-anisaldehyde staining solution followed by heating. ESI-HRMS spectra were recorded on Waters QTof API US spectrometer using the direct flow injection in the positive mode (capillary=3000 kV, cone=35, source temperature=120° C., and desolvation temperature=350° C.). $^1$H and $^{13}$C NMR spectra were recorded at room temperature on Varian spectrometers, and chemical shifts in ppm are referenced to the residual solvent peaks. Coupling constants are given in Hertz. Signal splitting patterns are described as singlet (s), doublet (d), triplet (t), quartet (q), broad signal (br), or multiplet (m). 31P NMR spectra were recorded under proton-decoupled mode; chemical shifts are referenced to external $H_3PO_4$ (80%).

Nucleoside 2a was syntehszied as follows:

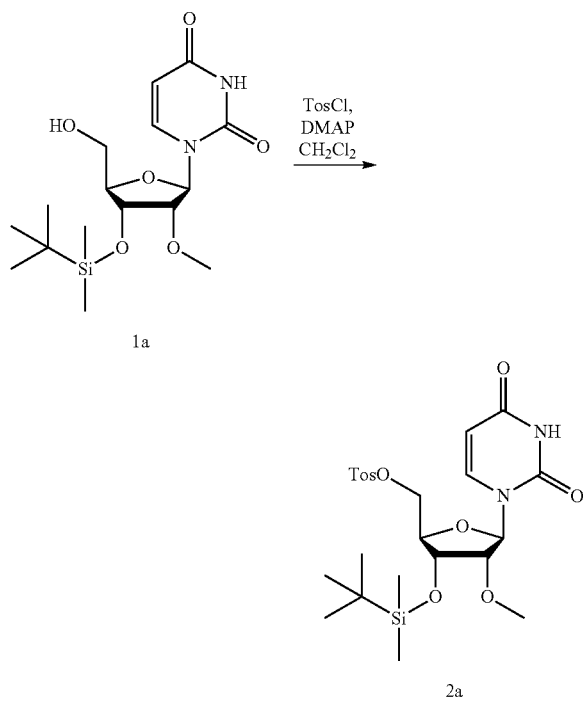

Alcohol 1a (7.45 g, 20 mmol) and 4-dimethyaminopyridine (DMAP, 4.89 g, 40 mmol) were dissolved in dry $CH_2Cl_2$. 4-Methylbenzenesufonyl chloride (TosCl, 5.72 g, 30 mmol) was added at 0° C. (ice bath), and the reaction mixture was stirred at 0° C. for 1 h and then at room temperature for 2 h. The reaction was quenched by adding saturated aqueous $NaHCO_3$ (150 mL) and extracted with $CH_2Cl_2$ (2×100 mL). The combined organic phases were dried ($MgSO_4$), and the crude product was purified by flash chromatography using a gradient of 0-70% EtOAc in hexanes to afford nucleoside 2a (8.40 g, 79%) as a white form. MS (ESI$^+$) m/z calcd for $C_{23}H_{35}N_2O_8SSi$ [M+H]$^+$ 527.1878, found 527.1883. $^1$H (400 MHZ, dmso) δ 11.40 (d, J=2.2 Hz, 1H), 7.88-7.73 (m, 2H), 7.52 (d, J=8.1 Hz, 1H), 7.48 (d, J=8.0 Hz, 2H), 5.73 (d, J=4.3 Hz, 1H), 5.60 (dd, J=8.1, 2.2 Hz, 1H), 4.21 (dd, J=8.9, 4.5 Hz, 2H), 4.15 (d, J=5.4 Hz, 1H), 3.92-3.90 (m, J=5.5, 3.5 Hz, 1H), 3.86 (t, J=4.8 Hz, 1H), 3.30 (s, 3H), 2.40 (s, 3H), 0.81 (s, 9H), 0.03 (s, 3H), 0.01 (s, 3H). $^{13}$C (126 MHz, dmso) δ 162.97, 150.27, 145.31, 140.47, 131.82, 130.24, 127.69, 102.04, 87.49, 80.90, 80.77, 69.49, 68.88, 57.63, 25.51, 21.09, 17.66, −4.89, −5.25.

Nucleoside2 b was syntehszied as follows:

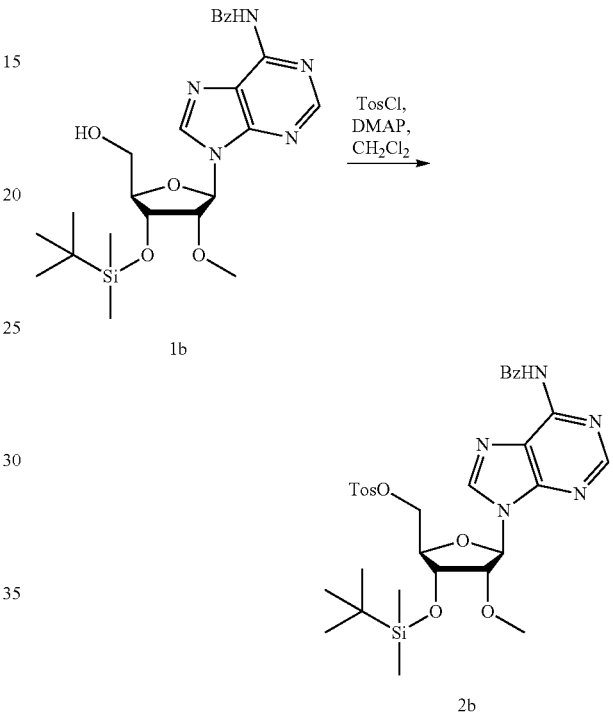

Alcohol 1b (1.00 g, 2.00 mmol) and 4-dimethylaminopyridine (DMAP, 0.49 g, 3.00 mmol) were dissolved in dry $CH_2Cl_2$ (20 mL), and the reaction mixture was cooled to 0-4° C. (ice bath). 4-Toluenesulfonyl chloride (TosCl, 0.48 g, 2.50 mmol) was added, and reaction mixture was stirred at 0° C. (ice bath) for 1 h and then at room temperature for 3 h. The reaction was diluted with $CH_2Cl_2$ (100 mL), washed with saturated aqueous $NaHCO_3$ (100 mL), dried, and concentrated. The residue was purified by column chromatography using a gradient of 0-4% MeOH in $CH_2Cl_2$ to obtain 2b (1.10 g, 84%) as a white foam. MS (ESI$^+$) m/z calcd for $C_{31}H_{40}N_5O_7SSi$ [M+H]$^+$ 654.2412, found 654.2423. $^1$H (400 MHZ, dmso) δ 11.24 (s, 1H), 8.69 (s, 1H), 8.61 (s, 1H), 8.11-7.99 (m, 2H), 7.73-7.68 (m, 2H), 7.68-7.62 (m, 1H), 7.56 (dd, J=8.3, 6.8 Hz, 2H), 7.42-7.29 (m, 2H), 6.10 (d, J=5.2 Hz, 1H), 4.61 (t, J=4.4 Hz, 1H), 4.55 (t, J=5.0 Hz, 1H), 4.37-4.28 (m, 2H), 4.09-4.06 (m, 1H), 3.29 (s, 3H), 2.35 (s, 3H), 0.87 (s, 9H), 0.10 (s, 3H), 0.08 (s, 3H). $^{13}$C (126 MHz, dmso) δ 165.59, 151.73, 151.60, 150.53, 145.09, 143.34, 133.25, 132.46, 131.85, 129.99, 128.47, 128.44, 127.49, 125.90, 85.93, 81.98, 80.90, 69.93, 69.23, 57.71, 25.54, 20.99, 17.70, −4.92, −5.12.

Nucleoside 2c was syntehszied as follows:

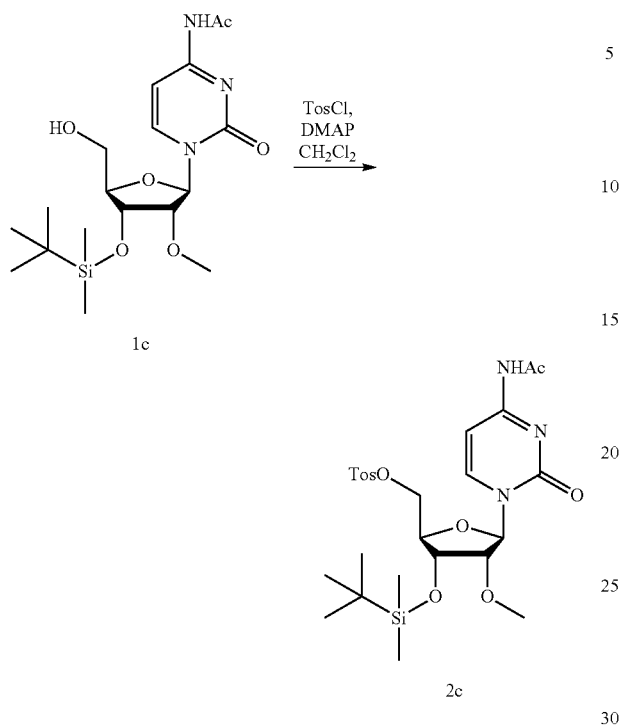

Alcohol 1c (2.50 g, 6.04 mmol) and 4-dimethylamino-pyridine (DMAP, 1.47 g, 12.03 mmol) were taken in dry CH$_2$Cl$_2$ (50 mL) and reaction mixture was cooled to 0-4° C. (ice bath). 4-Toluenesulfonyl chloride (TosCl, 1.44 g, 7.55 mmol) was added and reaction mixture was stirred in ice bath for 3 h. The reaction was diluted with CH$_2$Cl$_2$ (100 mL), washed with saturated aqueous NaHCO$_3$ (2×30 mL), dried, and concentrated. The residue was purified by column chromatography using a gradient of 0-5% MeOH in CH$_2$Cl$_2$ to obtain 2c (2.71 g, 79%) as a white foam. MS (ESI$^+$) m/z calcd for C$_{25}$H$_{38}$N$_3$O$_8$SSi [M+H]$^+$ 568.2143, found 568.2144. 1H (400 MHZ, dmso) δ 10.94 (s, 1H), 7.85 (d, J=7.5 Hz, 1H), 7.81 (d, J=8.3 Hz, 2H), 7.49 (d, J=8.1 Hz, 2H), 7.12 (d, J=7.5 Hz, 1H), 5.78 (d, J=2.2 Hz, 1H), 4.30 (dd, J=11.4, 2.8 Hz, 1H), 4.24 (dd, J=11.4, 4.9 Hz, 1H), 4.09 (dd, J=7.6, 4.9 Hz, 1H), 4.05-3.98 (m, 1H), 3.80 (dd, J=4.9, 2.3 Hz, 1H), 3.40 (s, 3H), 2.41 (s, 3H), 2.10 (s, 3H), 0.79 (s, 9H), 0.02 (s, 3H), −0.01 (s, 3H). $^{13}$C (101 MHZ, dmso) δ 171.04, 162.45, 154.18, 145.40, 144.50, 131.73, 130.28, 127.66, 95.43, 89.09, 81.95, 80.29, 69.12, 68.37, 57.78, 25.46, 24.34, 21.09, 17.59, −4.88, −5.39.

Nucleoside 2d was syntehszied as follows:

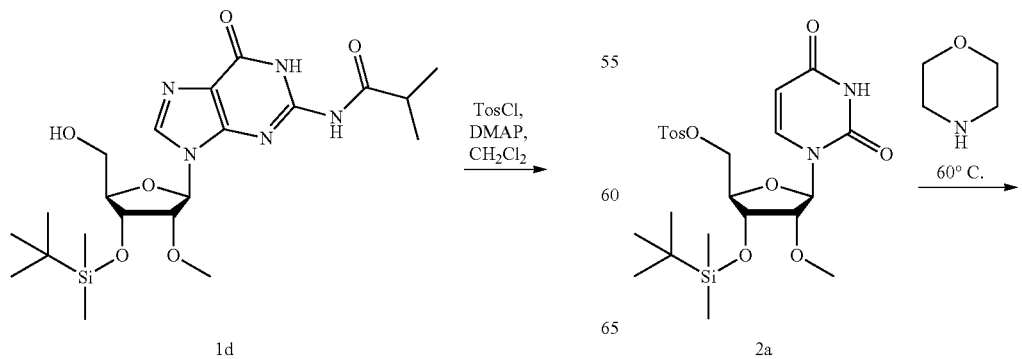

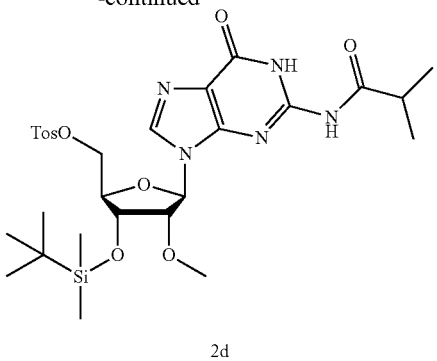

Alcohol 1d (4.81 g, 10 mmol) and 4-dimethylaminopyridine (DMAP, 2.45 g, 20 mmol) were dissolved in dry CH$_2$Cl$_2$ (40 mL). 4-Toluenesulfonyl chloride (TosCl, 2.86 g, 15 mmol) was added at 0° C. (ice bath) and the reaction mixture was stirred at 0° C. for 1 h and then at room temperature for 2 h. The reaction was quenched by adding saturated aqueous NaHCO$_3$ (100 mL) and extracted with CH$_2$Cl$_2$ (2× 60 mL). The combined organic phases were dried (MgSO$_4$), and the crude product was purified by column chromatography using a gradient of 0-4% MeOH in CH$_2$Cl$_2$ to afford nucleoside 2d (3.60 g, 56%) as a white form. MS (ESI$^+$) m/z calcd for C$_{28}$H$_{42}$N$_5$O$_8$SSi [M+H]$^+$ 636.2518, found 636.2521. 1H (400 MHZ, dmso) δ 12.08 (s, 1H), 11.53 (s, 1H), 8.17 (s, 1H), 7.81-7.70 (m, 2H), 7.40 (d, J=8.1 Hz, 2H), 5.83 (d, J=5.3 Hz, 1H), 4.37-4.30 (m, 2H), 4.27-4.22 (m, 2H), 4.03-4.00 (m, 1H), 3.27 (s, 3H), 2.77-2.73 (m, 1H), 2.38 (s, 3H), 1.11 (d, J=6.8 Hz, 6H), 0.85 (s, 9H), 0.07 (s, 3H), 0.06 (s, 3H). $^{13}$C (126 MHz, dmso) δ 180.04, 154.75, 148.71, 148.24, 145.19, 137.33, 131.93, 130.10, 127.57, 120.19, 84.52, 82.49, 81.26, 69.92, 69.49, 57.83, 34.77, 25.56, 21.06, 18.85, 18.83, 17.72, −4.96, −5.12.

Nucleoside 3a was syntehszied as follows:

-continued

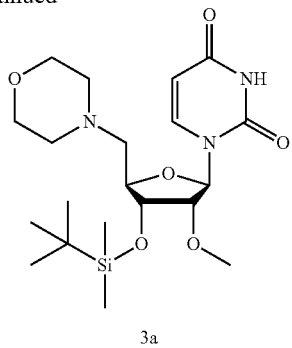

3a

Nucleoside 2a (2.0 g, 3.79 mmol) was dissolved in morpholine (25 mL), and the reaction mixture was stirred at 60° C. for 18 h. Solvent was removed at reduced pressure, and the residue was dissolved in CH$_2$Cl$_2$ (100 mL) and washed with H$_2$O (50 ml). The aqueous phase was back extracted with CH$_2$Cl$_2$ (2×30 mL), and the combined organic phases were dried (MgSO$_4$) and concentrated, and the crude was purified by column chromatography using a gradient of 0-5% MeOH in CH$_2$Cl$_2$ to afford nucleoside 3a (1.1 g, 66%) as white powder. MS (ESI$^+$) m/z calcd for C$_{20}$H$_{36}$N$_3$O$_6$Si [M+H]$^+$ 442.2368, found 442.2378. $^1$H (400 MHZ, dmso) δ 11.37 (s, 1H), 7.69 (d, J=8.1 Hz, 1H), 5.78 (d, J=4.5 Hz, 1H), 5.67 (d, J=8.0 Hz, 1H), 4.15 (t, J=5.2 Hz, 1H), 3.90-3.85 (m, 2H), 3.55 (t, J=4.6 Hz, 4H), 3.32 (s, 3H), 2.59 (dd, J=13.5, 5.1 Hz, 1H), 2.47-2.42 (m, 5H), 0.87 (s, 9H), 0.09 (s, 6H). $^{13}$C (101 MHz, DMSO) δ 162.96, 150.35, 140.90, 102.11, 87.07, 81.46, 80.92, 71.66, 66.14, 59.73, 57.42, 54.01, 25.61, 17.76, −4.70, −4.99.

Nucleoside 2b was syntehszied as follows:

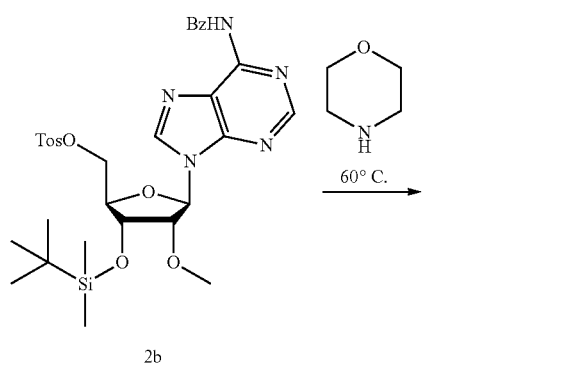

2b

3b

Nucleoside 2b (2.4 g, 3.6 mmol) was dissolved in morpholine (20 mL), and the reaction mixture was stirred at 60° C. for 16 h. Solvents were removed at reduced pressure, and the residue was dissolved in CH$_2$Cl$_2$ (50 mL) and washed with saturated aqueous NaHCO$_3$ (50 mL). The aqueous phase was back extracted with CH$_2$Cl$_2$ (2× 30 mL). The combined organic phases were concentrated, and the residue was purified by column chromatography using a gradient of 0-7% MeOH in CH$_2$Cl$_2$ to yield nucleoside 3b (1.35 g, 78%) as a white foam. MS (ESI$^+$) m/z calcd for C21H37N6O4Si [M+H]+ 465.2640, found 465.2630. 1H NMR (400 MHZ, CDCl$_3$) δ 8.33 (s, 1H), 7.94 (s, 1H), 5.99 (d, J=3.4 Hz, 1H), 5.79 (s, 2H), 4.50 (dd, J=6.2, 5.0 Hz, 1H), 4.37 (dd, J=5.1, 3.4 Hz, 1H), 4.24-4.15 (m, 1H), 3.70 (t, J=4.7 Hz, 4H), 3.46 (s, 3H), 2.69 (dd, J=5.5, 3.6 Hz, 2H), 2.63-2.45 (m, 4H); 0.94 (s, 9H), 0.14 (s, 3H), 0.13 (s, 3H). δ C (101 MHz, CDCl$_3$) 155.74, 153.18, 149.69, 140.18, 120.75, 87.98, 82.58, 81.99, 72.77, 67.05, 60.89, 58.67, 54.75, 25.97, 18.38, −4.28, −4.56.

Nucleoside 3c was syntehszied as follows:

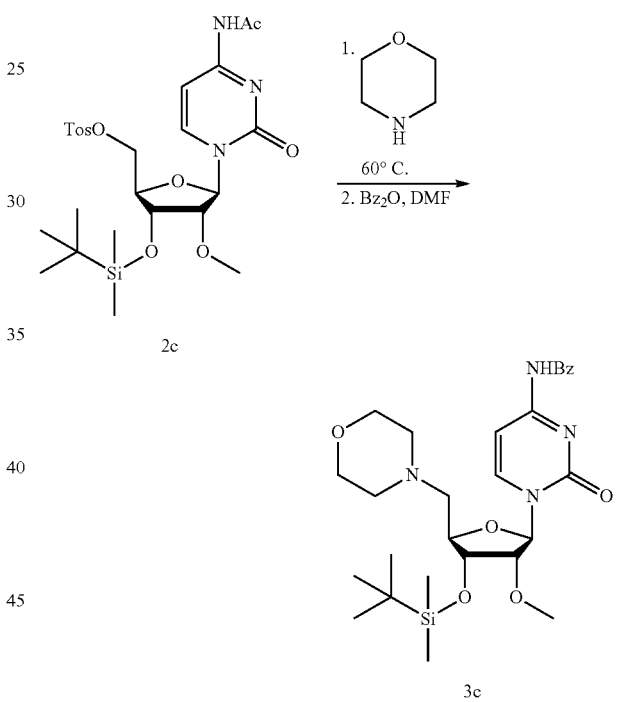

2c

3c

Nucleoside 2c (3.7 g, 6.51 mmol) was dissolved in morpholine (20 mL). The resulting solution was heated at 60° C. for 24 h. Solvents were removed, and the crude was purified by column chromatography using a gradient of 0-12% MeOH in CH$_2$Cl$_2$. The isolated product (3.5 g) was dissolved DMF (15 mL). To this solution was added benzoic anhydride (1.61 g, 7.11 mmol), and the reaction mixture was stirred at room temperature for 16 h. Solvent was removed, and the residue was dissolved in EtOAc (100 mL) and washed with H$_2$O (2×50 mL). The combined aqueous phases were back extracted with EtOAc (50 mL), and the combined organic phases were dried (MgSO$_4$) and concentrated at reduced pressure. The residue was purified by column chromatography using a gradient of 0-5% MeOH in CH$_2$Cl$_2$ to afford nucleoside 3c (2.35 g, 66% over 2 steps) as white foam. MS (ESI$^+$) m/z calcd for C$_{27}$H$_{41}$N$_4$O$_6$Si [M+H]+ 545.2790, found 545.2791. 1H (400 MHZ, dmso) δ 11.33 (s, 1H), 8.24 (d, J=7.5 Hz, 1H), 8.03-7.97 (m, 2H), 7.65-7.58 (m, 1H), 7.55-7.47 (m, 2H), 7.40 (d, J=7.5 Hz, 1H), 5.88 (d, J=2.8 Hz, 1H), 4.08 (dd, J=7.1, 4.9 Hz, 1H), 3.98 (dt, J=6.9, 5.1 Hz, 1H), 3.83 (dd, J=5.0, 2.8 Hz, 1H), 3.58 (t, J=4.6 Hz, 4H), 3.42 (s, 3H), 2.63 (d, J=5.1 Hz, 2H), 2.52-2.43 (m, 5H), 0.87 (s, 9H), 0.08 (s, 6H). $^{13}$C (101 MHz, dmso) δ 167.55, 163.09, 154.18, 145.29, 133.11, 132.71, 129.20, 128.43, 96.54, 88.72, 82.17, 81.29, 71.47, 66.17, 59.46, 57.57, 54.07, 25.59, 17.72, −4.65, −5.08.

Synthesis of nucleoside 3d: Nucleoside 2d (1.4 g, 2.20 mmol) was dissolved in morpholine (20 mL). The resulting solution was heated at 60° C. for 40 h. Solvent was removed, and the crude was dissolved in CHCl$_3$ (100 mL) and washed with H$_2$O (50 mL). The aqueous phase was back extracted with CHCl$_3$ (50 mL), and the combined organic phases were dried (MgSO$_4$) and concentrated at reduced pressure. The residue was dissolved in MeOH (15 mL) and to this was added dimethylformamide dimethyl acetal (DMF-DMA, 380 mg, 3.2 mmol). The resulting reaction mixture was stirred at room temperature for 18 h. The solvents were removed, and the crude was purified by column chromatography using a gradient of 0-6% MeOH in CH$_2$Cl$_2$ to afford nucleoside 3d (0.78 g, 66%) as a white foam. MS (ESI$^+$) m/z calcd for C$_{24}$H$_{42}$N$_7$O$_5$Si [M+H]$^+$ 536.3011, found 536.2994. 1H (400 MHZ, dmso) δ 11.37 (s, 1H), 8.51 (s, 1H), 8.06 (s, 1H), 5.87-5.86 (m, 1H), 4.41 (d, J=3.6 Hz, 2H), 3.96 (td, J=6.1, 2.6 Hz, 1H), 3.53 (t, J=4.6 Hz, 4H), 3.28 (s, 3H), 3.14 (s, 3H), 3.03 (s, 3H), 2.64 (dd, J=13.3, 5.9 Hz, 1H), 2.54-2.49 (m, 1H), 2.46-2.34 (m, 4H), 0.90 (s, 9H), 0.12 (s, 6H). $^{13}$C (101 MHz, DMSO) δ 157.76, 157.50, 157.23, 149.72, 137.28, 120.02, 85.23, 82.41, 81.05, 72.18, 66.15, 60.14, 57.54, 53.91, 40.69, 34.63, 25.66, 17.84, −4.68, −4.86.

Nucleoside 4a was syntehszied as follows:

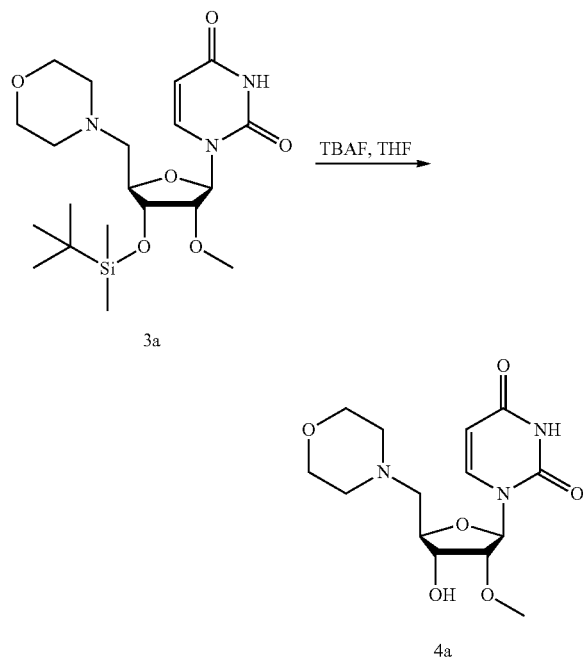

3a

4a

Nucleoside 3a (500 mg, 1.13 mmol) was dissolved in THF (5 mL). To this was added tetra-n-butylammonium fluoride (TBAF, 1 M in THF, 1.5 mL, 1.5 mmol). The reaction mixture was stirred at room temperature for 1 h. Solvents were removed, and the residue was purified by column chromatography using a gradient of 0-5% MeOH in EtOAc to obtain alcohol 4a (320 mg, 86%) as white amorphous powder. MS (ESI$^+$) m/z calcd for C$_{14}$H$_{22}$N$_3$O$_6$ [M+H]$^+$ 328.1503, found 328.1501. 1H NMR (500 MHz, DMSO) δ 11.35 (d, J=2.2 Hz, 1H), 7.71 (d, J=8.1 Hz, 1H), 5.76 (d, J=4.0 Hz, 1H), 5.65 (dd, J=8.0, 2.1 Hz, 1H), 5.18 (d, J=6.5 Hz, 1H), 3.94 (q, J=6.0 Hz, 1H), 3.88 (td, J=6.4, 3.9 Hz, 1H), 3.79 (dd, J=5.2, 4.1 Hz, 1H), 3.55 (t, J=4.7 Hz, 4H), 3.36 (s, 3H), 2.63 (dd, J=13.6, 3.9 Hz, 1H), 2.56-2.36 (m, 5H). δ C (101 MHz, DMSO) 163.00, 150.31, 140.79, 101.96, 87.07, 81.63, 81.48, 70.23, 66.14, 59.88, 57.63, 53.99.

Nucleoside 4b was syntehszied as follows:

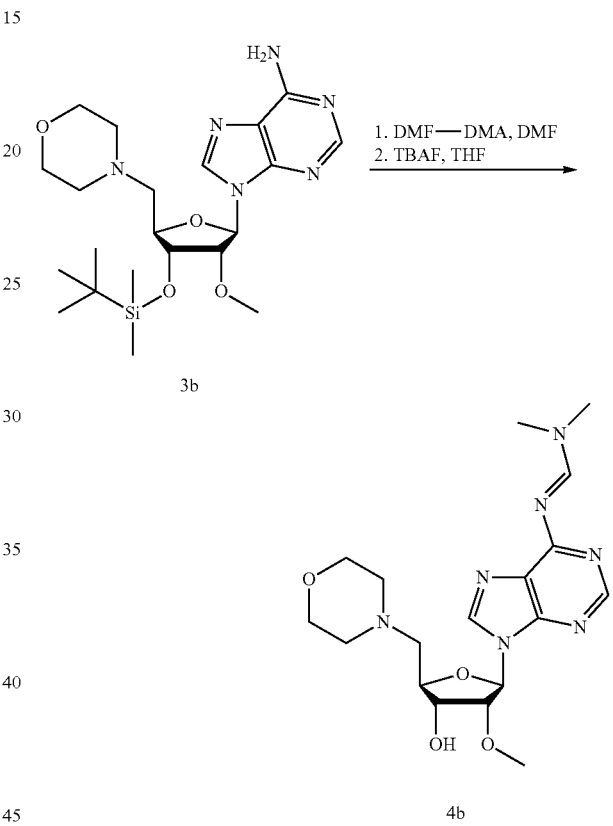

3b

4b

To a solution of nucleoside 3b (1.3 g, 2.79 mmol) in DMF (10 mL) was added dimethylformamide dimethyl acetal (DMF-DMA, 0.75 mL, 5.60 mmol). The reaction mixture was stirred at 50° C. for 5 h. The solvent was removed at reduced pressure, and the crude was dissolved in THF (6 mL). TBAF (1M in THF, 3.3 mL, 3.3 mmol) was added, and the reaction mixture was stirred at room temperature for 2 h. The solvent was removed at reduced pressure, and the residue was purified by column chromatography using a gradient of 0-7% MeOH in CH$_2$Cl$_2$ to yield 4b (0.81 g, 69%) as a white foam. MS (ESI$^+$) m/z calcd for C$_{18}$H$_{28}$N$_7$O$_4$ [M+H]$^+$ 406.2197, found 406.2209. 1H NMR (400 MHZ, DMSO) δ 8.90 (s, 1H), 8.47 (s, 1H), 8.42 (s, 1H), 6.02 (d, J=5.0 Hz, 1H), 5.29 (d, J=6.0 Hz, 1H), 4.41 (t, J=5.0 Hz, 1H), 4.31 (q, J=5.2 Hz, 1H), 4.04-4.00 (m, 1H), 3.52 (t, J=4.4 Hz, 4H), 3.34 (s, 3H), 3.19 (s, 3H), 3.12 (s, 3H), 2.67 (dd, J=13.4, 4.3 Hz, 1H), 2.54 (dd, J=13.4, 7.0 Hz, 1H), 2.44-2.33 (m, 4H). $^{13}$C (126 MHz, DMSO) δ 159.27, 157.97, 152.00, 151.19, 141.46, 125.68, 85.60, 82.28, 81.50, 70.51, 66.11, 60.39, 57.62, 53.85, 40.63, 34.53.

Nucleoside 4c was syntehszied as follows:

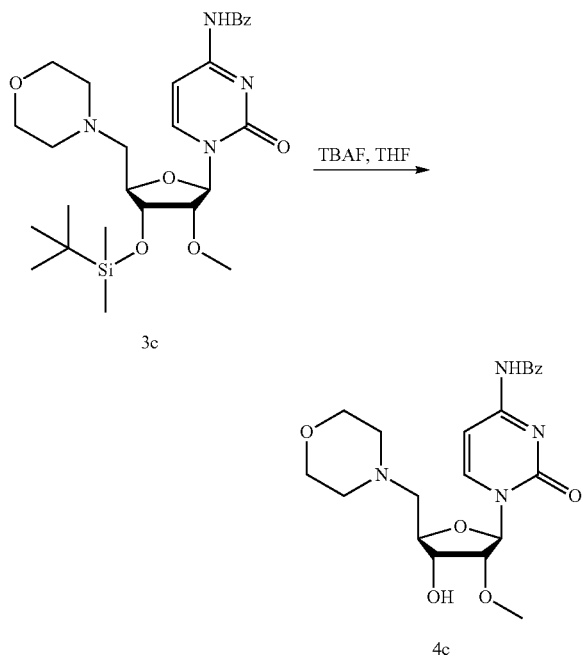

Protected nucleoside 3c (2.35 g, 1.13 mmol) was dissolved in THF (10 mL). To this was added tetra-n-butylammonium fluoride (TBAF, 1M in THF, 6.5 mL, 6.5 mmol). The reaction mixture was stirred at room temperature for 1 h. Solvents were removed, and the residue was purified by column chromatography using a gradient of 0-8% MeOH in EtOAc to obtain alcohol 4c (1.48 g, 80%) as a white foam. MS (ESI$^+$) m/z calcd for $C_{21}H_{27}N_4O_6$ [M+H]$^+$ 431.1925, found 431.1936. 1H NMR (500 MHz, DMSO) δ 11.30 (s, 1H), 8.30 (d, J=7.6 Hz, 1H), 8.04-7.94 (m, 2H), 7.62 (t, J=7.4 Hz, 1H), 7.51 (t, J=7.7 Hz, 2H), 7.39 (d, J=7.5 Hz, 1H), 5.84 (d, J=2.0 Hz, 1H), 5.18 (d, J=7.0 Hz, 1H), 3.99-3.95 (m, 1H), 3.90-3.86 (m, 1H), 3.73 (dd, J=5.0, 2.1 Hz, 1H), 3.58 (t, J=4.7 Hz, 4H), 3.47 (s, 3H), 2.71 (dd, J=13.8, 3.1 Hz, 1H), 2.63 (dd, J=14.0, 6.5 Hz, 1H), 2.56-2.41 (m, 4H), δ C (101 MHz, DMSO) 167.50, 163.07, 154.13, 145.19, 133.13, 132.70, 129.21, 128.43, 128.40, 96.36, 88.74, 82.81, 81.31, 70.09, 66.24, 59.36, 57.86, 54.12.

Nucleoside 4d was syntehszied as follows:

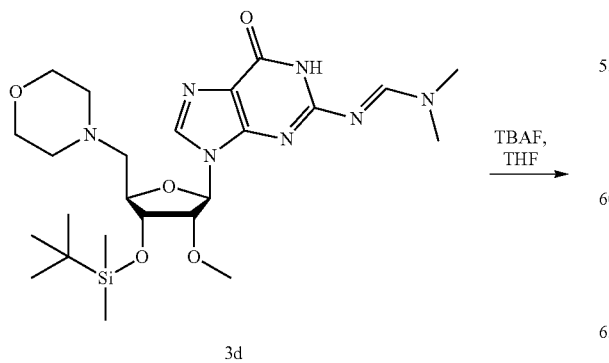

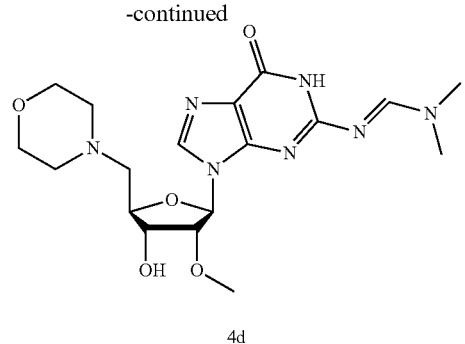

To a solution of 3 (0.63 g, 1.25 mmol) in THF (5 mL) was added tetra-n-butylammonium fluoride (TBAF, 1M in THF, 1.5 mL, 1.5 mmol). The reaction mixture was stirred at room temperature for 2 h. The solvent was removed at reduced pressure, and the residue was purified by column chromatography using a gradient of 0-8% MeOH in CH$_2$Cl$_2$ to yield 4d (0.46 g, 88%) as a white foam. MS (ESI$^+$) m/z calcd for $C_{18}H_{28}N_7O_5$ [M+H]$^+$ 422.2146, found 422.2154. 1H NMR (400 MHZ, DMSO) δ 11.35 (s, 1H), 8.54 (s, 1H), 8.03 (s, 1H), 5.87 (d, J=5.1 Hz, 1H), 5.28 (d, J=5.4 Hz, 1H), 4.24 (dt, J=12.5, 5.0 Hz, 2H), 4.00-3.96 (m, 1H), 3.53 (t, J=4.6 Hz, 4H), 3.34 (s, 3H), 3.15 (s, 3H), 3.03 (s, 3H), 2.65 (dd, J=13.3, 4.7 Hz, 1H), 2.55-2.50 (m, 1H), 2.40 (dt, J=9.2, 4.9 Hz, 4H). $^{13}$C NMR (126 MHz, DMSO) δ 157.87, 157.52, 157.28, 149.79, 136.79, 119.76, 84.84, 82.34, 81.87, 70.52, 66.12, 60.54, 57.55, 53.85, 40.70, 34.67.

Nucleoside 5a was syntehszied as follows:

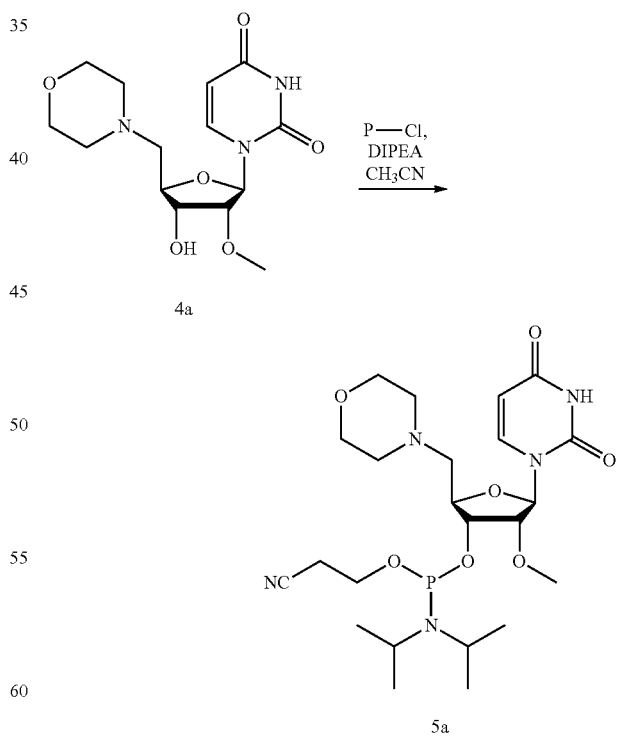

To a solution of 4a (6.2 gm, 18 mmol) in dry CH$_3$CN (60 mL) was added ethyl thiotetrazole (2.4 g, 18 mmol). 2-Cyanoethyl N, N, N',N'-tetraisopropylphosphordiamidite (6.8 gm, 22 mmol,) was added slowly to the reaction mixture and stirred at room temperature for 3 h. The reaction mixture was filtered and purified by column chromatography using a gradient of EtOAc in hexanes containing 0.2% triethylamine to yield 5a (5.0 g, 50%). MS (ESI$^+$) m/z calcd for C$_{23}$H$_{39}$N$_5$O$_7$P [M+H]+ 528.2582, found 528.2592. $^{31}$P NMR (202 MHZ CD$_3$CN) δ 151.04, 150.76.

Nucleoside 5a was syntehszied as follows:

Nucleoside 5ca was syntehszied as follows:

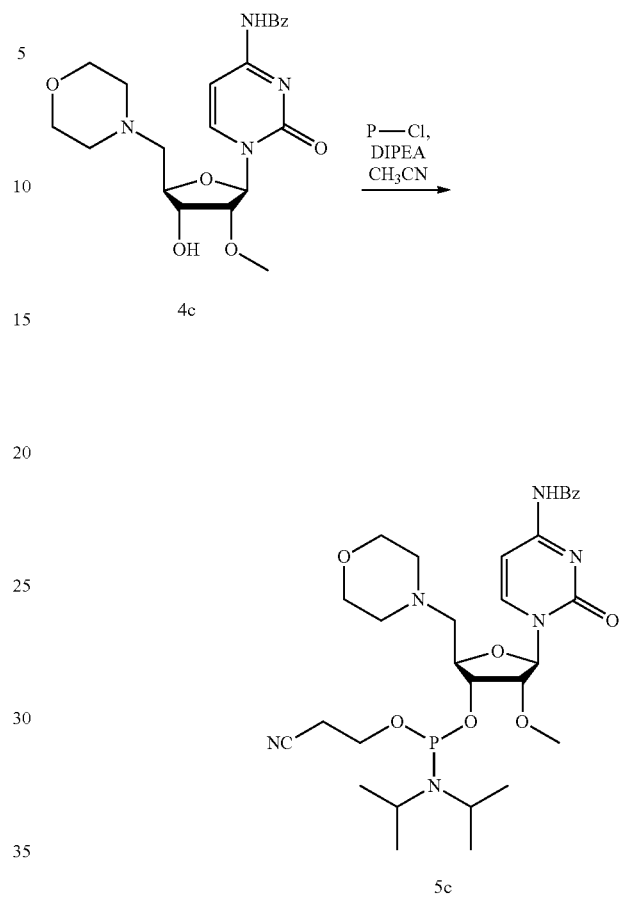

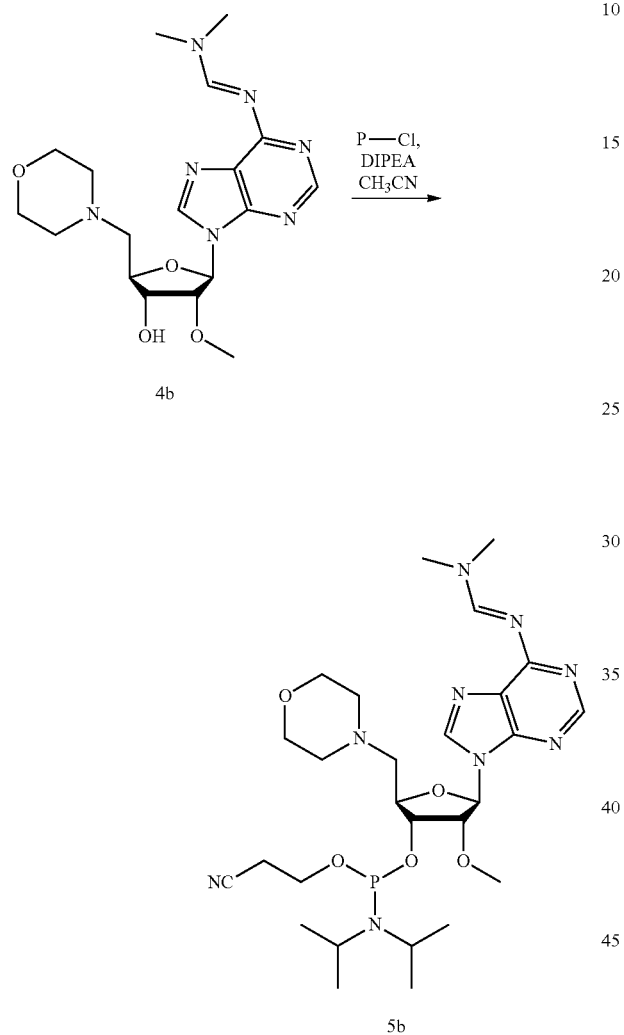

Nucleoside 4b (0.82 g, 1.35 mmol) was co-evaporated with dry CH$_3$CN and re-dissolved in dry CH$_3$CN (6 mL). N, N-diisopropylethylamine (DIPEA, 1.0 g, 7.73 mmol) and 2-cyanoethyl N,N-diisopropylchlorophosphoramidite (P—Cl, 0.95 g, 4.03 mmol) were added, and the reaction mixture was stirred at room temperature for 2 h. The reaction mixture was diluted with CH$_2$Cl$_2$ (50 mL) and washed with saturated aqueous NaHCO$_3$ (20 mL) followed by brine (20 mL). The combined aqueous phase was back extracted with CH$_2$Cl$_2$ (20 mL), and the combined organic phase was dried (MgSO$_4$) and concentrated under reduced pressure. The residue was purified by column chromatography using a gradient of 0-3% MeOH in CH$_2$Cl$_2$ (containing 0.2% Et$_3$N) to obtain phosphoramidite 5b (0.90 g, 73%) as a white foam. MS (ESI$^+$) m/z calcd for C$_{27}$H$_{45}$N$_9$O$_5$P [M+H]$^+$ 606.3276, found 606.3286. $^{31}$P (202 MHz, CD$_3$CN) δ 151.04, 150.70

Nucleoside 4c (0.50 g, 1.16 mmol) was co-evaporated with dry CH$_3$CN (5 mL) and re-dissolved in dry CH$_3$CN (5 mL). N, N-diisopropylethylamine (DIPEA, 0.60 g, 4.64 mmol) and 2-cyanoethyl N,N-diisopropylchlorophosphoramidite (P-Cl, 0.55 g, 2.32 mmol) were added, and the reaction mixture was stirred at room temperature for 2 h. The solvents were evaporated under reduced pressure, and the crude was purified by column chromatography using a gradient of 0-2% MeOH in CH$_2$Cl$_2$ (containing 0.2% Et$_3$N) to obtain phosphoramidite 5c (0.40 g, 57%) as a white foam. MS (ESI$^+$) m/z calcd for C$_{30}$H$_{44}$N$_6$O$_7$P [M+H]$^+$ 631.3004, found 631.3034. 31P (202 MHz, CD$_3$CN) δ 151.25, 150.89.

Nucleoside 5d was syntehszied as follows:

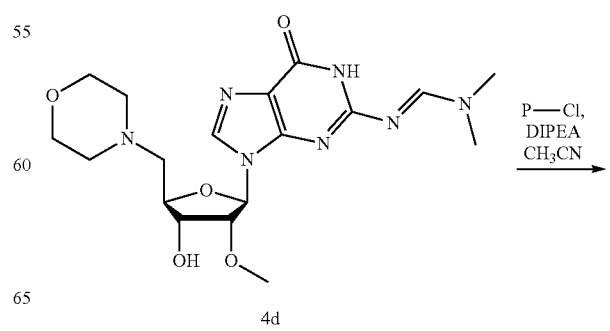

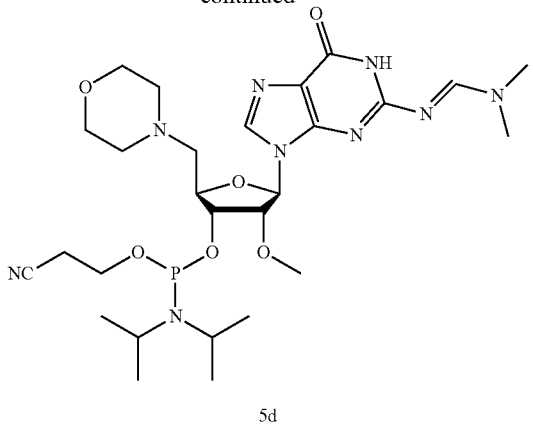

5d

Nucleoside 4d (0.40 g, 0.95 mmol) was co-evaporated with dry CH$_3$CN and re-dissolved in dry CH$_3$CN (5 mL). N,N-diisopropylethylamine (DIPEA, 0.60 g, 4.64 mmol) and 2-cyanoethyl N,N-diisopropylchlorophosphoramidite (P-Cl, 0.66 g, 2.78 mmol) were added, and the reaction mixture was stirred at room temperature for 2 h. The reaction mixture was diluted with CH$_2$Cl$_2$ (50 mL) and washed with saturated aqueous NaHCO$_3$ (20 mL) followed by brine (20 mL). The combined aqueous phase was back extracted with CH$_2$Cl$_2$ (20 mL), and the combined organic phases were dried (MgSO$_4$) and concentrated under reduced pressure. The residue was purified by column chromatography using a gradient of 0-3% MeOH in CH$_2$Cl$_2$ (containing 0.2% Et$_3$N) to obtain phosphoramidite 5d (460 mg, 77%). MS (ESI$^+$) m/z calcd for C$_{27}$H$_{45}$N$_9$O$_6$P [M+H]$^+$ 622.3225, found 622.3240. $^{31}$P (202 MHz, CD$_3$CN) δ 151.24, 150.89.

Nucleoside 7a was syntehszied as follows:

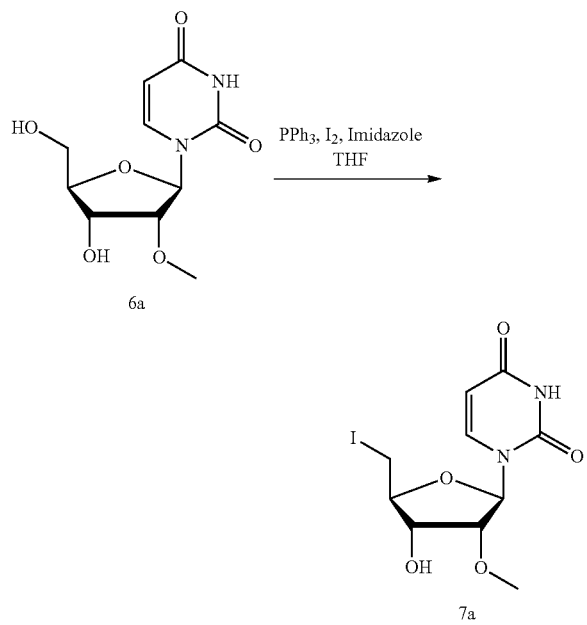

2'-O-Methyluridine (6a, 2.58 g, 10 mmol), imidazole (1.36 g, 20 mmol), and triphenylphosphine (3.93 g, 15 mmol) were suspended in dry THF (50 mL). To this was added a solution of iodine (3.16 g, 12.5 mmol) in THF (20 mL) dropwise at 0° C. The reaction mixture was slowly warmed to room temperature and stirred for another 3 h. The solvent was removed at reduced pressure, and the residue was purified by column chromatography using a gradient of 0-7% MeOH in CH$_2$Cl$_2$ to afford the desired nucleoside 7a (3.26 g, 86%) as a pale-yellow foam. MS (ESI$^+$) m/z calcd for C10H14IN2O5 [M+H]$^+$ 368.9942, found 368.9951. 1H NMR (400 MHZ, DMSO) δ 11.40 (d, J=2.1 Hz, 1H), 7.67 (d, J=8.1 Hz, 1H), 5.85 (d, J=5.4 Hz, 1H), 5.68 (dd, J=8.1 Hz, 2.2 Hz, 1H), 5.44 (d, J=6.0 Hz, 1H), 4.04-4.00 (m, 1H), 3.97 (t, J=5.4 Hz, 1H), 3.88-3.79 (m, 1H), 3.54 (dd, J=10.6 Hz, 5.4 Hz, 1H), 3.39 (dd, J=10.6 Hz, 6.8 Hz, 1H), 3.33 (s, 3H). $^{13}$C NMR (101 MHz, DMSO) δ 162.87, 150.41, 140.86, 102.31, 86.70, 83.31, 81.22, 71.44, 57.60, 7.23.

Nucleoside 7b was syntehszied as follows:

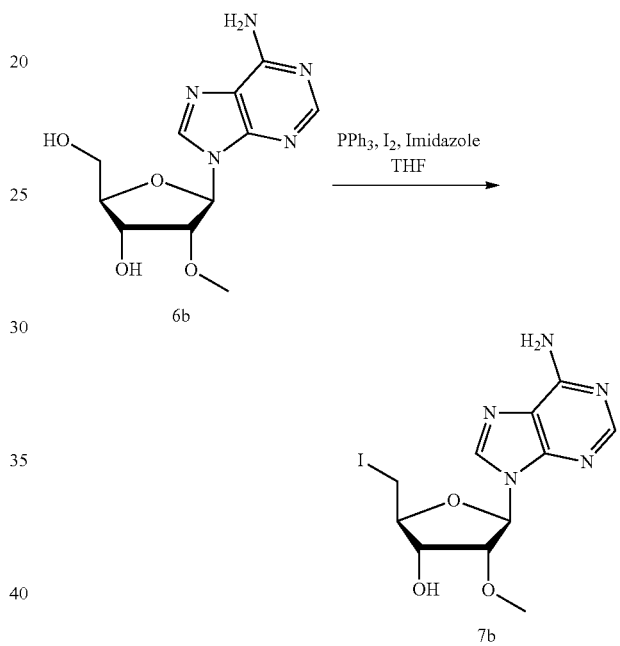

Nucleoside 6b (1.44 g, 5.0 mmol), imidazole (0.70 g, 10.0 mmol) and triphenylphosphine (2.00 g, 7.5 mmol) were suspended in dry THF (30 mL). To this was added a solution of iodine (1.60 g, 6.3 mmol) in THF (10 mL) dropwise at 0° C. The reaction mixture was slowly warmed to room temperature and stirred for another 3 h. The solvent was removed at reduced pressure, and the residue was purified by column chromatography using a gradient of 0-8% MeOH in CH$_2$Cl$_2$ to afford the nucleoside 7b (1.60 g, 82%) as an amorphous solid. MS (ESI$^+$) m/z calcd for C$_{11}$H$_{15}$IN$_5$O$_3$ [M+H]$^+$ 392.0214, found 392.0222. $^1$H NMR (400 MHZ, DMSO) δ 8.37 (s, 1H), 8.15 (s, 1H), 7.32 (s, 2H), 6.02 (d, J=5.9 Hz, 1H), 5.54 (d, J=5.5 Hz, 1H), 4.59 (t, J=5.4 Hz, 1H), 4.38-4.34 (m, 1H), 4.02-3.98 (m, 1H), 3.60 (dd, J=10.5, 5.9 Hz, 1H), 3.47 (dd, J=10.4, 7.0 Hz, 1H), 3.31 (s, 3H, OCH3). $^{13}$C NMR (126 MHz, DMSO) 156.12, 152.78, 149.27, 139.80, 119.11, 85.58, 84.42, 81.45, 71.45, 57.63, 7.52. Note: The compound was found to be unstable in solution. NMR samples were prepared at the time of the experiment.

Alternative Synthesis of Nucleoside 4a

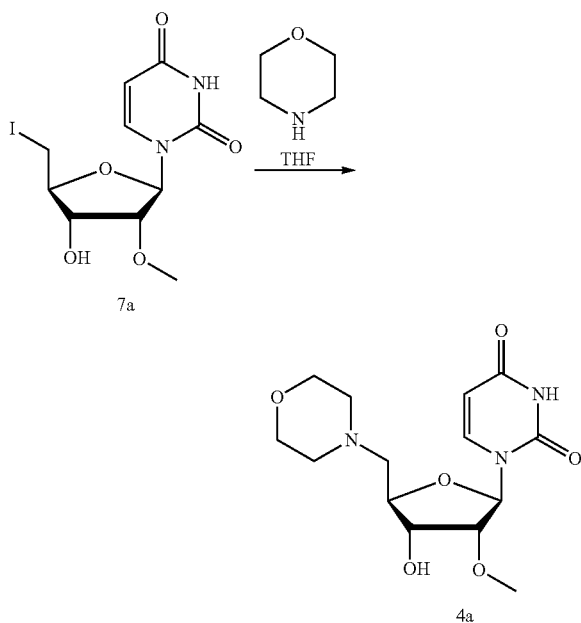

5'-Iodo-2'-O-methyluridine 7a (1.0 g, 2.71 mmol) was dissolved in THF (5 mL). Morpholine (5 mL) was added, and the reaction mixture was stirred at room temperature for 16 h. A white solid precipitated during this period. The solid was removed by filtration and washed with $CH_2Cl_2$ (50 mL). The filtrate was purified by column chromatography using a gradient of 0-8% MeOH in $CH_2Cl_2$ to afford the nucleoside 4a (0.55 g, 62%) as a white powder.

Alternative Synthesis of Nucleoside 4b

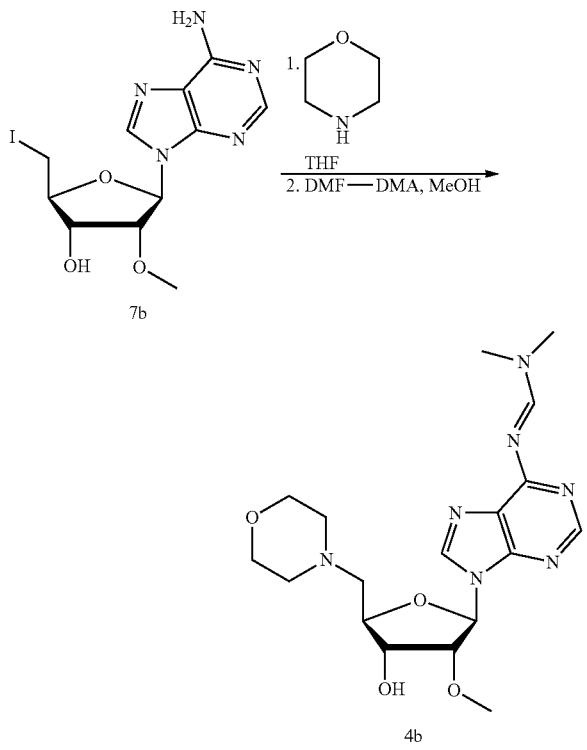

Nucleoside 7b (1.0 g, 2.55 mmol) was dissolved in THF (5 mL) and morpholine (5 mL). The reaction mixture was then stirred for 2 days at room temperature. A white solid precipitated. The solid was removed by filtration, washed with $CH_2Cl_2$ (50 mL), and purified by column chromatography using a gradient of 0-8% MeOH in $CH_2Cl_2$ to obtain white solid (0.7 g). The solid was dissolved in dry MeOH (6 mL) and to this solution was added dimethylformamide dimethyl acetal (DMF-DMA, 0.80 g, 6.7 mmol). The resulting solution was stirred for 16 h at room temperature. The solvents were removed, and the crude was purified by column chromatography using a gradient of 0-7% MeOH in $CH_2Cl_2$ to afford nucleoside 4b (550 mg, 48% over 2 steps) as a white solid material.

Oligonucleotide synthesis: Oligonucleotides were synthesized on an ABI-394 DNA/RNA synthesizer using standard synthesis cycles. A solution of 0.25 M 5-(S-ethylthio)-1 Htetrazole in acetonitrile was used as the activator. The phosphoramidite solutions were 0.15 M in anhydrous acetonitrile. The oxidizing reagent was 0.02 M $I_2$ in THF/pyridine/$H_2O$. N,N-Dimethyl-N'-(3-thioxo-3H-1,2,4-dithiazol-5-yl)methanimidamide (DDTT), 0.1 M in pyridine, was used as the sulfurizing reagent. The detritylation reagent was 3% dichloroacetic acid (DCA) in $CH_2Cl_2$. After completion of the automated synthesis, the oligonucleotide was manually released from support and deprotected using a mixture of 30% $NH_4OH$ containing 5% diethylamine for 6 h at 55° C. Solvent was collected by filtration, and the support was rinsed with $H_2O$. Crude oligonucleotides were purified by anion exchange HPLC using a linear gradient of gradient of mobile phase (0.15 M NaCl, 10% MeCN and 1.0 M NaBr, 10% MeCN) and desalted using size-exclusion chromatography with water as an eluent. Hybridization to generate siRNA duplexes was performed by mixing equimolar amounts of complementary strands in 1×PBS buffer, pH 7.4, and by heating in an over at 100° C. for 45 min followed by slow cooling to room temperature.

In vitro RNAi activity: To 5 µL of siRNA in each well of a 384-well collagen-coated plate were added 4.9 µL of Opti-MEM and 0.1 µL of Lipofectamine RNAiMax (Invitrogen). The final siRNA concentrations were 0.1 or 10 nM. Plates were incubated at room temperature for 15 min, and 40 µL of William's E Medium (Life Technologies) containing ~5×103 primary mouse hepatocytes cells were added. Each condition was assessed in quadruplicate. Cells were incubated for 24 h prior to RNA purification. RNA was isolated with DynaBeads (ThermoFisher), and reverse transcribed into cDNA according to manufacturer's protocol (Applied Biosystems). Multiplex qPCR reactions were performed in duplicate using a gene-specific TaqMan assay for apob (ThermoFisher Scientific, #Mm01545156_m1) and mouse Gapdh (#4352339E) as an endogenous control. Real-Time PCR was performed on a Roche LightCycler 480 using LightCycler 480 Probes Master Mix (Roche). Data were analyzed using the ΔΔCt method, normalizing apob expression to Gapdh, followed by normalization to the average of the control siRNA-transfected wells. Data were expressed as mean log difference from cells treated with the parent siRNA. Various designs were compared to parent design by multiple linear regression using the software package R.

Quantification of whole liver and Ago2-associated siRNA levels: Mice (n=3 per group) were sacrificed on days 3, 7, and 15 post-dose, and livers were snap-frozen in liquid nitrogen and ground into powder for downstream analysis. Total siRNA liver levels and Ago2-bound siRNA were measured by SL-qPCR based on previously published methods. 1 For SL-qPCR of apob-targeting siRNAs, the following probes and primers were used:

Sense Stem Loop Primer:

```
sense forward primer:
                                    (SEQ ID NO: 13)
5'-GTCGTATCCAGTGCAGGGTCCGAGGTATTCGCACTGGATACGACTG
ATGCCCAT-3', sense forward primer:
                                    (SEQ ID NO: 14)
5'-gccgcgcTGTGACAAATATG-3', sense probe:
                                    (SEQ ID NO: 15)
5'-CTGGATACGACTGATGCCC-3' antisense stem loop primer:
                                    (SEQ ID NO: 16)
5'-GTCGTATCCAGTGCAGGGTCCGAGGTATTCGCACTGGATACGACTT
TGTGACAA-3' antisense forward primer:
                                    (SEQ ID NO: 17)
5'-gccgcgcTTGATGCCCATA-3', antisense probe:
                                    (SEQ ID NO: 18)
5'-CTGGATACGACTTTGTGAC-3', and universal reverse primer:
                                    (SEQ ID NO: 19)
5'-GTGCAGGGTCCGAGGT-3'.
```

Table 2 shows siRNAs targeting Factor IX (FIX) gene.

TABLE 2 siRNAs targeting FIX gene

| Entry | siRNA | siRNA duplex | SEQ ID NO: |
|---|---|---|---|
| 1 | Parent | 5'-u•g•gaagCfaGfUfAfuguugaugga-GalNAc₃ | 20 |
|   |   | 5'-u•Cf•cauCfaAfCfauacUfgCfuucca•a•a | 21 |
| 2 | S5'-Mo | 5'-Mou•g•gaagCfaGfUfAfuguugaugga-GalNAc₃ | 22 |
|   |   | 5'-u•Cf•cauCfaAfCfauacUfgCfuucca•a•a | 21 |
| 3 | AS5'-Mo | 5'-u•g•gaagCfaGfUfAfuguugaugga-GalNAc₃ | 20 |
|   |   | 5'-Mou•Cf•cauCfaAfCfauacUfgCfuucca-a•a | 23 |

REFERENCES

1. R. G. Parmar, C. R. Brown, S. Matsuda, J. L. S. Willoughby, C. S. Theile, K. Charisse, D. J. Foster, I. Zlatev, V. Jadhav, M. A. Maier, M. Egli, M. Manoharan and K. G. Rajeev, *J Med Chem*, 2018, 61, 734-744.
2. R. Parmar, J. L. S. Willoughby, J. Liu, D. J. Foster, B. Brigham, C. S. Theile, K. Charisse, A. Akinc, E. Guidry, Y. Pei, W. Strapps, M. Cancilla, M. G. Stanton, K. G. Rajeev, L. Sepp-Lorenzino, M. Manoharan, R. Meyers, M. A. Maier and V. Jadhav, *ChemBioChem*, 2016, 17, 985-989.

Example 2

5'-Morpholine Phosphoramidite (u5mo) was synthesized as follows:

Scheme 3

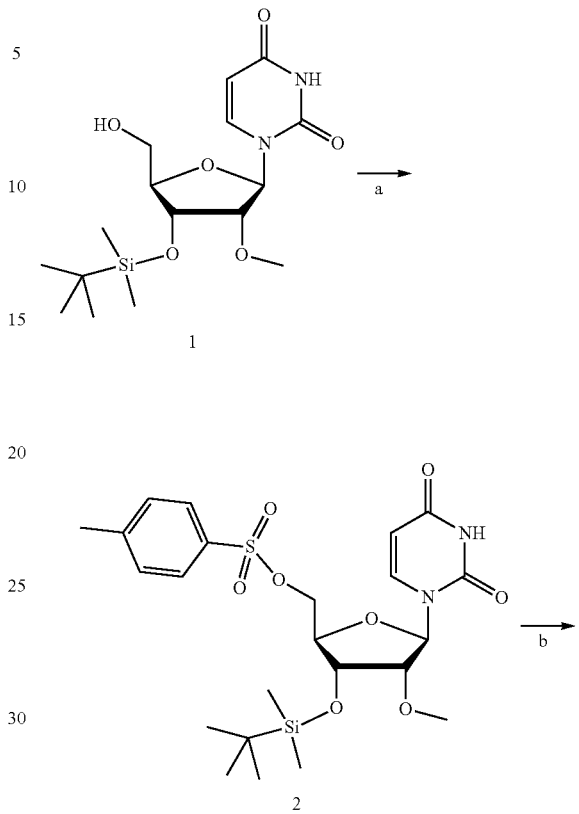

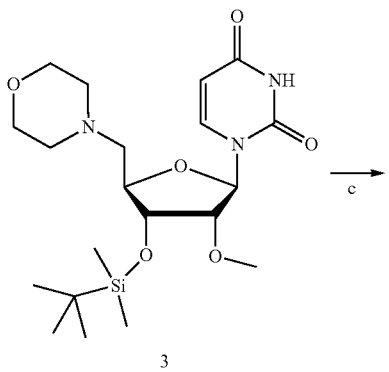

-continued

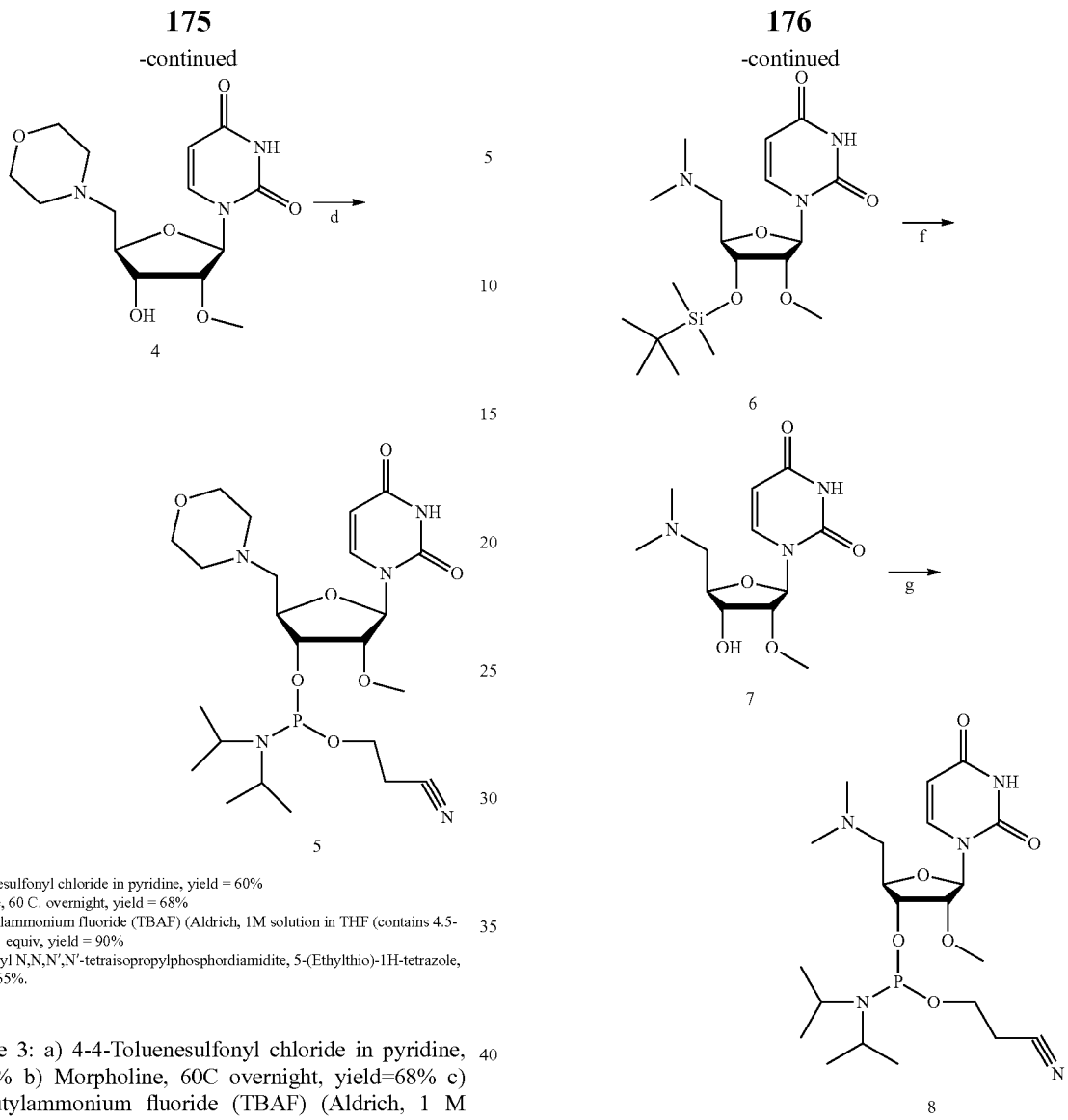

a) 4-4-Toluenesulfonyl chloride in pyridine, yield = 60%
b) Morpholine, 60 C. overnight, yield = 68%
c) tetra-n-butylammonium fluoride (TBAF) (Aldrich, 1M solution in THF (contains 4.5-5% water), 1.1 equiv, yield = 90%
d) 2-Cyanoethyl N,N,N',N'-tetraisopropylphosphordiamidite, 5-(Ethylthio)-1H-tetrazole, ACN, 6 h, rt, 65%.

Scheme 3: a) 4-4-Toluenesulfonyl chloride in pyridine, yield=60% b) Morpholine, 60C overnight, yield=68% c) tetra-n-butylammonium fluoride (TBAF) (Aldrich, 1 M solution in THF (contains 4.5-5% water), 1.1 equiv, yield=90% d) 2-Cyanoethyl N,N,N',N'-tetraisopropylphosphordiamidite, 5-(Ethylthio)-1H-tetrazole, ACN, 6 h, rt, 65%.

5'-dimethylamine phosphoramidite (u5a) was synthesized as follows:

Scheme 4

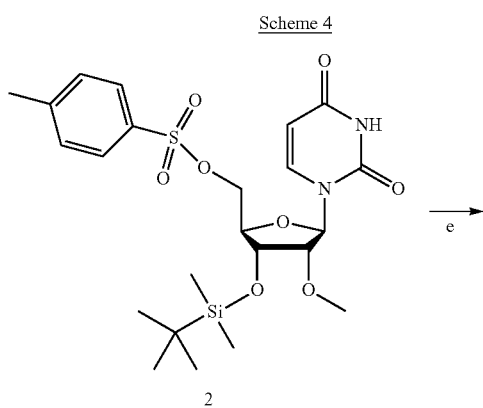

e) 2M dimethylamine in THF, 60 C. overnight, yield = 68%; f) tetra-n-butylammonium fluoride (TBAF) (Aldrich, 1M solution in THF (contains 4.5-5% water), 1.1 equiv, yield = 90%; g) 2-Cyanoethyl N,N,N',N'-tetraisopropylphosphordiamidite, 5-(Ethylthio)-1H-tetrazole, ACN, 6 h, rt, 65%

Synthesis of 6: A mixture of compound 2 (17 gm, 32 mmol) and morpholine (200 ml) was heated at 60° C. After 48 hours, TLC (8:2 ethylacetate: hexane) confirmed the formation of product. The reaction mixture was cooled to room temperature and diluted with ethylacetate (600 mL). The ethylacetate solution was washed with water (3× 600 mL), separated, dried over anhydrous $Na_2SO_4$, and filtered. The filtrate was evaporated to dryness and the solid residue was purified over a silica gel column in ethylacetate/hexane to afford compound 3. Yield=10 gm, 68%

Synthesis of 5' deoxy phosphoramidite (u5h): The 5' deoxy phosphroamidite was synthesized following the procedure described in US 2009/0280567.

Inverted abasic (ib) and locked nucleic acid (Tln) were commercially available.

RESULTS AND DISCUSSION: To eliminate the sense strand loading into RISC complex and to enhance the metabolic stability of siRNA duplex, we investigated different modifications that can block the RISC loading of sense strand and enhance exonuclease stability. The criteria for the selection of these modifications were to reduce the phosphorylation at 5' end of strand. For efficient RISC loading, 5' end of strand is phosphorylated with cellular kinases (Ref). Five modifications (Table-1) used here either have sterically hindered 5' OH or replaced with other moieties: example morpholine. These modifications were evaluated at 5' end of sense as well as antisense strands. The blocking of 5' end of antisense strand was evaluated to see how efficiently these modifications can block the RISC loading. Screening of these modification were done using in vitro transfection of the conjugates in primary mouse hepatocyte.

TABLE 3

| Blocking Sense Strand Loading: U•g•UgAcAaAUAuGgGcAuCaA-GalNAc$_3$ (SEQ ID NO: 1) | | | |
|---|---|---|---|
| Conjugate # | Target | Sense Strand (S) (5'-3') | Antisense Strand (AS) (5'-3') |
| I | Apo B | U•g•UgAcAaAUAuGgGcAuCaA-GalNAc$_3$ (SEQ ID NO: 24) | u•U•gAuGcCcAuauUuGuCaCa•a•a (SEQ ID NO: 25) |
| I-S-u5mo | Apo B | u5mo•g•UgAcAaAUAuGgGcAuCaA-GalNAc$_3$ (SEQ ID NO: 27) | u•U•gAuGcCcAuauUuGuCaCa•a•a (SEQ ID NO: 25) |
| I-AS-u5mo | Apo B | U•g•UgAcAaAUAuGgGcAuCaA-GalNAc$_3$ (SEQ ID NO: 24) | u5mo•U•gAuGcCcAuauUuGuCaCa•a•a (SEQ ID NO: 28) |
| I-S-AS-u5mo | Apo B | u5mo•g•UgAcAaAUAuGgGcAuCaA-GalNAc$_3$ (SEQ ID NO: 27) | u5mo•U•gAuGcCcAuauUuGuCaCa•a•a (SEQ ID NO: 28) |
| I-S-u5a | Apo B | u5a•g•UgAcAaAUAuGgGcAuCaA-GalNAc$_3$ (SEQ ID NO: 29) | u•U•gAuGcCcAuauUuGuCaCa•a•a (SEQ ID NO: 25) |
| I-AS-u5a | Apo B | U•g•UgAcAaAUAuGgGcAuCaA-GalNAc$_3$ (SEQ ID NO: 24) | u5a•U•gAuGcCcAuauUuGuCaCa•a•a (SEQ ID NO: 30) |
| I-S-u5h | Apo B | u5h•g•UgAcAaAUAuGgGcAuCaA-GalNAc$_3$ (SEQ ID NO: 31) | u•U•gAuGcCcAuauUuGuCaCa•a•a (SEQ ID NO: 25) |
| I-AS-u5h | Apo B | U•g•UgAcAaAUAuGgGcAuCaA-GalNAc$_4$ (SEQ ID NO: 32) | u5h•U•gAuGcCcAuauUuGuCaCa•a•a (SEQ ID NO: 33) |
| I-S-Tln | Apo B | Tln•g•UgAcAaAUAuGgGcAuCaA-GalNAc$_3$ (SEQ ID NO: 34) | u•U•gAuGcCcAuauUuGuCaCa•a•a (SEQ ID NO: 25) |
| I-AS-Tln | Apo B | U•g•UgAcAaAUAuGgGcAuCaA-GalNAc$_5$ (SEQ ID NO: 35) | Tln•U•gAuGcCcAuauUuGuCaCa•a•a (SEQ ID NO: 36) |
| I-S-ib | Apo B | ib•U•gUgAcAaAUAuGgGcAuCaA-GalNAc$_3$ (SEQ ID NO: 37) | u•U•gAuGcCcAuauUuGuCaCa•a•a (SEQ ID NO: 25) |
| I-AS-ib | Apo B | U•g•UgAcAaAUAuGgGcAuCaA-GalNAc$_6$ (SEQ ID NO: 38) | ib.u•U•gAuGcCcAuauUuGuCaCa•a•a (SEQ ID: 39) |
| II | Factor 9 | u•g•gaagCaGUAuguugaugga-GalNAc$_3$ (SEQ ID NO: 40) | u•C•cauCaACauacUgCuucca•a•a (SEQ ID NO: 41) |
| II-S-u5mo | Factor 9 | u5mo•g•gaagCaGUAuguugaugga-GalNAc$_3$ (SEQ ID NO: 42) | u•C•cauCaACauacUgCuucca•a•a (SEQ ID NO: 43) |
| II-AS-u5mo | Factor 9 | u•g•gaagCaGUAuguugaugga-GalNAc$_3$ (SEQ ID NO: 40) | u5mo•C•cauCaACauacUgCuucca•a•a (SEQ ID NO: 44) |
| II-S-AS-u5mo | Factor 9 | u5mo•g•gaagCaGUAuguugaugga-GalNAc$_4$ (SEQ ID NO: 45) | u5mo•C•cauCaACauacUgCuucca•a•a (SEQ ID NO: 44) |
| II-a | Factor 9 | uggaagCaGUAuguugaugga-GalNAc$_3$ (SEQ ID NO: 46) | u•C•cauCaACauacUgCuucca•a•a (SEQ ID NO: 41) |
| II-a-S-u5mo | Factor 9 | u5moggaagCaGUAuguugaugga-GalNAc3 (SEQ ID NO: 47) | u•C•cauCaACauacUgCuucca•a•a (SEQ ID NO: 43) |
| II-a-S-u5a | Factor 9 | u5aggaagCaGUAuguugaugga-GalNAc3 (SEQ ID NO: 48) | u•C•cauCaACauacUgCuucca•a•a (SEQ ID NO: 43) |
| II-a-S-ib | Factor 9 | ibggaagCaGUAuguugaugga-GalNAc3 (SEQ ID NO: 49) | u•C•cauCaACauacUgCuucca•a•a (SEQ ID NO: 43) |
| III | Factor 9 | u•g•ugcaAuGAAaggcaaauaa-GalNAc3 (SEQ ID NO: 50) | u•U•auuUgCCuuucAuUgcaca•c•u (SEQ ID NO: 51) |
| III-S-u5mo | Factor 9 | u5mo•g•ugcaAuGAAaggcaaauaa-GalNAc3 (SEQ ID NO: 52) | u•U•auuUgCCuuucAuUgcaca•c•u (SEQ ID NO: 53) |
| III-AS-u5mo | Factor 9 | u•g•ugcaAuGAAaggcaaauaa-GalNAc4 (SEQ ID NO: 54) | u5mo•U•auuUgCCuuucAuUgcaca•c•u (SEQ ID NO: 55) |

TABLE 3-continued

Blocking Sense Strand Loading: U•g•UgAcAaAUAuGgGcAuCaA-GalNAc₃ (SEQ ID NO: 1)

| Conjugate # | Target | Sense Strand (S) (5'-3') | Antisense Strand (AS) (5'-3') |
|---|---|---|---|
| III-S-AS-u5mo | Factor 9 | u5mo•g•ugcaAuGAAaggcaaauaa-GalNAc5 (SEQ ID NO: 56) | u5mo•U•auuUgCCuuucAuUgcaca•c•u (SEQ ID NO: 55) |
| IV | Factor 9 | c•a•guacCuUAGaguuccacua-GalNAc3 (SEQ ID NO: 57) | u•A•gugGaACucuaAgGuacug•a•a (SEQ ID NO: 58) |
| IV-S-c5mo | Factor 9 | c5mo•a•guacCuUAGaguuccacua-GalNAc3 (SEQ ID NO: 59) | u•A•gugGaACucuaAgGuacug•a•a (SEQ ID NO: 60) |
| IV-ASu5mo | Factor 9 | c•a•guacCuUAGaguuccacua-GalNAc3 (SEQ ID NO: 57) | u5mo•A•gugGaACucuaAgGuacug•a•a (SEQ ID NO: 61) |
| IV-ASu5mo | Factor 9 | c5mo•a•guacCuUAGaguuccacua-GalNAc4 (SEQ ID NO: 62) | u5mo•A•gugGaACucuaAgGuacug•a•a (SEQ ID NO: 61) |

Italicized upper case and more lower case letters indicate 2'-fluoro (2'-F), and 2'-O-methyl (2'-OMe) sugar modifications, respectively to adenosine (A), cytidine (C), guanosine (G), and uridine (U). • indicates phosphorothioate (PS) linkage; GalNAc3 indicates hydroxyprolynyl tri-valent N-Acetyl-Galactosamine ligand

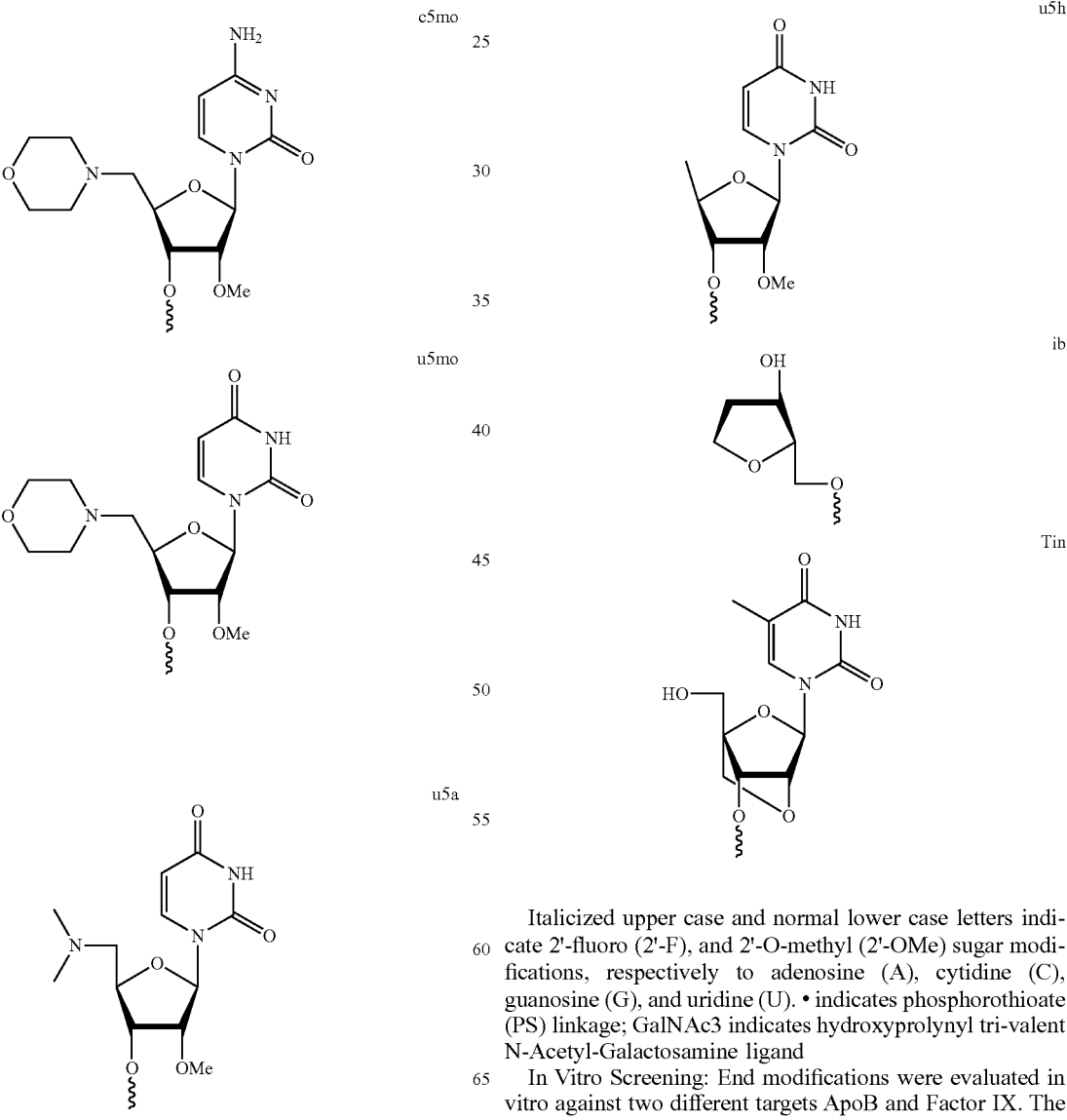

Italicized upper case and normal lower case letters indicate 2'-fluoro (2'-F), and 2'-O-methyl (2'-OMe) sugar modifications, respectively to adenosine (A), cytidine (C), guanosine (G), and uridine (U). • indicates phosphorothioate (PS) linkage; GalNAc3 indicates hydroxyprolynyl tri-valent N-Acetyl-Galactosamine ligand In Vitro Screening: End modifications were evaluated in vitro against two different targets ApoB and Factor IX. The modified conjugates were evaluated in primary mouse hepatocytes by transfection and gene silencing was measured as a function of siRNA concentration. FIG. 1, shows the adjusted mean difference in log (efficacy) from parent compound.

As show in FIG. 26, siRNA conjugates targeting ApoB when modified at sense strand with morpholino I-S-u5mo, inverted abasic I-S-ib, deoxy I-S-u5h, locked nucleic acid I—S-Tln, dimethyl amine I-S-u5a show the activity similar parent I, trending towards slight improvement in activity.

In Vivo Screening: Synthesis of the above described modifications on the 5' of the anti-sense strand showed complete RNAi activity loss consistent with the notion that the modification specifically inhibited RISC strand loading. To translate these observations in vivo and confirm that the observed activity loss was specifically due to the lack of RISC loading, we chose to thoroughly evaluate a single modification. The morpholino modification was selected as it showed the greatest loss of activity when synthesized to the 5' of the anti-sense and activity improvement when synthesized on the 5' end of the sense strand. To evaluate the ability of the morpholino modification to impact RISC strand loading in vivo, an experiment was executed to evaluate both the pharmacodynamic activity and RISC loading at multiple time points in wild-type mice. The previously described ApoB targeting siRNA was synthesized with the 5' morpholino modification on the sense strand, anti-sense strand or on both strands as an experimental control. Animals received a single subcutaneous dose of 3 mg/kg of each conjugate and cohorts were sacrificed on days 3, 7 and 15 for each group. FIG. 27 shows the remaining hepatic gene expression of ApoB following administration with the previously described conjugates (#s). The parent compound (Conjugate ApoB parent) resulted in approximately 65% target knockdown with maximum knockdown observed 7 days post treatment. The 5' Morpholino modification on the anti-sense strand resulted in complete loss of activity at the 3 mg/kg dose, whereas, the conjugate with the 5' Morpholino on the sense strand, resulted in greater activity at day 3 with comparable activity at days 7 and 15. This observation was consistent with the in vitro activity shown in FIG. 26. A control was included where the 5' Morpholino modified sense and anti-sense strands were annealed evaluated at the same dose level. The dually modified conjugate showed a complete loss of activity. To confirm that the modification prevents RISC loading of the relevant strand, the RISC loaded levels for each duplex were evaluated within the same samples.

Similarly, in vivo experiment was performed with another target Factor IX (F9). To investigate whether the 5'-Morpholino would block anti-sense strand loading would translate to additional siRNA sequences in vivo, two additional siRNA conjugates targeting F9 were synthesized with the 5' Morpholino on the sense or anti-sense strand. Here, the inventors included sequences that were deemed phosphate independent versus phosphate dependant as determined through RNAi activity improvement with the addition of a 5' Vinyl phosphonate (VP). Wild-type rodents were dosed 1 mg/kg and circulating FIX activity levels were assayed on days 7, 14, and 21 post a single subcutaneous dose. The sequences with the 5' Morpholino modification on the AS showed complete activity loss in direct comparison to the parent, as expected. Sequences with the 5' morpholino modification had activity comparable to the parent. These data were consistent at all time-points evaluated. See. FIG. 29.

In Vitro Stability Assay

Sample Preparation: Samples were prepared in triplicate using two time points. For the 24-hour time point, modified oligonucleotide was added at 0.1 mg/mL to a solution of female rat tritosome (Xenotech cat. R$^{0610}$.LT), 0.5U/mL acid phosphatase in tritosome dilution buffer (20 mM sodium citrate, pH 5.0), then adjusted to pH 4.5 using citric acid. Control (zero time point) samples were prepared using the same method, except oligonucleotide was not added. Then, 24-hour samples were incubated at 37° C. for 24 hours at 100 RPM, and control samples were stored at −80° C. After incubation, control samples were thawed to room temperature. Proteinase K (Qiagen cat. 19133) at 3.5 mg/mL in buffer (1 mg/mL 5% tween 20, 0.36% Triton X-100, 30 mM Tris-HCl, pH 8.0) was added to all samples, which were then incubated for one hour at 50° C., 60 RPM. Lysis buffer (Phenomenex cat. ALO-8579) spiked with 21-nt oligonucleotide internal standard was then added to all samples and mixed briefly. Samples were filtered using ion-exchange phase extraction columns (Phenomenex cat. 8E-S103-EGA). The resulting eluents were evaporated and reconstituted in ionized water for analysis by LC-MS.

Sample Analysis: Samples were analyzed using RP LC-MS, with Dionex Ultimate 3000 RS pump coupled with Thermo Q orbitrap, using a RP BEH column (Waters cat. 186006041). The system ran in negative ion mode under the following conditions: 30 uL injection volume, 0.7 mL/minute flow rate, gradient 0-O-35% mobile phase B in 0-0.4-10 minutes (mobile phase A: 16 mM triethylamine, 200 mM hexafluoroisopropanol, mobile phase B: 100% methanol). Xcalibur (Thermo Fisher, version 3.0) software was used to interface instrumentation. For data processing, Promass (Novatia) was used to deconvolute m/z to mass. Metabolites were identified using an internal program to predict masses of cleaved oligonucleotides.

Results: All duplexes showed parent masses remaining with loss of 3 GalNAC sugars from sense strand after 24 hours, indicating lack of siRNA degradation.

In vivo screen: To confirm the stability of the above described modifications, the compounds were screened in wild-type mice. Animals received a single dose of conjugates (numbers) on Day 0 and the animals were sacrificed on Day 10 post conjugate administration.

Figure 5:
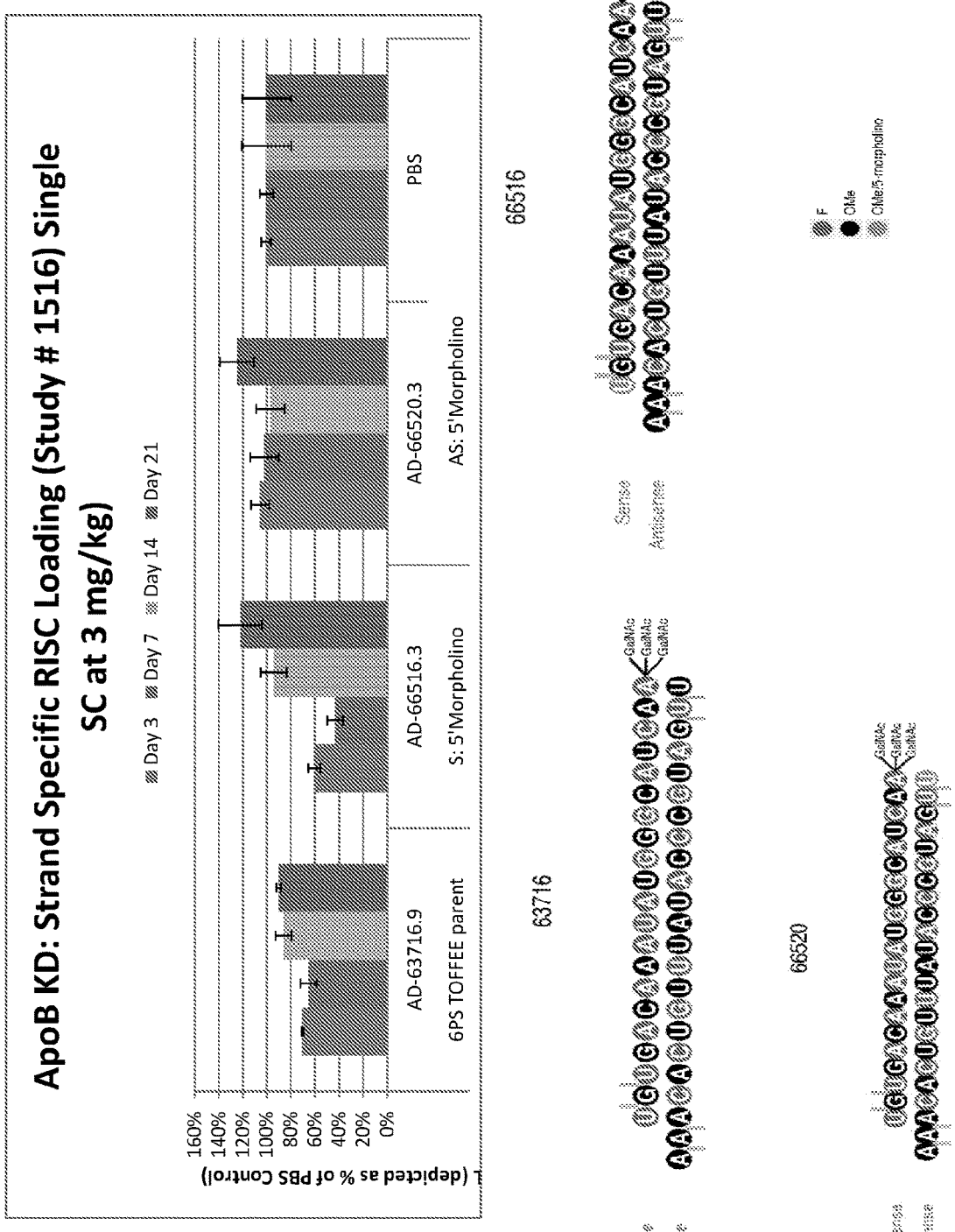
Figure 7:
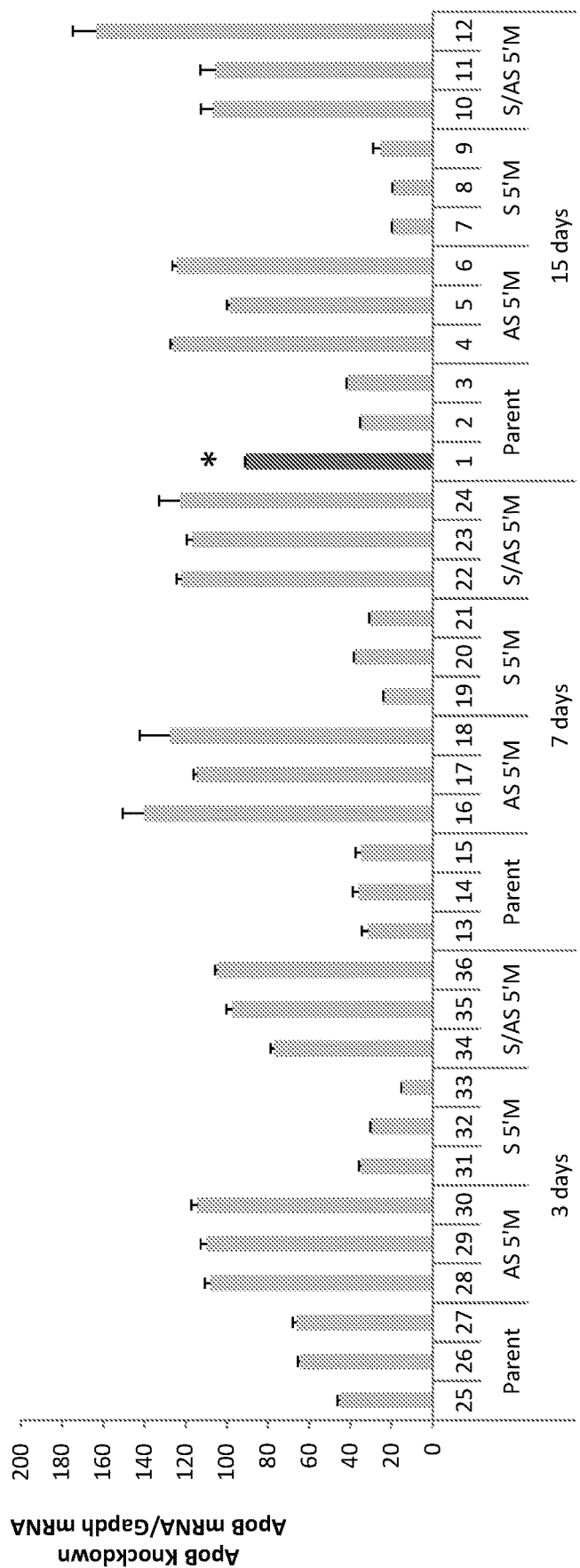
FIGS. 7 and 8 are bar graphs showing ApoB knockdown in liver post single SC dose in WT mice demonstrating 5'-morpholino modification ablates in vivo activity of ApoB conjugates (5'AS).
Figure 8:
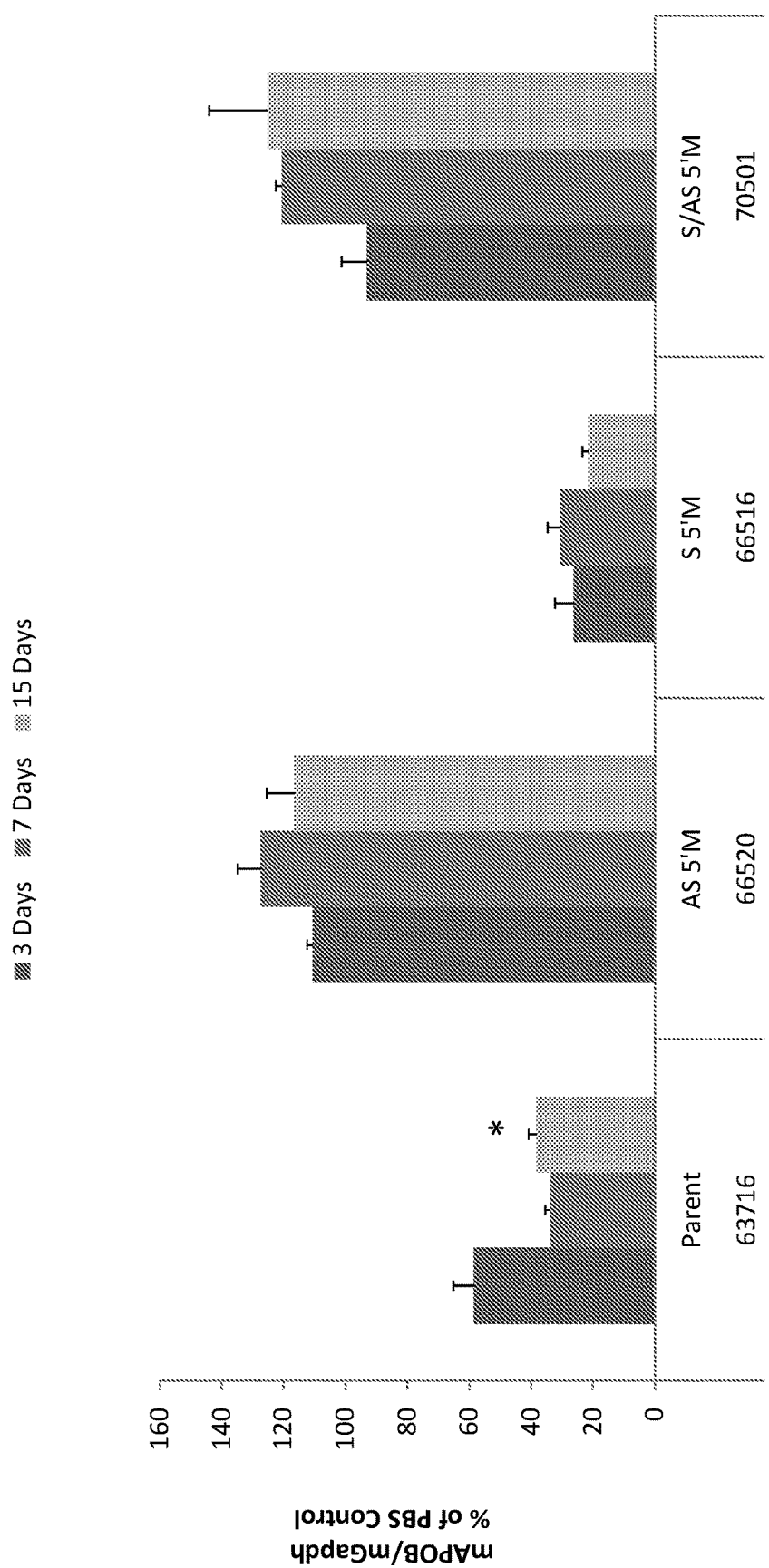
Figure 9:
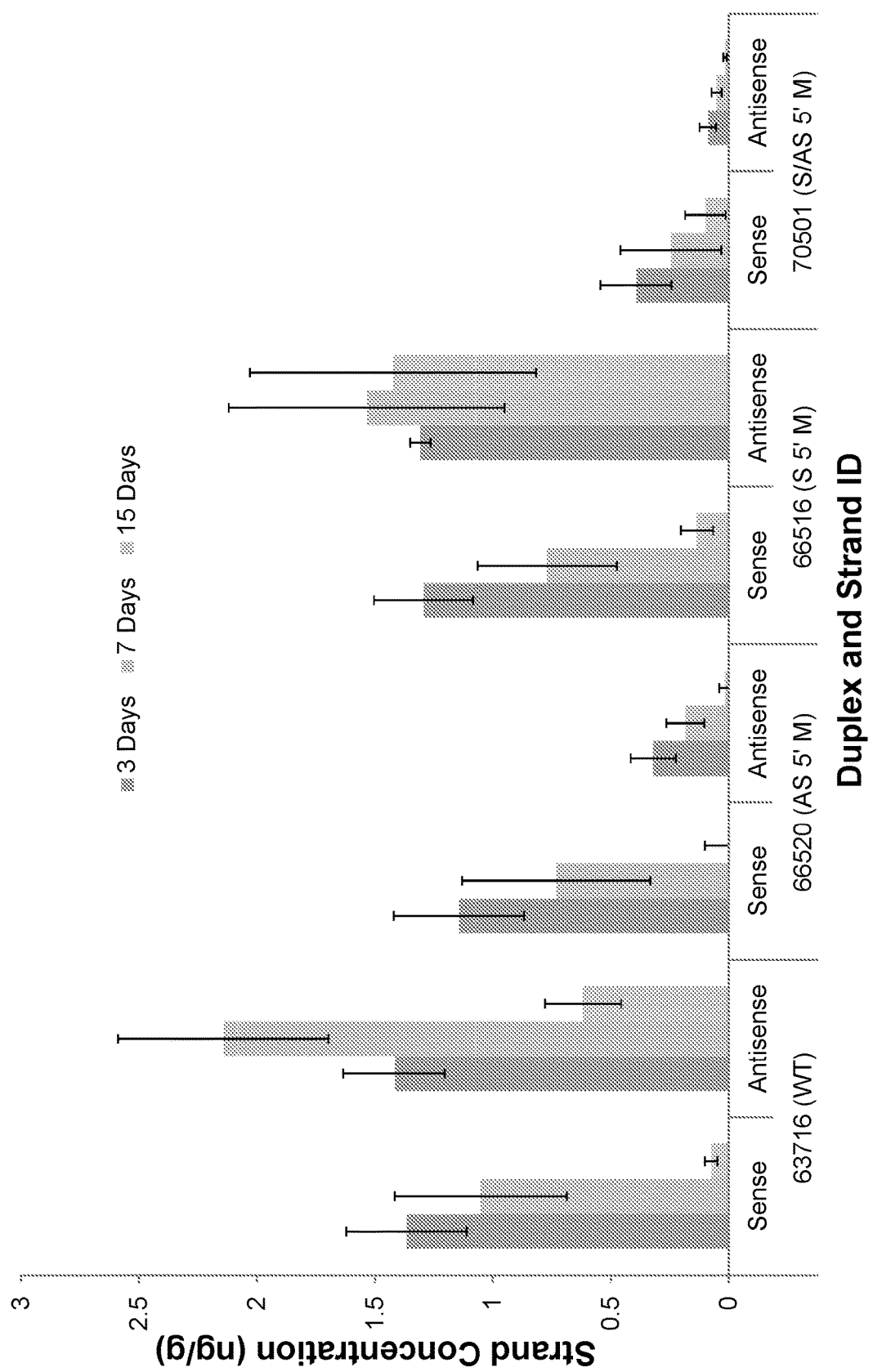
Figure 11:
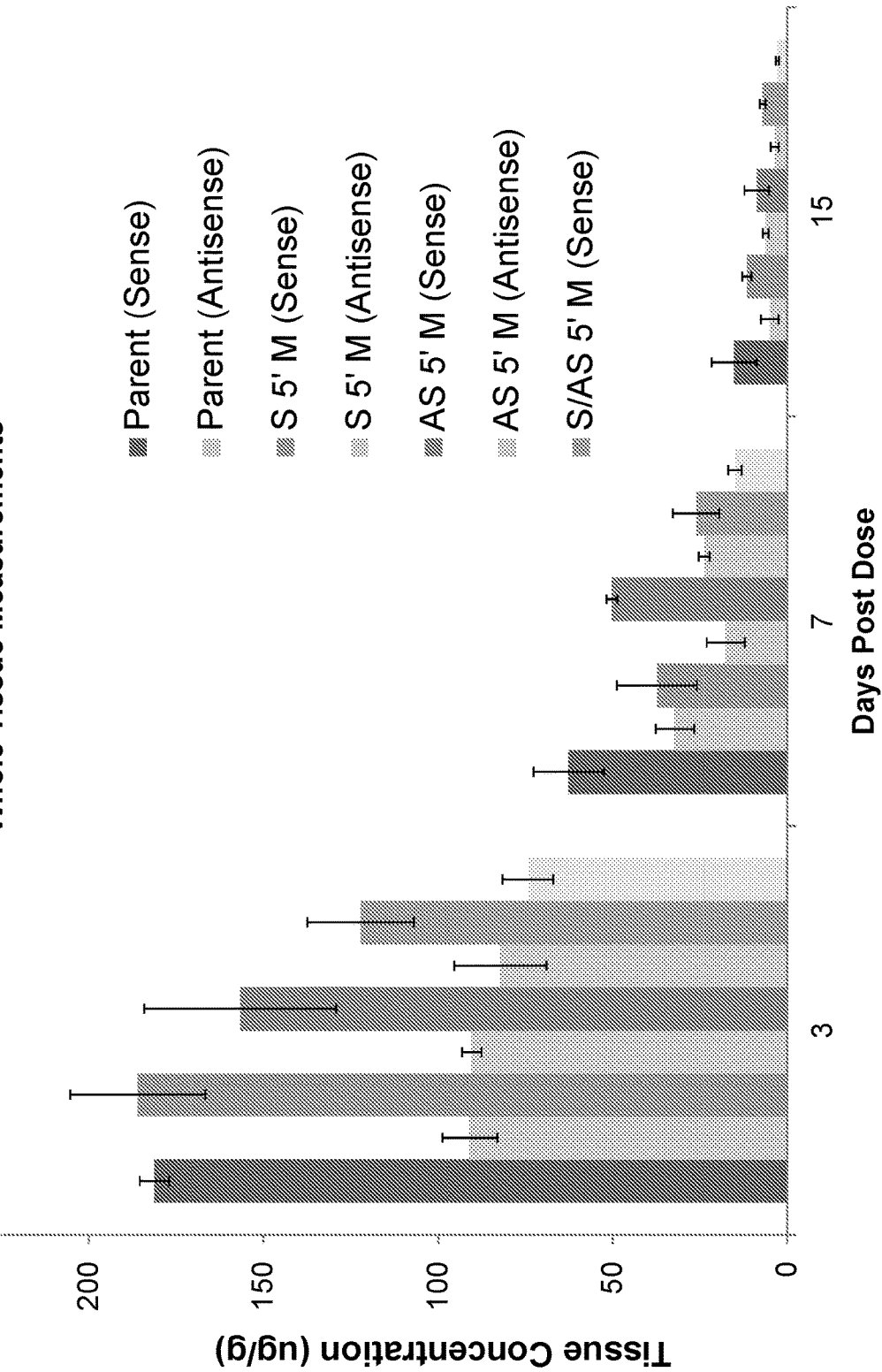
FIG. 11 shows whole tissue loads siRNA are similar across exemplary ApoB conjugates.
Figure 12:
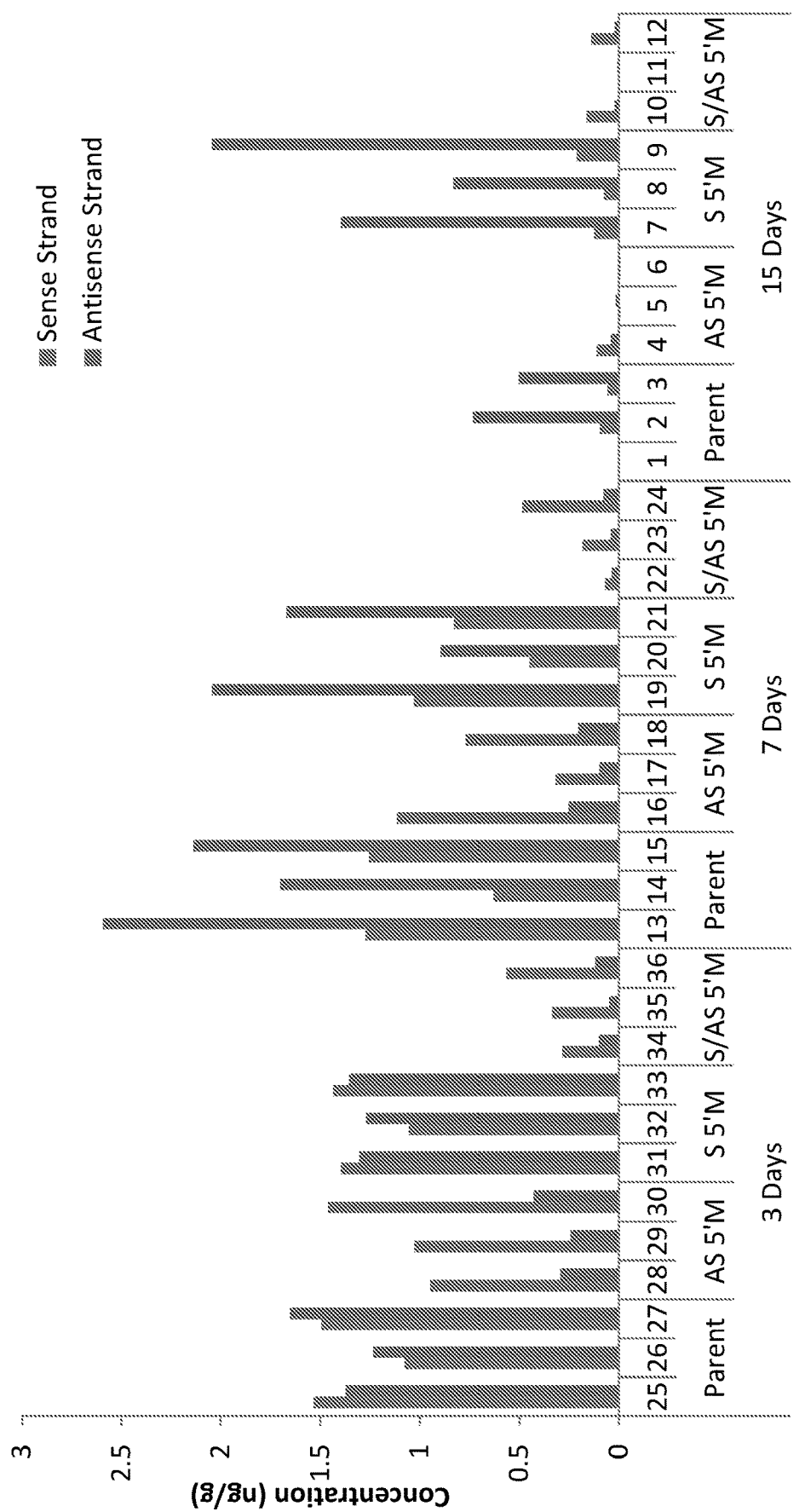
FIGS. 12 and 13 are bar graphs of individual animal data showing that 5'-morpholion modifications alter the RISC loading of and exemplary RNAi agent (ApoB) sense and antisense strands.
Figure 13:
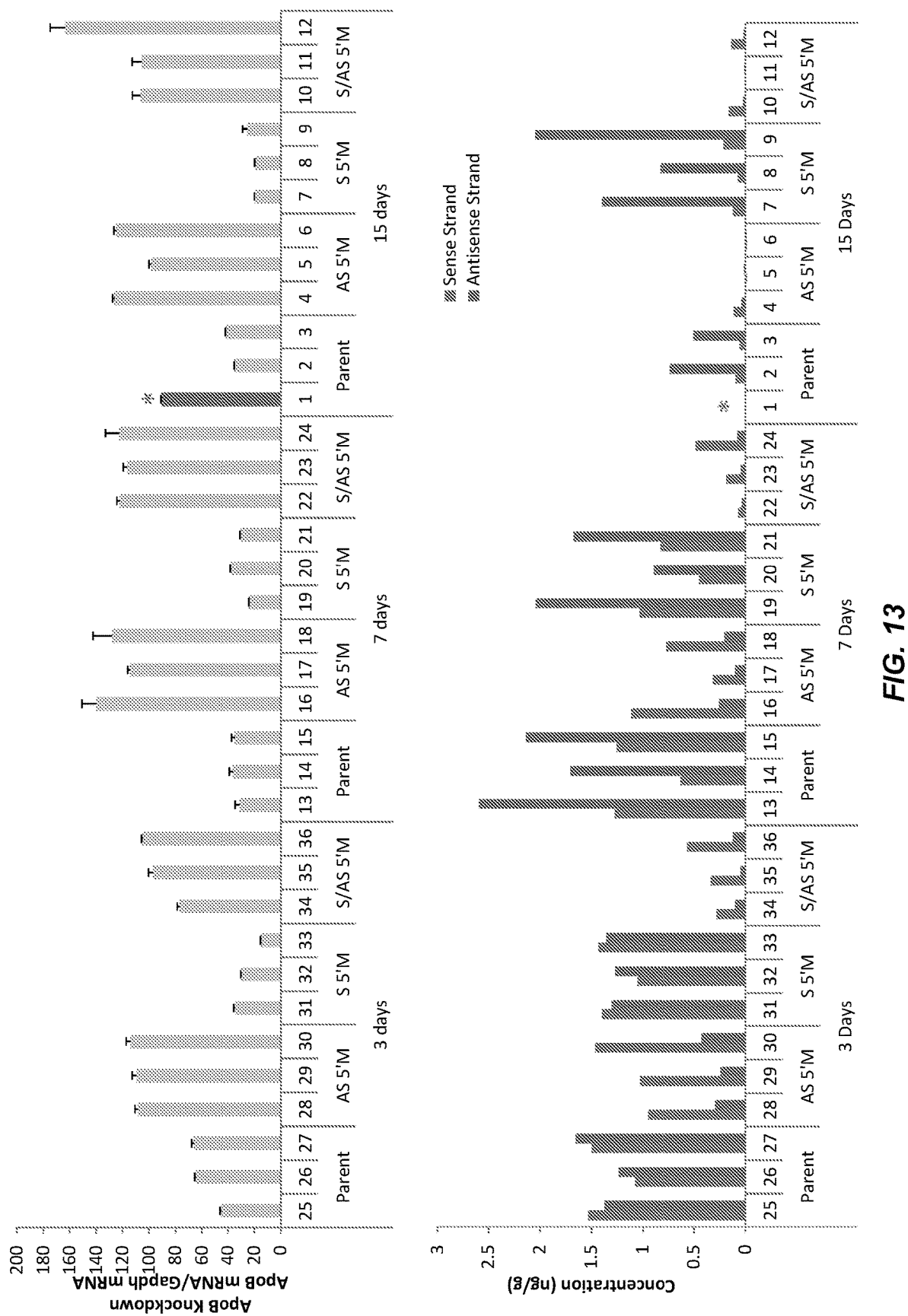
Figure 14:
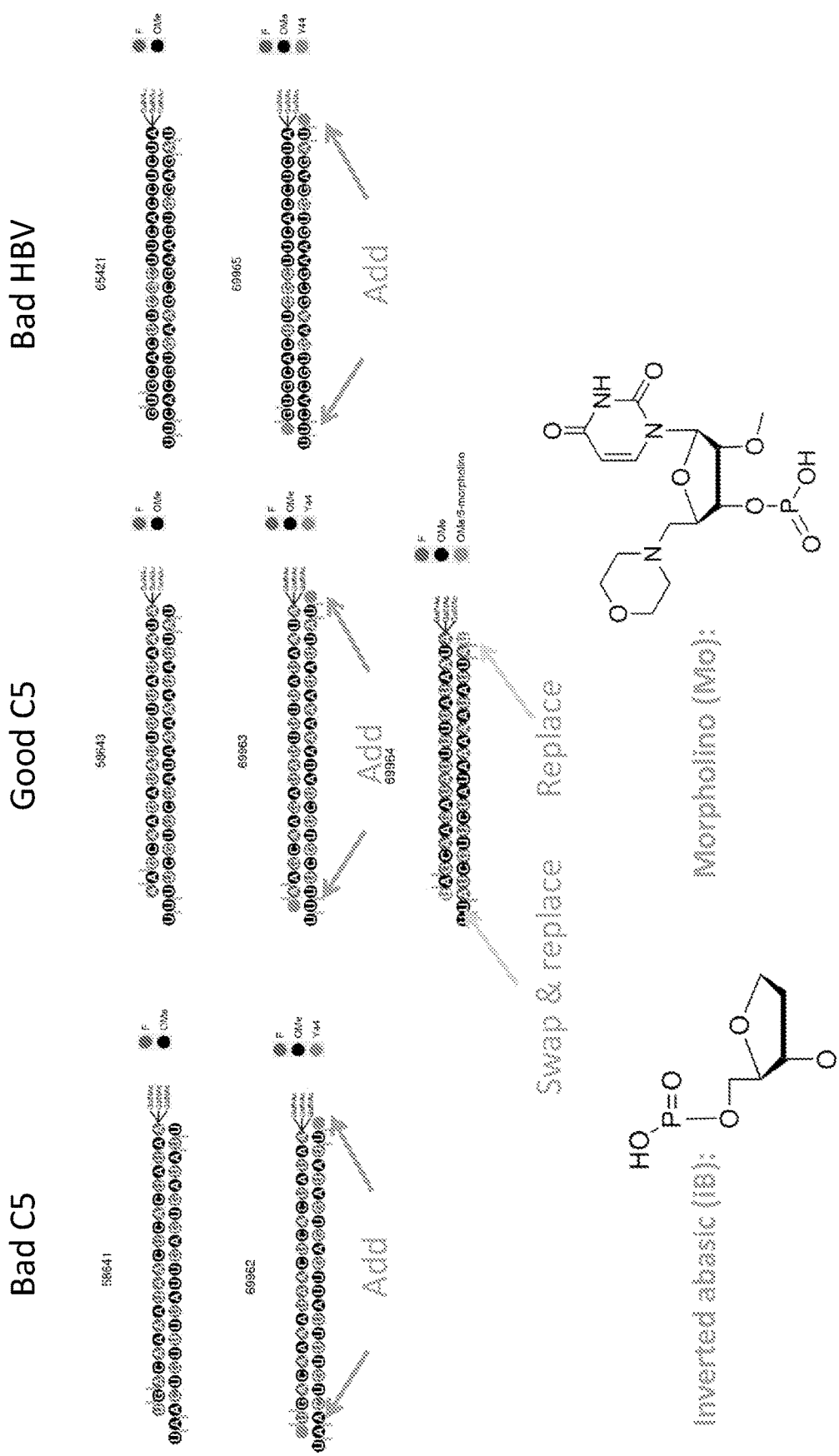
FIG. 14 is a schematic representation showing exemplary 5'-modifications of some exemplary RNAi agents.
Figure 16:
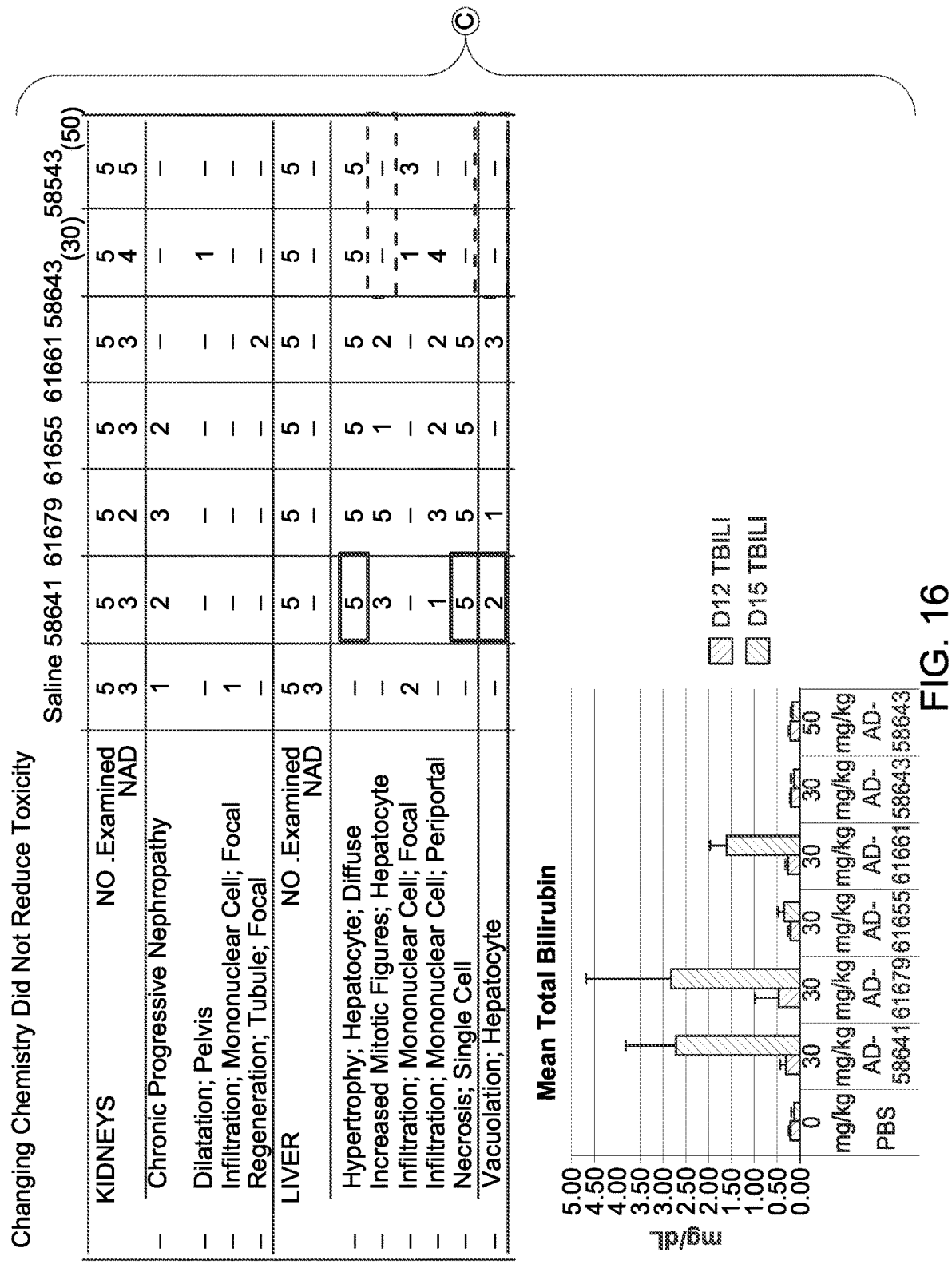
FIG. 16 shows changing chemistry did not reduce toxicity of exemplary C5 RNAi agents.
Figure 17:
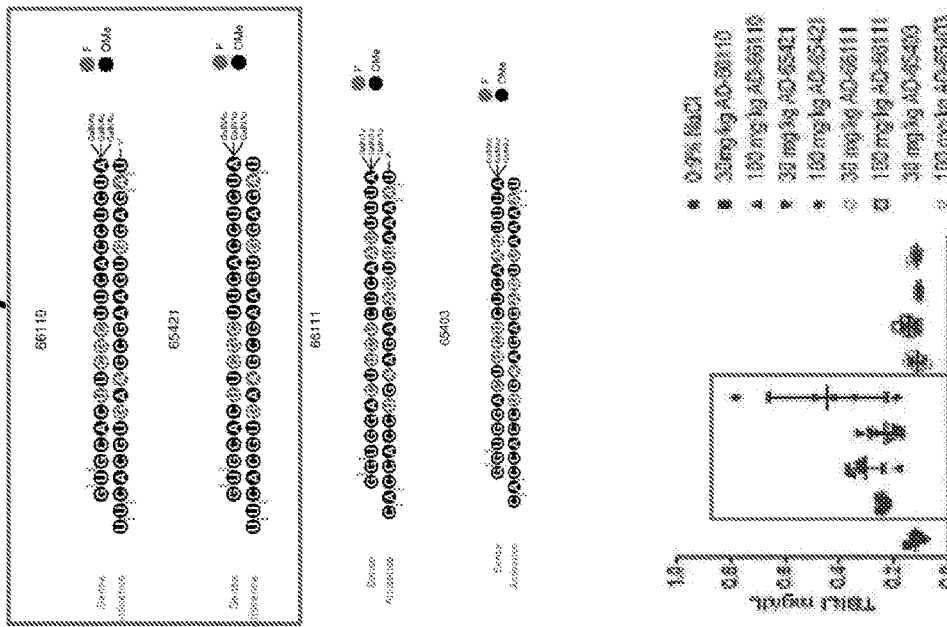
FIG. 17 shows that increasing RISC loading of exemplary HBV RNAi agents increased toxicity independent of chemistry.
Figure 18:
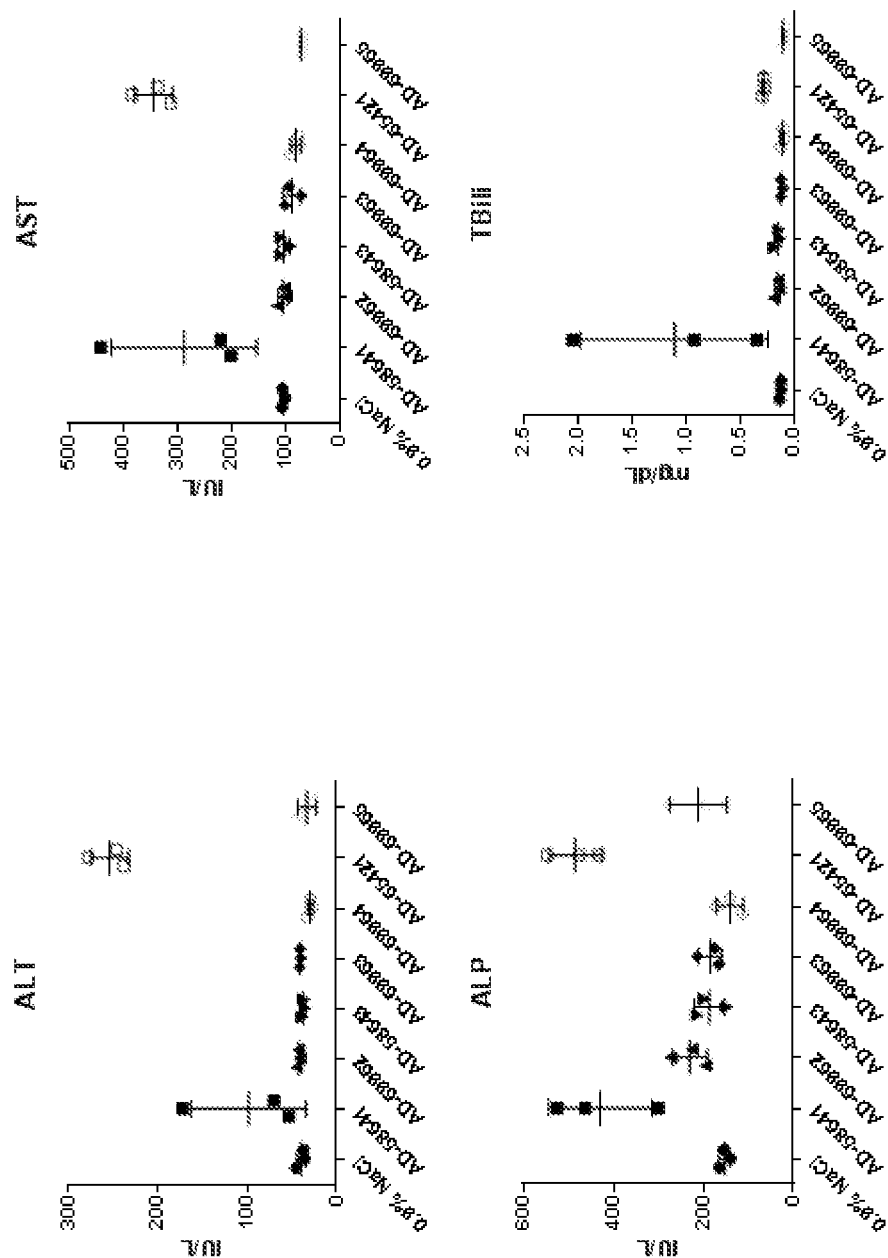
FIG. 18 shows clinical pathology of the exemplary RNAi agents shown in FIG. 14.
Figure 19:
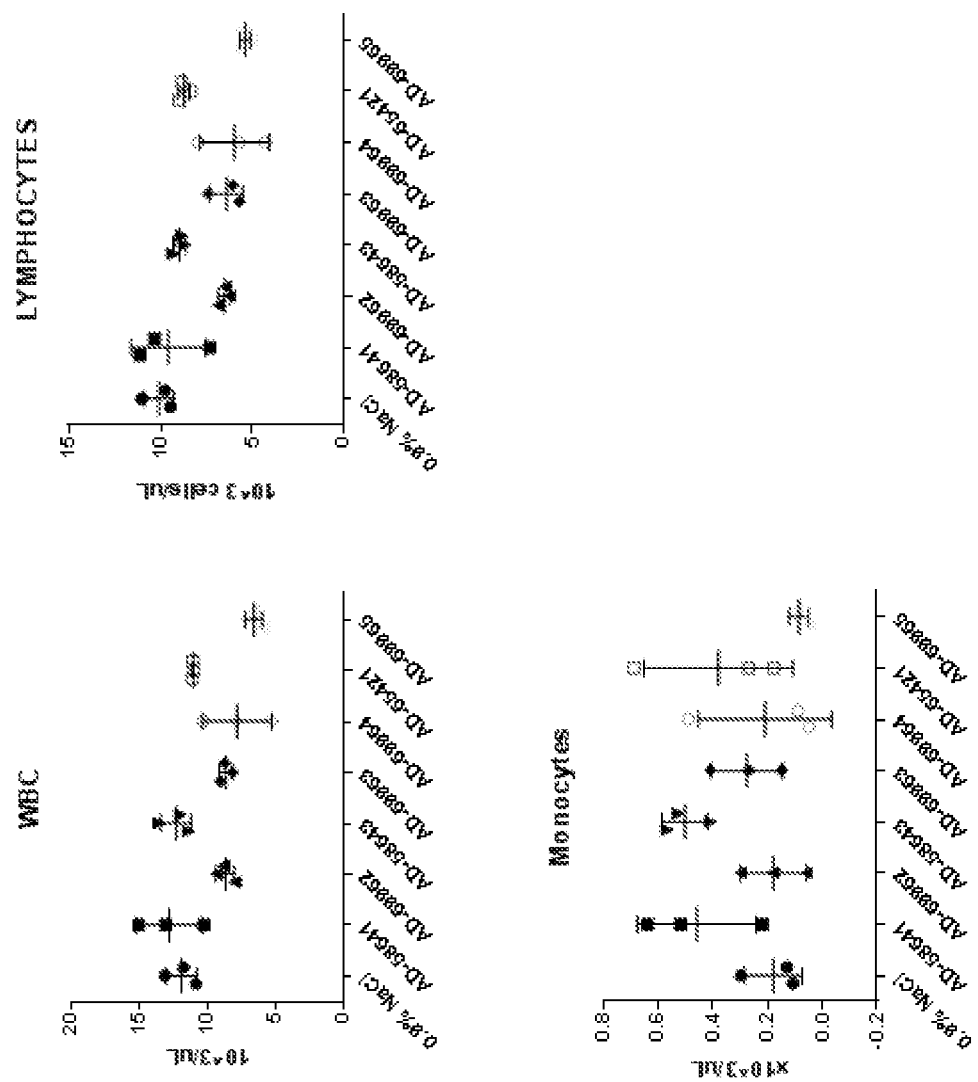
FIG. 19 shows hematology results of the exemplary RNAi agents shown in FIG. 14. Decreased white blood cells and lymphocytes were seen only with abasic and morpholino modifications for all sequences.
Figure 20:
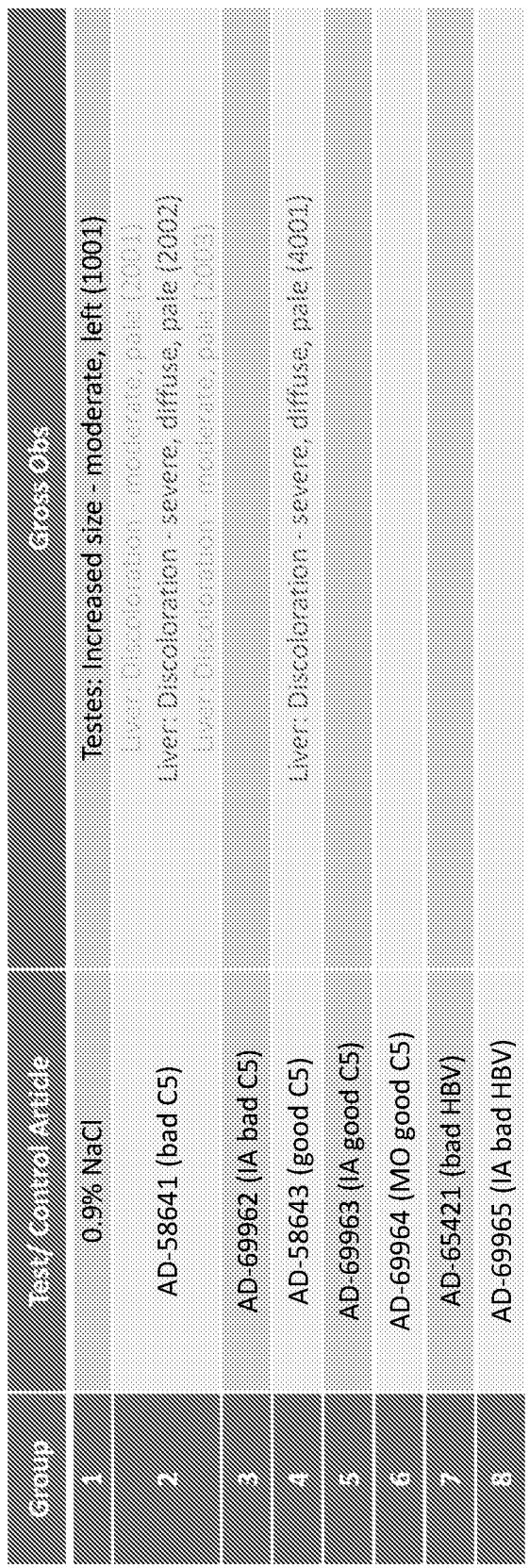
FIG. 20 shows gross observations for the exemplary RNAi agents shown in FIG. 14.

Hepatic F9 gene expression was assayed to evaluate RNAi mediated knockdown. FIG. 5 shows that selected modifications did provide exonuclease stability in comparison to the negative control where the stabilizing phosphorothioate modifications were removed without the replacement of the above described stabilizing modifications. The u5Mo and u5a modifications were able to restore some of the activity loss observed at this time point.

Example 3

Commercially available starting materials, reagents, and solvents were used as received. All moisture-sensitive reactions were carried under anhydrous conditions under argon atmosphere. Flash chromatography was performed on a Teledyne ISCO Combi Flash system using pre-packed ReadySe.p Teledyne ISCO silica gel columns. TLC was performed on Merck silica-coated plates 60 $F_{254}$. Compounds were visualized under UV light (254 nm) or after spraying with the p-anisaldehyde staining solution followed by heating. ESI-HRMS spectra were recorded on Waters QTof API US spectrometer using the direct flow injection in the positive mode (capillary=3000 kV, cone=35, source temperature=120° C., and desolvation temperature=350° C.). $^1$H and $^{13}$C NMR spectra were recorded at room temperature on Varian spectrometers, and chemical shifts in ppm are referenced to the residual solvent peaks. Coupling constants are given in Hertz. Signal splitting patterns are described as singlet (s), doublet (d), triplet (t), quartet (q), broad signal (br), or multiplet (m). $^{31}$P NMR spectra were recorded under proton-decoupled mode; chemical shifts are referenced to external $H_3PO_4$ (80%).

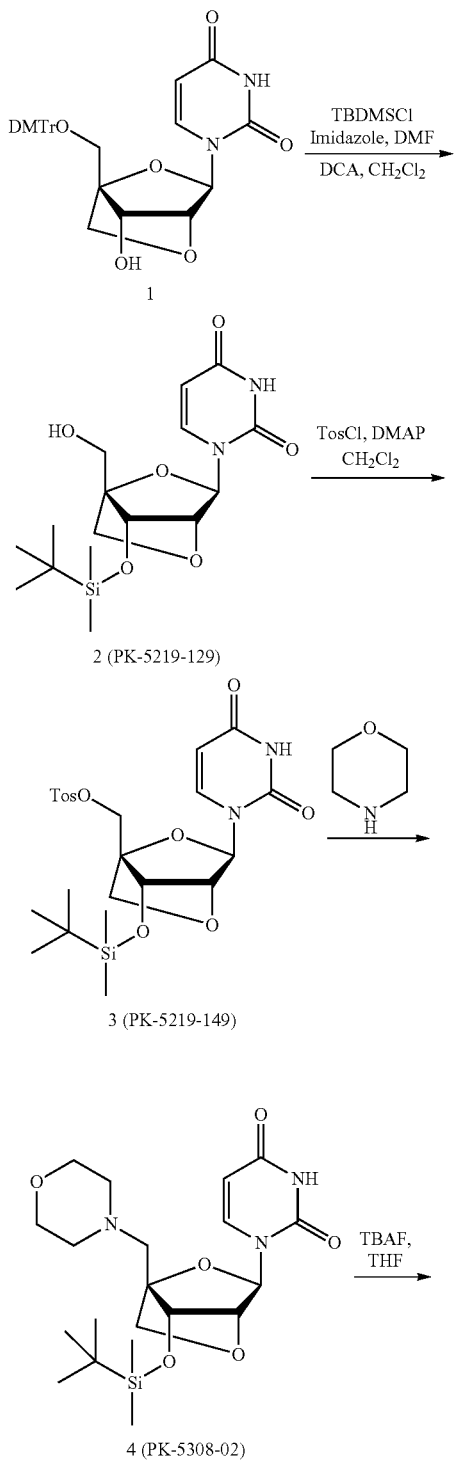

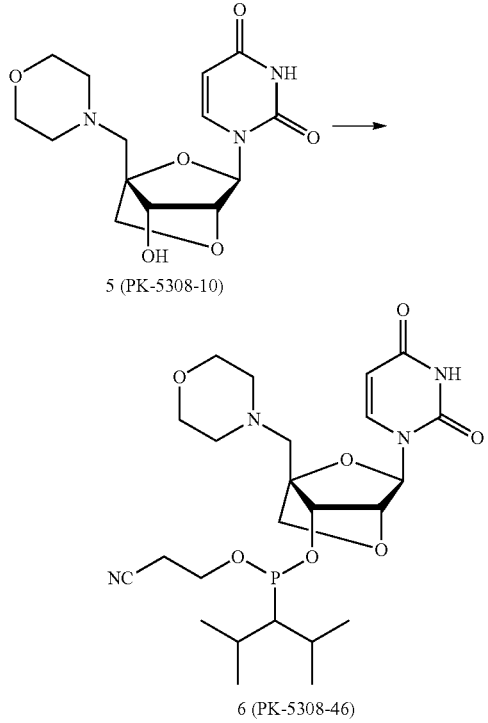

Nucleoside 2 (PK-5219-129) was synthesized as follows:

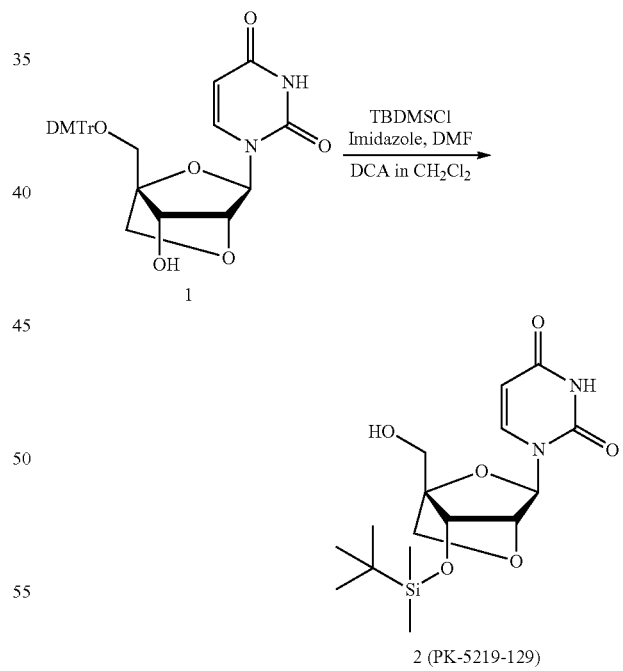

Nucleoside 11 (11.0 g, 19.7 mmol) was dissolved in dry DMF (30 mL). To this was added imidazole (1.70 g, 24.9 mmol) followed by tert-butyldimethylsilyl chloride (3.6 g, 23.8 mmol) and the mixture was stirred at room temperature for 18 h. The reaction mixture was diluted with EtOAc (200 mL) and washed with saturated aqueous solution of NaHCO$_3$ (2×50 mL). The organic phase was dried (MgSO$_4$) and concentrated under reduced pressure. The crude was purified by column chromatography using a gradient of 0-70% EtOAc in hexane to obtain fully protected nucleoside (10.7 g). To this was added a solution of dichloroacetic acid in CH$_2$Cl$_2$ (3% wt/v, 120 mL). The reaction mixture was stirred for 1 h whereupon MeOH (5 mL) was added and stirring was continued for another 20 minutes. The solvents were removed, and the residue was purified by column chromatography using a gradient of 0-12% MeOH in CH$_2$Cl$_2$ to afford PK-5219-129 (4.95 g, 70%). $^1$H NMR (400 MHZ, DMSO) δ 11.36 (s, 1H), 7.74 (d, J=8.1 Hz, 1H), 5.63 (dd, J=8.1, 2.2 Hz, 1H), 5.44 (d, J=0.7 Hz, 1H), 5.20 (t, J=5.3 Hz, 1H), 4.14 (s, 1H), 4.00 (s, 1H), 3.79 (d, J=7.7 Hz, 1H), 3.76-3.67 (m, 2H), 3.65 (d, J=7.8 Hz, 1H), 0.84 (s, 9H), 0.07 (s, 3H), 0.05 (s, 3H).

Nucleoside 3 (PK-5308-149) was synthesized as follows:

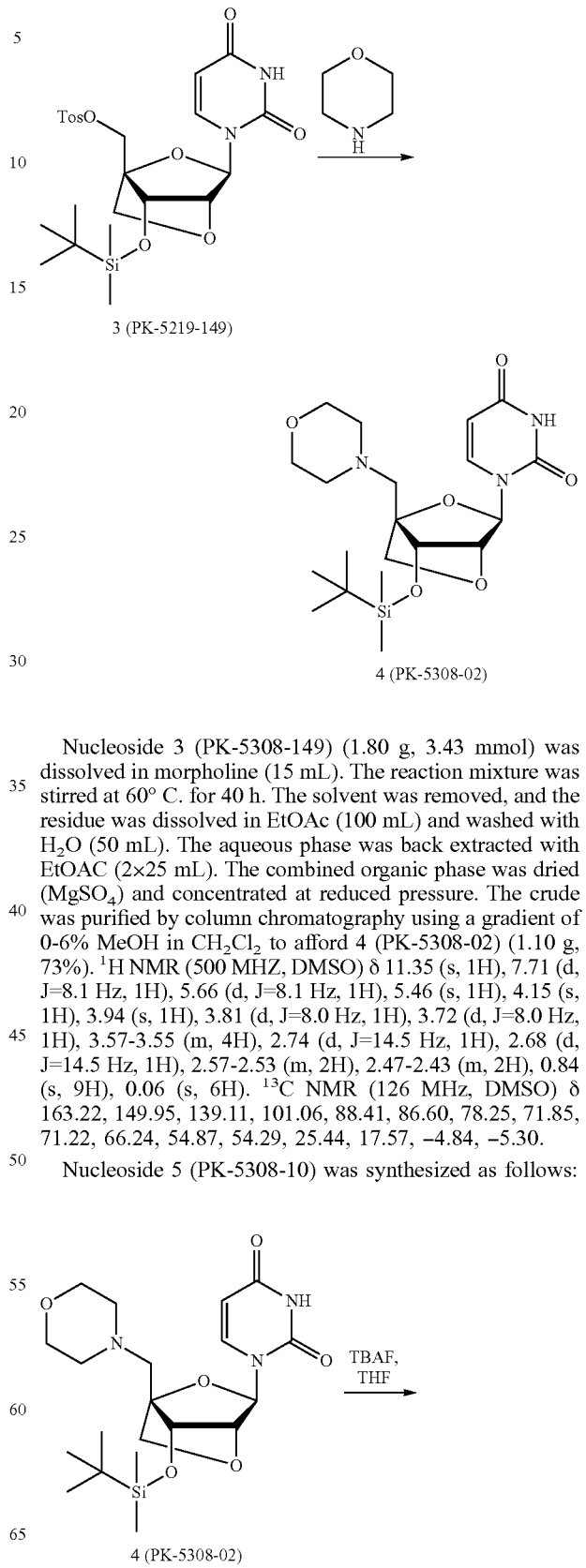

To a solution of 2 (PK-5219-129) (2.0 g, 5.39 mmol) in CH$_2$Cl$_2$ was added 4-dimethylaminopyridine (DMAP, 1.32 g, 10.78 mmol) and 4-toluenesulfonyl chloride (TosCl, 1.28, 6.74 mmol) at 0° C. The reaction mixture was slowly warm to room temperature and stirred for 2 h. The reaction mixture was diluted with CH$_2$Cl$_2$ (100 mL) and washed with saturated aqueous solution of NaHCO$_3$ (50 mL). The aqueous phase was back extracted with CH$_2$Cl$_2$ (50 mL), and combined organic phase was dried (MgSO$_4$) and concentrated at reduced pressure. The residue was purified by column chromatography using a gradient of 0-4% MeOH in CH$_2$Cl$_2$ to afford nucleoside 3 (PK-5219-149) (2.15 g, 75%). $^1$H NMR (400 MHZ, DMSO) δ 11.37 (d, J=2.1 Hz, 1H), 7.86-7.73 (m, 2H), 7.51-7.49 (m, 3H), 5.56 (dd, J=8.1, 2.2 Hz, 1H), 5.45 (s, 1H), 4.62 (d, J=11.8 Hz, 1H), 4.23-4.20 (d, 2H), 4.00 (s, 1H), 3.79-3.63 (m, 2H), 2.41 (s, 3H), 0.75 (s, 9H), 0.02 (s, 3H), 0.01 (s, 3H). $^{13}$C NMR (126 MHz, DMSO) δ 163.17, 149.90, 145.43, 138.95, 131.44, 130.29, 127.71, 101.00, 86.84, 85.26, 78.65, 70.96, 70.82, 66.03, 25.29, 21.07, 17.41, −5.00, −5.49.

Nucleoside 4 (PK-5308-02) was synthesized as follows:

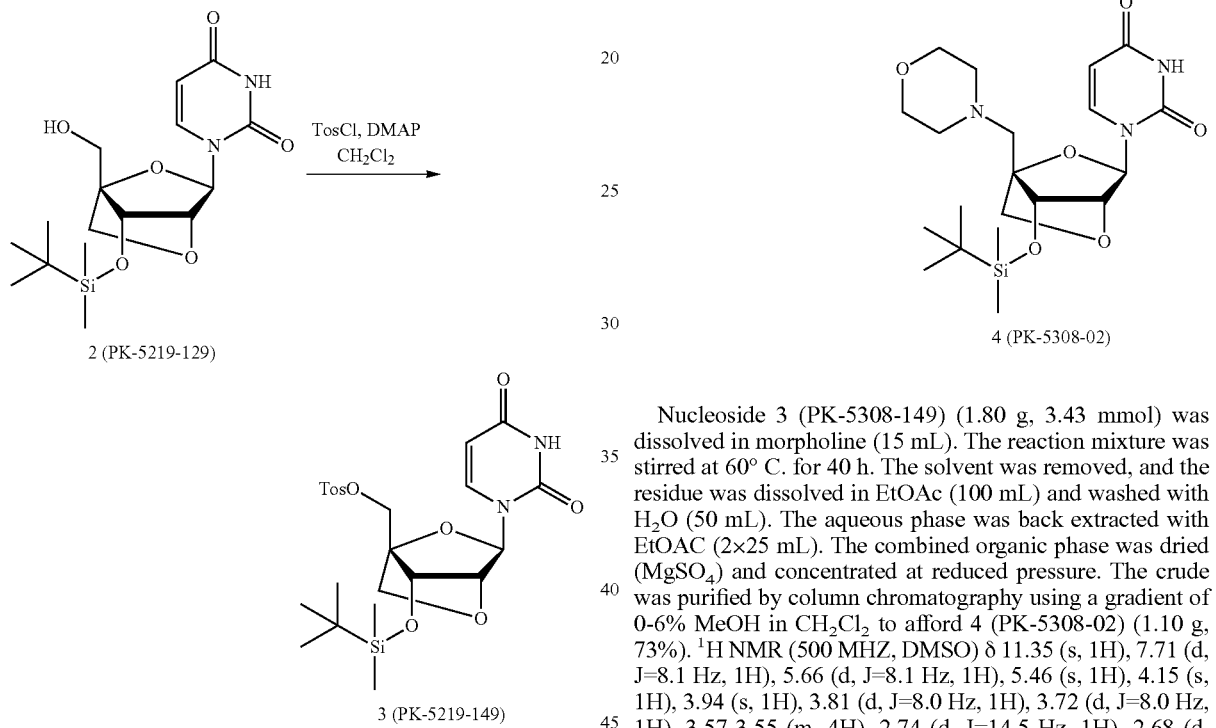

Nucleoside 3 (PK-5308-149) (1.80 g, 3.43 mmol) was dissolved in morpholine (15 mL). The reaction mixture was stirred at 60° C. for 40 h. The solvent was removed, and the residue was dissolved in EtOAc (100 mL) and washed with H$_2$O (50 mL). The aqueous phase was back extracted with EtOAC (2×25 mL). The combined organic phase was dried (MgSO$_4$) and concentrated at reduced pressure. The crude was purified by column chromatography using a gradient of 0-6% MeOH in CH$_2$Cl$_2$ to afford 4 (PK-5308-02) (1.10 g, 73%). $^1$H NMR (500 MHZ, DMSO) δ 11.35 (s, 1H), 7.71 (d, J=8.1 Hz, 1H), 5.66 (d, J=8.1 Hz, 1H), 5.46 (s, 1H), 4.15 (s, 1H), 3.94 (s, 1H), 3.81 (d, J=8.0 Hz, 1H), 3.72 (d, J=8.0 Hz, 1H), 3.57-3.55 (m, 4H), 2.74 (d, J=14.5 Hz, 1H), 2.68 (d, J=14.5 Hz, 1H), 2.57-2.53 (m, 2H), 2.47-2.43 (m, 2H), 0.84 (s, 9H), 0.06 (s, 6H). $^{13}$C NMR (126 MHz, DMSO) δ 163.22, 149.95, 139.11, 101.06, 88.41, 86.60, 78.25, 71.85, 71.22, 66.24, 54.87, 54.29, 25.44, 17.57, −4.84, −5.30.

Nucleoside 5 (PK-5308-10) was synthesized as follows:

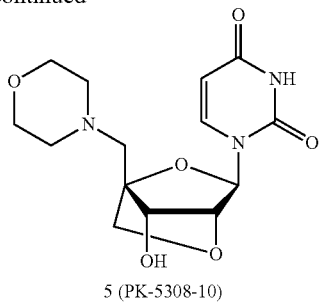

5 (PK-5308-10)

To a solution of 4 (PK-5308-02) (1.05 g, 2.38 mmol) in THF was added tetrabutylammonium fluoride (TBAF, 1M in THF, 3.60 mL, 3.60 mmol). The reaction mixture was stirred at room temperature for 1 h. The solvent was removed, and the crude was purified by column chromatography using a gradient of 0-5% MeOH in EtOAc to afford 5 (PK-5308-10) (0.70 g, 90%). $^1$H NMR (500 MHz, DMSO) δ 11.34 (s, 1H), 7.76 (d, J=8.1 Hz, 1H), 5.77-5.71 (m, 1H), 5.65 (d, J=8.1 Hz, 1H), 5.42 (s, 1H), 4.12 (s, 1H), 3.84 (d, J=8.0 Hz, 1H), 3.77 (d, J=3.2 Hz, 1H), 3.70 (d, J=8.0 Hz, 1H), 3.56 (t, J=4.7 Hz, 4H), 2.74 (s, 2H), 2.65-2.54 (m, 2H), 2.48-2.38 (m, 2H). $^{13}$C NMR (126 MHz, DMSO) δ 163.20, 149.95, 139.19, 100.92, 88.40, 86.48, 78.58, 71.60, 69.91, 66.31, 54.78, 54.50.

Nucleoside 6 (PK-5308-46) was synthesized as follows:

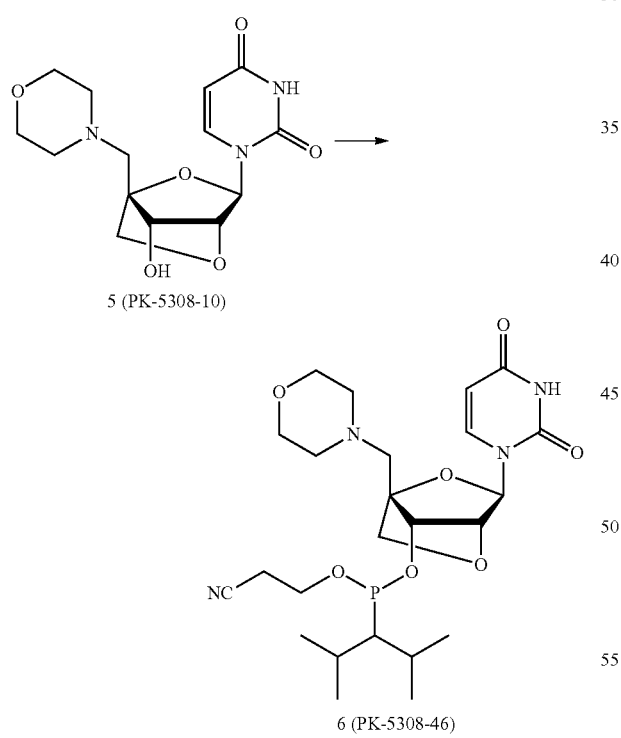

To a suspension of nucleoside 5 (PK-5308-10) (0.65 g, 2.0 mmol) in anhydrous CH$_2$Cl2 (5 mL) was added 2-Cyanoethyl N, N, N',N'-tetraisopropylphosphordiamidite (PN$_2$ 1.20 g, 4 mmol) followed by 4,5 dicyanoimidazole (DCI, 0.29 mg, 2.5 mmol). The reaction mixture was stirred at room temperature for 3 h whereupon it was diluted with CH$_2$Cl$_2$ (50 mL) and washed with saturated aqueous NaHCO$_3$(25 mL). The aqueous phase was back extracted with CH$_2$Cl$_2$ (25 mL), and the combined organic phase was dried (MgSO$_4$) and concentrated at reduced pressure. The residue was purified by column chromatography using a gradient of 0-2% MeOH in CH$_2$Cl$_2$ (containing 0.2% Et$_3$N) to afford 6 (PK-5308-46) (0.88 g, 84%). $^{31}$P NMR (202 MHZ, CD$_3$CN) δ 149.90, 149.58.

Scheme 6: Synthesis of 5'-morpholino LNA A

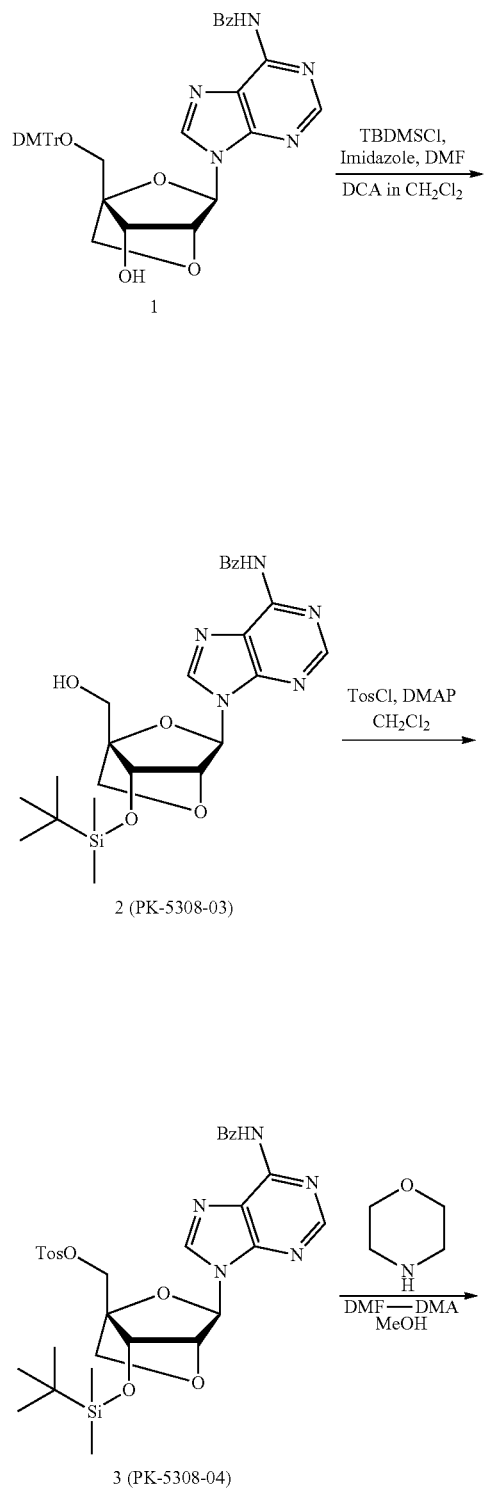

-continued

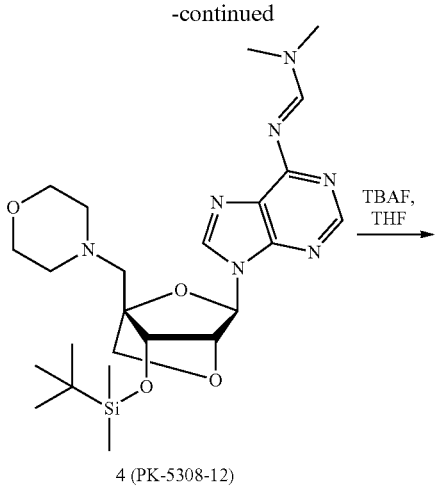

4 (PK-5308-12)

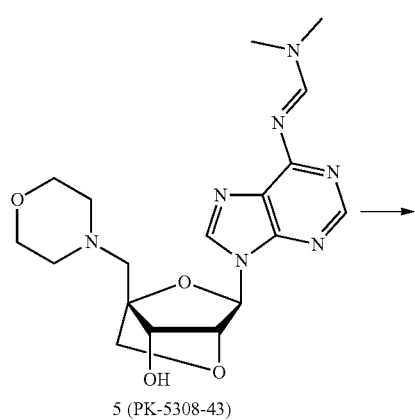

5 (PK-5308-43)

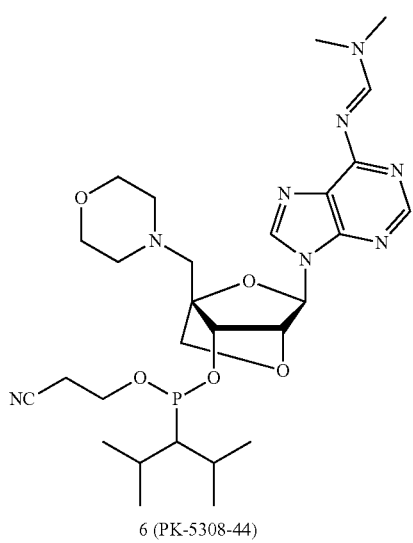

6 (PK-5308-44)

Synthesis of PK-5308-03:

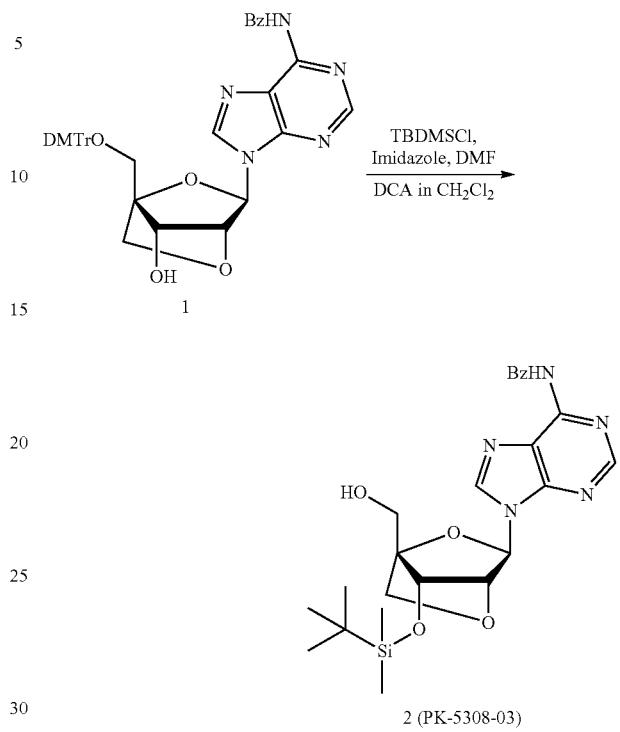

2 (PK-5308-03)

To a solution of nucleoside 12 (5.0 g, 7.29 mmol) in anhydrous DMF (20 mL) was added imidazole (0.74 g, 10.9 mmol), and tert-butyldimethylsilyl chloride (1.64 g, 10.9 mmol). The reaction mixture was stirred at room temperature for 20 h, diluted with EtOAc (200 mL) and washed with saturated aqueous solution of $NaHCO_3$ (2×100 mL). The combined aqueous phase was back extracted with EtOAc (100 mL). The combined organic phase was dried ($MgSO_4$) and concentrated under reduced pressure. To the residue was added a solution of dichloroacetic acid in $CH_2Cl_2$ (3% wt/v, 200 mL). The reaction mixture was stirred at room temperature for 1 h whereupon MeOH (5 mL was added). The reaction mixture was stirred again for 1 h. The reaction mixture was reduced to half under reduced pressure and neutralized with saturated aqueous solution of $NaHCO_3$ (200 mL) in an open flask. The content was transferred to a separating funnel and organic phase was washed with $NaHCO_3$ (200 mL). The combined aqueous phase was back extracted with $CH_2Cl_2$ (2×100 mL). The combined organic phase was dried ($MgSO_4$) and concentrated under reduced pressure. The residue was purified by column chromatography using a gradient of 0-2% MeOH in $CH_2Cl_2$ to afford 2 (PK-5308-03) (2.60 g, 72%). $^1$H NMR (500 MHZ, DMSO) δ 11.22 (s, 1H), 8.74 (s, 1H), 8.54 (s, 1H), 8.07-8.01 (m, 2H), 7.64 (t, J=7.4 Hz, 1H), 7.54 (t, J=7.7 Hz, 2H), 6.07 (s, 1H), 4.66 (s, 1H), 4.57 (s, 1H), 3.94 (d, J=7.8 Hz, 1H), 3.83 (d, J=7.8 Hz, 1H), 2.43 (d, J=7.2 Hz, 1H), 2.40 (d, J=7.1 Hz, 1H), 0.85 (s, 9H), 0.08 (s, 3H), 0.07 (s, 3H).

192

Synthesis of Nucleoside 4 (PK-5308-12):

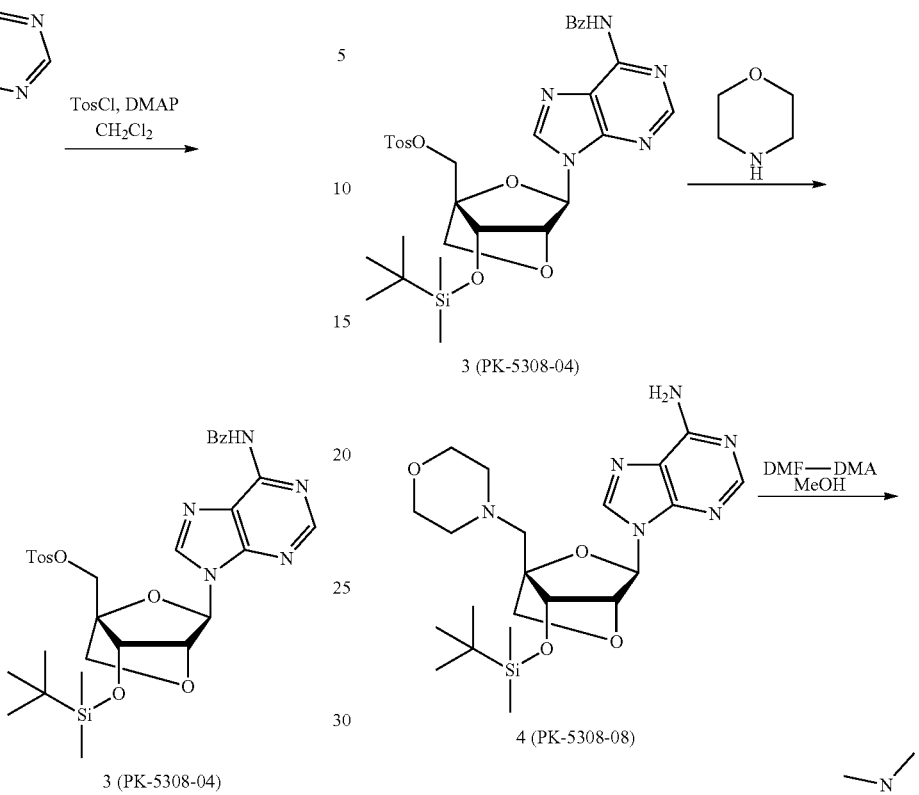

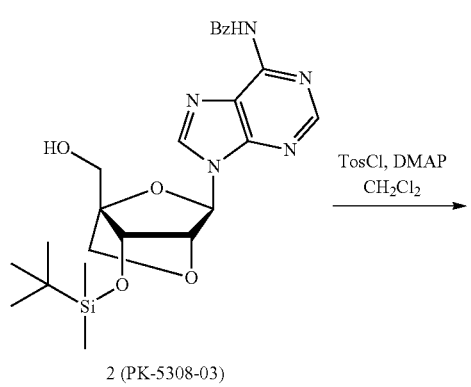

To a solution of nucleoside 2 (PK-5308-3) (2.60 g, 5.22 mmol) in dry $CH_2Cl_2$ was added 4-dimethylaminopyridine (DMAP, 1.27 g, 10.44 mmol) and 4-toluenesulfonyl chloride (TosCl, 1.24, 6.53 mmol) at 0° C. The reaction mixture was slowly warm to room temperature and stirred for 3 h. The reaction mixture was diluted with $CH_2Cl_2$ (100 mL) and washed with saturated aqueous solution of $NaHCO_3$ (50 mL). The aqueous phase was back extracted with $CH_2Cl_2$ (50 mL), and combined organic phase was dried ($MgSO_4$) and concentrated at reduced pressure. The residue was purified by column chromatography using a gradient of 0-5% MeOH in $CH_2Cl_2$ to afford nucleoside 3 (PK-5308-4) (2.65 g, 77%). $^1$H NMR (400 MHZ, DMSO) δ 11.25 (s, 1H), 8.73 (s, 1H), 8.48 (s, 1H), 8.12-7.96 (m, 2H), 7.76 (d, J=8.4 Hz, 2H), 7.66-7.62 (m, 1H), 7.57-7.53 (m, 2H), 7.47-7.40 (m, 2H), 6.07 (s, 1H), 4.74 (s, 1H), 4.72 (s, 1H), 4.59 (d, J=11.7 Hz, 1H), 4.23 (d, J=11.7 Hz, 1H), 3.84 (d, J=8.1 Hz, 1H), 3.79 (d, J=8.1 Hz, 1H), 2.38 (s, 3H), 0.78 (s, 9H), 0.07 (s, 3H), 0.05 (s, 3H). $^{13}$C NMR (126 MHz, DMSO) δ 165.55, 151.52, 151.31, 150.44, 145.31, 142.56, 133.26, 132.45, 131.46, 130.16, 128.45, 128.44, 127.68, 125.59, 85.61, 85.03, 78.88, 72.37, 71.31, 66.39, 25.34, 21.03, 17.43, −4.94, −5.37.

Nucleoside 3 (PK-5308-4) (2.5 g, 3.83 mmol) was taken in morpholine (30 mL). The reaction mixture for stirred at 60° C. for 2 days. The solvent was evaporated, and the crude was purified by column chromatography using a gradient of 0-8% MeOH in $CH_2Cl_2$ to afford PK-5308-08 (tentatively assigned by LCMS). To a solution of PK-5308-8 in MeOH (5 mL) was added DMF-DMA (400 μL, 3.01 mmol). The reaction mixture was stirred at room temperature for 18 h. Solvent was removed, and the residue was taken in $CH_2Cl_2$ (50 mL) and $H_2O$ (50 mL). The layers were separated out and the aqueous phase was back extracted with $CH_2Cl_2$ (2×25 mL). The combined organic phase was dried ($MgSO_4$) and concentrated at reduced pressure. The residue was purified by column chromatography using a using a gradient of 0-5% MeOH in $CH_2Cl_2$ to afford 4 (PK-5308-12) (0.50 g, 25% from 3). $^1$H NMR (400 MHZ, DMSO) δ 8.90 (s, 1H), 8.40 (s, 1H), 8.29 (s, 1H), 5.98 (s, 1H), 4.70 (s, 1H), 4.55 (s, 1H), 3.92 (d, J=8.0 Hz, 1H), 3.86 (d, J=8.0 Hz, 1H), 3.53 (t, J=4.8 Hz, 4H), 3.19 (s, 3H), 3.12 (s, 3H), 2.74 (d, J=14.2 Hz, 1H), 2.69 (d, J=14.2 Hz, 1H), 2.57-2.50 (m, 2H), 2.45-2.36 (m, 2H), 0.85 (s, 9H), 0.09 (s, 3H), 0.08 (s, 3H). $^{13}$C NMR (126 MHz, DMSO) δ 159.25, 157.97, 151.83, 150.48, 140.75, 125.58, 88.06, 85.53, 78.73, 73.03, 72.30, 66.17, 55.06, 54.73, 40.67, 34.56, 25.52, 17.64, −4.83, −5.14.

Synthesis of Nucleoside 5 (PK-5308-43):

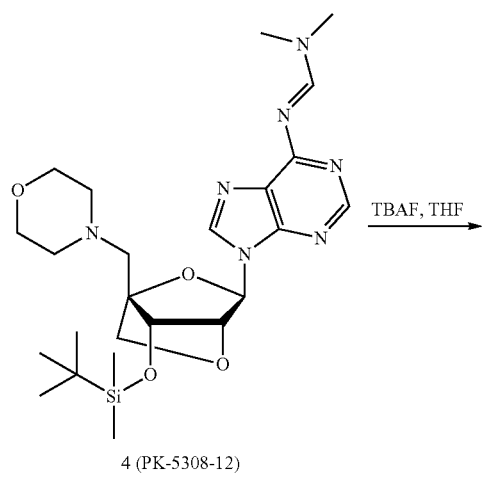

4 (PK-5308-12)

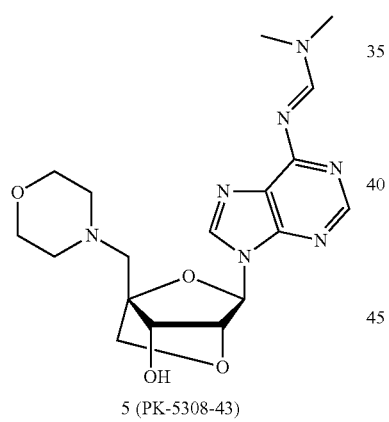

5 (PK-5308-43)

Nucleoside 4 (PK-5308-12) (1.0 g, 1.93 mmol) was dissolved in THF (5 mL). To this was added TBAF (1M in THF, 2.4 mL, 2.4 mmol), and the reaction mixture was stirred at room temperature for 1 h. Solvent was removed, and the residue was purified by column chromatography using a using a gradient of 0-6% MeOH in EtOAc to afford 5 (PK-5308-43) (0.58 g, 74%). $^1$H NMR (500 MHz, DMSO) δ 8.90 (s, 1H), 8.41 (s, 1H), 8.31 (s, 1H), 5.95 (s, 1H), 5.78 (d, J=4.4 Hz, 1H), 4.41 (s, 1H), 4.26 (d, J=4.4 Hz, 1H), 3.95 (d, J=8.1 Hz, 1H), 3.85 (d, J=8.1 Hz, 1H), 3.56 (t, J=4.8 Hz, 4H), 3.19 (s, 3H), 3.12 (s, 3H), 2.82 (d, J=14.3 Hz, 1H), 2.77 (d, J=14.3 Hz, 1H), 2.66-2.57 (m, 2H), 2.46-2.35 (m, 2H). $^{13}$C NMR (126 MHz, DMSO) δ 159.16, 157.95, 152.01, 150.47, 139.72, 125.51, 88.06, 85.24, 78.89, 71.94, 71.38, 66.21, 55.26, 54.66, 40.64, 34.53.

Synthesis of Nucleoside 6 (PK-5308-44)

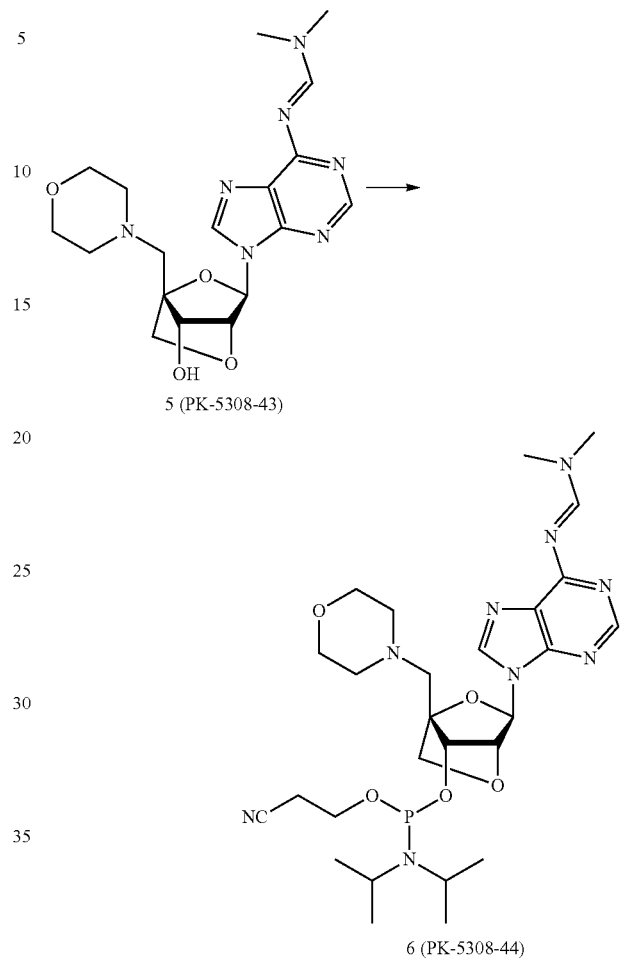

To a suspension of nucleoside 5 (PK-5308-43) (0.55 g, 1.36 mmol) in anhydrous CH$_2$Cl$_2$ (5 mL) was added 2-Cyanoethyl N, N, N′,N′-tetraisopropylphosphordiamidite (PN$_2$ 0.82 g, 2.72 mmol) followed by 4,5 dicyanoimidazole (DCI, 0.20 mg, 1.7 mmol). The reaction mixture was stirred at room temperature for 3 h whereupon it was diluted with CH$_2$Cl$_2$ (50 mL) and washed with saturated aqueous NaHCO$_3$ (25 mL). The aqueous phase was back extracted with CH$_2$Cl$_2$ (20 mL), and the combined organic phase was dried (MgSO$_4$) and concentrated at reduced pressure. The residue was purified by column chromatography using a gradient of 0-2% MeOH in CH$_2$Cl$_2$ (containing 0.2% Et$_3$N) to afford 6 (PK-5308-44) (0.65 g, 79%). $^{31}$P NMR (202 MHZ, CD$_3$CN) δ 149.80, 149.71.

Scheme 7: Synthesis of 5′-piperazinotrizolyl LNA U

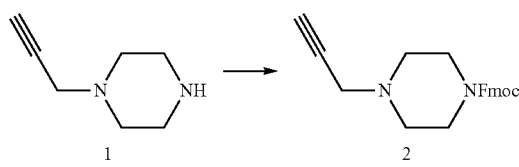

-continued
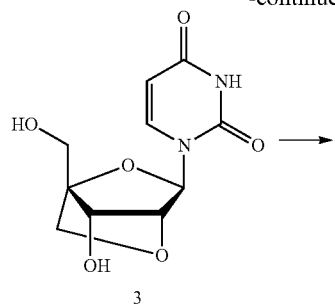
3
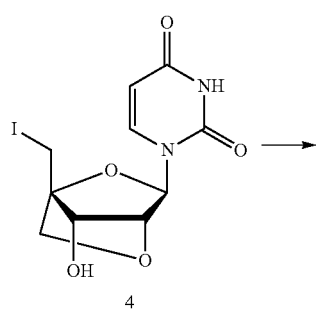
4
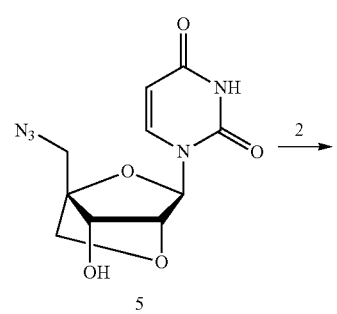
5
-continued
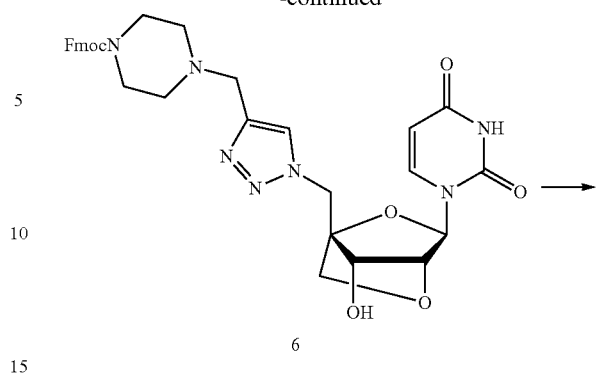
6
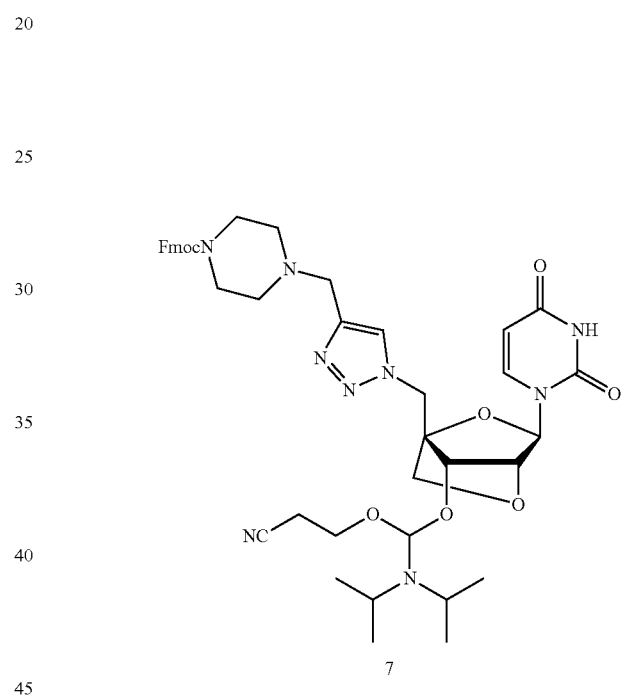
7
Scheme 8: Synthesis of 5′-piperazinotrizoly LNA U Conjugates
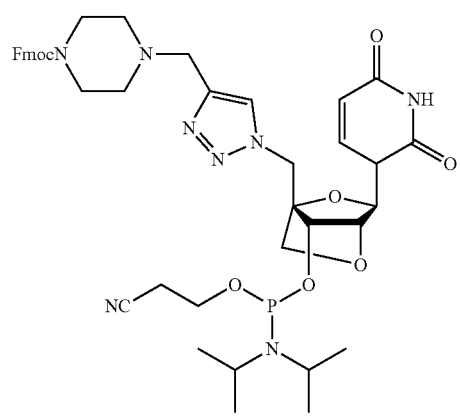
7

-continued
8
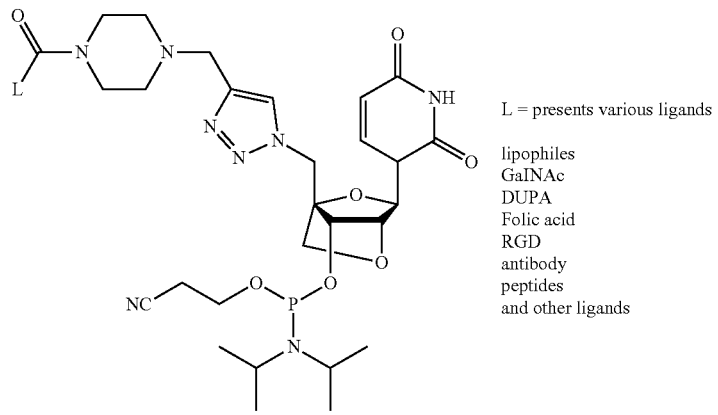
L = presents various ligands
lipophiles
GalNAc
DUPA
Folic acid
RGD
antibody
peptides
and other ligands
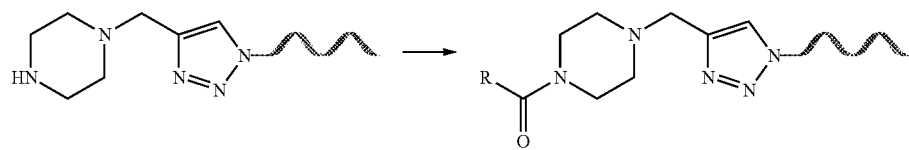
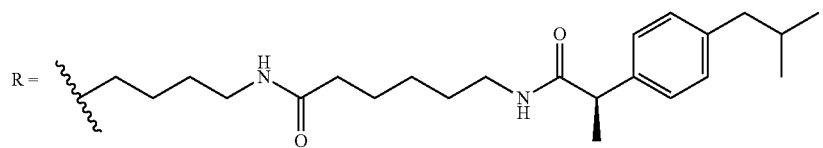
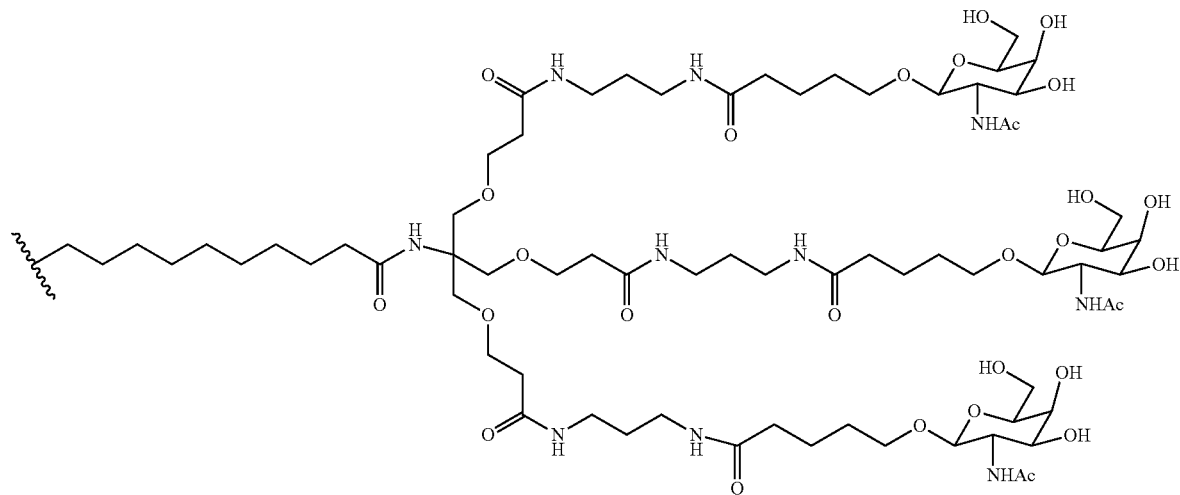
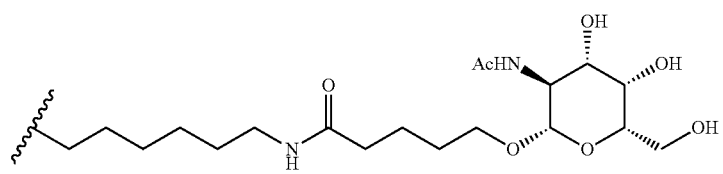

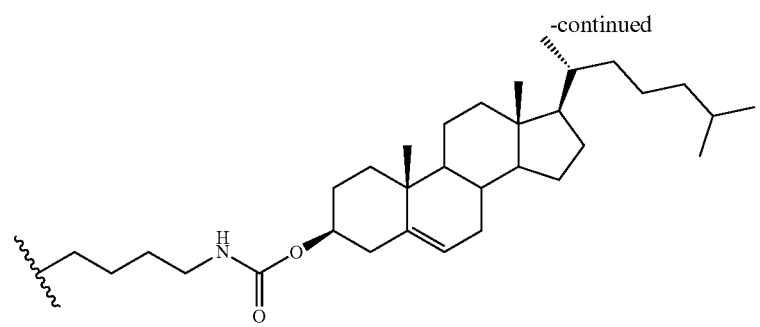
Alkyl (C16, C12 etc)
Alkenyl
Alkynyl
Scheme 9: Scheme 3: Synthesis of 5′-piperazinotrizolyl LNA U Conjugates
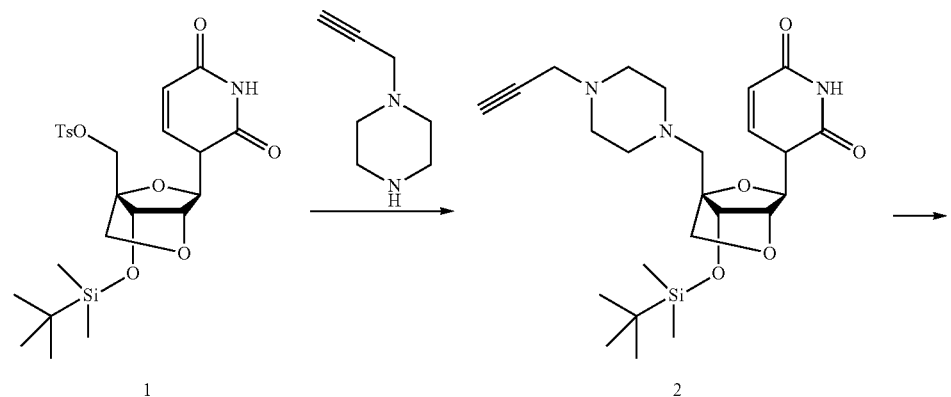
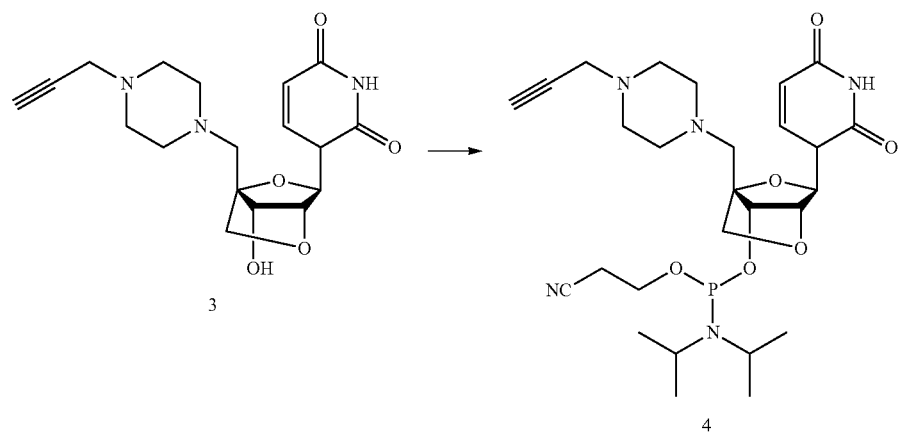

-continued
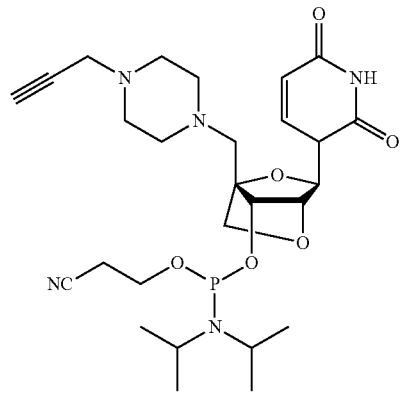
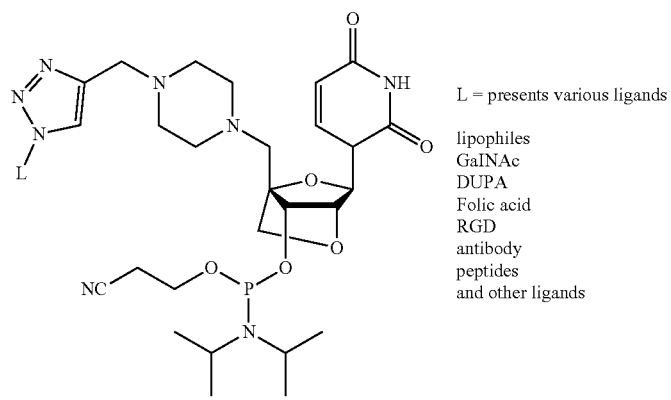
L = presents various ligands
lipophiles
GalNAc
DUPA
Folic acid
RGD
antibody
peptides
and other ligands
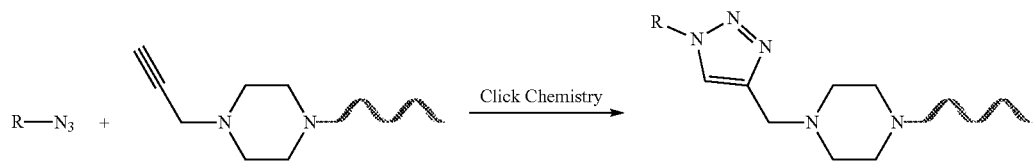
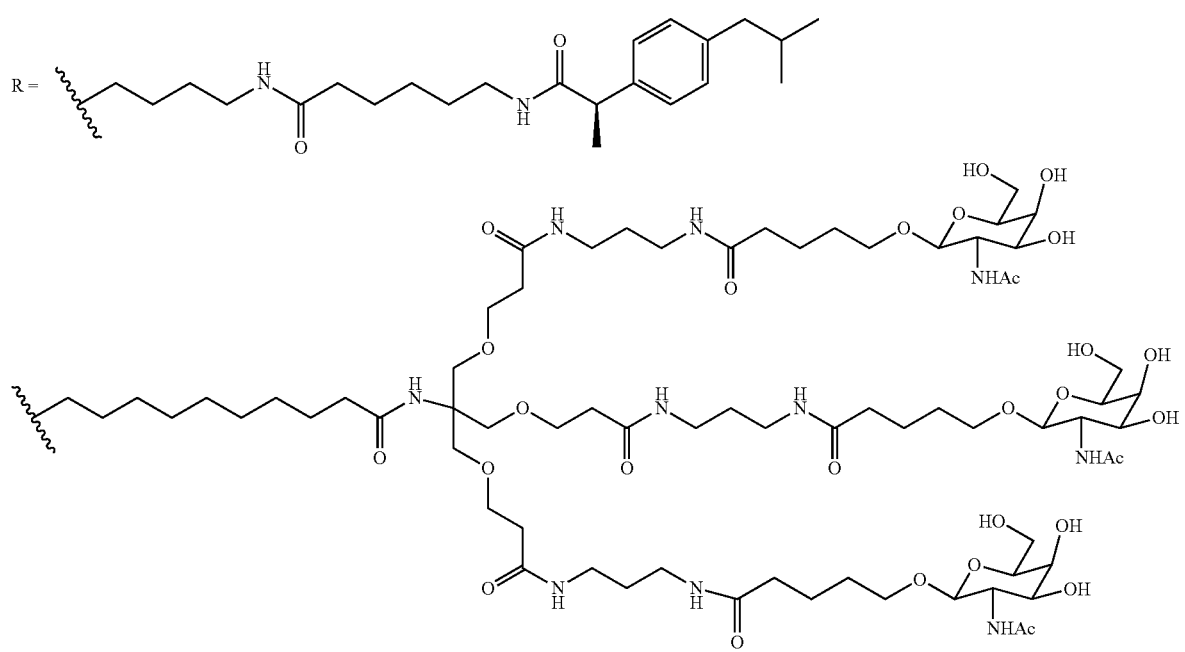

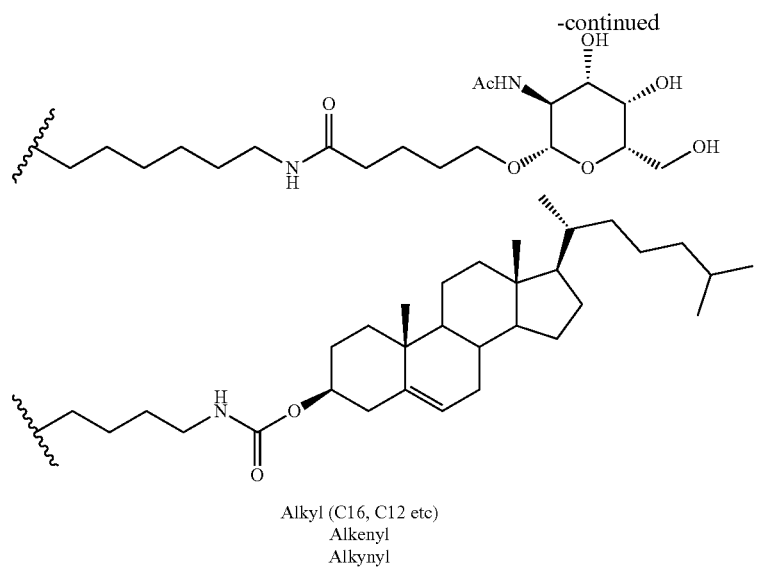
Alkyl (C16, C12 etc)
Alkenyl
Alkynyl
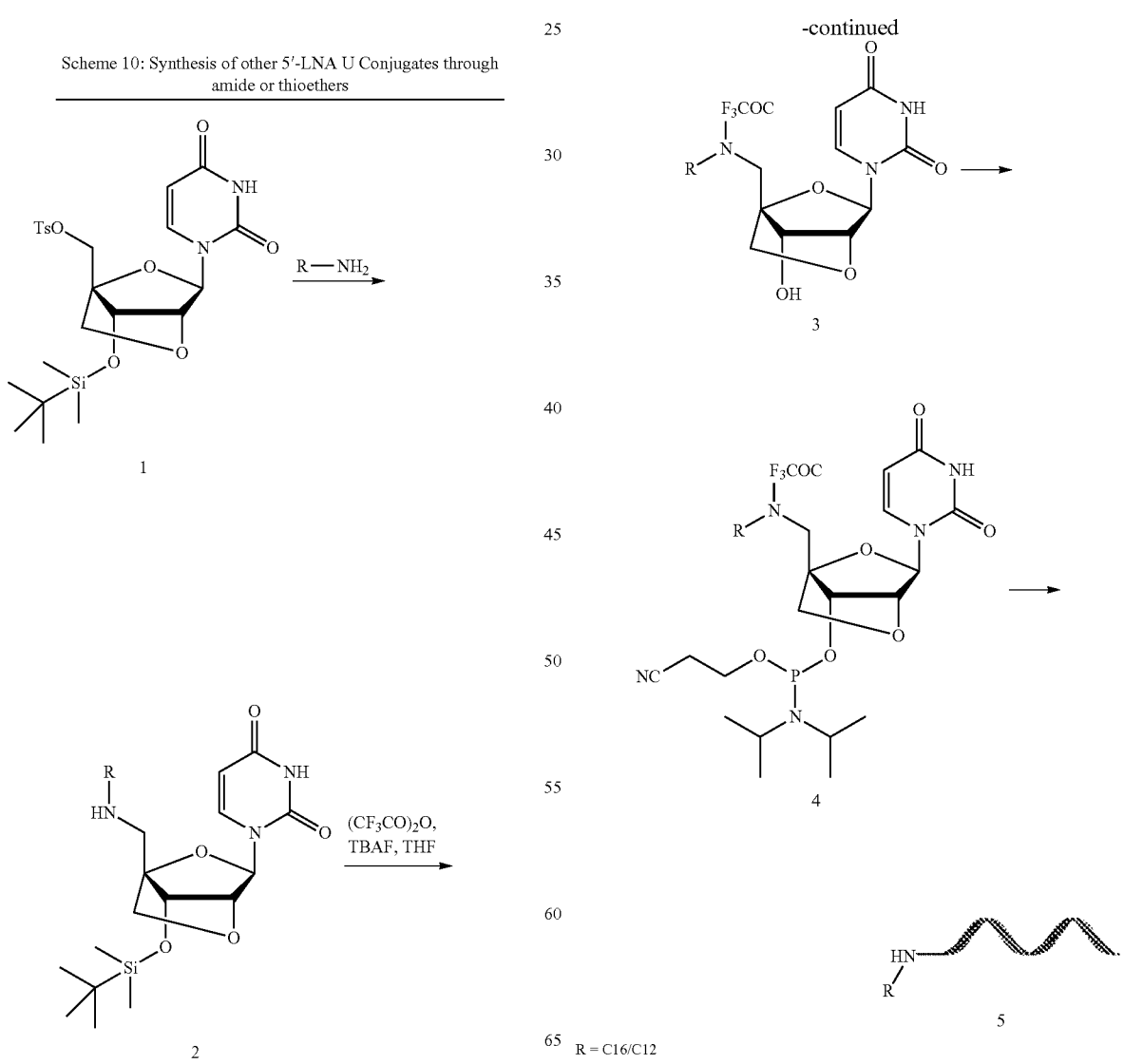
R = C16/C12

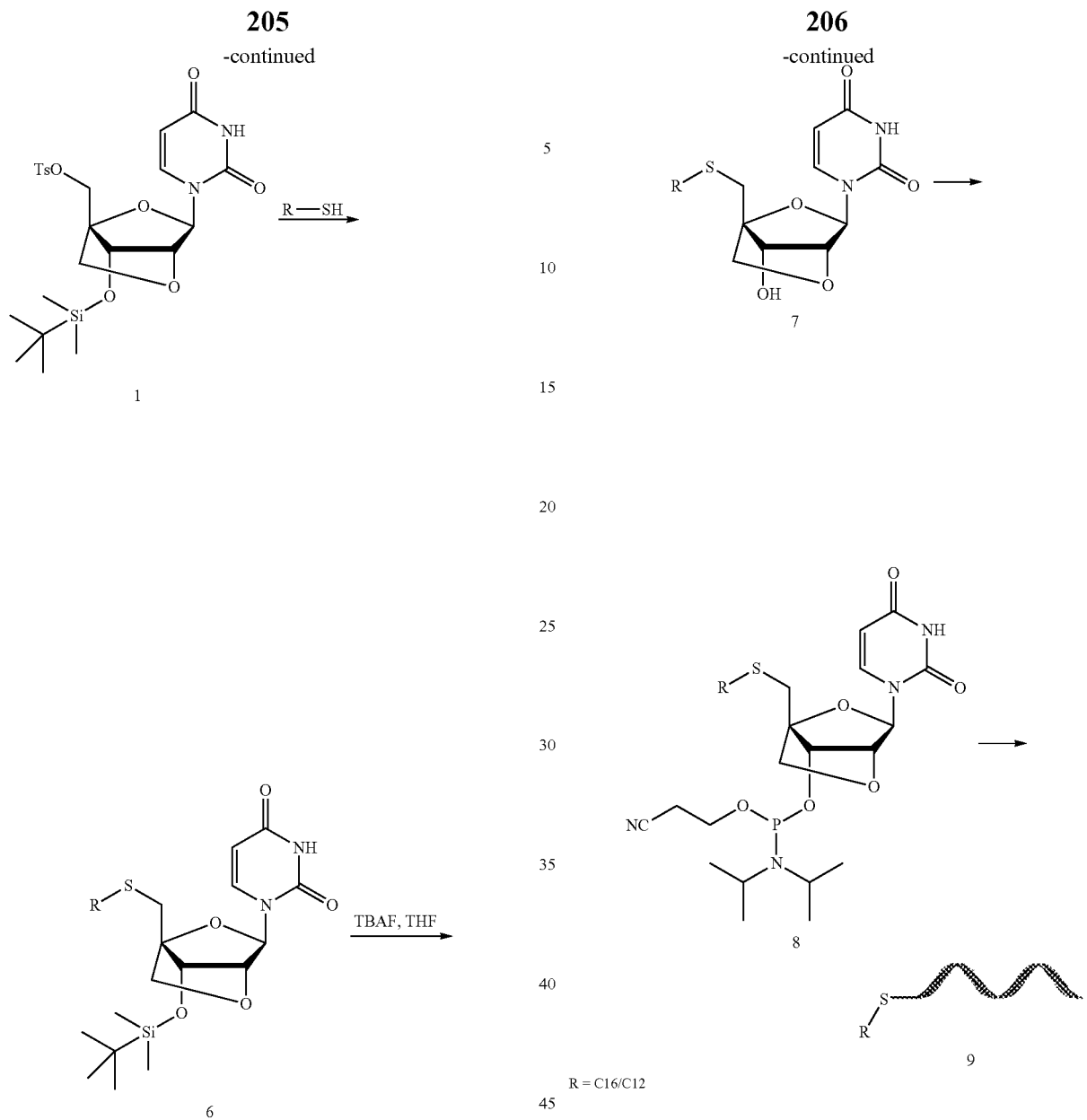
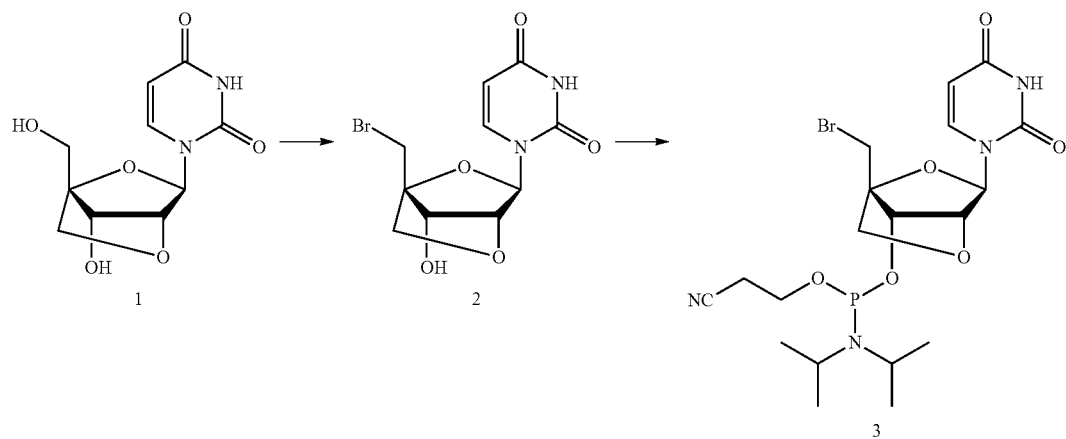
Scheme 11: Synthesis of 5'-triazolyl-LNA U Conjugates

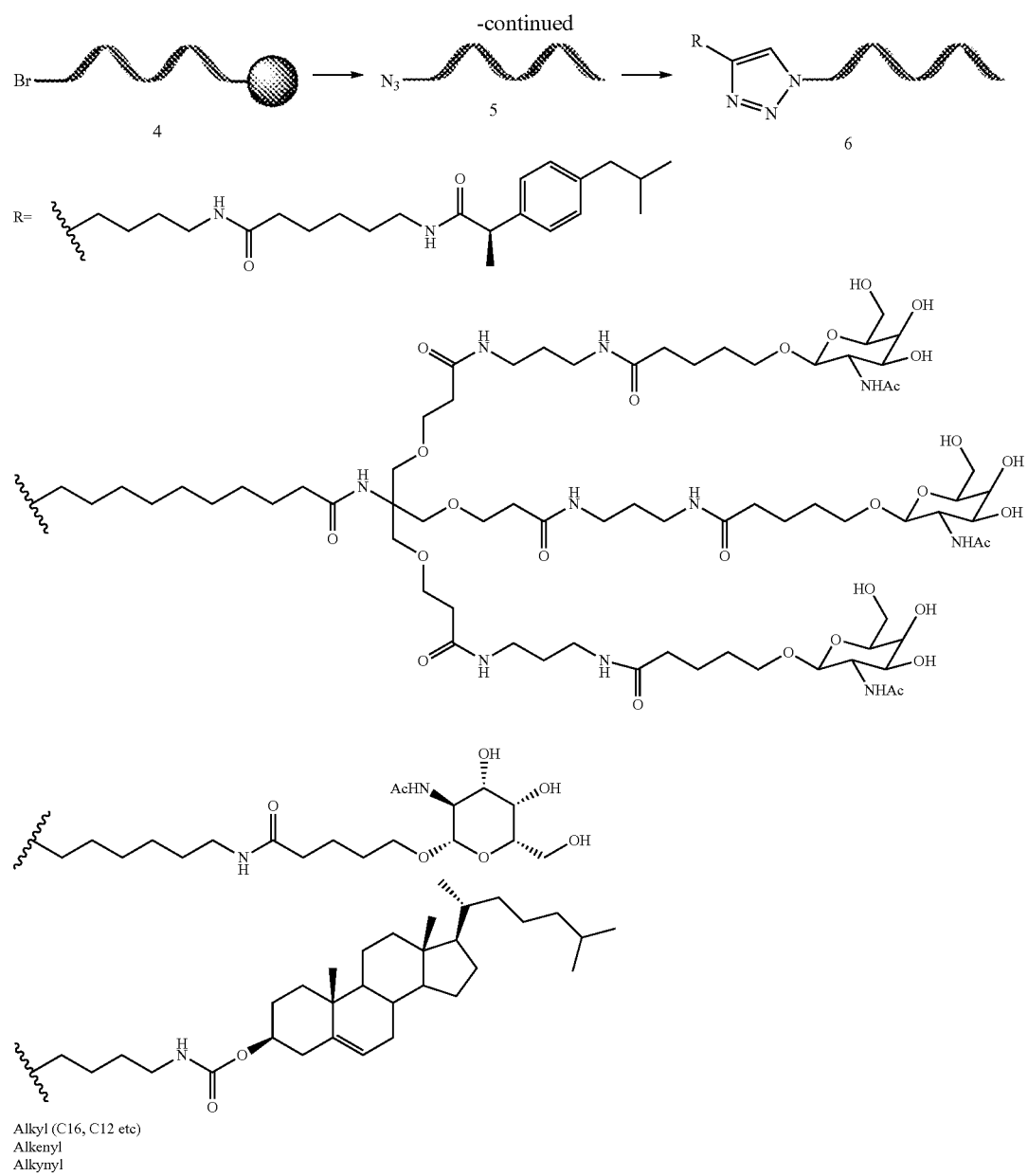
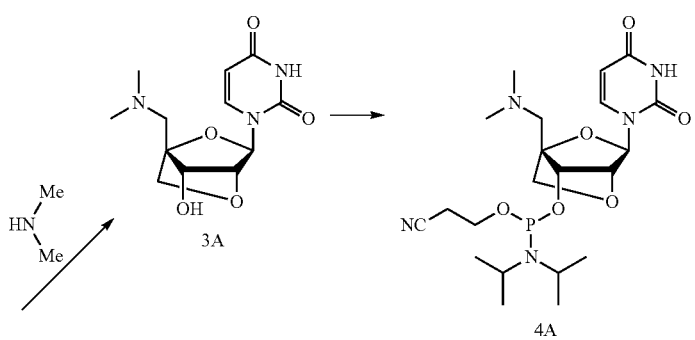
Scheme 12: Synthesis of 5'-other modifications of LNA

-continued

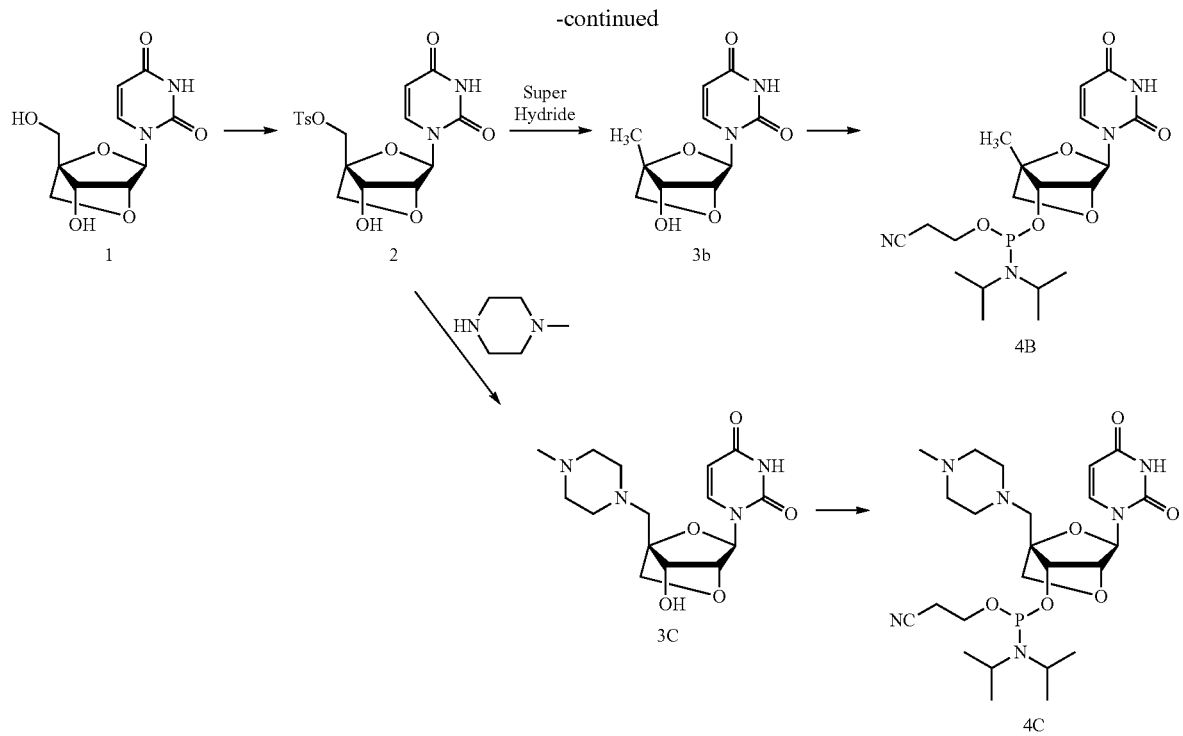

Example 4: Synthesis and Biophysical Characterization of RNAs Containing 2'-Fluorinated Northern Methanocarbacyclic Nucleotides 2'-Fluorinated Northern methanocarbacyclic (2'-F-NMC) nucleosides and phosphoramidites, based on a bicyclo[3.1.0] hexane scaffold and bearing all four natural nucleobases (U, C, A, and G), were synthesized to enable exploration of this novel nucleotide modification related to the clinically-validated, 2'-deoxy-2'-fluororibonucleotides (2'-F-RNA). A duplex of an 2'-F-NMC-modified oligonucleotide with RNA exhibited thermal stability similar to that of the parent RNA duplex, and 2'-F-NMC-modified oligonucleotides had higher stability against 5'- and 3'-exonucleolytic degradation than oligonucleotides modified with 2'-F-RNA.

Therapeutics based on RNA interference (RNAi) have great potential for treating human diseases. The FDA recently approved the first small interfering RNA (siRNA) drug, patisiran, for treatment of polyneuropathy caused by transthyretin-mediated amyloidosis (Adams, D.; Gonzalez-Duarte, A.; O'Riordan, W. D.; Yang, C. C.; Ueda, M.; Kristen, A. V.; Tourney, I.; Schmidt, H. H.; Coelho, T.; Berk, J. L.; Lin, K. P.; Vita, G.; Attarian, S.; Plante-Bordeneuve, V.; Mezei, M. M.; Campistol, J. M.; Buades, J.; Brannagan, T. H., 3rd; Kim, B. J.; Oh, J.; Parman, Y.; Sekijima, Y.; Hawkins, P. N.; Solomon, S. D.; Polydefkis, M.; Dyck, P. J.; Gandhi, P. J.; Goyal, S.; Chen, J.; Strahs, A. L.; Nochur, S. V.; Sweetser, M. T.; Garg, P. P.; Vaishnaw, A. K.; Gollob, J. A.; Suhr, O. B. N Engl J Med 2018, 379, 11). The oligonucleotides used in nucleic acid-based therapeutics require use of artificial nucleoside building blocks to stabilize the agents against nuclease degradation, to enhance cell-membrane permeability, and to limit immune responses (Bumcrot, D.; Manoharan, M.; Koteliansky, V.; Sah, D. W. Nat Chem Biol 2006, 2, 711). The 2'-deoxy-2'-fluororibonucleotide (2'-F-RNA, FIG. 36A) and 2'-O-methyl (2'-OMe) modifications have been used to modify siRNAs, (Allerson, C. R.; Sioufi, N.; Jarres, R.; Prakash, T. P.; Naik, N.; Berdeja, A.; Wanders, L.; Griffey, R. H.; Swayze, E. E.; Bhat, B. J Med Chem 2005, 48, 901; Manoharan, M.; Akinc, A.; Pandey, R. K.; Qin, J.; Hadwiger, P.; John, M.; Mills, K.; Charisse, K.; Maier, M. A.; Nechev, L.; Greene, E. M.; Pallan, P. S.; Rozners, E.; Rajeev, K. G.; Egli, M. Angewandte Chemie International Edition 2011, 50, 2284; Pallan, P. S.; Greene, E. M.; Jicman, P. A.; Pandey, R. K.; Manoharan, M.; Rozners, E.; Egli, M. Nucleic Acids Res 2011, 39, 3482) antisense oligonucleotides, (Kawasaki, A. M.; Casper, M. D.; Freier, S. M.; Lesnik, E. A.; Zounes, M. C.; Cummins, L. L.; Gonzalez, C.; Cook, P. D. J Med Chem 1993, 36, 831; Monia, B. P.; Lesnik, E. A.; Gonzalez, C.; Lima, W. F.; McGee, D.; Guinosso, C. J.; Kawasaki, A. M.; Cook, P. D.; Freier, S. M. J Biol Chem 1993, 268, 14514) aptamers, (Ng, E. W.; Shima, D. T.; Calias, P.; Cunningham, E. T., Jr.; Guyer, D. R.; Adamis, A. P. Nat Rev Drug Discov 2006, 5, 123) microRNAs, (Davis, S.; Propp, S.; Freier, S. M.; Jones, L. E.; Serra, M. J.; Kinberger, G.; Bhat, B.; Swayze, E. E.; Bennett, C. F.; Esau, C. Nucleic Acids Res 2009, 37, 70) and ribozymes (Pieken, W. A.; Olsen, D. B.; Benseler, F.; Aurup, H.; Eckstein, F. Science 1991, 253, 314). Incorporation of 2'-F-RNA and 2'-O-Me residues stabilizes an A-form RNA duplex (Patra, A.; Paolillo, M.; Charisse, K.; Manoharan, M.; Rozners, E.; Egli, M. Angew Chem Int Ed Engl 2012, 51, 11863). Specifically, 2'-F preorganizes the sugar into a C3'-endo or North conformation; this modification reduces the entropic penalty for formation of the A-form duplex and increases base stacking and Watson-Crick hydrogen-bond stabilities due to its electron-withdrawing power. Furthermore, 2'-F-RNA-modified siRNAs, which are used in several siRNAs in clinical development, have reduced immune stimulation and improved activity in vitro and in vivo compared with unmodified siRNA. The 2'-F-RNA-modified oligonucleotides are, however, more sensitive to nucleolytic degradation than other 2'-modified oligonucleotides; moreover, these monomers are recognized, albeit poorly, by human RNA polymerases at high concentrations (Peng, C. G.; Damha, M. J. Canadian Journal of Chemistry 2008, 86, 881; Arnold, J. J.; Sharma, S. D.; Feng, J. Y.; Ray, A. S.; Smidansky, E. D.; Kireeva, M. L.; Cho, A.; Perry, J.; Vela, J. E.; Park, Y.; Xu, Y.; Tian, Y.; Babusis, D.; Barauskus, O.; Peterson, B. R.; Gnatt, A.; Kashlev, M.; Zhong, W.; Cameron, C. E. PLOS Pathog 2012, 8, e1003030). Hence, chemically modified building blocks that retain the advantages of 2'-F-RNA but overcome these limitations have the potential to improve pharmacological properties of oligonucleotides. A number of fluorine-containing building blocks have been synthesized and evaluated in the context of oligonucleotide-based therapeutics (Egli, M.; Pallan, P. S.; Allerson, C. R.; Prakash, T. P.; Berdeja, A.; Yu, J.; Lee, S.; Watt, A.; Gaus, H.; Bhat, B.; Swayze, E. E.; Seth, P. P. J Am Chem Soc 2011, 133, 16642; Seth, P. P.; Yu, J.; Jazayeri, A.; Pallan, P. S.; Allerson, C. R.; Ostergaard, M. E.; Liu, F.; Herdewijn, P.; Egli, M.; Swayze, E. E. J Org Chem 2012, 77, 5074; Pallan, P. S.; Yu, J.; Allerson, C. R.; Swayze, E. E.; Seth, P.; Egli, M. Biochemistry 2012, 51, 7; Seth, P. P.; Pallan, P. S.; Swayze, E. E.; Egli, M. Chembiochem 2013, 14, 58; Jung, M. E.; Dwight, T. A.; Vigant, F.; Ostergaard, M. E.; Swayze, E. E.; Seth, P. P. Angew Chem Int Ed Engl 2014, 53, 9893; Ostergaard, M. E.; Dwight, T.; Berdeja, A.; Swayze, E. E.; Jung, M. E.; Seth, P. P. J Org Chem 2014, 79, 8877; Istrate, A.; Medvecky, M.; Leumann, C. J. Org Lett 2015, 17, 1950; Martinez-Montero, S.; Deleavey, G. F.; Dierker-Viik, A.; Lindovska, P.; Ilina, T.; Portella, G.; Orozco, M.; Parniak, M. A.; Gonzalez, C.; Damha, M. J. J Org Chem 2015, 80, 3083; Martinez-Montero, S.; Deleavey, G. F.; Martin-Pintado, N.; Fakhoury, J. F.; Gonzalez, C.; Damha, M. J. ACS Chem Biol 2015, 10, 2016; Kel'in, A. V.; Zlatev, I.; Harp, J.; Jayaraman, M.; Bisbe, A.; O'Shea, J.; Taneja, N.; Manoharan, R. M.; Khan, S.; Charisse, K.; Maier, M. A.; Egli, M.; Rajeev, K. G.; Manoharan, M. J Org Chem 2016, 81, 2261; Ostergaard, M. E.; Nichols, J.; Dwight, T. A.; Lima, W.; Jung, M. E.; Swayze, E. E.; Seth, P. P. Mol Ther Nucleic Acids 2017, 7, 20; Istrate, A.; Katolik, A.; Istrate, A.; Leumann, C. J. Chemistry 2017, 23, 10310; Malek-Adamian, E.; Guenther, D. C.; Matsuda, S.; Martinez-Montero, S.; Zlatev, I.; Harp, J.; Burai Patrascu, M.; Foster, D. J.; Fakhoury, J.; Perkins, L.; Moitessier, N.; Manoharan, R. M.; Taneja, N.; Bisbe, A.; Charisse, K.; Maier, M.; Rajeev, K. G.; Egli, M.; Manoharan, M.; Damha, M. J. J Am Chem Soc 2017, 139, 14542; Harp, J. M.; Guenther, D. C.; Bisbe, A.; Perkins, L.; Matsuda, S.; Bommineni, G. R.; Zlatev, I.; Foster, D. J.; Taneja, N.; Charisse, K.; Maier, M. A.; Rajeev, K. G.; Manoharan, M.; Egli, M. Nucleic Acids Res 2018, 46, 8090; Malek-Adamian, E.; Patrascu, M. B.; Jana, S. K.; Martinez-Montero, S.; Moitessier, N.; Damha, M. J. The Journal of Organic Chemistry 2018, 83, 9839; Frei, S.; Istrate, A.; Leumann, C. J. Beilstein J Org Chem 2018, 14, 3088).

However, none of these modifications have been made with all four nucleobases. As nucleotide pharmacology in a therapeutic oligonucleotide like siRNA depends both on sequence and position, it is necessary to have all four nucleosides for evaluation of therapeutic potential (Schlegel, M. K.; Foster, D. J.; Kel'in, A. V.; Zlatev, I.; Bisbe, A.; Jayaraman, M.; Lackey, J. G.; Rajeev, K. G.; Charisse, K.; Harp, J.; Pallan, P. S.; Maier, M. A.; Egli, M.; Manoharan, M. J Am Chem Soc 2017, 139, 8537).

Conformationally restricted nucleic acids bearing bicyclic or tricyclic scaffolds that exhibit high affinity for complementary RNA have also been widely explored as potential oligonucleotide modifications (Goyenvalle, A.; Leumann, C.; Garcia, L. J Neuromuscul Dis 2016, 3, 157; Shen, X.; Corey, D. R. Nucleic Acids Res 2018, 46, 1584). Nucleosides with a carbocyclic bicyclo[3.1.0]hexane system, here referred to as Northern methanocarbacyclic (NMC) nucleosides, are constrained to an RNA-like sugar pucker (FIG. 36B) (Altmann, K.-H.; Kesselring, R.; Francotte, E.; Rihs, G. Tetrahedron Letters 1994, 35, 2331; Siddiqui, M. A.; Ford, H.; George, C.; Marquez, V. E. Nucleosides and Nucleotides 1996, 15, 235; Marquez, V. E.; Siddiqui, M. A.; Ezzitouni, A.; Russ, P.; Wang, J.; Wagner, R. W.; Matteucci, M. D. J Med Chem 1996, 39, 3739; Maier, M. A.; Choi, Y.; Gaus, H.; Barchi, J. J., Jr.; Marquez, V. E.; Manoharan, M. Nucleic Acids Res 2004, 32, 3642; Terrazas, M.; Ocampo, S. M.; Perales, J. C.; Marquez, V. E.; Eritja, R. Chembiochem 2011, 12, 1056; Pallan, P. S.; Marquez, V. E.; Egli, M. Biochemistry 2012, 51, 2639). The bicyclic NMC sugar is predicted to adopt a pseudoboat C2'-exo conformation due to the methylene bridge between the C4' and C6' positions. Consequently, NMC-modified oligonucleotides form more stable duplexes with RNA than do unmodified DNA.

Jung and co-workers recently synthesized thymidine analogs 2'-F-NMC T (FIG. 36C) and ara-2'-F-NMC T and oligonucleotides containing these building blocks. Deoxyoligonucleotides containing 2'-F-NMC T have higher RNA binding affinity than do oligonucleotides containing 2'-deoxy-2'-fluoro uridine or non-fluorinated NMC thymidine. This duplex stabilization is presumed to result from stabilization of Watson-Crick hydrogen-bonding and base-stacking interactions due to the 2'-fluoro incorporation and demonstrates the potential of 2'-F-NMC analogs in oligonucleotide-based therapeutics.

The inventors have systematically evaluated the role of chemical modifications in siRNA activity. To assess 2'-F-NMC analogs in terms of their sequence- and position-dependent RNAi activity we required all RNA nucleobase analogs. Here, the synthesis of 2'-F-NMC phosphoramidites bearing the four natural RNA nucleobases (i.e., A, U, G, C) from a common starting material in a convergent approach is reported. The binding affinities to a target RNA and susceptibilities to exonuclease degradation of oligonucleotides containing 2'-F-NMC is also reported.

The 2'-F-NMC U and 2'-F-NMC C phosphoramidites were synthesized as depicted in Scheme 13. The starting amine I was prepared according to the procedure reported by Jung et al. and was coupled with 3-methoxyacryloyl isocyanate and cyclized under acidic conditions to afford the uridine derivative 2 (Shaw, G.; Warrener, R. N. Journal of the Chemical Society (Resumed) 1958, 157; Umemiya, H.; Kagechika, H.; Hashimoto, Y.; Shudo, K. Nucleosides and Nucleotides 1996, 15, 465). The 5'—OH group of the nucleoside 2 was protected with 4,4'-dimethoxytriphenylmethyl chloride (DMTrCl) to give compound 3. Subsequent phosphitylation of the 3'—OH group of 3 gave the desired phosphoramidite 4. For the synthesis of 2'-F-NMC C, fully protected nucleoside 5 was obtained by tert-butyldimethylsilyl (TBS) protection of 3. Compound 5 was then converted into the cytidine derivative 6 by reacting with 1,2,4-triazole in the presence of $Et_3N$ and $POCl_3$, followed by treatment with aqueous $NH_3$. The exocyclic amine of 6 was benzoylated using benzoyl chloride (BzCl), and the resulting protected cytidine derivative 7 was treated with tetra-n-butylammonium fluoride (TBAF) to obtain alcohol 8. Phosphitylation of 8 gave the desired phosphoramidite 9.

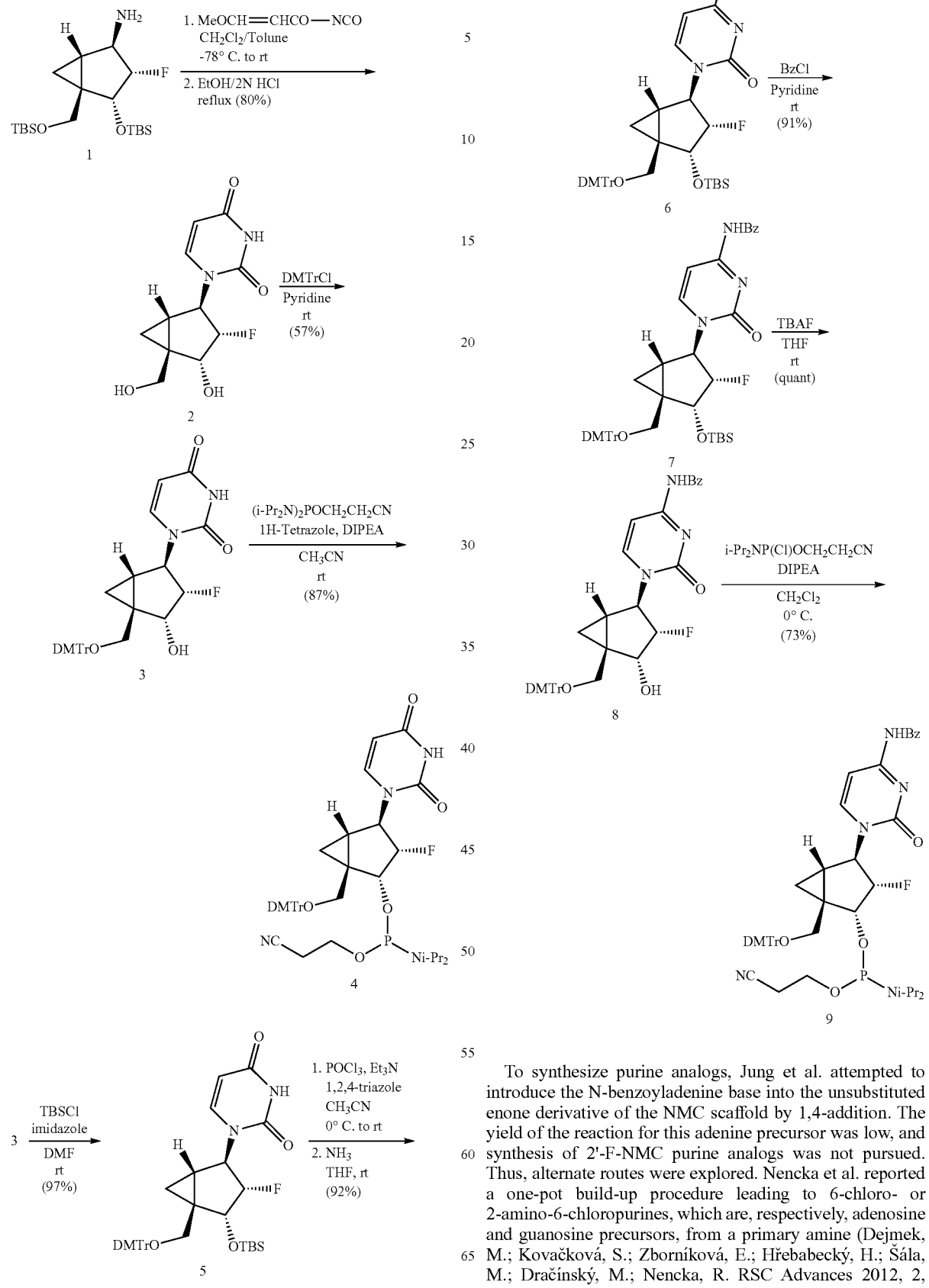

To synthesize purine analogs, Jung et al. attempted to introduce the N-benzoyladenine base into the unsubstituted enone derivative of the NMC scaffold by 1,4-addition. The yield of the reaction for this adenine precursor was low, and synthesis of 2'-F-NMC purine analogs was not pursued. Thus, alternate routes were explored. Nencka et al. reported a one-pot build-up procedure leading to 6-chloro- or 2-amino-6-chloropurines, which are, respectively, adenosine and guanosine precursors, from a primary amine (Dejmek, M.; Kovačková, S.; Zborníková, E.; Hřebabecký, H.; Šála, M.; Dračínský, M.; Nencka, R. RSC Advances 2012, 2, 6970). Marquez et al. also achieved excellent yields of bicyclo[3,1,0]hexane carbocyclic nucleosides, which involve 6-chloropurines on a primary amine, using a microwave reactor (Saneyoshi, H.; Deschamps, J. R.; Marquez, V. E. J Org Chem 2010, 75, 7659). Therefore, the synthesis of the 2'-F-NMC purine phosphoramidites from the starting amine 1 was evaluated. As shown in Scheme 14, the reaction of 1 with 4,6-dichloro-5-formamidopyrimidine followed by cyclization of the formamido intermediate 10 in the presence of diethoxymethyl acetate gave the 6-chloropurine derivative 11 in 54% yield over two steps. Ammonolysis of the obtained compound 11 using a microwave reactor produced the desired adenine nucleoside 12 in 91% yield. The amino group was then protected with BzCl to furnish the dibenzoyl derivative 13 (19%) and mono-benzoyl derivative 14 (65%). Compound 13 was readily converted to 14 by treatment with aqueous $NH_3$ in THF. Silyl protection was then removed by treating 14 with $Et_3N·3HF$ at 55° C., to obtain diol 15 in 98% yield. Subsequent dimethoxytritylation of the 5'-OH followed by phosphitylation of 16 yielded the desired phosphoramidite 17 (82%).

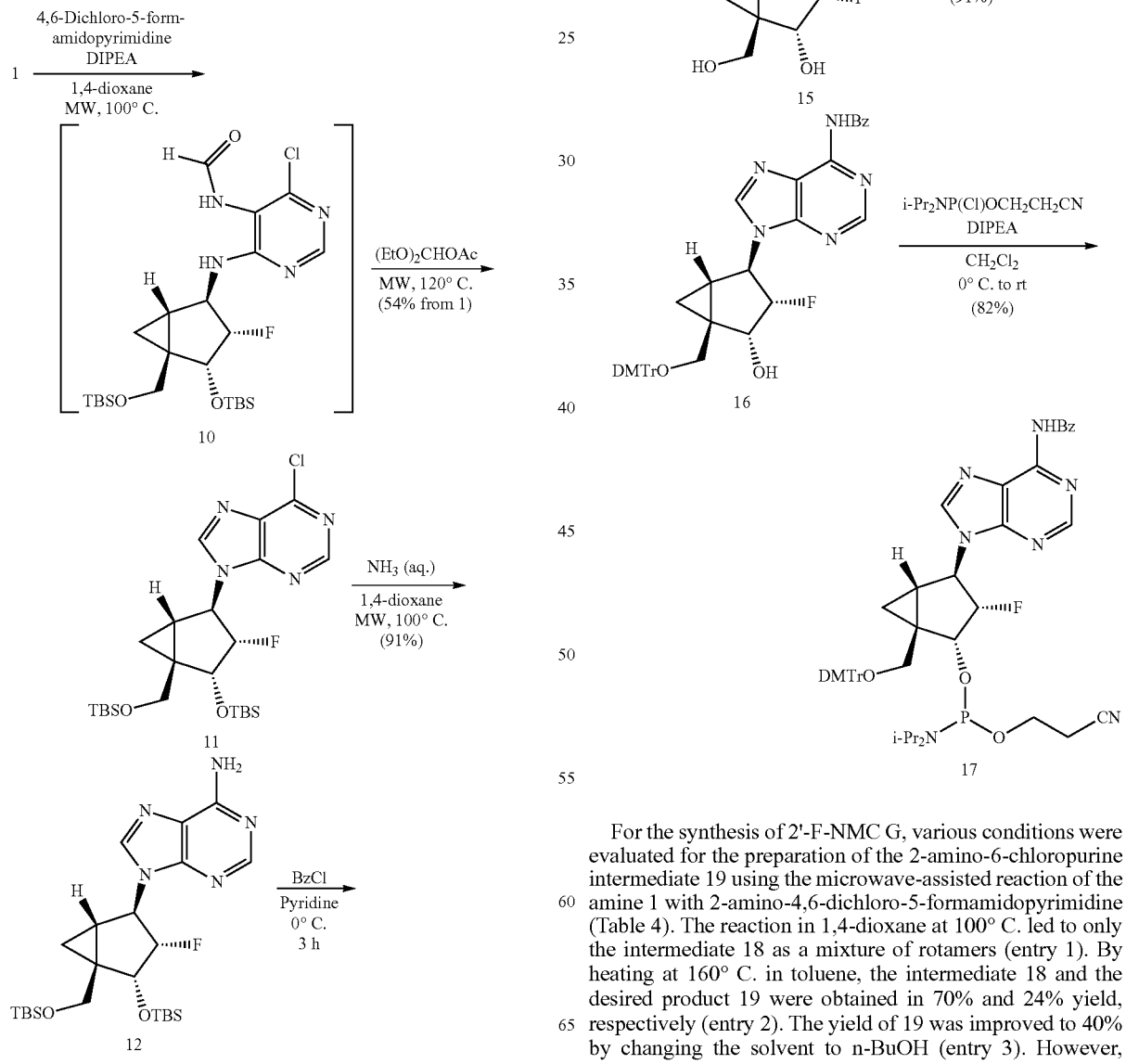

For the synthesis of 2'-F-NMC G, various conditions were evaluated for the preparation of the 2-amino-6-chloropurine intermediate 19 using the microwave-assisted reaction of the amine 1 with 2-amino-4,6-dichloro-5-formamidopyrimidine (Table 4). The reaction in 1,4-dioxane at 100° C. led to only the intermediate 18 as a mixture of rotamers (entry 1). By heating at 160° C. in toluene, the intermediate 18 and the desired product 19 were obtained in 70% and 24% yield, respectively (entry 2). The yield of 19 was improved to 40% by changing the solvent to n-BuOH (entry 3). However, longer reaction times resulted only in substitution of 6-Cl groups by n-BuOH. Attempts to cyclize intermediate 18 in 1,4-dioxane by heating under microwave conditions resulted in disappointingly low yields (17%). The presence of the bulky 5'-O-TBDMS group may hinder imidazole-ring closure, resulting in poor yields. Attempts to use diethoxymethyl acetate for the cyclization yielded a complex mixture, including 19, as shown by LC-MS (data not shown). 2'-F-NMC G was eventually synthesized from the 2-amino-6-chloropurine derivative 19 by reacting with 3-hydroxypropionitrile in the presence of NaH (Scheme 15). Standard protection of exocyclic amine using isobutyryl chloride afforded protected nucleoside 21 (95%). Desilylation using Et$_3$N·3HF gave diol 22 in 98% yield. Dimethoxytritylation gave DMTr-protected compound 23 (66%), which was converted to the corresponding phosphoramidite 24 in 61% yield.

TABLE 4

Construction of 2'-F-NMC G precursor 19

| entry | solvent | temperature (° C.) | time (h) | yield (%) 18 | 19 |
|---|---|---|---|---|---|
| 1 | 1,4-dioxane | 100 | 12 | 88 | trace |
| 2 | toluene | 160 | 2 | 70 | 24 |
| 3 | n-BuOH | 160 | 2 | 59 | 40 |

Scheme 15. Synthesis of 2'-F-NMC G amidite

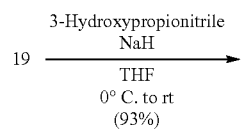

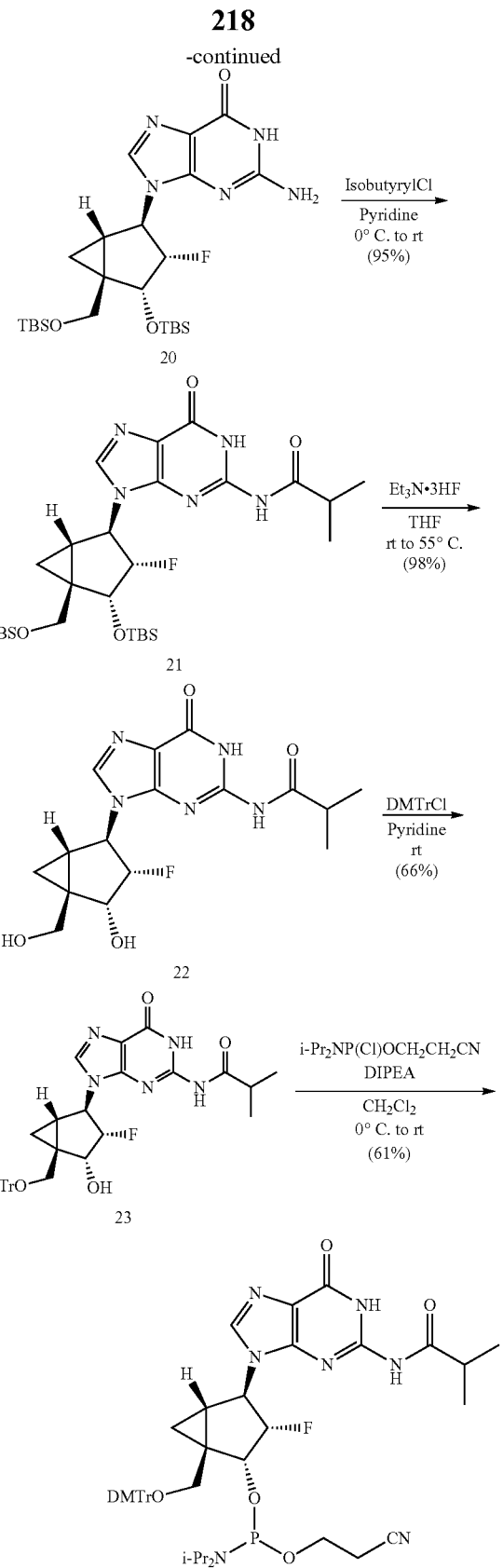

To gauge the effect of modified nucleotides on RNA affinity, the 2'-F-NMC modifications were incorporated into 12-mer oligoribonucleotides via standard solid-phase synthesis. The 2'-F-NMC-modified oligonucleotides were mixed with complementary RNA in PBS buffer, and the melting temperatures (Tm) were determined (Table 5). Modified duplexes containing a single 2'-F-NMC nucleotide at the center showed a decrease of at most 1.3° C. in the melting temperature compared to the unmodified duplex (Table 5). In a similar context, incorporation of 2'-F-RNA-modified nucleotides resulted in slight improvements in the thermal stability. These experiments demonstrate that the 2'-F-NMC modification is well tolerated in an RNA duplex. The slight loss in thermal stability may prove advantageous in RNAi-based applications where high binding affinities in the seed region can induce undesirable off-target effects (Janas, M. M.; Schlegel, M. K.; Harbison, C. E.; Yilmaz, V. O.; Jiang, Y.; Parmar, R.; Zlatev, I.; Castoreno, A.; Xu, H.; Shulga-Morskaya, S.; Rajeev, K. G.; Manoharan, M.; Keirstead, N. D.; Maier, M. A.; Jadhav, V. Nat Commun 2018, 9, 723).

TABLE 5

UV melting temperatures of modified duplexes

| entry | duplex | SEQ ID NO: | $T_m{}^a$ ($\Delta T_m$) (° C.)[b] F-NMC | 2'-F |
|---|---|---|---|---|
| 1 | 5'-UACAGUCUAUGU<br>3'-AUGUCAGAUACA | 63<br>64 | 53.4 (-0.2) | 54.1 (0.5) |
| 2 | 5'-UACAGUCUAUGU<br>3'-AUGUCAGAUACA | 65<br>66 | 53.4 (-0.2) | 54.2 (0.6) |
| 3 | 5'-UACAGUCUAUGU<br>3'-AUGUCAGAUACA | 67<br>64 | 52.3 (-1.3) | 54.3 (0.7) |
| 4 | 5'-UACAGUCUAUGU<br>3'-AUGUCAGAUACA | 65<br>68 | 53.1 (-0.5) | 54.5 (0.9) |

[a]Tm values were obtained in PBS (pH 7.4) using 2.0 µM concentrations of each strand. [b]ΔTm is the difference in melting temperature between the duplex with the modified strand and the unmodified reference duplex (5'-UACAGUCUAUGU-3' (SEQ ID NO: 65) ':3'-AUGUCAGAUACA-5' (SEQ ID NO: 64), Tm = 53.6° C.).

The global conformations of RNA duplexes with one or two 2'-F-NMC nucleotides were evaluated using circular dichroism (CD) spectroscopy. The CD spectra of modified duplexes were comparable to that of unmodified RNA and featured a strong positive band at around 260 nm and a negative band at around 210 nm characteristic of a A-type duplex (FIG. 37). This indicates that the 2'-F-NMC modification does not significantly distort the global geometry of an RNA:RNA duplex.

To determine the effect of the 2'-F-NMC modification on degradation of oligonucleotides by exonucleases, 2'-F-NMC C ($C^{F-NMC}$) or 2'-F-RNA C ($C^F$) was incorporated at the terminus or at the penultimate position of a dT oligonucleotide. The oligonucleotide modified at the 3' end with 2'-F-NMC ($dT_{19}C^{F-NMC}$ (SEQ ID NO: 75)) was more resistant to degradation by snake venom phosphodiesterase (SVPD) than was the oligonucleotide modified with 2'-F-RNA (FIG. 38A). The half-life of the 2'-F-NMC-modified oligonucleotide was around 90 min, whereas the half-life of $dT_{19}C^F$ (SEQ ID NO: 80) was 15 min. The 3'-terminal dT in the oligonucleotide with the 2'-F-NMC residue at the penultimate position relative to the 3' end ($dT_{18}C^{F-NMC}dT$ (SEQ ID NO: 77)) was lost within an hour; however, $dT_{18}C^{F-NMC}$ (SEQ ID NO: 95) had a half-life of 170 min. while $dT_{18}C^FdT$ (SEQ ID NO: 81) and $dT_{19}C^F$ (SEQ ID NO: 80) had a half-life of around 15 min.

Oligonucleotides modified at 5' ends were incubated with the 5'-exonuclease phosphodiesterase II (PDE-II). Unlike the 3' end-modified $dT_{18}C^{F-NMC}dT$ (SEQ ID NO: 77), removal of the 5'-terminal dT was not observed when $dTC^{F-NMC}dT_{18}$ (SEQ ID NO: 79) was incubated with PDE-II. Rather, the full-length 20-mer oligonucleotide with a penultimate $C^{F-NMC}$ was very stable with a half-life of 5 h (FIG. 38B). Surprisingly, $C^{F-NMC}dT$ 19 (SEQ ID NO: 78) was degraded rapidly with a half-life of 12 min. This indicates that 2'-F-NMC modification improves stability at the penultimate position. Nevertheless, the 2'-F-RNA-modified oligonucleotides are more stable than 2'-F-RNA-modified oligonucleotides as $C^FdT$ 19 (SEQ ID NO: 82) and $dTC^FdT$ 18 (SEQ ID NO: 83) were completely degraded by the first time point (1 min) after addition of PDE-II.

In summary, efficient routes for convergent synthesis of the four 2'-F-NMC ribonucleosides are presented. 2'-F-NMC residues are well accommodated in double-stranded RNAs and do not alter the global structure of the duplex. 2'-F-NMC oligonucleotides are more resistant to nuclease degradation than are oligonucleotides modified with 2'-F-RNA. Due to the presence of methanocarbacyclic ring, the 2'-F-NMC residue showed more lipophilicity than 2'-F-RNA residue in oligonucleotides, and this may improve cellular uptake and endosomal release of RNAs. Having access to all four amidites will allow exploration of the full potential of 2'-F-NMC modification in therapeutic oligonucleotides such as siRNAs.

Synthetic Procedures and Compound Characterization

General conditions: TLC was performed on Merck silica gel 60 plates coated with F254. Compounds were visualized under UV light (254 nm) or after spraying with the p-anisaldehyde staining solution followed by heating. Flash column chromatography was performed using a Teledyne ISCO Combi Flash system with pre-packed RediSep Teledyne ISCO silica gel cartridges. All moisture-sensitive reactions were carried out under anhydrous conditions using dry glassware, anhydrous solvents, and argon atmosphere. The microwave reactions were performed using a Discover® SP microwave system (CEM corporation) and heated in sealed glass tubes at 200 W with a 30 sec premixing time. The reaction temperature was monitored with an internal infrared probe. All commercially available reagents and solvents were purchased from Sigma-Aldrich unless otherwise stated and were used as received. ESI-MS spectra were recorded on a Waters Qtof Premier instrument using the direct flow injection mode. $^1$H NMR spectra were recorded at 400 or 500 MHz. $^{13}$C NMR spectra were recorded at 101 or 126 MHz. $^{19}$F NMR spectra were recorded at 470 MHz. $^{31}$P NMR spectra were recorded at 202 MHz. Chemical shifts are given in ppm referenced to the solvent residual peak (DMSO-$d_6$-1H: δ at 2.50 ppm and $^{13}$C δ at 39.5 ppm; acetone-$d_6$-1H: δ at 2.05 ppm and $^{13}$C δ at 29.8 and 206.3 ppm; CD$_3$CN-$^1$H: δ at 1.94 ppm and $^{13}$C δ at 1.32 and 118.3 ppm). Coupling constants are given in Hertz. Signal splitting patterns are described as singlet (s), doublet (d), triplet (t), septet (sept), broad signal (brs), or multiplet (m).

Synthesis of Compound 2:

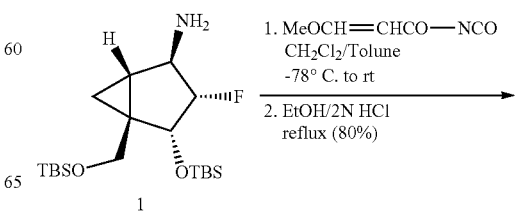

-continued

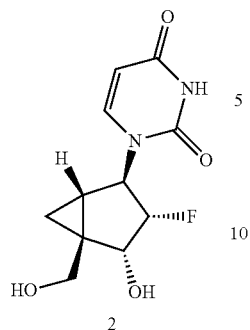

2

3'-Methoxy acrylic acid (1.07 g, 10.5 mmol) was dissolved in CH$_2$Cl$_2$ (15 mL). It was cooled to 0° C. in an ice bath, and oxalyl chloride (4.43 mL, 52.3 mmol) was added to the solution dropwise. The solution was allowed to warm to room temperature and was stirred for 16 h. Solvent was removed, and the residual solid was kept under high vacuum for 10 min. This acid chloride was dissolved in toluene (30 mL). To the solution was added silver cyanate (1.88 g, 12.6 mmol) followed by refluxing for 2 h. After cooling to room temperature, the liquid was carefully filtered through 0.2-μm syringe filter and then cooled to −78° C. Compound 1, which was made following Jung et al., 1 (1.36 g, 3.49 mmol) in CH$_2$Cl$_2$ (10 mL) was added dropwise to this solution over 5 min. The solution was then warmed to room temperature and stirred for 18 h. The reaction was quenched by adding EtOH. The mixture was filtered and evaporated to a syrup. The residue was dissolved in 2 N HCl (8 mL) and MeOH (25 mL) and was refluxed at 90° C. for 16 hours. After excess solvent was removed, the crude residue was purified by column chromatography on silica gel (0-15% MeOH in CH$_2$Cl$_2$) to provide compound 2 as white powder (710 mg, 80%).

$^1$H NMR (500 MHz, DMSO-d$_6$) δ 11.31 (s, 1H), 7.89 (d, J=8.0 Hz, 1H), 5.55 (dd, J=8.0 and 1.8 Hz, 1H), 4.98 (brs, 2H), 4.75 (d, J=17.6 Hz, 1H), 4.41-4.58 (m, 2H), 4.01 (d, J=11.4 Hz, 1H), 3.08 (d, J=11.5 Hz, 1H), 1.33 (dd, J=8.9 and 3.6 Hz, 1H), 0.95-0.97 (m, 1H), 0.65-0.69 (m, 1H). $^{13}$C NMR (126 MHz, DMSO-d$_6$) δ 163.2, 150.8, 141.4, 101.4, 95.3 (d, J=190.3 Hz), 69.9 (d, J=16.4 Hz), 61.31, 59.9 (d, J=27.7 Hz), 36.2, 20.6, 10.9 (d, J=3.8 Hz). $^{19}$F NMR (470 MHZ, DMSO-d$_6$) δ −187.57--187.37 (m). HRMS calc. for C$_{11}$H$_{14}$FN$_2$O$_4$ [M+H]$^+$ 257.0932, found 257.0948.

Synthesis of Compound 3:

-continued

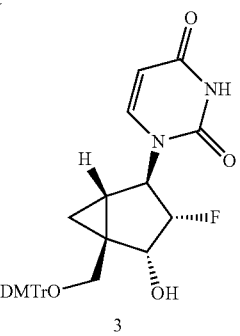

3

To a solution of compound 2 (0.858 g, 3.35 mmol) in pyridine (5 mL), 4,4'-dimethoxytrityl chloride (1.48 g, 4.36 mmol) was added. The mixture was stirred at room temperature for 4 h. The reaction was quenched by addition of MeOH. After excess solvent was removed, the residue was dissolved in CH$_2$Cl$_2$ and washed with saturated NaHCO$_3$ (aq.) and brine. The organic layer was dried with Na$_2$SO$_4$ and purified by column chromatography on silica gel (30-80% ethyl acetate in hexanes). Compound 3 was obtained as white foam (1.07 g, 57%).

$^1$H NMR (400 MHZ, acetone-d$_6$) δ 10.07 (s, 1H), 8.11 (d, J=8.1 Hz, 1H), 7.48-7.50 (m, 2H), 7.24-7.38 (m, 7H), 6.91 (d, J=8.5 Hz, 4H), 5.26 (d, J=8.0 Hz, 1H), 4.96-5.06 (m, 2H), 4.74 (dd, J=50.5 and 5.4 Hz, 1H), 4.01-4.15 (m, 2H), 3.79 (s, 6H), 2.76 (d, J=10.1 Hz, 1H), 1.39 (dd, J=8.9 and 3.7 Hz, 1H), 1.13-1.16 (m, 1H), 0.60-0.65 (m, 1H). $^{13}$C NMR (126 MHz, acetone-d$_6$) δ 163.6, 159.8, 159.7, 151.7, 150.7, 146.2, 142.2, 136.9, 136.6, 131.1, 131.0, 129.0, 128.8, 127.8, 124.6, 114.1, 114.1, 102.8, 96.3 (d, J=190.3 Hz), 87.4, 72.5 (d, J=16.4 Hz), 65.0, 61.1 (d, J=26.5 Hz), 55.6, 35.6, 22.9, 11.5 (d, J=7.6 Hz). $^{19}$F NMR (470 MHz, acetone-d$_6$) δ −187.37 (ddd, J=52.5, 19.4 and 19.4 Hz). HRMS calc. for C$_{32}$H$_{31}$FN$_2$NaO$_6$ [M+Na]$^+$ 581.2064, found 581.2062.

Synthesis of Compound 4:

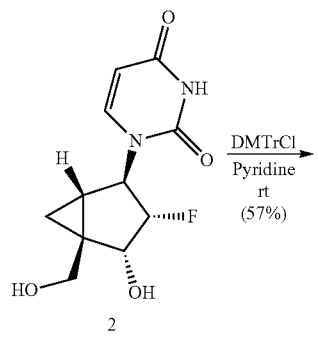

2

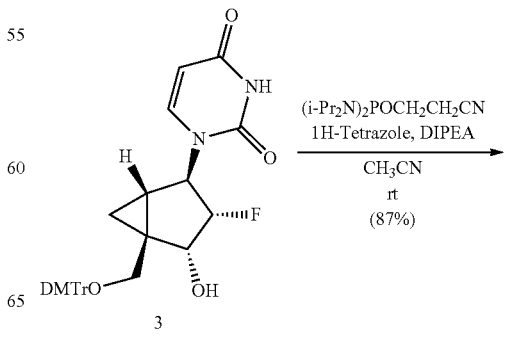

3

223
-continued

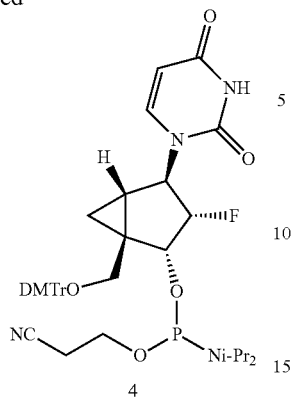
4

To a solution of compound 3 (1.12 g, 2.00 mmol) in CH₃CN (20 mL) were added DIPEA (0.418 mL, 2.40 mmol), 2-cyanoethyl N,N,N',N'-tetraisopropylphosphordiamidite (0.669 mL, 3.00 mmol) and 1H-tetrazole (0.45 M in CH₃CN, 4.88 mL, 2.20 mmol). The solution was stirred at room temperature for 3 h. The reaction was quenched with MeOH. The solvents were removed under reduced pressure, and the residue was dissolved in CH₂Cl₂, washed with saturated NaHCO₃ (aq.), and dried with Na₂SO₄. The volume of CH₂Cl₂ was reduced to 5 mL, and the mixture was added dropwise to 300 mL stirring hexanes. The precipitated white solid was collected and dried under high vacuum. Compound 4 was obtained as white powder (1.31 g, 87%).

¹H NMR (500 MHZ, CD₃CN) δ 9.29 (brs, 1H), 7.98-8.03 (m, 1H), 7.42-7.47 (m, 2H), 7.25-7.35 (m, 7H), 6.86-6.89 (m, 4H), 5.13-5.16 (m, 1H), 4.89-5.09 (m, 2H), 4.67-4.80 (m, 1H), 3.57-3.93 (m, 11H), 2.74 (d, J=10.3 Hz, 0.5H), 2.68 (d, J=10.2 Hz, 0.5H), 2.65 (t, J=6.0 Hz, 1H), 2.55 (t, J=6.0 Hz, 1H), 1.22-1.26 (m, 1H), 1.08-1.20 (m, 13H), 0.61-0.66 (m, 1H). ¹³C NMR (101 MHz, CD₃CN) δ 164.1, 164.1, 159.8, 159.8, 151.9, 151.9, 146.1, 146.1, 142.8, 142.6, 136.7, 136.7, 136.5, 131.2, 129.1, 129.1, 129.0, 129.0, 128.1, 128.0, 119.8, 119.5, 114.2, 114.2, 102.9, 97.0, 96.0, 95.1, 94.1, 87.5, 87.5, 74.3, 74.2, 74.1, 74.0, 73.5, 73.4, 73.2, 64.2, 61.9, 61.6, 59.9, 59.7, 59.2, 59.0, 56.0, 56.0, 44.3, 44.2, 44.1, 44.1, 44.0, 43.9, 35.5, 35.4, 35.4, 35.3, 25.2, 25.1, 25.1, 25.1, 25.0, 24.9, 24.9, 22.7, 21.2, 21.1, 21.1, 12.1, 12.1, 12.1, 12.0. 19F NMR(470 MHZ, CD₃CN) δ −186.32--186.10 (m), −185.78--185.57 (m). ³¹P NMR (202 MHz, CD₃CN) δ 151.49 (d, J=12.1 Hz), 151.37 (d, J=8.1 Hz). HRMS calc. for C₄₁H₄₉FN₄O₇P [M+H]⁺ 759.3317, found 759.3344.

Synthesis of Compound 5:

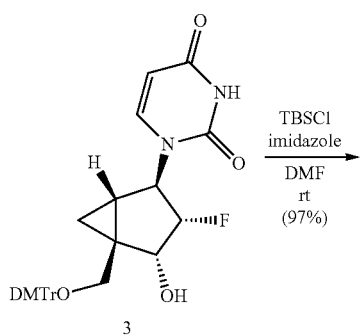
3

224
-continued

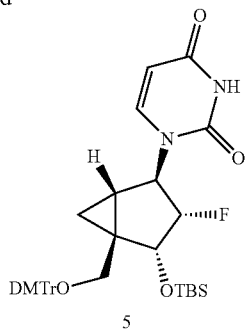
5

To a solution of compound 3 (1.70 g, 3.04 mmol) in DMF (30 mL) were added tert-butyldimethylsilyl chloride (688 mg, 4.56 mmol) and imidazole (622 mg, 9.13 mmol). The reaction mixture was stirred at room temperature overnight. The reaction mixture was quenched with water and then diluted with diethyl ether. The organic layer was washed with water and brine, dried with Na₂SO₄, and concentrated under vacuum. The crude residue was purified by column chromatography on silica gel (0-50% ethyl acetate in hexanes). Compound 5 was isolated as a white foam (1.98 g, 97%).

¹H NMR (400 MHZ, DMSO-d₆) δ 11.40 (s, 1H), 8.03 (d, J=8.0 Hz, 1H), 7.17-7.33 (m, 9H), 6.87-6.90 (m, 4H), 5.12 (d, J=8.0 Hz, 1H), 4.67-4.85 (m, 3H), 3.72 (s, 6H), 3.61 (d, J=10.1 Hz, 1H), 2.78 (d, J=10.1 Hz, 1H), 1.41-1.44 (m, 1H), 0.93-0.95 (m, 1H), 0.73 (s, 9H), 0.62-0.67 (m, 1H), −0.02 (s, 3H), −0.08 (s, 3H). ¹³C NMR (101 MHz, DMSO-d₆) δ 163.2, 158.2, 158.2, 150.8, 144.5, 141.4, 135.1, 134.9, 129.9, 129.7, 127.9, 127.7, 126.9, 113.2, 113.1, 101.4, 93.9 (d, J=193.9 Hz), 85.7, 71.6 (d, J=16.2 Hz), 63.2, 60.3 (d, J=26.3 Hz), 55.0, 34.7, 25.5, 21.0, 17.7, 10.8 (d, J=7.1 Hz), −4.86, −5.37. 19F NMR (470 MHz, DMSO-d₆) δ −187.66 (ddd, J=50.0, 18.0 and 18.0 Hz). HRMS calc. for C₃₈H₄₅FN₂NaO₆Si [M+Na]⁺ 695.2923, found 695.2959.

Synthesis of Compound 6:

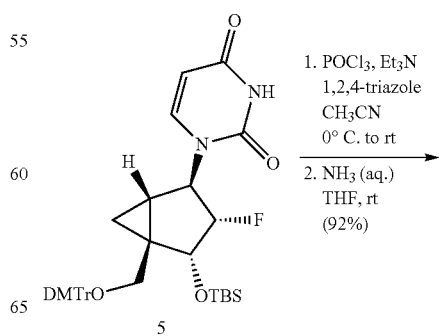
5

-continued

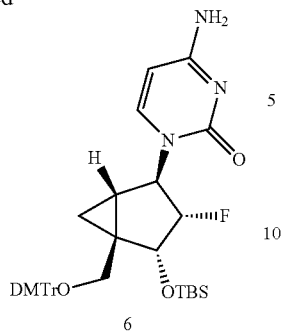

6

Phosphorus oxychloride (0.353 mL, 3.79 mmol) was added dropwise to a solution of 1,2,4-triazole (2.09 g, 30.3 mmol) and triethylamine (4.23 mL, 30.3 mmol) in CH₃CN (10 mL) maintained in an ice bath. After stirring for 30 min, a solution of compound 5 (850 mg, 1.26 mmol) in CH₃CN (5 mL) was added dropwise to the reaction. After stirring for 10 min at 0° C., the reaction was stirred at room temperature for 4 h. The solvent was then removed under vacuum, and the residue was partitioned between ethyl acetate and water. The organic layer was washed with saturated NaHCO₃ (aq.) and brine, dried (Na₂SO₄), and concentrated under vacuum. The crude residue was dissolved in THF (10 mL), and NH₃ (aq.) (2.5 mL) was added. The reaction mixture was stirred at room temperature overnight and diluted with ethyl acetate. The solution was sequentially washed with water and brine, dried (Na₂SO₄), and concentrated under vacuum. The crude residue was purified by column chromatography on silica gel (0-10% MeOH in CH₂Cl₂) to give compound 6 as a white foam (779 mg, 92%).

¹H NMR (400 MHZ, DMSO-d₆) δ 8.08 (d, J=7.4 Hz, 1H), 7.17-7.34 (m, 11H), 6.88-6.90 (m, 4H), 5.54 (d, J=7.4 Hz, 1H), 4.94 (d, J=18.2 Hz, 1H), 4.82 (dd, J=18.2 and 5.7 Hz, 1H), 4.51 (dd, J=50.6 and 5.7 Hz, 1H), 3.73 (s, 6H), 3.54 (d, J=10.1 Hz, 1H), 2.78 (d, J=10.1 Hz, 1H), 1.41-1.44 (m, 1H), 0.92-0.96 (m, 1H), 0.60-0.71 (m, 10H), −0.04 (s, 3H), −0.12 (s, 3H). ¹³C NMR (101 MHZ, DMSO-d₆) δ 165.5, 158.2, 155.2, 144.5, 141.7, 135.2, 129.8, 129.7, 127.9, 127.7, 126.9, 113.3, 113.2, 94.4 (d, J=194.9 Hz), 94.1, 85.6, 71.5 (d, J=15.2 Hz), 63.4, 60.6 (d, J=25.3 Hz), 55.0, 34.6, 25.5, 21.4, 17.7, 10.9 (d, J=7.1 Hz), −4.86, −5.37. ¹⁹F NMR (470 MHZ, DMSO-d₆) δ −186.59 (ddd, J=50.4, 18.4 and 18.4 Hz). HRMS calc. for C₃₈H₄₇FN₃O₅Si [M+H]⁺ 672.3264, found 672.3278.

Synthesis of Compound 7:

-continued

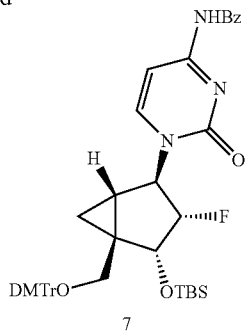

7

To a solution of compound 6 (650 mg, 0.967 mmol) in pyridine (10 mL) at 0° C. was added dropwise benzoyl chloride (0.168 mL, 1.45 mmol). The mixture was stirred at 0° C. for 3 h. The reaction mixture was diluted with ethyl acetate and washed with saturated NaHCO₃ (aq.), water, and brine, dried (Na₂SO₄), and concentrated under vacuum. The crude residue was purified by column chromatography on silica gel (25-75% ethyl acetate in hexanes) to give compound 7 as a white foam (663 mg, 88%).

¹H NMR (400 MHZ, DMSO-d₆) δ 11.33 (s, 1H), 8.60 (d, J=7.6 Hz, 1H), 7.99-8.01 (m, 2H), 7.49-7.64 (m, 3H), 7.22-7.36 (m, 10H), 6.90-6.92 (m, 4H), 5.02 (d, J=17.6 Hz, 1H), 4.88 (dd, J=5.8 and 17.6 Hz, 1H), 4.68 (dd, J=5.8 and 50.6 Hz, 1H), 3.75 (s, 6H), 3.61 (d, J=10.0 Hz, 1H), 2.81 (d, J=10.0 Hz, 1H), 1.63-1.66 (m, 1H), 1.01-1.04 (m, 1H), 0.68-0.71 (m, 10H), −0.03 (s, 3H), −0.12 (s, 3H). ¹³C NMR (101 MHZ, DMSO-d₆) δ 167.7, 163.2, 158.7, 158.7, 155.3, 150.8, 146.5, 144.5, 135.7, 135.65, 133.5, 133.2, 130.2, 128.9, 128.8, 128.4, 128.4, 127.4, 113.8, 113.7, 95.9 (d, J=219.2 Hz), 93.3, 86.2, 71.8 (d, J=13.1 Hz), 63.8, 62.1 (d, J=21.2 Hz), 55.4, 35.3, 26.0, 21.4, 18.2, 11.5 (d, J=6.1 Hz), −4.37, −4.94. ¹⁹F NMR (470 MHz, DMSO-d₆) δ −187.76 (ddd, J=50.7, 17.8 and 17.8 Hz). HRMS calc. for C₄₅H₅₁FN₃O₆Si [M+H]⁺ 776.3526, found 776.3508.

Synthesis of Compound 8:

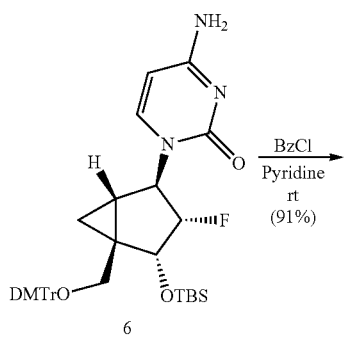

6

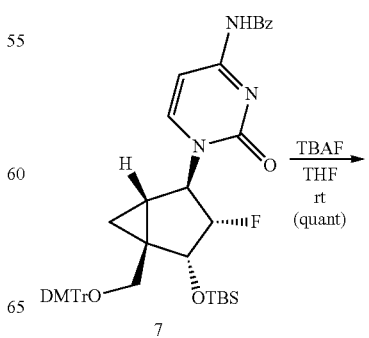

7

227
-continued

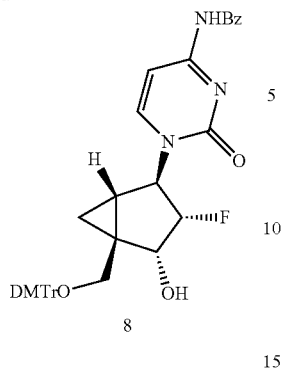

8

To a solution of compound 7 (570 mg, 0.735 mmol) in THF (10 mL) at 0° C. was added dropwise tetra-n-butylammonium fluoride (1 M in THF, 1.10 mL, 1.10 mmol), and the mixture was stirred at room temperature overnight. The reaction mixture was concentrated under vacuum. The crude residue was purified by column chromatography on silica gel (50-100% ethyl acetate in hexanes) to give compound 8 as a white foam (485 mg, quant.).

$^1$H NMR (400 MHZ, DMSO-d$_6$) δ 11.29 (s, 1H), 8.50 (d, J=7.5 Hz, 1H), 8.00-8.02 (m, 2H), 7.23-7.64 (m, 13H), 6.90-6.94 (m, 4H), 5.09 (d, J=8.1 Hz, 1H), 4.99 (d, J=17.6 Hz, 1H), 4.79 (ddd, J=8.1, 8.1 and 22.2 Hz, 1H), 4.60 (dd, J=1 and 50.4 Hz, 1H), 3.76-4.81 (m, 7H), 2.62 (d, J=10.1 Hz, 1H), 1.47-1.49 (m, 1H), 1.04-1.07 (m, 1H), 0.59-0.61 (m, 1H). $^{13}$C NMR (101 MHz, DMSO-d$_6$) δ 167.8, 163.3, 158.6, 158.6, 155.2, 146.4, 144.9, 136.3, 136.0, 133.6, 133.2, 130.2, 130.0, 128.9, 128.9, 128.4, 128.3, 127.3, 113.8, 97.1, 95.0 (d, J=191.9 Hz), 86.3, 70.7 (d, J=17.2 Hz), 64.4, 61.8 (d, J=27.3 Hz, 1H), 55.4 (d, J=2.0 Hz), 34.6, 21.86, 11.5 (d, J=7.1 Hz). $^{19}$F NMR (470 MHz, DMSO-d$_6$) δ −187.19 (ddd, J=50.1, 18.8 and 18.8 Hz). HRMS calc. for C$_{39}$H$_{37}$FN$_3$O$_6$ [M+H]$^+$ 662.2661, found 662.2690.

Synthesis of Compound 9:

228
-continued

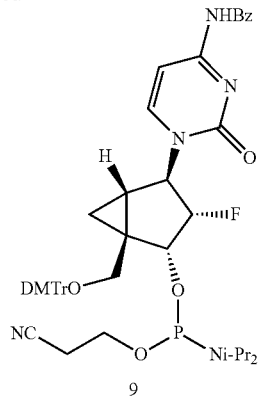

9

To a solution of compound 8 (500 mg, 0.756 mmol) and DIPEA (0.395 mL, 2.27 mmol) in CH$_2$Cl$_2$ (9 mL) at 0° C. was added dropwise 2-cyanoethyl N,N-diisopropylchlorophosphoramidite (0.202 mL, 0.907 mmol) and the mixture was stirred at 0° C. for 1 h. The reaction mixture was diluted with ethyl acetate and washed with saturated NaHCO$_3$ (aq.), water, and brine, dried (Na$_2$SO$_4$), and concentrated under vacuum. The crude residue was purified by column chromatography on silica gel (50-65% ethyl acetate in hexanes) to give compound 9 as a white foam (479 mg, 73%).

$^1$H NMR (400 MHZ, CD$_3$CN) δ 9.31 (brs, 1H), 8.55-8.59 (m, 1H), 7.95-7.97 (m, 2H), 7.18-7.64 (m, 13H), 6.89-6.92 (m, 4H), 4.98-5.14 (m, 2H), 4.66-4.80 (m, 1H), 3.90-3.96 (m, 1H), 3.59-3.87 (m, 10H), 2.74 (d, J=8.2 Hz, 0.4H), 2.69 (d, J=8.2 Hz, 0.6H), 2.62 (t, J=4.6 Hz, 0.8H), 2.53 (t, J=4.6 Hz, 1.2H), 1.38-1.41 (m, 1H), 1.07-1.19 (m, 13H), 0.65-0.66 (m, 1H). $^{13}$C NMR (101 MHz, CD$_3$CN) δ 168.20, 163.43, 163.36, 159.74, 156.11, 147.39, 147.24, 145.55, 145.50, 136.99, 136.84, 136.81, 136.78, 134.43, 133.85, 133.83, 131.07, 131.04, 131.00, 130.97, 129.61, 129.26, 129.19, 129.06, 129.04, 129.02, 128.04, 128.01, 119.67, 119.45, 114.21, 114.20, 97.76, 96.62, 95.57, 95.54, 94.69, 93.63, 93.61, 87.49, 87.43, 74.16, 74.03, 74.00, 73.88, 73.23, 73.08, 64.46, 63.28, 63.23, 63.01, 62.96, 59.77, 59.57, 59.09, 58.88, 55.91, 55.88, 44.18, 44.06, 44.01, 43.89, 35.48, 35.43, 35.35, 25.10, 25.06, 25.03, 24.99, 24.92, 24.84, 24.78, 22.78, 22.68, 21.08, 21.01, 12.34, 12.28, 12.21. $^{19}$F NMR (470 MHz, CD$_3$CN) δ −186.47−−186.24 (m), −185.74−−185.53 (m). $^{31}$P NMR (202 MHZ, CD$_3$CN) δ 151.61 (d, J=13.9 Hz), 151.48 (d, J=6.9 Hz). HRMS calc. for C$_{48}$H$_{54}$FN$_5$O$_7$P [M+H]$^+$ 862.3739, found 862.3726.

Synthesis of Compound 11:

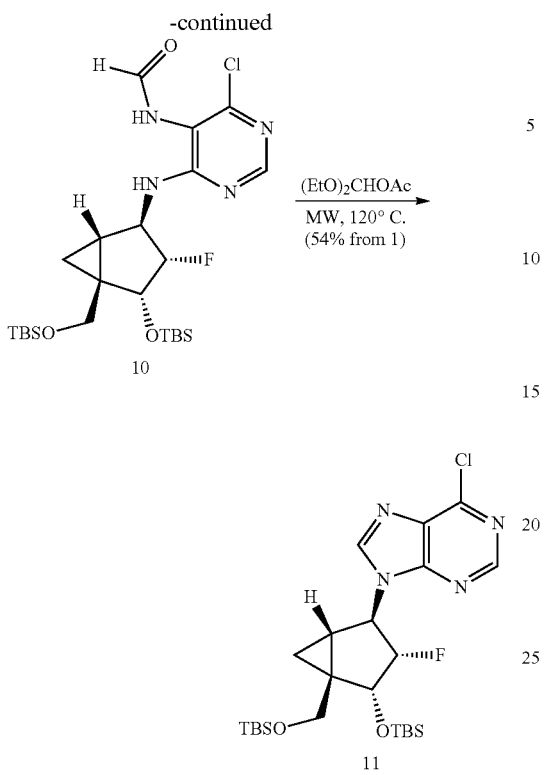

10

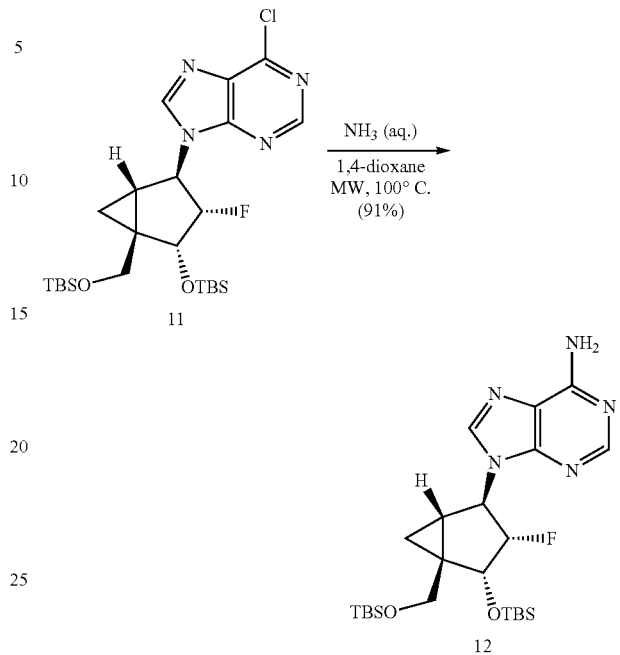

11

Synthesis of Compound 12:

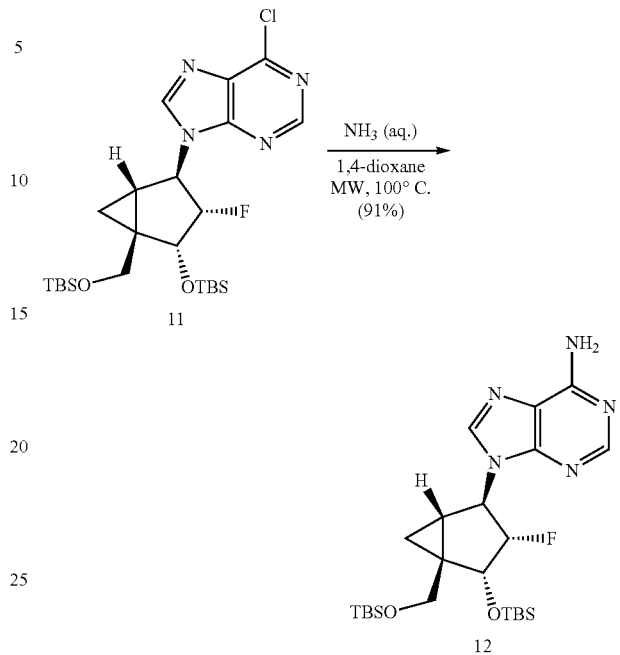

11

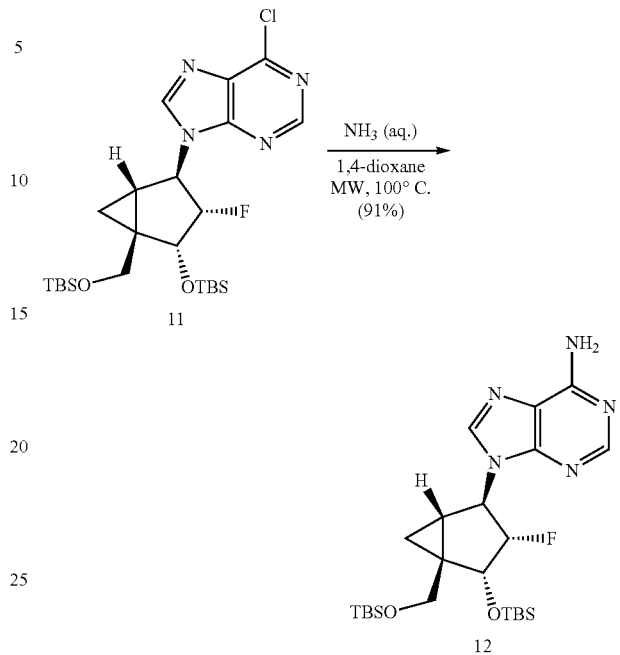

12

To a solution of compound 1 (1.80 g, 4.62 mmol) and DIPEA (2.41 mL, 13.9 mmol) in 1,4-dioxane (20 mL) was added 4,6-dichloro-5-formamidopyrimidine (1.06 g, 5.54 mmol). The reaction mixture was stirred and heated in microwave reactor at 100° C. for 6 h. The reaction was cooled to room temperature and concentrated under vacuum. The residue containing compound 10 was dissolved in diethoxymethyl acetate (10 mL), and the solution was stirred and heated in a microwave reactor at 120° C. for 2 h. After concentration under vacuum, the crude residue was purified by column chromatography on silica gel (0-15% ethyl acetate in hexanes) to afford compound 11 as a yellow foam (1.32 g, 54%).

$^1$H NMR (400 MHZ, DMSO-$d_6$) δ 8.78 (s, 1H), 8.76 (s, 1H), 5.12 (d, J=15.6 Hz, 1H), 4.89 (brs, 1H), 4.80 (dd, J=32.4 and 5.4 Hz, 1H), 4.19 (d, J=10.8 Hz, 1H), 3.36 (d, J=10.8 Hz, 1H), 1.79 (dd, J=8.8 and 3.9 Hz, 1H), 1.15-1.18 (m, 1H), 0.93 (s, 9H), 0.85-0.90 (m, 10H), 0.10 (s, 6H), 0.06 (s, 3H), 0.00 (s, 3H). $^{13}$C NMR (126 MHZ, DMSO-$d_6$) δ 151.5, 151.5, 158.2, 148.9, 144.5, 131.1, 93.4 (d, J=192.8 Hz), 70.7 (d, J=15.1 Hz), 63.3, 59.0 (d, J=27.7 Hz), 35.9, 25.8, 25.6, 22.0, 17.9, 17.8, 10.8 (d, J=7.6 Hz), −4.88, −5.27, −5.59, −5.66. $^{19}$F NMR (470 MHz, DMSO-$d_6$) δ −189.95-−189.76 (m). HRMS calc. for $C_{24}H_{41}ClFN_4O_2Si_2$ [M+H]$^+$ 527.2435, found 527.2441.

A mixture of compound 11 (100 mg, 0.190 mmol), ammonium hydroxide solution (2 mL), and 1,4-dioxane (2 mL) was stirred and heated in a microwave reactor at 100° C. for 6 h. After the mixture was concentrated under vacuum, the crude residue was purified by column chromatography on silica gel (50-100% ethyl acetate in hexanes). Compound 12 was isolated as a white solid (87.3 mg, 91%).

$^1$H NMR (500 MHZ, DMSO-$d_6$) δ 8.25 (s, 1H), 8.15 (s, 1H), 7.28 (brs, 2H), 4.98 (d, J=16.3 Hz, 1H), 4.87 (dd, J=19.9 and 5.1 Hz, 1H), 4.82 (dd, J=50.7 and 5.1 Hz, 1H), 4.17 (d, J=10.8 Hz, 1H), 3.33 (d, J=10.8 Hz, 1H), 1.67 (dd, J=8.4 and 3.9 Hz, 1H), 1.12 (dd, J=3.9 and 3.9 Hz, 1H), 0.92 (s, 9H), 0.82-0.86 (m, 10H), 0.09 (s, 6H), 0.07 (s, 3H), 0.02 (s, 3H). $^{13}$C NMR (126 MHz, DMSO-$d_6$) δ 156.0, 152.6, 149.0, 137.8, 118.7, 94.1 (d, J=194.0 Hz), 70.7 (d, J=16.4 Hz), 63.4, 58.1 (d, J=26.5 Hz), 35.8, 25.8, 25.6, 22.3, 18.0, 17.9, 10.8 (d, J=7.6 Hz), −4.85, −5.21, −5.50, −5.60. $^{19}$F NMR (470 MHz, DMSO-$d_6$) δ −188.53-−188.34 (ddd, J=50.4, 18.4 and 18.4 Hz). HRMS calc. for $C_{24}H_{43}FN_5O_2Si_2$ [M+H]$^+$ 508.2934, found 508.2929.

Syntheses of Compounds 13 and 14:

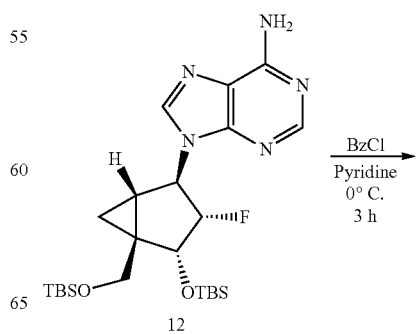

12

-continued

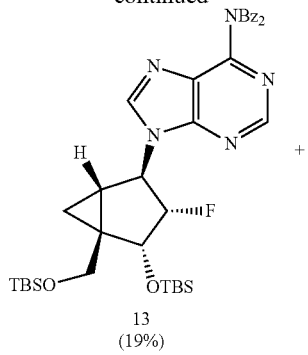

13
(19%)

+

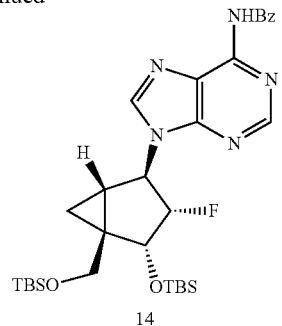

14

A mixture of compound 13 (180 mg, 0.251 mmol), ammonium hydroxide solution (2 mL), and THF (2 mL) was stirred at 0° C. for 3 h. The reaction mixture was diluted with ethyl acetate and washed with water and brine, dried (Na$_2$SO$_4$), and concentrated under vacuum. The crude residue was purified by column chromatography on silica gel (20-50% ethyl acetate in hexanes). The desired compound 14 was isolated as a white foam (152 mg, 99%).

Compound 13: $^1$H NMR (500 MHZ, DMSO-d$_6$) δ 8.71 (s, 1H), 8.62 (s, 1H), 7.76 (d, J=7.3 Hz, 4H), 7.57 (dd, J=7.3 and 7.3 Hz, 2H), 7.44 (dd, J=7.3 and 7.3 Hz, 4H), 5.10 (d, J=16.1 Hz, 1H), 4.93 (dd, J=19.8 and 5.6 Hz, 1H), 4.68 (dd, J=14.0 and 5.6 Hz, 1H), 4.12 (d, J=10.8 Hz, 1H), 3.38 (d, J=10.8 Hz, 1H), 1.69 (dd, J=8.9 and 3.9 Hz, 1H), 1.11-1.13 (m, 1H), 0.87 (s, 9H), 0.84-0.86 (m, 10H), 0.09 (s, 3H), 0.04 (s, 6H), 0.02 (s, 3H). $^{13}$C NMR (101 MHz, DMSO-d$_6$) δ 172.0, 152.5, 151.6, 150.7, 144.5, 133.6, 133.2, 128.9, 128.9, 127.0, 93.8 (d, J=194.9 Hz), 70.9 (d, J=16.2 Hz), 63.2, 59.2 (d, J=26.3 Hz), 35.9, 25.8, 25.6, 22.1, 17.9, 17.8, 10.9 (d, J=7.1 Hz), −4.85, −5.17, −5.51, −5.63. 19F NMR (470 MHz, DMSO-d$_6$) δ −187.76 (dddd, J=51.2, 39.5, 39.5 and 4.7 Hz). HRMS calc. for C$_{38}$H$_{51}$FN$_5$O+Si$_2$ [M+H]$^+$ 716.3458, found 716.3480.

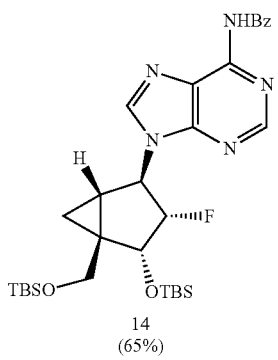

14
(65%)

To a solution of compound 12 (1.00 g, 1.97 mmol) in pyridine (20 mL) was added dropwise benzoyl chloride (0.274 mL, 2.36 mmol) at 0° C., and the mixture was stirred at 0° C. for 3 h. The reaction was quenched with MeOH and concentrated under vacuum. The residue was dissolved in ethyl acetate and washed with saturated NaHCO$_3$ (aq.), water, and brine, dried (Na$_2$SO$_4$), and concentrated under vacuum. The crude residue was purified by column chromatography on silica gel (0-100% ethyl acetate in hexanes). Compound 13 was isolated as a white foam (270 mg, 19%), and compound 14 was isolated as a white foam (786 mg, 65%).

Conversion of 13 to 14:

Compound 14: $^1$H NMR (500 MHz, DMSO-d$_6$) δ 11.19 (s, 1H), 8.75 (s, 1H), 8.53 (s, 1H), 8.03 (d, J=7.4 Hz, 2H), 7.64 (dd, J=7.4 and 7.4 Hz, 1H), 7.54 (dd, J=7.4 and 7.4 Hz, 2H), 5.13 (d, J=16.0 Hz, 1H), 4.78-4.92 (m, 2H), 4.18 (d, J=10.9 Hz, 1H), 3.38 (d, J=10.9 Hz, 1H), 1.76 (dd, J=8.8 and 3.7 Hz, 1H), 1.14-1.16 (m, 1H), 0.91 (s, 9H), 0.86-0.87 (m, 10H), 0.09 (s, 6H), 0.08 (s, 3H), 0.03 (s, 3H). $^{13}$C NMR (126 MHz, DMSO-d$_6$) δ 165.6, 152.0, 151.5, 150.2, 141.7, 133.5, 132.4, 128.5, 128.4, 125.5, 93.9 (d, J=194.0 Hz), 70.8 (d, J=15.1 Hz), 63.4, 58.6 (d, J=26.5 Hz), 36.0, 25.9, 25.6, 22.0, 18.0, 17.8, 10.9 (d, J=7.6 Hz), −4.83, −5.20, −5.46, −5.56. $^{19}$F NMR (470 MHz, DMSO-d$_6$) δ −188.93-−188.73 (m). HRMS calc. for C$_{31}$H$_{47}$FN$_5$O$_3$Si$_2$ [M+H]$^+$ 612.3196, found 612.3206.

Synthesis of Compound 15:

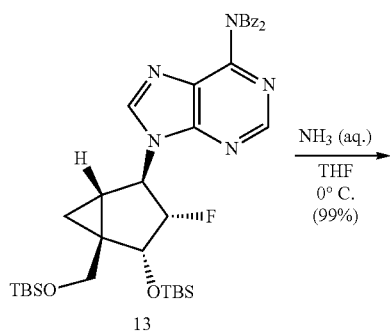

13

NH$_3$ (aq.)
───────→
THF
0° C.
(99%)

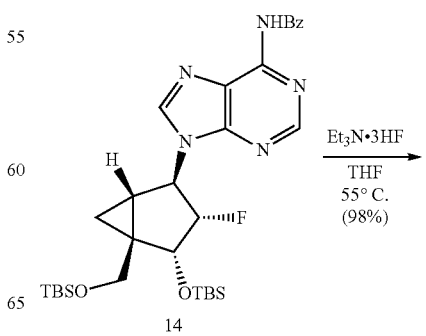

14

Et$_3$N·3HF
───────→
THF
55° C.
(98%)

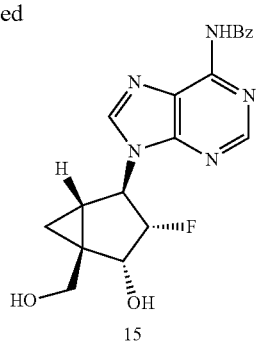

15

To a solution of compound 14 (750 mg, 1.23 mmol) in THF (12 mL) was added dropwise triethylamine trihydrofluoride (0.999 mL, 6.13 mmol) at room temperature, and the mixture was stirred at 55° C. for 6 h. The reaction mixture was concentrated under vacuum. The crude residue was purified by column chromatography on silica gel (0-10% MeOH in CH$_2$Cl$_2$). Compound 15 was isolated as a white foam (463 mg, 98%).

$^1$H NMR (500 MHZ, DMSO-d$_6$) δ 11.18 (s, 1H), 8.75-8.76 (m, 2H), 8.03 (d, J=7.4, 2H), 7.63 (dd, J=7.4 and 7.4, 1H), 7.54 (dd, J=7.4 and 7.4, 2H), 5.10-5.15 (m, 3H), 4.63-4.74 (m, 2H), 4.11 (dd, J=11.5 and 5.4 Hz, 1H), 4.60 (dd, J=11.5 and 4.7 Hz, 1H), 1.71 (dd, J=8.7 and 3.7 Hz, 1H), 1.15-1.17 (m, 1H), 0.79-0.82 (m, 1H). $^{13}$C NMR (126 MHZ, DMSO-d$_6$) δ 165.6, 151.8, 151.5, 150.3, 142.2, 133.4, 132.4, 128.5, 128.4, 125.4, 94.9 (d, J=191.5 Hz), 70.0 (d, J=16.4 Hz), 61.5, 58.6 (d, J=26.5 Hz, 1H), 35.8, 21.9, 11.2 (d, J=7.6 Hz). 19F NMR (470 MHZ, DMSO-d$_6$) δ −188.79−−188.59 (m). HRMS calc. for C$_{19}$H$_{19}$FN$_5$O$_3$ [M+H]$^+$ 384.1466, found 384.1471.

Synthesis of Compound 16:

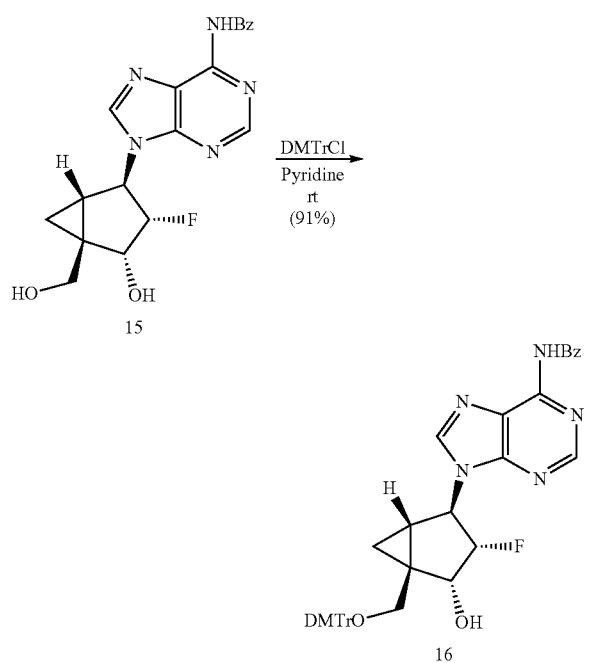

To a solution of compound 15 (400 mg, 1.04 mmol) in pyridine (10 mL) was added 4,4'-dimethoxytrityl chloride (424 mg, 1.25 mmol), and the mixture was stirred at room temperature overnight. The reaction was quenched with dry MeOH and concentrated under vacuum. The residue was dissolved in ethyl acetate and washed with saturated NaHCO$_3$ (aq.), water, and brine, dried (Na$_2$SO$_4$), and concentrated under vacuum. The crude residue was purified by column chromatography on silica gel (50-100% ethyl acetate in hexanes) to give compound 16 as a white foam (650 mg, 91%).

$^1$H NMR (500 MHZ, DMSO-d$_6$) δ 11.22 (s, 1H), 8.71 (s, 1H), 8.61 (s, 1H), 8.04 (d, J=7.3 Hz, 1H), 7.64 (dd, J=7.3 and 7.3 Hz, 1H), 7.54 (dd, J=7.3 and 7.3 Hz, 1H), 7.37-7.39 (m, 2H), 7.19-7.30 (m, 7H), 6.85-6.87 (m, 4H), 5.12-5.16 (m, 2H), 4.86-5.02 (m, 2H), 3.69-3.71 (m, 7H), 2.83 (d, J=9.9 Hz, 1H), 1.67-1.69 (m, 1H), 1.12-1.14 (m, 1H), 0.74-0.78 (m, 1H). $^{13}$C NMR (126 MHZ, DMSO-d$_6$) δ 165.6, 158.0, 158.0, 151.9, 151.5, 150.3, 144.7, 142.3, 135.8, 135.6, 133.4, 132.4, 129.7, 129.6, 128.5, 128.4, 127.9, 127.7, 126.7, 125.6, 113.2, 94.7 (d, J=190.3 Hz), 85.5, 70.9 (d, J=16.4 Hz), 63.4, 59.2 (d, J=27.7 Hz, 1H), 33.9, 22.5, 10.8 (d, J=6.3 Hz). $^{19}$F NMR (470 MHz, DMSO-d$_6$) δ −188.07−−187.87 (m). HRMS calc. for C$_{40}$H$_{37}$FN$_5$O$_5$ [M+H]$^+$ 686.2773, found 686.2790.

Synthesis of Compound 17

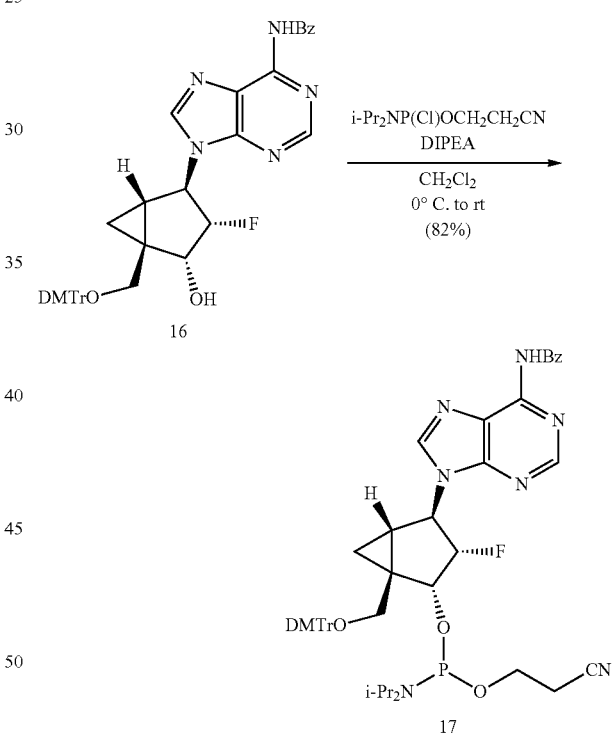

To a solution of compound 16 (560 mg, 0.817 mmol) and DIPEA (0.427 mL, 2.45 mmol) in CH$_2$Cl$_2$ (8 mL) was added dropwise 2-cyanoethyl N,N-diisopropylchlorophosphoramidite (0.219 mL, 0.980 mmol) at 0° C., and the mixture was stirred at room temperature for 2 h. The reaction mixture was quenched with saturated NaHCO$_3$ (aq.) and washed with saturated NaHCO$_3$ (aq.), water, and brine, dried (Na$_2$SO$_4$), and concentrated under vacuum. The crude residue was purified by column chromatography on silica gel (50% ethyl acetate in hexanes) to give compound 17 as a white foam (593 mg, 82%).

$^1$H NMR (400 MHZ, CD$_3$CN) δ 9.51 (brs, 1H), 8.61-8.63 (m, 1H), 8.49-8.53 (m, 1H), 8.00 (d, J=7.3 Hz, 2H), 7.61-

7.65 (m, 1H), 7.53 (dd, J=7.3 and 7.3 Hz, 2H), 7.41-7.47 (m, 2H), 7.19-7.34 (m, 7H), 6.82-6.86 (m, 4H), 5.15-5.37 (m, 2H), 5.02 (dd, J=50.3 and 5.8 Hz, 1H), 3.55-3.86 (m, 11H), 2.94 (d, J=10.0 Hz, 0.3H), 2.89 (d, J=10.1 Hz, 0.7H), 2.57 (t, J=5.9 Hz, 0.6H), 2.51 (t, J=6.1 Hz, 1.4H), 1.63-1.69 (m, 1H), 1.20-1.23 (m, 1H), 1.07-1.18 (m, 12H), 0.79-0.87 (m, 1H). $^{13}$C NMR (101 MHz, CD$_3$CN) δ 159.7, 159.7, 153.1, 152.7, 151.0, 146.1, 143.4, 143.3, 136.9, 136.9, 135.1, 133.6, 131.2, 131.1, 129.7, 129.2, 129.1, 129.0, 128.0, 127.9, 125.6, 119.6, 119.5, 114.2, 96.7, 96.0, 95.9, 94.8, 94.0, 94.0, 87.2, 74.7, 74.6, 74.4, 73.9, 73.8, 73.6, 64.2, 64.1, 61.3, 61.3, 61.1, 59.9, 59.7, 59.4, 59.2, 56.0, 56.0, 44.2, 44.1, 44.0, 35.3, 35.3, 35.2, 25.2, 25.1, 25.1, 25.1, 25.0, 25.0, 24.9, 23.9, 23.9, 23.9, 21.1, 21.1, 12.1, 12.0, 12.0. $^{19}$F NMR (470 MHZ, CD$_3$CN) δ 151.47 (d, J=12.1 Hz), 151.19 (d, J=16.0 Hz). HRMS calc. for C$_{49}$H$_{54}$FN$_7$O$_6$P [M+H]$^+$ 886.3852, found 886.3837.

Synthesis of Compound 18 and 19:

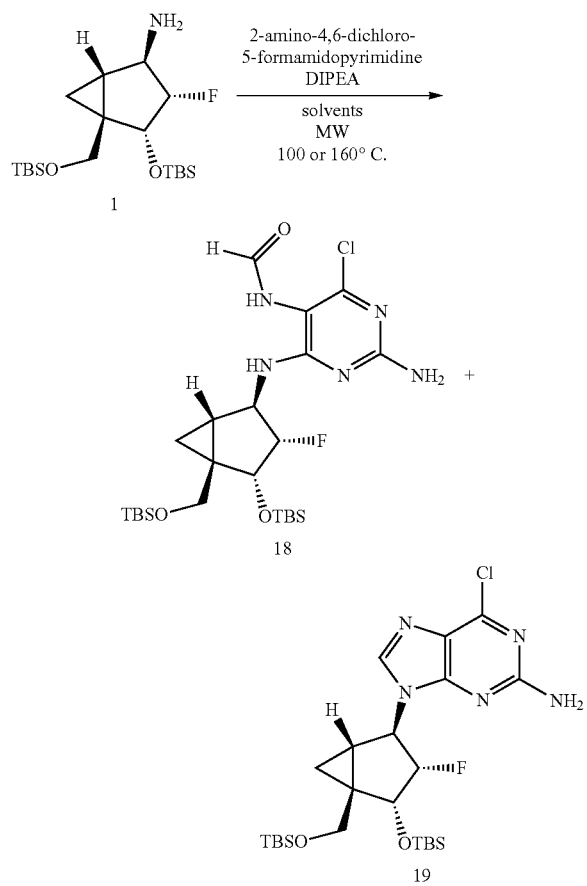

Reaction using 1,4-dioxane: To a solution of compound 1 (100 mg, 0.257 mmol) and DIPEA (0.134 mL, 0.770 mmol) in 1,4-dioxane (3 mL) was added 2-amino-4,6-dichloro-5-formamidopyrimidine (79.7 mg, 0.385 mmol). The reaction mixture was stirred and heated in a microwave reactor at 100° C. for 12 h. The reaction was cooled to room temperature, and the solution was concentrated under vacuum. The crude residue was purified by column chromatography on silica gel (0-50% ethyl acetate in hexanes). Compound 18 was isolated as a yellow solid (127 mg, 88%).

Reaction using toluene: To a solution of compound 1 (100 mg, 0.257 mmol) and DIPEA (0.134 mL, 0.770 mmol) in toluene (3 mL) was added 2-amino-4,6-dichloro-5-formamidopyrimidine (79.7 mg, 0.385 mmol). The reaction mixture was stirred and heated in microwave reactor at 160° C. for 2 h. The reaction was cooled to room temperature, and the solution was concentrated under vacuum. The crude residue was purified by column chromatography on silica gel (20-50% ethyl acetate in hexanes). Compound 18 was isolated as a yellow solid (100.8 mg, 70%), and compound 19 was isolated as a white solid (33.0 mg, 24%).

Reaction using n-BuOH: To a solution of compound 1 (100 mg, 0.257 mmol) and DIPEA (0.134 mL, 0.770 mmol) in n-butanol (3 mL) was added 2-amino-4,6-dichloro-5-formamidopyrimidine (79.7 mg, 0.385 mmol). The reaction mixture was stirred and heated in microwave reactor at 160° C. for 2 h. The reaction was cooled to room temperature and the solution was concentrated under vacuum. The crude residue was purified by column chromatography on silica gel (20-50% ethyl acetate in hexanes). Compound 18 was isolated as a yellow solid (84.2 mg, 59%), and compound 19 was isolated as a white solid (55.9 mg, 40%).

Conversion of 18 to 19:

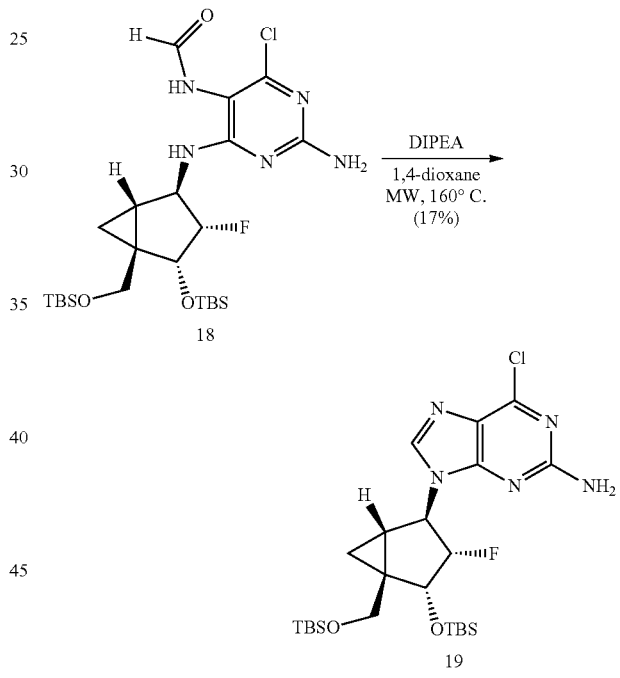

A solution of compound 18 (84.0 mg, 0.150 mmol) and DIPEA (52.2 μL, 0.300 mmol) in 1,4-dioxane (2 mL) was stirred and heated in microwave reactor at 160° C. for 48 h. The reaction was cooled to room temperature and the solution was concentrated in vacuo. The crude residue was purified by column chromatography on silica gel (0-50% ethyl acetate in hexanes). Compound 19 was isolated as a white solid (14.0 mg, 17%), and starting material 18 was collected as a yellow solid (54.6 mg, 65%).

Compound 18 (mixture of rotamers): $^1$H NMR (500 MHZ, DMSO-d$_6$) δ 9.11 (brs, 0.8H), 8.51 (d, J=11.4 Hz, 0.2H), 8.15 (brs, 0.8H), 7.79 (d, J=11.4 Hz, 0.2H), 6.59-6.67 (m, 2.2H), 4.30-4.66 (m, 3H), 3.84-3.87 (m, 1H), 3.41-3.45 (m, 1H), 1.11-1.19 (m, 1H), 4.79-4.87 (m, 2H), 0.86-0.89 (m, 19H), 0.62-0.68 (m, 1H), 0.08-0.09 (m, 3H), 0.05-0.06 (m, 3H), −0.01−0.01 (m, 6H). $^{13}$C NMR (101 MHz, DMSO-d$_6$) δ 165.6, 160.9, 160.7, 160.7, 160.2, 159.3, 156.9, 155.6, 101.9, 101.3, 95.3 (d, J=193.9 Hz), 95.1 (d, J=195.9 Hz), 71.8 (d, J=19.2 Hz), 71.7 (d, J=16.2 Hz), 63.1, 56.3 (d, J=25.3 Hz), 55.9 (d, J=25.3 Hz), 34.9, 34.7, 25.8, 25.8, 25.6, 22.6, 22.3, 18.0, 18.0, 17.9, 10.6 (d, J=6.1 Hz), 10.4 (d, J=6.1 Hz), −4.73, −4.79, −4.96, −4.99, −5.28, −5.32, −5.45. $^{19}$F NMR (470 MHz, DMSO-d$_6$) δ −188.06–−187.84 (m). HRMS calc. for $C_{24}H_{44}ClFN_5O_3Si_2$ [M+H]$^+$ 560.2650, found 560.2647.

Compound 19: $^1$H NMR (500 MHZ, DMSO-d$_6$) δ 8.26 (s, 1H), 6.99 (s, 1H), 4.79-4.87 (m, 2H), 4.69 (dd, J=50.6 and 5.5 Hz, 1H), 4.17 (d, J=10.8 Hz, 1H), 3.32 (d, J=10.8 Hz, 1H), 1.68 (dd, J=8.5 and 3.1 Hz, 1H), 1.10-1.12 (m, 1H), 0.93 (s, 9H), 0.80-0.86 (m, 10H), 0.10 (s, 6H), 0.07 (s, 3H), 0.01 (s, 3H). $^{13}$C NMR (101 MHZ, DMSO-d$_6$) δ 159.8, 153.6, 149.4, 139.9, 123.4, 93.6 (d, J=192.9 Hz), 70.6 (d, J=16.2 Hz), 63.4, 58.0 (d, J=27.3 Hz), 35.8, 25.8, 25.6, 22.1, 18.0, 17.8, 10.7 (d, J=8.1 Hz), −4.84, −5.26, −5.57, −5.65. $^{19}$F NMR (470 MHz, DMSO-d$_6$) δ −189.95–−189.06 (m). HRMS calc. for $C_{24}H_{42}ClFN_5O_2Si_2$ [M+H]$^+$ 542.2544, found 542.2551.

Synthesis of Compound 20:

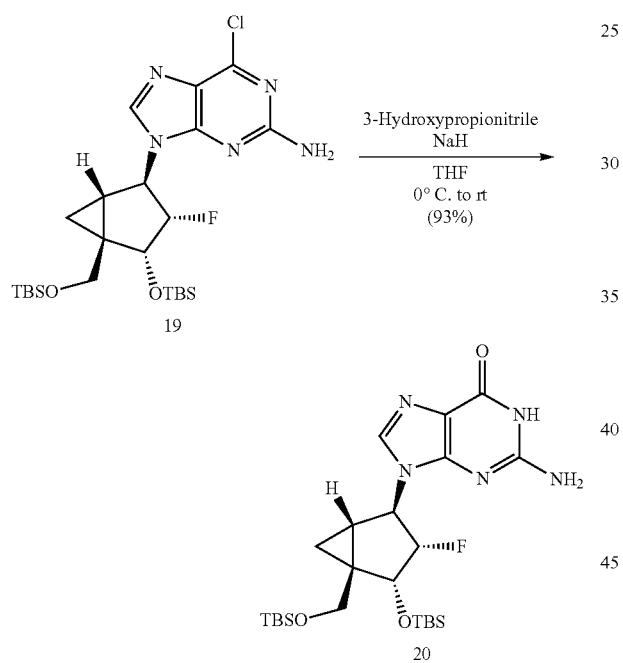

3-Hydroxypropionitrile (0.272 mL, 3.98 mmol) was dissolved in THF (5 mL) and cooled to 0° C. Sodium hydride (60% in mineral oil, 159 mg, 3.98 mmol) was added in portions, and the mixture was stirred at room temperature for 30 min and cooled to 0° C. A solution of compound 19 (480 mg, 0.885 mmol) in THF (5 mL) was added dropwise at 0° C., and the mixture was stirred at room temperature. After 16 h, the reaction was quenched by addition of saturated NH$_4$Cl (aq.). The reaction mixture was extracted with CH$_2$Cl$_2$ and ethyl acetate. The combined organic layers were washed with brine, dried (Na$_2$SO$_4$), and concentrated under vacuum. The crude residue was purified by column chromatography on silica gel (0-10% MeOH in CH$_2$Cl$_2$) to give compound 20 as a white solid (430 mg, 93%).

$^1$H NMR (400 MHZ, DMSO-d$_6$) δ 10.55 (brs, 1H), 7.90 (s, 1H), 6.52 (brs, 2H), 4.73-4.83 (m, 2H), 4.57 (dd, J=50.6 and 5.2 Hz, 1H), 4.15 (d, J=11.0 Hz, 1H), 3.28-3.31 (m, 1H), 1.67 (dd, J=8.8 and 3.8 Hz, 1H), 1.06-1.08 (m, 1H), 0.92 (s, 9H), 0.77-0.86 (m, 10H), 0.08 (s, 6H), 0.07 (s, 3H), 0.02 (s, 3H). $^{13}$C NMR (126 MHz, DMSO-d$_6$) δ 156.8, 153.7, 150.6, 134.3, 116.5, 94.2 (d, J=192.8 Hz), 70.7 (d, J=16.4 Hz), 63.3, 57.7 (d, J=26.5 Hz), 35.7, 25.8, 25.6, 22.4, 17.9, 17.8, 10.7 (d, J=7.6 Hz), −4.85, −5.21, −5.58, −5.66. $^{19}$F NMR (470 MHz, DMSO-d$_6$) δ −188.37–−188.18 (m). HRMS calc. for $C_{24}H_{43}FN_5O_3Si_2$ [M+H]$^+$524.2883, found 524.2894.

Synthesis of Compound 21:

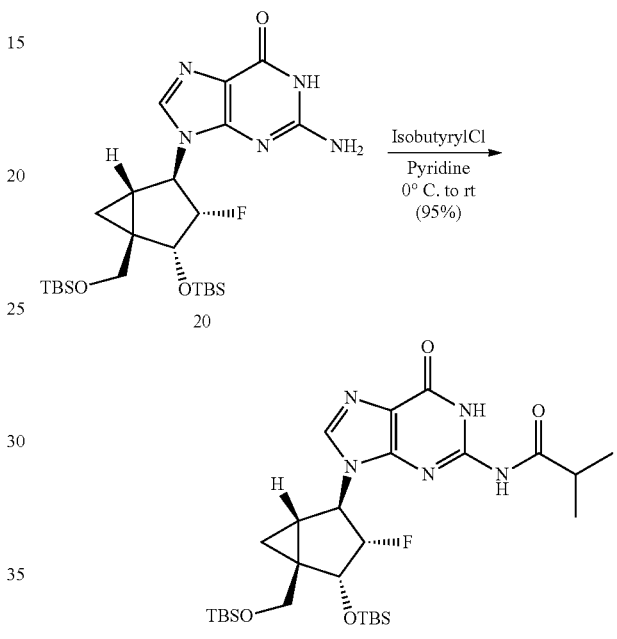

To a solution of compound 20 (430 mg, 0.821 mmol) in pyridine (8 mL) was added dropwise isobutyryl chloride (0.103 mL, 0.985 mmol) at 0° C., and the mixture was stirred at room temperature overnight. The reaction was quenched with MeOH and concentrated under vacuum. The residue was dissolved in ethyl acetate and washed with saturated NaHCO$_3$ (aq.). The aqueous layer was extracted with CH$_2$Cl$_2$, and the combined organic layers were concentrated under vacuum. The crude residue was purified by column chromatography on silica gel (0-50% ethyl acetate in hexanes). Compound 21 was isolated as a white foam (464 mg, 95%).

$^1$H NMR (500 MHZ, DMSO-d$_6$) δ 12.09 (s, 1H), 11.72 (s, 1H), 8.19 (s, 1H), 4.79-4.87 (m, 2H), 4.67 (dd, J=50.5 and 5.3 Hz, 1H), 4.17 (d, J=10.8 Hz, 1H), 3.31-3.32 (m, 1H), 2.78 (sept, J=6.8 Hz, 1H), 1.68-1.70 (m, 1H), 1.10-1.12 (m, 7H), 0.94 (s, 9H), 0.84-0.88 (m, 10H), 0.10 (s, 6H), 0.07 (s, 3H), 0.02 (s, 3H). $^{13}$C NMR (126 MHz, DMSO-d$_6$) δ 180.2, 154.9, 148.2, 148.0, 136.7, 120.1, 93.9 (d, J=194.0 Hz), 706 (d, J=15.1 Hz), 63.3, 58.2 (d, J=26.5 Hz), 35.8, 34.7, 25.8, 25.6, 22.4, 18.9, 18.8, 18.0, 17.8, 10.8 (d, J=7.6 Hz), −4.83, −5.24, −5.58, −5.65. 19F NMR (470 MHz, DMSO-d$_6$) δ −188.86–−188.67 (m). HRMS calc. for $C_{28}H_{49}FN_5O_4Si_2$ [M+H]$^+$ 594.3302, found 594.3312.

Synthesis of Compound 22:

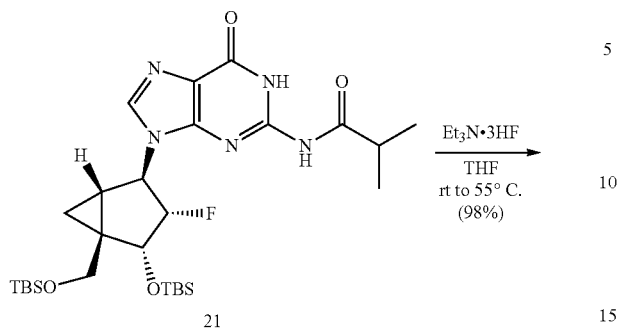

To a solution of compound 21 (300 mg, 0.505 mmol) in THF (5 mL) was added dropwise triethylamine trihydrofluoride (0.247 mL, 1.52 mmol) at room temperature and the mixture was stirred at 55° C. for 6 hours. The reaction mixture was concentrated in vacuo. The crude residue was purified by column chromatography on silica gel (0-10% MeOH in $CH_2Cl_2$). Compound 22 was isolated as a white solid (181 mg, 98%).

$^1$H NMR (500 MHZ, DMSO-$d_6$) δ 12.08 (brs, 1H), 11.70 (brs, 1H), 8.29 (s, 1H), 5.13 (t, J=5.0 Hz, 1H), 5.07 (d, J=7.2 Hz, 1H), 4.83 (d, J=15.9 Hz, 1H), 4.53-4.67 (m, 2H), 4.09 (dd, J=11.5 and 5.0 Hz, 1H), 3.15 (dd, J=11.5 and 5.0 Hz, 1H), 2.78 (sept, J=6.8 Hz, 1H), 1.62 (dd, J=8.6 and 3.7 Hz, 1H), 1.08-1.12 (m, 7H), 0.73-0.77 (m, 1H). $^{13}$C NMR (126 MHz, DMSO-$d_6$) δ 180.2, 154.9, 148.1, 148.0, 137.2, 120.1, 95.0 (d, J=190.3 Hz), 69.7 (d, J=16.4 Hz), 61.4, 58.3 (d, J=26.5 Hz, 1H), 35.7, 34.7, 21.9, 18.9, 18.8, 11.1 (d, J=7.6 Hz). $^{19}$F NMR (470 MHz, DMSO-$d_6$) δ −188.50−−188.30 (m). HRMS calc. for $C_{16}H_{21}FN_5O_4$ [M+H]$^+$366.1572, found 366.1562.

Synthesis of Compound 23:

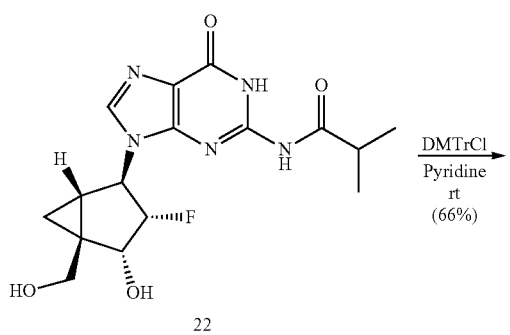

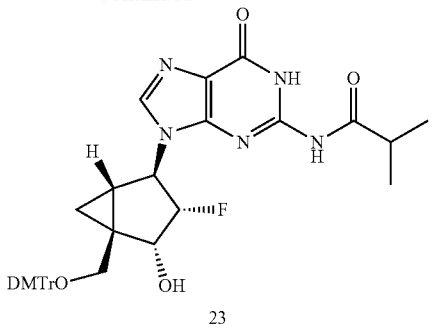

To a solution of compound 22 (380 mg, 1.04 mmol) in pyridine (10 mL) was added 4,4'-dimethoxytrityl chloride (423 mg, 1.25 mmol) and the mixture was stirred at room temperature overnight. The reaction was quenched with dry MeOH and concentrated in vacuo. The residue was dissolved in ethyl acetate and washed with saturated $NaHCO_3$ (aq.), water, and brine, dried ($Na_2SO_4$) and concentrated in vacuo. The crude residue was purified by column chromatography on silica gel (50-100% ethyl acetate in hexanes). Compound 23 was isolated as a white foam (455 mg, 66%).

$^1$H NMR (500 MHZ, DMSO-$d_6$) δ 12.12 (brs, 1H), 11.70 (brs, 1H), 8.18 (s, 1H), 7.36 (d, J=7.5 Hz, 2H), 7.29 (dd, J=7.5 and 7.5 Hz, 2H), 7.21-7.25 (m, 5H), 6.85-6.87 (m, 4H), 5.11 (d, J=8.0 Hz, 1H), 4.85-4.95 (m, 2H), 4.74 (dd, J=50.4 and 5.7 Hz, 1H), 3.71-3.73 (m, 7H), 2.74-2.79 (m, 2H), 1.58 (d, J=9.0 and 3.8 Hz, 1H), 1.10 (t, J=6.5 Hz, 6H), 1.04-1.06 (m, 1H), 0.67-0.71 (m, 1H). $^{13}$C NMR (126 MHz, DMSO-$d_6$) δ 180.2, 158.0, 154.9, 148.2, 148.0, 144.9, 137.0, 135.6, 135.4, 129.7, 129.7, 127.8, 127.6, 126.7, 120.2, 113.2, 94.7 (d, J=190.3 Hz), 85.6, 70.7 (d, J=16.4 Hz), 63.3, 58.7 (d, J=26.5 Hz, 1H), 34.7, 33.8, 22.7, 18.8, 18.8, 10.7 (d, J=7.6 Hz). $^{19}$F NMR (470 MHz, DMSO-$d_6$) δ −187.75−−187.55 (m). HRMS calc. for $C_{16}H_{21}FN_5O_4$ [M+H]$^+$668.2879, found 668.2894.

Synthesis of Compound 24:

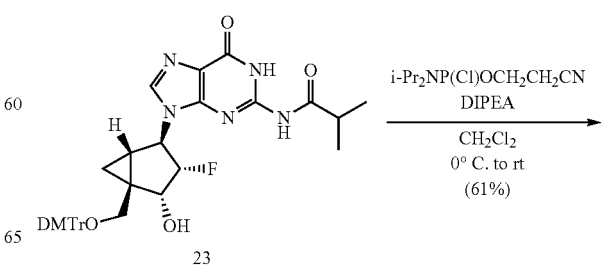

-continued

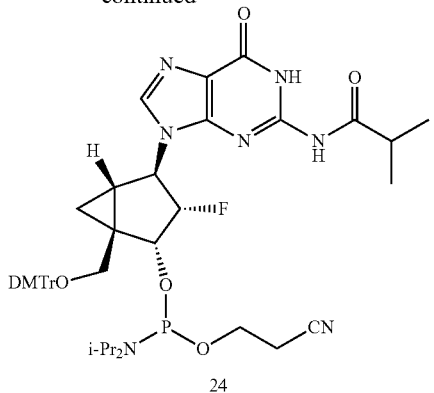

24

To a solution of compound 23 (450 mg, 0.674 mmol) and DIPEA (0.352 mL, 2.02 mmol) in $CH_2Cl_2$ 7 mL) was added dropwise 2-cyanoethyl N,N-diisopropylchlorophosphoramidite (0.180 mL, 0.809 mmol) at 0° C. and the mixture was stirred at room temperature overnight. The reaction mixture was quenched with saturated $NaHCO_3$ (aq.). The organic layer was washed with water and brine, dried ($Na_2SO_4$) and concentrated in vacuo. The crude residue was purified by column chromatography on silica gel (60% ethyl acetate in hexanes) to give compound 24 as a white foam (354 mg, 61%).

$^1$H NMR (500 MHZ, $CD_3CN$) δ 8.15 (s, 0.8H), 8.11 (s, 0.2H), 7.45-7.48 (m, 2H), 7.23-7.37 (m, 7H), 6.84-6.87 (m, 1H), 5.13-5.19 (m, 0.8H), 5.02-5.08 (m, 0.2H), 4.79-4.92 (m, 2H), 3.75-3.86 (m, 7H), 3.55-3.67 (m, 4H), 2.84-2.88 (m, 1H), 2.49-2.58 (m, 3H), 1.61-1.64 (m, 1H), 1.05-1.19 (m, 19H), 0.78-0.81 (m, 1H). $^{13}$C NMR (126 MHz, $CD_3CN$) δ 180.4, 180.4, 159.3, 159.2, 156.0, 149.0, 148.6, 148.5, 145.7, 145.7, 137.9, 136.3, 136.3, 136.3, 136.3, 130.7, 130.7, 130.7, 130.6, 128.6, 128.6, 128.5, 128.5, 127.5, 127.5, 121.6, 121.6, 119.1, 119.0, 113.7, 113.7, 113.7, 96.2, 95.5, 95.5, 94.7, 94.0, 93.9, 86.7, 86.7, 73.7, 73.6, 73.6, 73.5, 73.1, 73.0, 72.9, 63.8, 63.7, 60.2, 60.2, 60.0, 59.9, 59.2, 59.0, 58.7, 58.6, 55.5, 55.4, 43.7, 43.6, 43.6, 43.5, 36.2, 36.2, 34.7, 34.7, 34.5, 34.5, 24.7, 24.6, 24.6, 24.5, 24.5, 24.5, 24.4, 24.3, 23.2, 23.2, 20.6, 20.6, 20.6, 20.5, 18.7, 18.7, 11.9, 11.8, 11.7, 11.6. 19F NMR (470 MHZ, $CD_3CN$) δ −186.46−−186.25 (m), −186.92−−186.70 (m). $^{31}$P NMR (202 MHz, $CD_3CN$) δ 151.31 (d, J=12.1 Hz), 151.31 (d, J=12.1 Hz). HRMS calc. for $C_{46}H_{56}FN_7O_7P$ [M+H]$^+$ 868.3957, found 868.3962.

Oligonucleotide synthesis and characterization: Oligonucleotides were synthesized on an ABI-394 DNA/RNA synthesizer using standard solid-phase synthesis and deprotection protocols. A solution of 0.25 M 5-(S-ethylthio)-1H-tetrazole in acetonitrile ($CH_3CN$) was used as the activator. The phosphoramidite solutions (commercially available 2'-F-RNA amidites and standard RNA and DNA amidites and synthesized 2'-F-NMC amidities) were prepared at 0.15 M in anhydrous $CH_3CN$. The oxidizing reagent was 0.02 M $I_2$ in THF/pyridine/$H_2O$. The detritylation reagent was 3% dichloroacetic acid (DCA) in $CH_2Cl_2$. After completion of the automated synthesis, the oligonucleotides were manually released from support and deprotected using 30% $NH_4OH$ and 5% diethylamine for 6 h at 55° C. After filtration through a nylon syringe filter (0.45 µm), oligonucleotides were either stored until purification or, in the case of RNA, the 2'-hydroxyl groups were deprotected by treating with $Et_3N·3HF$ at 60° C. for 10 min. Oligonucleotides were purified using anion-exchange high-performance liquid chromatography (IEX-HPLC) using an appropriate gradient of mobile phase (0.15 M NaCl, 10% $CH_3CN$ and 1.0 M NaBr, 10% $CH_3CN$) and desalted using size-exclusion chromatography with water as an eluent. Oligonucleotides were then quantified by measuring the absorbance at 260 nm using the following extinction coefficients: (A, 13.86 L/mol/cm; T/U, 7.92 L/mol/cm; C, 6.57 L/mol/cm; and G, 10.53 L/mol/cm). The purities and identities of modified oligonucleotides were verified by analytical anion exchange chromatography and mass spectrometry, respectively (Table 6).

TABLE 6

MS (m/z) analysis of modified oligonucleotides[a]

| oligo-nucleo-tide no. | sequence (5'-3') | mass (m/z) calc. | obs. |
|---|---|---|---|
| 1 | rUACAGU$^{F-NMC}$CUAUGU | 3769.3 | 3768.1 |
| 2 | rUACAGUC$^{F-NMC}$UAUGU | 3769.3 | 3768.3 |
| 3 | rACAUAG$^{F-NMC}$ACUGUA | 3815.4 | 3814.3 |
| 4 | rACAUAGA$^{F-NMC}$CUGUA | 3815.4 | 3814.6 |
| 5 | rGCG$^{F-NMC}$A$^{F-NMC}$U$^{F-NMC}$C$^{F-NMC}$U$^{F-NMC}$C$^{F-NMC}$AC | 3192.1 | 3191.2 |
| 6 | rGCG$^F$A$^F$U$^F$C$^F$U$^F$C$^F$AC | 3131.9 | 3130.9 |
| 7 | dTTTTTTTTTTTTTTTTTTTC$^{F-NMC}$ | 6034.9 | 6033.6 |
| 8 | dTTTTTTTTTTTTTTTTTTTC$^{F-NMC}$T | 6034.9 | 6033.6 |
| 9 | dCFNMC$^{F-NMC}$TTTTTTTTTTTTTTTTTTT | 6034.9 | 6033.5 |
| 10 | dTC$^{F-NMC}$TTTTTTTTTTTTTTTTTTT | 6034.9 | 6033.6 |
| 11 | dTTTTTTTTTTTTTTTTTTTC$^F$ | 6024.9 | 6023.6 |
| 12 | dTTTTTTTTTTTTTTTTTTTC$^F$T | 6024.9 | 6023.6 |
| 13 | dC$^F$TTTTTTTTTTTTTTTTTTT | 6024.9 | 6023.6 |
| 14 | dTC$^F$TTTTTTTTTTTTTTTTTTT | 6024.9 | 6023.5 |

[a]Prefix r indicates ribonucleotide, prefix d indicates deoxyribonucleotide, superscript F indicates 2'-F-RNA, superscript F-NMC indicates 2'-F-NMC. SEQ ID NOs are, from top to bottom, as follows: Oligonucleotide No. 1 (SEQ ID NO: 84), 2 (SEQ ID NO: 85), 3 (SEQ ID NO: 71), 4 (SEQ ID NO: 72), 5 (SEQ ID NO: 73), 6 (SEQ ID NO: 74), 7 (SEQ ID NO: 75), 8 (SEQ ID NO: 77), 9 (SEQ ID NO: 78), 10 (SEQ ID NO: 79), 11 (SEQ ID NO: 80), 12 (SEQ ID NO: 81), 13 (SEQ ID NO: 82) and 14 (SEQ ID NO: 83).

Thermal melting studies: UV melting curves were recorded using a Cary 4000 Scan UV-Visible Spectrophotometer. The concentration of oligonucleotide was 2 µM, and samples were prepared in PBS buffer (137 mM sodium chloride, 2.7 mM potassium chloride, 8 mM sodium phosphate dibasic, and 2 mM potassium phosphate monobasic, pH 7.4). Samples were annealed by heating to 85° C. and then slowly cooled to 10° C. Samples were then heated to 85° C. at a gradient of 1° C./min, and the change in UV absorbance at 260 nm was recorded. The melting temperature was calculated from the first derivative of the melting curve.

TABLE 7

UV melting temperatures of self-complementary modified duplexes

| entry | duplex | $T_m^a$ ($\Delta T_m$) (° C.)[b] F-NMC | $T_m^a$ ($\Delta T_m$) (° C.)[b] 2'-F |
|---|---|---|---|
| 1 | 5'-UACAGUCUAUGU<br>3'-AUGUCAGAUACA | 53.2 (-0.4) | 55.0 (1.4) |
| 2 | 5'-UACAGUCUAUGU<br>3'-AUGUCAGAUACA | 51.4 (-2.2) | 55.6 (2.0) |

[a] $T_m$ values were obtained in PBS (pH 7.4) using 2.0 µM concentrations of each strand. [b] $\Delta T_m$ is the difference in melting temperature between the duplex with the modified strand and the unmodified reference duplex (5'-UACAGUCUAUGU-3' (SEQ ID NO: 65); 3'-AUGUCAGAUACA-5' (SEQ ID NO: 64), $T_m$ = 53.6° C.). SEQ ID NOs are from to bottom SEQ ID NO: 63, SEQ ID NO: 66, SEQ ID NO: 67 and SEQ ID NO: 68)

TABLE 8

UV melting temperatures of duplexes containing multiple modified RNAs

| entry | duplex | $T_m^a$ ($\Delta T_m$) (° C.)[b] F-NMC | $T_m^a$ ($\Delta T_m$) (° C.)[b] 2'-F |
|---|---|---|---|
| 1 | 5'-GCGAUCUCAC<br>3'-CGCUAGAGUG | 57.4 (-0.2) | 65.3 (7.7) |

[a] $T_m$ values were obtained in PBS (pH 7.4) using 2.0 µM concentrations of each strand. [b] $\Delta T_m$ is the difference in melting temperature between the duplex with the modified strand and the unmodified reference duplex (5'-GCGAUCUCAC-3' (SEQ ID NO: 69); 3'-CGCUAGAGUG-5' (SEQ ID NO: 70), Tm = 57.6° C.). Two sequences in the table are from top to bottom SEQ ID NO: 90 and SEQ ID no: 70).

TABLE 9

Duplexes analyzed for $T_m$ studies[a] (Table 9 discloses SEQ ID NOS 65, 64, 84, 64, 85, 64, 65, 72, 65, 71, 86, 64, 87, 64-65, 88, 65, 89, 84, 72, 85, 71, 86, 88, 87, 89, 69, 70, 73, 70, 74 and 70, respectively, in order of appearance)

| duplex no. | duplex type | duplex[b] |
|---|---|---|
| 1 | RNA¹:CRNA¹ | 5'-UACAGUCUAUGU<br>3'-AUGUCAGAUACA |
| 2 | RNA(U$^{F-NMC}$):cRNA¹ | 5'-UACAGU$^{F-NMC}$CUAUGU (1)<br>3'-AUGUCAGAUACA |
| 3 | RNA(C$^{F-NMC}$):cRNA¹ | 5'-UACAGUC$^{F-NMC}$UAUGU (2)<br>3'-AUGUCAGAUACA |
| 4 | RNA¹:cRNA(G$^{F-NMC}$) | 5'-UACAGUCUAUGU<br>3'-AUGUCA$^{F-NMC}$GAUACA (3) |
| 5 | RNA¹:cRNA(A$^{F-NMC}$) | 5'-UACAGUCUAUGU<br>3'-AUGUCAG$^{F-NMC}$AUACA (4) |
| 6 | RNA(U$^F$):cRNA¹ | 5'-UACAGU$^F$CUAUGU<br>3'-AUGUCAGAUACA |
| 7 | RNA(C$^F$):cRNA¹ | 5'-UACAGUC$^F$UAUGU<br>3'-AUGUCAGAUACA |
| 8 | RNA¹:cRNA(G$^F$) | 5'-UACAGUCUAUGU<br>3'-AUGUCA$^F$GAUACA |
| 9 | RNA¹:cRNA(A$^F$) | 5-UACAGUCUAUGU<br>3'-AUGUCAG$^F$AUACA |
| 10 | RNA(U$^{F-NMC}$):cRNA(A$^{F-NMC}$) | 5'-UACAGU$^{F-NMC}$CUAUGU (1)<br>3'-AUGUCA$^{F-NMC}$GAUACA (4) |
| 11 | RNA(C$^{F-NMC}$):cRNA(G$^{F-NMC}$) | 5'-UACAGUC$^{F-NMC}$UAUGU (2)<br>3'-AUGUCAG$^{F-NMC}$AUACA (3) |
| 12 | RNA(U$^F$):cRNA(A$^F$) | 5'-UACAGU$^F$CUAUGU<br>3'-AUGUCA$^F$GAUACA |
| 13 | RNA(C$^F$):cRNA(G$^F$) | 5' UACAGUC$^F$UAUGU<br>3'-AUGUCAG$^F$AUACA |
| 14 | RNA²:cRNA² | 5'-GCGAUCUCAC<br>3'-CGCUAGAGUG |
| 15 | RNA(B$^{F-NMC}$):cRNA² | 5'-GCG$^{F-NMC}$A$^{F-NMC}$U$^{F-NMC}$C$^{F-NMC}$U$^{F-NMC}$C$^{F-NMC}$AC (5)<br>3'-CGCUAGAGUG |
| 16 | RNA(B$^F$):cRNA² | 5'-GCG$^F$A$^F$U$^F$C$^F$U$^F$C$^F$AC (6)<br>3'-CGCUAGAGUG |

[a] Superscript F indicates 2'-F-RNA, superscript F-NMC indicates 2'-F-NMC. [b] Numbers in parentheses indicate numbers from Table S1.

Circular dichroism spectroscopy: The circular dichroism (CD) spectra were obtained on a Jasco J-815 spectropolarimeter equipped with a Julabo F25 circulating bath. The sample was allowed to equilibrate for 5 min at 15° C. in PBS (137 mM sodium chloride, 2.7 mM potassium chloride, 8 mM sodium phosphate dibasic, and 2 mM potassium phosphate monobasic, pH 7.4) at a final concentration of 2.61 µM of duplex. The spectrum was an average of 5 scans. Spectra were collected at a rate of 50 nm/min with a bandwidth of 1 nm and at a sampling wavelength of 0.2 nm using fused quartz cells (Starna 29-Q-10) at a temperature of 15° C. The CD spectra were recorded from 350 to 200 nm. The molar ellipticity was calculated from the equation $[\theta]=\theta/10Cl$, where $\theta$ is the ellipticity (mdeg), C is the molar concentration of oligonucleotides (M), and l is the path length of the cell (cm). The data were processed using software supplied by JASCO and were transferred into Microsoft Excel for presentation.

TABLE 10

Modified duplexes for CD spectroscopy[a] (Table 10 discloses SEQ ID NOS 65, 64, 84, 64, 84 and 72, respectively, in order of appearance)

| duplex no. | duplex type | duplex[b] |
|---|---|---|
| 1 | RNA:cRNA | 5'-UACAGUCUAUGU<br>3'-AUGUCAGAUACA |

TABLE 10-continued

Modified duplexes for CD spectroscopy[a] (Table 10 discloses SEQ ID NOS 65, 64, 84, 64, 84 and 72, respectively, in order of appearance)

| duplex no. | duplex type | duplex[b] | |
|---|---|---|---|
| 2 | RNA($U^{F-NMC}$):cRNA | 5'-UACAGU$^{F-NMC}$CUAUGU<br>3'-AUGUCAGAUACA | (1) |
| 3 | RNA($U^{F-NMC}$):cRNA($A^{F-NMC}$) | 5'-UACAGU$^{F-NMC}$CUAUGU<br>3'-AUGUCA$^{F-NMC}$GAUACA | (1)<br>(4) |

[a]Superscript F-NMC indicates 2'-F-NMC. [b]Numbers in parentheses indicate numbers from Table 6

Exonuclease assays: Oligonucleotides were prepared at a final concentration of 0.1 mg/mL in either 50 mM Tris (pH 7.2) and 10 mM $MgCl_2$ or 50 mM sodium acetate (pH 6.5) and 10 mM $MgCl_2$ for assays in the presence of 3'-specific or 5'-specific exonucleases, respectively. The exonuclease (75 mU/mL SVPD or 500 mU/mL PDE-II) was added to oligonucleotide solution immediately prior to the first injection onto the HPLC column, and enzymatic degradation kinetics were monitored for 24 h at 25° C. Samples collected over 24 h were injected directly onto a Dionex DNAPac PA200 analytical column at 30° C. column temperature. The gradient was from 37% to 52%1 M NaBr, 10% $CH_3CN$, 20 mM sodium phosphate buffer at pH 11 over 10 min with a flow rate of 1 mL/min. The amount of 20-mer or 19-mer (for experiment with $dT_{18}C^{F-NMC}dT$ (SEQ ID NO: 77)) was determined as the area under the curve of the peak detected at $A_{260}$. Percent full-length ON was calculated by dividing the area under the curve at the first time point and multiplying by 100. Activity of enzyme was verified for each experiment by including a oligodeoxythymidylate with a terminal phosphorothioate linkage $dT_{20}$ (SEQ ID NO: 96) in each experiment. Each aliquot of enzyme was thawed just prior to the experiment. The half-life was determined by fitting to first-order kinetics. Each degradation experiment was run in duplicate.

Modeling study: The model shown in FIG. 36A-36D was built using the program UCSF Chimera (Pettersen, E. F.; Goddard, T. D.; Huang, C. C.; Couch, G. S.; Greenblatt, D. M.; Meng, E. C.; Ferrin, T. E. J. Comput. Chem. 2004, 25, 1605) starting from an RNA duplex, riboses in one strand were replaced by 2'-F-NMC sugars with a C2'-exo pucker without altering backbone or glycosidic torsion angles.

All of the U.S. patents, U.S. patent application publications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A double-stranded RNA (dsRNA) molecule capable of inhibiting the expression of a target gene, comprising: a sense strand and an antisense strand, each stranding having 14 to 40 nucleotides, wherein the antisense strand has sufficient complementarity to the target sequence to mediate RNA interference, wherein said sense strand, at position 1 of the 5' end, comprises a 5'-deoxynucleoside with a morpholino at the 5'-carbon.

2. The dsRNA molecule of claim 1, wherein said antisense strand comprises at least one thermally destabilizing modification of the duplex within the first 9 nucleotide positions of the 5' region, wherein said sense strand comprises an asialoglycoprotein receptor (ASGPR) ligand.

3. The dsRNA molecule according to claim 2, wherein the dsRNA comprises at least four 2'-fluoro.

4. The dsRNA molecule according to claim 3, wherein there are no 2'-fluoro modifications at nucleotide positions 3-9 of the antisense strand.

5. The dsRNA molecule according to claim 1, further having the following characteristics:

a) the thermally destabilizing modification of the duplex is located in position 4-8 of the 5' region of the antisense strand;
b) and each of the sense and antisense strands comprise at least two 2'-fluoro modifications; and
c) an ASGPR ligand attached to either end of the sense strand.

6. The dsRNA molecule according to claim 5, wherein there are no 2'-fluoro modifications at nucleotide positions 3-9 of the antisense strand.

7. The dsRNA molecule according to claim 1, wherein the antisense strand has at least two of the following characteristics:

a) the thermally destabilizing modification of the duplex modification is located in position 4 to 8 of the antisense strand;
b) at least two 2'-fluoro modifications;
c) phosphorothioate internucleotide linkages between nucleotide positions 1 and 2 (counting from the 5' end);
d) it has a length of 18 to 35 nucleotides.

8. The dsRNA molecule according to claim 7, wherein there are no 2'-fluoro modifications at nucleotide positions 3-9 of the antisense strand.

9. The dsRNA molecule according to claim 1, wherein the sense strand has at least one of the following characteristics:
   a) the ASGPR ligand attached to either end of the sense strand;
   b) at least two 2'-fluoro modifications;
   c) the sense strand and the antisense strand show sufficient complementarity to form a double stranded region spanning at least 19 nucleotide positions and wherein the thermally destabilizing modification of the duplex is located within said double-stranded region.

10. The dsRNA molecule according to claim 9, wherein there are no 2'-fluoro modifications at nucleotide positions 3-9 of the antisense strand.

11. The dsRNA molecule according to claim 2, wherein the thermally destabilizing modification of the duplex is selected from the group consisting of

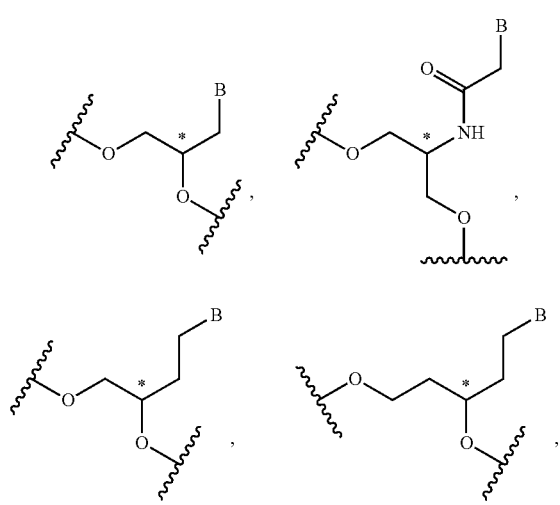

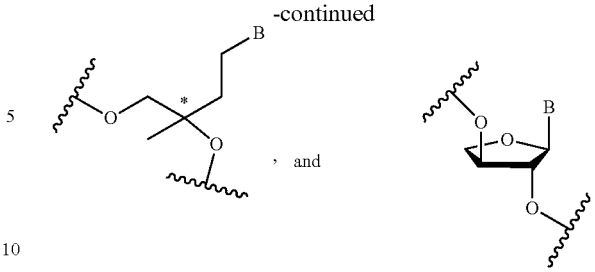

wherein B is nucleobase.

12. The dsRNA molecule according to claim 2, wherein the thermally destabilizing modification is located in position 7 of the antisense strand.

13. The dsRNA molecule according to claim 2, wherein the ASGPR ligand is one or more N-acetylgalactosamine (GalNAc) derivatives attached through a bivalent or trivalent branched linker.

14. The dsRNA molecule of claim 9, wherein the ASGPR ligand is:

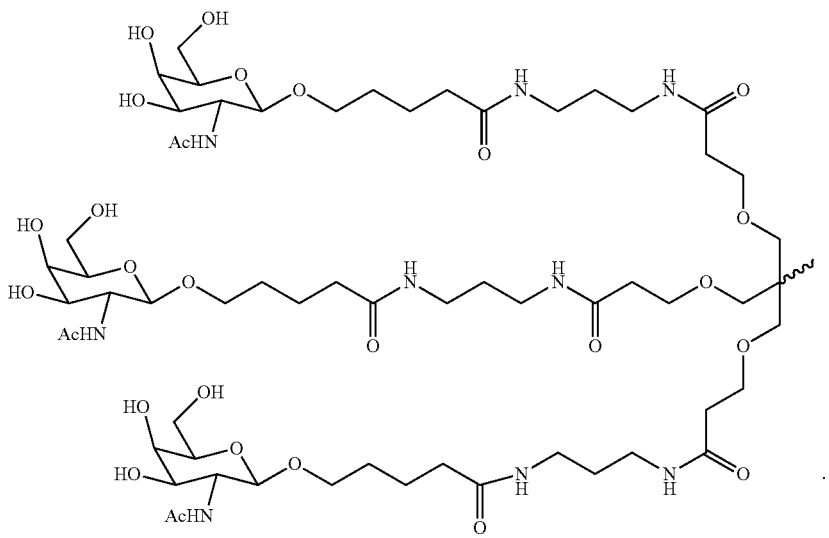 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

15. The dsRNA molecule according to claim 1, wherein the antisense strand comprises at least one thermally destabilizing modification of the duplex within the first 9 nucleotide positions of the 5' region, and the dsRNA has a melting temperature of from about 40° C. to about 80° C.

16. The dsRNA of claim 1, wherein the dsRNA further has at least one of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; (vii) the dsRNA comprises a duplex region of 12-40 nucleotide pairs in length; (viii) a blunt end at 5' end of the antisense strand; and (ix) the sense strand comprises one or more LNA modifications.

17. The dsRNA of claim 16, wherein there are no 2'-fluoro modifications at positions 3-9 of the antisense strand.

18. The dsRNA molecule according to claim 1, wherein the sense strand has 21 nucleotides, and the antisense strand has 23 nucleotides.

19. A method for silencing a target gene in a cell, the method comprising a step of introducing the dsRNA molecule of claim 1 into the cell.

20. A method for suppressing off-target effects caused by the sense strand of dsRNA molecules, the method comprising a step of introducing the dsRNA molecule of claim 1 into a cell.

* * * * *